United States Patent
Tie et al.

(10) Patent No.: US 9,631,002 B2
(45) Date of Patent: Apr. 25, 2017

(54) METHODS AND COMPOSITIONS FOR PRODUCING ACTIVE VITAMIN K-DEPENDENT PROTEINS

(75) Inventors: Jianke Tie, Chapel Hill, NC (US); Darrel W. Stafford, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/997,008

(22) PCT Filed: Dec. 21, 2011

(86) PCT No.: PCT/US2011/066379
§ 371 (c)(1),
(2), (4) Date: Aug. 28, 2013

(87) PCT Pub. No.: WO2012/088222
PCT Pub. Date: Jun. 28, 2012

(65) Prior Publication Data
US 2013/0337504 A1  Dec. 19, 2013

Related U.S. Application Data

(60) Provisional application No. 61/425,652, filed on Dec. 21, 2010, provisional application No. 61/506,436, filed on Jul. 11, 2011, provisional application No. 61/540,374, filed on Sep. 28, 2011.

(51) Int. Cl.
*C07K 14/47* (2006.01)
*C12N 9/04* (2006.01)
*C12P 21/02* (2006.01)
*C12Q 1/26* (2006.01)

(52) U.S. Cl.
CPC ............ *C07K 14/47* (2013.01); *C12N 9/0006* (2013.01); *C12P 21/02* (2013.01); *C12Q 1/26* (2013.01); *C12Y 101/04* (2013.01); *G01N 2333/35* (2013.01); *G01N 2333/904* (2013.01); *G01N 2500/04* (2013.01)

(58) Field of Classification Search
CPC ....... C07K 14/47; C12N 9/0006; C12P 21/02; C12Q 1/26
See application file for complete search history.

(56) References Cited

U.S. PATENT DOCUMENTS

| | | | |
|---|---|---|---|
| 3,662,406 A | 5/1972 | Giglio | |
| 4,736,866 A | 4/1988 | Leder et al. | |
| 4,770,999 A | 9/1988 | Kaufman et al. | |
| 4,816,397 A | 3/1989 | Boss et al. | |

(Continued)

FOREIGN PATENT DOCUMENTS

| | | |
|---|---|---|
| DE | 39 08 009 A1 | 9/1990 |
| DE | 196 25 049 | 1/1998 |

(Continued)

OTHER PUBLICATIONS

ED043588 (Created on Aug. 22, 2007).*

(Continued)

*Primary Examiner* — Alexander Kim
(74) *Attorney, Agent, or Firm* — Myers Bigel, P.A.

(57) ABSTRACT

The present invention provides methods and compositions for the production of vitamin K dependent proteins.

2 Claims, 35 Drawing Sheets

(56) References Cited

U.S. PATENT DOCUMENTS

| | | | |
|---|---|---|---|
| 4,816,567 A | 3/1989 | Cabilly et al. | |
| 5,268,275 A | 12/1993 | Stafford et al. | |
| 5,460,950 A | 10/1995 | Barr et al. | |
| 5,547,835 A | 8/1996 | Koster et al. | |
| 5,583,278 A | 12/1996 | Alt et al. | |
| 5,625,122 A | 4/1997 | Mak | |
| 5,686,631 A | 11/1997 | Li et al. | |
| 5,698,765 A | 12/1997 | Mak | |
| 5,750,825 A | 5/1998 | Yazaki et al. | |
| 5,888,809 A | 3/1999 | Allison | |
| 6,043,031 A | 3/2000 | Koster et al. | |
| 6,270,022 B1 | 8/2001 | Knapp | |
| 6,453,244 B1 | 9/2002 | Oefner | |
| 6,492,115 B1 | 12/2002 | Guida et al. | |
| 7,220,849 B2 | 5/2007 | High et al. | |
| 7,445,896 B2 | 11/2008 | Rieder et al. | |
| 7,482,141 B2* | 1/2009 | Stafford | C12N 9/0006 435/189 |
| 7,524,665 B2 | 4/2009 | Stafford et al. | |
| 7,645,602 B2 | 1/2010 | Stafford et al. | |
| 7,687,233 B2 | 3/2010 | Stafford et al. | |
| 7,858,318 B2 | 12/2010 | Stafford et al. | |
| 8,097,410 B2 | 1/2012 | Stafford et al. | |
| 8,603,823 B2* | 12/2013 | Stafford | C12N 9/0006 435/183 |
| 2002/0102649 A1 | 8/2002 | Hillman et al. | |
| 2003/0220247 A1 | 11/2003 | High et al. | |
| 2005/0164367 A1 | 7/2005 | Fenge et al. | |
| 2005/0271644 A1 | 12/2005 | Oldenburg et al. | |
| 2006/0084070 A1 | 4/2006 | Rieder et al. | |
| 2006/0084081 A1 | 4/2006 | Rieder et al. | |
| 2006/0166239 A1 | 7/2006 | Chen et al. | |
| 2006/0194284 A1 | 8/2006 | Scheiflinger et al. | |
| 2006/0240440 A1 | 10/2006 | Stafford et al. | |
| 2007/0009950 A1 | 1/2007 | Stafford et al. | |
| 2007/0190614 A1 | 8/2007 | Stafford et al. | |
| 2007/0269866 A1 | 11/2007 | Stafford et al. | |
| 2007/0298426 A1 | 12/2007 | Chen et al. | |
| 2008/0045453 A1 | 2/2008 | Drohan et al. | |
| 2008/0050732 A1 | 2/2008 | Rieder et al. | |
| 2008/0050733 A1 | 2/2008 | Rieder et al. | |
| 2008/0057500 A1 | 3/2008 | Rieder et al. | |
| 2008/0318219 A1 | 12/2008 | Rieder et al. | |
| 2009/0215045 A1 | 8/2009 | Stafford et al. | |
| 2009/0215061 A1 | 8/2009 | Stafford et al. | |
| 2009/0325226 A1* | 12/2009 | Stafford et al. | 435/69.1 |
| 2010/0255586 A1 | 10/2010 | Stafford et al. | |
| 2011/0124000 A1 | 5/2011 | Stafford et al. | |

FOREIGN PATENT DOCUMENTS

| | | |
|---|---|---|
| EP | 0 127 839 | 12/1984 |
| EP | 0 154 133 | 9/1985 |
| EP | 0 368 684 | 5/1990 |
| EP | 0 549 721 | 7/1993 |
| EP | 1 273 724 A1 | 1/2003 |
| EP | 1 842 920 | 10/2007 |
| EP | 2 380 985 | 10/2011 |
| GB | 1 216 155 | 12/1970 |
| GB | 2 104 625 | 3/1983 |
| GB | 2 145 499 | 3/1985 |
| JP | 2003-292404 | 10/2003 |
| WO | WO 88/01649 | 3/1988 |
| WO | WO 88-03926 | 6/1988 |
| WO | WO 89/12685 A | 12/1989 |
| WO | WO 90/03496 A1 | 4/1990 |
| WO | WO 91/01372 | 2/1991 |
| WO | WO 92/01795 | 2/1992 |
| WO | WO 92-09698 | 6/1992 |
| WO | WO 92/19636 | 11/1992 |
| WO | WO 93/06213 | 4/1993 |
| WO | WO 95/34679 | 12/1995 |
| WO | WO 96-34966 | 11/1996 |
| WO | WO 97/49802 | 12/1997 |
| WO | WO 98/24884 | 6/1998 |
| WO | WO 98/49289 A1 | 11/1998 |
| WO | WO 99/33983 | 8/1999 |
| WO | WO 99/43003 | 8/1999 |
| WO | WO 00/03015 | 1/2000 |
| WO | WO 00/43003 A1 | 7/2000 |
| WO | WO 02/29045 | 4/2002 |
| WO | WO 02/40544 A2 | 5/2002 |
| WO | WO 02/102994 A2 | 12/2002 |
| WO | WO 03/006477 A1 | 1/2003 |
| WO | WO 2005/030039 | 4/2005 |
| WO | WO 2005-038019 | 4/2005 |
| WO | WO2005/040367 | 5/2005 |
| WO | WO 2006/044686 | 4/2006 |
| WO | WO 2006/067116 A | 6/2006 |
| WO | WO 2006/089613 A | 8/2006 |
| WO | WO 2006/101474 | 9/2006 |
| WO | WO 2006-110083 | 10/2006 |
| WO | WO 2007/065173 | 6/2007 |
| WO | WO 2007/075976 | 7/2007 |

OTHER PUBLICATIONS

Kulman et al., Vitamin K-dependent proteins in Ciona intestinalis, a basal chordate lacking a blood coagulation cascade., Proc Natl Acad Sci U S A. (2006), vol. 103(43), pp. 15794-15799.*
Rettie et al. "A common genetic basis for idiosyncratic toxicity of warfarin and phenytoin" *Epilepsy Res.* 35(3):253-255 (1999).
Rettie et al. "Hydroxylation of warfarin by human cDNA-expressed cytochrome P-450: a role for P-4502C9 in the etiology of (S)-warfarin-drug interactions" *Chem Res Toxicol.* 5(1):54-59 (1992).
Rieder et al. "Effect of VKORC1 Haplotypes on Transcriptional Regulation and Warfarin Dose" *N Engl J Med* 352(22):2285-2293 (2005).
Rieder et al. GenBank Accession No. AY 587020 "*Homo sapiens* vitamin K epoxide reductase complex, subunit 1 (VKORC1) gene, complete cds" May 14, 2004.
Risch. "Searching for Genetic Determinants in the New Millennium" *Nature* 405:847-856 (2000).
Robertson, "Genes Encoding Vitamin-K Epoxide Reductase are Present in *Drosophila* and Trypanosomatid Protists", *Genetics* 168:1077-1080 (2004).
Rost et al. "Mutations in VKORC1 cause warfarin resistance and multiple coagulation factor deficiency type 2" *Nature* 427:537-541 (2004).
Roth et al. "Expression of Bovine Vitamin K-Dependent Carboxylase Activity in Baculovirus-Infection Insect Cells" *PNAS USA* 90:8372-8376 (1993).
Roth et al. "Human Recombinant Factor IX: Safety and Efficacy Studies in Hemophilia B Patients Previously Treated with Plasma-Derived Factor IX Concentrates" *Blood* 98(13):3600-3606 (2001).
Running Deer and Allison. "High-Level Expression of Proteins in Mammalian Cells Using Transcription Regulatory Sequences from the Chinese Hamster EF-1α Gene" *Biotechnol Prog* 20:880-889 (2004).
Rusconi et al. "RNA aptamers as reversible antagonists of coagulation factor IXa" *Nature* 419:90-94 (2002).
Russell et al. "Nucleotide Sequence of the Yeast Alcohol Dehydrogenase II Gene" *The Journal of Biological Chemistry* 258(4):2674-2682 (1983).
Scahill et al. "Expression and characterization of the product of a human immune interferon cDNA gene in Chinese hamster ovary cells" *Proc. Natl. Acad. Sci. USA* 80:4654-4658 (1993).
Schmidt-Krey et al. "Two dimensional crystallization of human vitamin K-dependent γ-glutamyl carboxylase" *Journal of Structural Biology* 157:437-442 (2007).
Sconce et al. "The impact of CYP2C9 and VKORC1 genetic polymorphism and patient characteristics upon warfarin dose requirements: proposal for a new dosing regimen" *Blood* 106(7):2329-2333 (2005).
Scott et al. "Warfarin Pharmacogenetics: *CYP2C9* and *VKORC1* Genotypes Predict Different Sensitivity and Resistance Frequencies in the Ashkenazi and Sephardi Jewish Populations" *American Journal of Human Genetics* 82:495-500 (2008).

(56) References Cited

OTHER PUBLICATIONS

Seffernick et al. "Melamine Deaminase and Atrazine Chlorohydrolase: 98 Percent Identical but Functionally Different" *Journal of Bacteriology* 183(8):2405-2410 (2001).
Sen et al. "Developments in Directed Evolution for Improving Enzyme Functions" *Appl. Biochem. Biotechnol.* 143:212-223 (2007).
Shah et al. "Vitamin K-Dependent Carboxylase: Effect of Detergent Concentrations, Vitamin K Status, and Added Protein Precursors on Activity" *Archives of Biochemistry and Biophysics* 222(1):216-221 (1983).
Single Nucleotide Polymorphism (SNP) RefSNP (rs#) rs7294; GenBank Accession No. AA708782, Aug. 23, 1999.
Single Nucleotide Polymorphism (SNP) RefSNP (rs#) rs8359612; GenBank Accession No. AACN010884940, Sep. 14, 2003.
Single Nucleotide Polymorphism (SNP) RefSNP(rs#) rs8050394; GenBank Accession No. NT_010393, Jul. 4, 2003.
Single Nucleotide Polymorphism (SNP) RefSNP(rs#) rs9923231; GenBank Accession No. NT_024812.10, Nov. 5, 2003.
Single Nucleotide Polymorphism (SNP) RefSNP(rs#) rs9934438; GenBank Accession No. NC_000016.5, Aug. 10, 2004.
Single Nucleotide Polymorphism (SNP) RefSNP(rs#) rs9934438; GenBank Accession No. NT_024812.10, Mar. 19, 2004, Details: ss21323934.
Single Nucleotide Polymorphism (SNP) RefSNP(rs#) rs9934438; GenBank Accession No. NT_024812.10, Nov. 5, 2003, Details: ss13773513.
Single Nucleotide Polymorphism (SNP) RefSNP(rs#) rs9934438; GenBank Accession No. NT_024812.10, Feb. 20, 2004, Details: ss19348150.
Sinha et al. "Effect of Gamma Carboxylation on Prothrombinase Inhibitory Activity of Catalytically Inactive Factor XA" *Thromb Res* 75(4):427-436 (1994) (Abstract only).
Soute et al. "Characteristics of recombinant W501S mutated human γ-glutamyl carboxylase" *Journal of Thrombosis and Haemostasis* 2:597-604 (2004).
Sperling et al. "Metal Binding Properties of γ-Carboxyglutamic Acid" *The Journal of Biological Chemistry* 253(11):3898-3906 (1978).
Spier. "Genetic Engineering: Animal Cell Technology" *Encyclopedia of Cell Technology*, vol. 2 (John Wiley & Sons), excerpt pp. 737-757 (2000).
Spohn et al. "VKORC1 Deficiency in Mice Causes Early Postnatal Lethality Due to Severe Bleeding" *Thromb Haemost* 101:1044-1050 (2009).
Spronk et al. "Novel mutation in the γ-glutamyl carboxylase gene resulting in congenital combined deficiency of all vitamin K-dependent blood coagulation factors" *Blood* 96(10):3650-3652 (2000).
Stafford et al. "The vitamin K Cycle" *Journal of Thrombosis and Haemostasis* 3:1873-1878 (2005).
Stanley et al. "Amino Acids Responsible for Reduced Affinities of Vitamin K-Dependent Propeptides for the Carboxylase" *Biochemistry* 38:15681-15687 (1999).
Stanley et al. Identification of a vitamin K-dependent carboxylase in the venom duct of a *Conus* snail *FEBS letters* 407(1):85-88 (1997).
Stanley et al. "Role of the Propeptide and γ-Glutamic Acid Domain of Factor IX for in Vitro Carboxylation by the Vitamin K-Dependent Carboxylase" *Biochemistry* 37:13262-13268 (1998).
Stanley et al. "The Propeptides of the Vitamin K-dependent Proteins Possess Different Affinities for the Vitamin K-dependent Carboxylase" *The Journal of Biological Chemistry* 274:16940-16944 (1999).
Stein et al. "Antithrombotic therapy in patients with mechanical and biological prosthetic heart valves" *Chest* 108:371S-379S (1995).
Stenflo et al. "Vitamin K-dependent formation of gamma-carboxyglutamic acid" *Annu Rev Biochem.* 46:157-72 (1977).
Stitt et al. "The Anticoagulation Factor Protein S and its Relative, Gas6, are Ligands for the Tyro 3/Axl Family of Receptor Tyrosine Kinases" *Cell* 80:661-670 (1995).
Strausberg et al. "Generation and initial analysis of more than 15,000 full-length human and mouse cDNA sequences" *PNAS* 99(26):16899-16903 (2002).
Sun et al. "Vitamin K epoxide reductase significantly improves carboxylation in a cell line overexpressing factor X" *Blood* 106(12):3811-3815 (2005).
Suttie "The Biochemical Basis of Warfarin Therapy" *Adv. Exp. Med. Bio.* 214:3-16 (1987).
Suttie et al. "Mechanism of action of vitamin K: synthesis of gamma-carboxyglutamic acid" *CRC Crit Rev Biochem.* 8(2):191-223 (1980).
Suttie. "Synthesis of Vitamin K-Dependent Proteins" *FASEB J.* 7:445-452 (1993).
Swiss-Prot Accession No. Q9CRC0, Vitamin K epoxide reductase complex subunit 1 (Vitamin K1 2,3-epoxide reductase subunit 1), Jun. 1, 2001.
Takahashi et al. "Population differences in S-warfarin metabolism between CYP2C9 genotype-matched Caucasian and Japanese patients" *Clin Pharmacol Ther.* 73(3):253-63 (2003).
Taniguchi et al. "Protein-Protein and Lipid-Protein Interactions in a Reconstituted Cytochrome P-450 Dependent Microsomal Monooxygenase" *Biochemistry* 26:7084-7090 (1987).
Taube et al. "Influence of Cytochrome P-450 CYP2C9 Polymorphisms on Warfarin Sensitivity and Risk of Over-Anticoagulation in Patients on Long-Term Treatment" *Blood* 96(5):1816-1819 (2000).
Terai et al. "Human homologue of maid: A dominantly inhibitory helix-loop-helix protein associated with liver-specific gene expression" *Hepatology* 32(2):357-66 (2000).
Tie et al. "A topological study of the human γ-glutamyl carboxylase" *Blood* 96:973-978 (2000).
Tie et al. "Chemical Modification of Cysteine Residues is a Misleading Indicator of Their Status as Active Site Residues in the Vitamin K-dependent γ-Glutamyl Carboxylation" *The Journal of Biological Chemistry* 279:54079-54087 (2004).
Tie et al. "Determination of Disulfide Bond Assignment of Human Vitamin K-dependent γ-Glutamyl Carboxylase by Matrix-assisted Laser Desorption/Ionization Time-of-Flight Mass Spectrometry" *The Journal of Biological Chemistry* 278:45468-45475 (2003).
Tie et al. "Identification of the N-Linked Glycosylation Sites of Vitamin K-Dependent Carboxylase and Effect of Glycosylation on Carboxylase Function" *Biochemistry* 45:14755-14763 (2006).
Tie et al. "Membrane Topology Mapping of Vitamin K Epoxide Reductase by in Vitro Translation/Cotranslocation" *The Journal of Biological Chemistry* 280:16410-16416 (2005).
Tie et al. "Functional Study of the Vitamin K Cycle in Mammalian Cells" *Blood* 117(10)2967-2974 (2011).
Jin et al. "The Conversion of Vitamin K Epoxide to Vitamin K Quinone and Vitamin K Quinone to Vitamin K Hydroquinone Uses the Same Active Site Cysteines" *Biochemistry* 46:7279-7283 (2007).
Wajih et al. "Engineering of a Recombinant Vitamin K-Dependent γ-Carboxylation System with Enhanced γ-Carboxyglutamic Acid Forming Capacity" *The Journal of Biological Chemistry* 260(11):10540-10547 (2005).
PCT International Search Report for International Application No. PCT/US2011/066379, mailed Jul. 6, 2012 (4 pages).
PCT Written Opinion of the International Searching Authority for International Application No. PCT/US2011/066379, mailed Jul. 6, 2012 (6 pages).
Absher et al. "Patient-specific factors predictive of warfarin dosage requirements" *Ann Pharmacother.* 36(10):1512-7 (2002).
Accession AAX84611. Human V201 Coding Sequence. (2 pages) (Sep. 14, 1999).
Accession AAY22213. Human V201 Protein Sequence. (2 pages) (Sep. 14, 1999).
Aithal et al. "Association of polymorphisms in the cytochrome P450 CYP2C9 with warfarin dose requirement and risk of bleeding complication" *Lancet* 353(9154):717-719 (1999).
Altschul et al. "Gapped Blast and PSI-Blast: a new generation of protein database search programs" *Nucleic Acids Research* 25(17):3389-3402 (1997).

(56) References Cited

OTHER PUBLICATIONS

Aquilante et al. "Influence of coagulation factor, vitamin K epoxide reductase complex subunit 1, and cytochrome P450 2C9 gene polymorphisms on warfarin dose requirements" *Clinical Pharmacology & Therapeutics* 79(4):291-302 (2006).
Bandyopadhyay et al. "γ-Glutamyl carboxylation: An extracellular posttranslational modification that antedates the divergence of mollusks, arthropods, and chordates" *PNAS* 99(3):1264-1269 (2002).
Begent et al. "Characterization and Purification of the Vitamin $K_1$ 2,3 Epoxide Reductase System From Rat Liver" *Journal of Pharmacy and Pharmacology* 53:481-486 (2001).
Bell and Matschiner. "Vitamin K Activity of Phylloquinone Oxide" *Archives of Biochemistry and Biophysics* 141:473-476 (1970).
Bell et al. "Warfarin and the inhibition of vitamin K activity by an oxide metabolite" *Nature* 237:32-33 (1972).
Berkner and Pudota. "Vitamin K-Dependent Carboxylation of the Carboxylase" *PNAS USA* 95:466-471 (1998).
Berkner et al. "The Vitamin K-Dependent Carboxylase" *J. Nutr.* 130:1877-1880 (2000).
Berkner. "Expression of Recombinant Vitamin K-Dependent Proteins in Mammalian Cells: Factors IX and VII" *Methods in Enzymology* 222:450-477 (1993).
Blann et al. "Racial background is a determinant of average warfarin dose required to maintain the INR between 2.0 and 3.0" *Br J Haematol.* 107(1):207-209 (1999).
Bodin et al. "Cytochrome P450 2C9 (CYP2C9) and vitamin K epoxide reductase (VKORC1) genotypes as determinants of acenocoumarol sensitivity" *Blood* 106(1):135-140 (2005).
Bogousslavsky et al. "Anticoagulant-induced intracerebral bleeding in brain ischemia" *Acta Neurol Scand.* 71:464-471 (1985).
Boneh et al. "Hereditary Deficiency of Vitamin K-Dependent Coagulation Factors With Skeletal Abnormalities" *American Journal of Medical Genetics* 65:241-243 (1996).
Brenner et al. "A Missense Mutation in γ-Glutamyl Carboxylase Gene Causes Combined Deficiency of All Vitamin K-Dependent Blood Coagulation Factors" *Blood* 92(12):4554-4559 (1998).
Butler. "Animal Cell Cultures: Recent Achievements and Perspectives in the Production of Biopharmaceuticals" *Appl Microbiol Biotechnol* 68(3):283-291 (2005).
Cain et al. "Assembly of the Warfarin-sensitive Vitamin K 2,3-Epoxide Reductase Enzyme Complex in the Endoplasmic Reticulum Membrane" *The Journal of Biological Chemistry* 272(46):29068-29075 (1997).
Cain et al. "Warfarin Resistance is Associated with a Protein Component of the Vitamin K 2,3-Epoxide Reductase Enzyme Complex in Rat Liver" *Thromb Haemost* 80:128-33 (1998).
Camire et al. "Enhanced γ-Carboxylation of Recombinant Factor X Using a Chimeric Construct Containing the Prothrombin Propeptide" *Biochemistry* 39:14322-14329 (2000).
Carter et al. "Prothrombin G20210A is a bifunctional gene polymorphism" *Thromb Haemost.* 87(5):846-853(2002).
Chen et al. "Calcium Phosphate-Mediated Gene Transfer: A Highly Efficient Transfection System for Stably Transforming Cells with Plasmid DNA" *BioTechniques* 6(7):632-638 (1988).
Chenhsu et al. "Long-term treatment with warfarin in Chinese population" *Ann Pharmacother.* 34(12):1395-401 (2000).
Cheung et al. "Localization of a Metal-Dependent Epitope to the Amino Terminal Residues 33-40 of Human Factor IX" *Thrombosis Research* 80(5):419-427 (1995).
Chica et al. "Semi-Rational Approaches to Engineering Enzyme Activity: Combining the Benefits of Directed Evolution and Rational Design" *Current Opinion in Biotechnology* 16:378-384 (2005).
Chu et al. "A Mutation in the Propeptide of Factor IX Leads to Warfarin Sensitivity by a Novel Mechanism" *J. Clin. Invest.* 98(7):1619-1625 (1996).
Chu et al. "Purified vitamin K epoxide reductase alone is sufficient for conversion of vitamin K epoxide to vitamin K and vitamin K to vitamin $KH_2$" *PNAS* 103(51):19308-19313 (2006).
Karimi et al., Gateway vectors for Agrobacterium-mediated plant transformation., Trends in Plant Science, 2002, vol. 7, pp. 193-195.

Kaufman et al. "Expression, Purification, and Characterization of Recombinant γ-Carboxylated Factor IX Synthesized in Chinese Hamster Ovary Cells" *The Journal of Biological Chemistry* 261(21):9622-9628 (1986).
Keller and Manak. "DNA Probes" $2^{nd}$ Ed., Macmillan Publishers Ltd., pp. 259 (1993).
Kimura et al. "Genotypes of Vitamin K Epoxide Reductase, γ-Glutamyl Carboxylase, and Cytochrome P450 2C9 as Determinants of Daily Warfarin Dose in Japanese Patients" *Thrombosis Research* 120:181-186 (2007).
Kirchheiner et al. "Clinical consequences of cytochrome P450 2C9 polymorphisms" *Clin Pharmacol Thera.* 77(1):1-16 (2005).
Kohn et al. "A gene-anchored map position of the rat warfarin-resistance locus, Rw, and its orthologs in mice and humans" *Blood* 96(5):1996-1998 (2000).
Kohn et al. "Genomic assignment of the warfarin resistance locus, Rw, in the rat" *Mammalian Genome* 10:696-698 (1999).
Kohn et al. "Locus-Specific Genetic Differentiation at Rw Among Warfarin-Resistant Rat (*Ratus norvegicus*) Populations" *Genetics* 164:1055-1070 (2003).
Kohn et al. "Natural selection mapping of the warfarin-resistance gene" *PNAS* 97(14):7911-7915 (2000).
Kojima et al. "The Function of GADD34 is a Recovery from a Shutoff of Protein Synthesis Induced by ER Stress: Elucidation by GADD34-Deficient Mice" *FASEB* 17:1573-1575 (2003).
Kozak et al. "An analysis of 5'-noncoding sequences from 699 vertebrate messenger RNAs" *Nucleic Acids Research* 15(20):8125-8148 (1987).
Kulman et al. "Primary Structure and Tissue Distribution of Two Novel Proline-Rich γ-Carboxyglutamic Acid Proteins" *PNAS USA* 94:9058-9062 (1997).
Landefeld et al. "Anticoagulant-related bleeding: clinical epidemiology, prediction, and prevention" *Am J Med.* 95(3):315-28 (1993).
Larson et al. "Structure/Function Analyses of Recombinant Variants of Human Factor Xa: Factor Xa Incorporation into Prothrombinase on the Thrombin-Activated Platelet Surface is not Mimicked by Synthetic Phospholipid Vesicles" *Biochemistry* 37:5029-5038 (1998).
Laupacis et al. "Antithrombotic therapy in atrial fibrillation" *Chest* 114:579s-589s (1998).
Lee et al. "Glucocorticoids regulate expression of dihydrofolate reductase cDNA in mouse mammary tumour virus chimaeric plasmids" *Nature* 294:228-232 (1981).
Lee et al. "Interethnic variability of warfarin maintenance requirement is explained by *VKORC1* genotype in an Asian population" *Clinical Pharmacology & Therapeutics* 79(3):197-205 (2006).
Lee et al. "Identification of a Warfarin-Sensitive Protein Component in a 200S Rat Liver Microsomal Fraction Catalyzing Vitamin K and Vitamin K 2,3-Epoxide Reduction" *Biochemistry* 24:7063-7070 (1985).
Lesko et al. "Translation of pharmacogenomics and pharmacogenetics: a regulatory perspective" *Nat Rev Drug Discov.* 3(9):763-769 (2004).
Li et al. "Identification of the gene for vitamin K epoxide reductase" *Nature* 427:541-544 (2004).
Li et al. "Indentification of a *Drosophila* Vitamin K-dependent γ-Glutamyl Carboxylase" *The Journal of Biological Chemistry* 275:18291-18296 (2000).
Li et al. "Polymorphisms in the VKORC1 gene are strongly associated with warfarin dosage requirements in patients receiving anticoagulation" *J. Med. Genet.* Online Publication Apr. 12, 2006.
Lin et al. "Binding of the Factor IX γ-Carboxyglutamic Acid Domain to the Vitamin K-dependent γ-Glutamyl Carboxylase Active Site Induces an Allosteric Effect That May Ensure Processive Carboxylation and Regulate the Release of Carboxylated Product" *The Journal of Biological Chemistry* 279(8):6560-6566 (2004).
Lin et al. "The Putative Vitamin K-dependent γ-Glutamyl Carboxylase Internal Propeptide Appears to Be the Propeptide Binding Site" *The Journal of Biological Chemistry* 277(32):28584-28591 (2002).

(56) References Cited

OTHER PUBLICATIONS

Liska and Suttie. "Location of γ-Carboxyglutamyl Residues in Partially Carboxylated Prothrombin Preparations" *Biochemistry* 27:8366-8641 (1988).
Loebstein et al. Common genetic variants of microsomal epoxide hydrolase affect warfarin dose requirements beyond the effect of cytochrome P450 2C9 *Clinical Pharmacology & Therapeutics* 77(5):365-372 (2005).
Loebstein et al. "Interindividual variability in sensitivity to warfarin—Nature or nurture?" *Clin Pharmacol Ther.* 70(2):159-164 (2001).
Lucentini. "Gene Association Studies Typically Wrong" The Scientist pp. 20 (Dec. 20, 2004).
Malhotra et al. "The Kinetics of Activation of Normal and γ-Carboxyglutamic Acid-deficient Prothrombins" *The Journal of Biological Chemistry* 260(1):279-287 (1985).
Manfioletti et al. "The Protein Encoded by a Growth Arrest-Specific Gene (gas6) is a New Member of the Vitamin K-Dependent Proteins Related to Protein S, a Negative Coregulator in the Blood Coagulation Cascade" *Molecular and Cellular Biology* 13(8):4976-4985 (1993).
Mann et al. "Cofactor proteins in the assembly and expression of blood clotting enzyme complexes" *Annu Rev Biochem.* 57:915-56 (1988).
Martin et al. "Warfarin-resistance genotype determination in the Norway rat, *Rattus norvegicus*" *Laboratory Animals* 13:209-214 (1979).
Massari et al. "Helix-Loop-Helix Proteins: Regulators of Transcription in Eucaryotic Organisms" *Molecular and Cellular Biology* 20(2):429-440 (2000).
McGraw et al. "Evidence for a prevalent dimorphism in the activation peptide of human coagulation factor IX" *Proc. Natl. Acad. Sci. USA* 82:2847-2851 (1985).
McManus et al. "Gene Silencing in Mammals by Small Interfering RNAs" *Nature Reviews* 3:737-747 (2002).
McMillan et al. "Congenital Combined Deficiency of Coagulation Factors II, VII, IX, and X" *Medical Intelligence* 274(23):1313-1315 (1966).
McVey et al. "Factor VII Deficiency and the FVII Mutation Database" *Human Mutation* 17:3-17 (2001).
Montes et al. "The c.-1639G>A polymorphism of the VKORC1 gene is a major determinant of the response to acenocoumarol in anticoagulated patients" *Br. J. Haematol.* 133(2):183-187 (2006).
Moor et al. "Coagulation Factor VII Mass and Activity in Young Men With Myocardial Infarction at a Young Age" *Arteriosclerosis, Thrombosis, and Vascular Biology* 15:655-664 (1995).
Morris et al. "Characterization of the Purified Vitamin K-dependent γ-Glutamyl Carboxylase" *The Journal of Biological Chemistry* 268(12):8735-8742 (1993).
Morris et al. "Processive Post-translational Modification" *The Journal of Biological Chemistry* 270(51):30491-30498 (1995).
Morrissey et al. "Quantitation of Activated Factor VII Levels in Plasma Using a Tissue Factor Mutant Selectively Deficient in Promoting Factor VII Activation" *Blood* 81(3):734-744 (1993).
Mountford et al. "Internal ribosome entry sites and dicistronic RNAs in mammalian transgenesis" *Trends Genet.* 11(5):179-84 (1995).
Mukharji et al. "Purification of a vitamin K epoxide reductase that catalyzes conversion of vitamin K 2,3-epoxide to 3-hydroxy-2-methyl-3-phytyl-2,3-dihydronaphthoquinone" *Proc. Natl. Acad. Sci. USA* 82:2713-2717 (1985).
Mumberg et al. "Regulatable promoters of *Saccharomyces cerevisiae*: comparison of transcriptional activity and their use for heterologous expression" *Nucleic Acids Research* 22(25):5767-5768 (1994).
Munns et al. "Vitamin K-Dependent Synthesis and Modification of Precursor Prothrombin in Cultured H-35 Hepatoma Cells" *PNAS USA* 73:2803-2807 (1976).

Mushiroda et al. "Association of VKORC1 and CYP2C9 polymorphisms with warfarin dose requirements in Japanese patients" *J. Hum. Genet.* 51(3):249-253 (2006).
Mutero et al. "Resistance-associated point mutations in insecticide-insensitive acetylcholinesterase" *Proc. Natl. Acad. Sci.* 91:5922-5926 (1994).
Mutucumarana et al. "A Conserved Region of Human Vitamin K-dependent Carboxylase Residues 393 and 404 is Important for its Interaction with the Glutamate Substrate" *The Journal of Biological Chemistry* 278:46488-46493 (2003).
Mutucumarana et al. "Expression and Characterization of the Naturally Occurring Mutation L394R in Human γ-Glutamyl Carboxylase" *The Journal of Biological Chemistry* 275(42):32572-32577 (2000).
Nasu et al. "Genetic analysis of *CYP2C9* polymorphism in a Japanese population" *Pharmacogenetics* 7:405-409 (1997).
Nellen et al. "What makes an mRNA anti-sense-itive" *TIBS* 18:419-423 (1993).
Nelsestuen et al. "Role of γ-Carboxyglutamic Acid" *The Journal of Biological Chemistry* 251(22):6886-6893 (1976).
Nelsestuen et al. "The Mode of Action of Vitamin K" *The Journal of Biological Chemistry* 249(19):6347-6350 (1974).
Oldenburg et al "Vitamin K Epoxide Reductase Complex Subunit 1 (VKORC1): The Key Protein of the Vitamin K Cycle" *Antioxidatns & Redox Signaling* 8(3 & 4):347-353 (2006).
Oldenburg et al. "Congenital Deficiency of Vitamin K Dependent Coagulation Factors in Two Families Presents as a Genetic Defect of the Vitamin K-Epoxide-Reductase-Complex" *Thromb Haemost* 84:937-941 (2000).
Olsen and Brooker. "Analysis of the Structural Specificity of the Lactose Permease Toward Sugars" *The Journal of Biological Chemistry* 264(27):15982-15987 (1989).
O'Reilly et al. "Hereditary Transmission of Exceptional Resistance to Coumarin Anticoagulant Drugs" *The New England Journal of Medicine* 271:809-815 (1964).
O'Reilly et al. "The Second Reported Kindred With Hereditary Resistance to Oral Anticoagulant Drugs" *The New England Journal of Medicine* 282:1448-1451 (1970).
Pao and Paulsen. "Major Facilitator" *Microbiology and Molecular Biology Reviews* 62(1):1-34 (1998).
Pauli et al. "Association of Congenital Deficiency of Multiple Vitamin K-dependent Coagulation Factors and the Phenotype of the Warfarin Embryopathy: Clues to the Mechanism of Teratogenicity of Coumarin Derivatives" *Am. J. Hum. Genet.* 41:566-583 (1987).
Pechlaner et al. "A new case of combined deficiency of vitamin K dependent coagulation factors" *Thromb Haemost* 68(5):617 (1992).
Pelz et al. "The Genetic Basis of Resistance to Anticoagulants in Rodents" *Genetics* 170:1839-1847 (2005).
Pennisi et al. "A Closer Look at SNPs Suggests Difficulties" *Science* 281:1787-1789 (1998).
Petersen et al. "Probing the Structure of the Warfarin-Binding Site on Human Serum Albumin Using Site-Directed Mutagenesis" *Proteins* 47:116-125 (2002).
Prentice "Acquired Coagulation Disorders" *Clin. Haematol.* 14(2):413-442 (1985).
Presnell et al. "A Novel Fluorescence Assay to Study Propeptide Interaction with γ-Glutamyl Carboxylase" *Biochemistry* 40:11723-11733 (2001).
Presnell et al. "The Vitamin K-dependent Carboxylase" *Thromb Haemost* 87:937-946 (2002).
Price "Role of Vitamin-K-Dependent Proteins in Bone Metabolism" *Ann Rev Nutr* 8:565-583 (1988).
Price et al. "Matrix Gla Protein, a New γ-Carboxyglutamic Acid-Containing Protein which is Associated with the Organic Matrix of Bone" *Biochemical and Biophysical Research Communications* 117(3):765-771 (1983).
Przweorski et al. "Adjusting the focus on human variation" *Trends Genet.* 16(7):296-302 (2000).
Quteineh et al. "Vitamin K epoxide reductase (VKORC1) genetic polymorphism is associated to oral anticoagulant overdose" *Thromb. Haemost.* 94(3):690-691 (2005).

(56) References Cited

OTHER PUBLICATIONS

Ratfcliffe et al. "The Importance of Specific γ-Carboxyglutamic Acid Residues in Prothrombin" *The Journal of Biological Chemistry* 268(32):24339-24345 (1993).
Rehemtulla et al. "In vitro and in vivo functional characterization of bovine vitamin K-dependent γ-carboxylase expressed in Chinese hamster ovary cells" *Proc. Natl. Acad. Sci. USA* 90:4611-4615 (1993).
Reitsma et al. "A C1173T Dimorphism in the VKORC1 Gene Determines Coumarin Sensitivity and Bleeding Risk" *PloS Medicine* 2(10):e312, published on-line Oct. 11, 2005.
Notification Concerning Transmittal of International Preliminary Report on Patentability and Written Opinion of the International Searching Authority in corresponding PCT Application No. PCT/US2011/066379 mailed Jul. 4, 2013 (8 pages).
Crawford et al. "Haplotype Diversity across 100 Candidate Genes for Inflammation, Lipid Metabolism, and Blood Pressure Regulation in Two Populations" *Am J. Hum. Genet.* 74:610-622 (2004).
D'Andrea et al. "A polymorphism in the VKORC1 gene is associated with an interindividual variability in the dose-anticoagulant effect of warfarin" *Blood* 106(1):645-649 (2005).
Database Accession No. ADA57411 "Human Secreted Protein #230", Nov. 20, 2003 (first entry)(reissued Jun. 15, 2007).
Davis et al. "A quantum chemical study of the mechanism of action of Vitamin K carboxylase (VKC)III. Intermediates and transition states" *Journal of Molecular Graphics and Modelling* (Nov. 6, 2006).
Davis et al. "A quantum chemical study of the mechanism of action of Vitamin K epoxide reductase (VKOR) II. Transition states" *Journal of Molecular Graphics and Modelling* (Nov. 6, 2006).
Derian et al. "Inhibitors of 2-Ketoglutarate-dependent Dioxygenases Block Aspartyl β-Hydroxylation of Recombinant Human Factor IX in Several Mammalian Expression Systems" *The Journal of Biological Chemistry* 264(12):6615-6618 (1989).
Devlin et al. "A Comparison of Linkage Disequilibrium Measures of Fine Scale Mapping" *Genomics* 29(2):311-322 (1995).
Dockal et al. "Five recombinant fragments of human serum albumin-tools for the characterization of the warfarin binding site" *Protein Sci.* 9:1455-1465 (2000).
Dockal et al. "The Three Recombinant Domains of Human Serum Albumin" *The Journal of Biological Chemistry* 274(41):29303-29310 (1999).
Dowd et al. "Vitamin K and Energy Transduction: A Base Strength Amplification Mechanism" *Science* 269:1684-1691 (1995).
Drysdale et al. "Complex promoter and coding region β2-adrenergic receptor haplotypes alter receptor expression and predict in vivo responsiveness" *PNAS* 97(19):10483-10488 (2000).
Durrin et al. "Vitamin D receptor 3'-untranslated region polymorphisms: lack of effect on mRNA stability" *Biochim Biophys Acta.* 1453(3):311-20 (1999).
Ekelund et al. "Combined Deficiency of Coagulation Factors II, VII, IX, and X: A Case of Probable Congenital Origin" *Pediatric Hematology and Oncology* 3:187-193 (1986).
Esmon and Suttie. "Vitamin K-Dependent Carboxylase" *The Journal of Biological Chemistry* 251(20):6238-6243 (1976).
Esmon et al. "The Functional Significance of Vitamin K Action" *The Journal of Biological Chemistry* 250(11):4095-4099 (1975).
Esmon et al. "The New Carboxylation Reaction" *The Journal of Biological Chemistry* 250(12):4744-4748 (1975).
European Pharmacopoeia 5.0; 2.7.10 Assay of Human Coagulation Factor VII; pp. 203-204 (2005).
Fair et al. "Biosynthesis and Secretion of Factor VII, Protein C, Protein S, and the Protein C Inhibitor from a Human Hepatoma Cell Line" *Blood* 67:64-70 (1986).
Fang et al. "National Trends in Antiarrhythmic and Antithrombotic Medication Use in Atrial Fibrillation" *Arch Intern Med.* 164(1):55-60 (2004).
Fasco and Principe. "Vitamin $K_1$ Hydroquinone Formation Catalyzed by a Microsomal Reductase System" *Biochemical and Biophysical Research Communications* 97(4):1487-1492 (1980).

Fasco et al. "Formation of Hydroxyvitamin K by Vitamin K Epoxide Reductase of Warfarin-resistant Rats" *The Journal of Biological Chemistry* 258(7):4372-4380 (1983).
Fasco et al. "Warfarin Inhibition of Vitamin K 2,3-Epoxide Reductase in Rat Liver Microsomes" *Biochemistry* 22:5655-5660 (1983).
Ferland. "The Vitamin K-Dependent Proteins: An Update" *Nutrition Reviews* 56(8):223-230 (1998).
Foster et al. "Propeptide of Human Protein C is Necessary for γ-Carboxylation" *Biochemistry* 26:7003-7011 (1987).
Fregin et al. "Homozygosity mapping of a second gene locus for hereditary combined deficiency of vitamin K-dependent clotting factors to the centromeric region of chromosome 16" *Blood* 100(9):3229-3232 (2002).
Furie et al. "The Molecular Basis of Blood Coagulation" *Cell* 53:505-518 (1988).
Furie et al. "Vitamin K-Dependent Biosynthesis of γ-Carboxyglutamic Acid" *Blood* 93(6):1798-1808 (1999).
Furie et al. "Molecular Basis of Vitamin K-Dependent γ-Carboxylation" *The Journal of the American Society of Hematology* 75(9): 1753-1762 (1990).
Furuya et al. "Genetic polymorphism of CYP2C9 and its effect on warfarin maintenance dose requirement in patients undergoing anticoagulation therapy" *Pharmacogenetics* 5:389-392 (1995).
Gage et al. "Adverse Outcomes and Predictors of Underuse of Antithrombic Therapy in Medicare Beneficiaries with Chronic Atrial Fibrillation" *Stroke* 31:822-827 (2000).
Gage et al. "Pharmacogenetics and Anticoagulant Therapy" *Journal of Thrombosis and Thrombolysis* 16(1/2):73-78 (2003).
Gage et al. "PharmGKB Submission Update: VIII. PBAT Submission of Genetic Variation in *VKORC1I* to the PharmGKB Network" *Pharmacol Rev* 58(2):138-139 (2006).
Gage et al. "Use of pharmacogenetics and clinical factors to predict the maintenance dose of warfarin" *Thromb Haemost.* 91(1):87-94 (2004).
Gainnelli et al. "Hemophilia B: Database of Point Mutations and Short Additions and Deletions—eighth edition" *Nucleic Acids Research* 26(1):265-268 (1998).
Gan et al. "Racial Background is a Determinant Factor in the Maintenance Dosage of Warfarin" *International Journal of Hematology* 78:84-86 (2003).
Gateway Cloning Technology Overview (2000, total 4 pages).
Geisen et al. "VKORC1 haplotypes and their impact on the inter-individual and inter-ethnical variability of oral anticoagulation" *Blood* 94(4):773-779 (2005).
GenBank Accession No. AC135050, *Homo sapiens* chromosome 16 clone RP11-196G11, complete sequence, Oct. 5, 2002.
GenBank Accession No. AK002742, *Mus musculus* adult male kidney cDNA, clone:0610033K05, Jul. 10, 2000.
GenBank Accession No. AK013996, *Mus musculus* 13 days embryo head cDNA, clone:3110005B16, Jul. 10, 2000.
GenBank Accession No. AV003686, *Mus musculus* C57BL/8J kidney *Mus musculus* cDNA, clone:0610033K05, Unpublished 1999.
GenBank Accession No. AV162712, *Mus musculus* head C57BL/6 13-dat embryo *Mus Musculus* cDNA, clone:3110005B16, Unpublished 1999.
GenBank Accession No. AY587020, *Homo sapiens* vitamin K epoxide reductase complex, Mar. 31, 2004.
GenBank Accession No. BC000828, *Homo sapiens* vitamin K epoxide reductase complex, CDNA clone Image:3455200, Aug. 11, 2006.
GenBank Accession No. BC000828, *Homo sapiens* vitamin K epoxide reductase complex, cDNA clone Image:3455200, Sep. 1, 2006.
GenBank Accession No. BC000828.1 *Homo sapiens* vitamin K epoxide reductase complex, CDNA clone Image: 3455200, Nov. 15, 2000.
GenBank Accession No. BC002911.1, *Homo sapiens*, clone MGC:11276, Feb. 5, 2001.
GenBank Accession No. BC002911.2, *Homo sapiens* vitamin K epoxide reductase complex, clone MGC:11276, Feb. 5, 2001.
GenBank Accession No. BC027734.1 *Homo sapiens* vitamin K epoxide reductase complex, clone MGC:29720, Apr. 8, 2002.

(56) References Cited

OTHER PUBLICATIONS

GenBank Accession No. BY703248, Adult male kidney *Mus musculus*, clone 0610033K05, Dec. 16, 2002.
GenBank Accession No. N63475 (2 pages) (Sep. 13, 2000).
GenBank Accession No. NG_005631, *Homo sapiens* vitamin K epoxide reductase complex, LOC441241, derived from AC073210. 8, *Homo sapiens* BAC clone RP11-460N20, complete sequence, Jun. 10, 2000.
GenBank Accession No. NG_005631.1, *Homo sapiens* vitamin K epoxide reductase complex, LOC441241, derived from AC073210. 8, *Homo sapiens* BAC clone RP11-460N20, complete sequence, Nov. 18, 2006.
GenBank Accession No. NM_178600.1 *Mus musculus* vitamin K epoxide reductase complex, LOC441241, Aug. 5, 2006.
GenBank Accession No. NM_024006.1, *Homo sapiens* hypothetical protein, Image 3455200, Oct. 5, 2003.
GenBank Accession No. NM_024006.4, *Homo sapiens* vitamin K epoxide reductase complex, VKORC1, Mar. 11, 2007.
GenBank Accession No. NM_178600, *Mus musculus* vitamin K epoxide reductase complex, Vkorc1, derived from AK003237.1, *Mus musculus* 18-day embryo whole body cDNA, clone:1110001K05, Jul. 10, 2000 and CD774813.1, NIH_BMAP_MHI *Mus musculus* cDNA clone, Jul. 2, 2003.
GenBank Accession No. NM_178600.2, *Mus musculus* vitamin K epoxide reductase complex, Vkorc1, Mar. 16, 2004.
GenBank Accession No. NM_203335.1, *Rattus norvegicus* vitamin K epoxide reductase complex, Vkorc1, Jan. 15, 2006.
GenBank Accession No. NM_203335.2, *Rattus norvegicus* vitamin K epoxide reductase complex, VKORC1, derived from CB314647. 1, NICHD_Rr_Pit1 *Rattus norvegicus* cDNA clone, Image:6890244, Mar. 3, 2003, AY423047.1, *Rattus norvegicus* vitamin K epoxide reductase complex subunit 1(Vkorc1) mRNA, complete cds, Sep. 25, 2003 and AW253787.1, UI-R-BJ0-acz-d-05-0-UI.s1 UI-R-BJ0 *Rattus norvegicus* cDNA clone, Dec. 17, 1999.
GenBank Accession No. NM_206807, *Gallus gallus* vitamin K epoxide reductase complex, VKORC1, derived from AW355622, *Gallus gallus* cDNA clone pftlc.pk003.d10, Jun. 23, 2006, and BU114821.1, CHSEQCHL14 *Gallus gallus* cDNA clone ChEST105p15, Nov. 25, 2002.
GenBank Accession No. NM_206807.1, *Gallus gallus* vitamin K epoxide reductase complex, VKORC1, Jun. 25, 2006.
GenBank Accession No. NM_206824, *Homo sapiens* vitamin K epoxide reductase complex, VKORC1, derived from BI822140.1, 603039843F1 NIH_MGC_115 *Homo sapiens* cDNA clone Image:5180554, Oct. 4, 2001, AK129513.1, *Homo sapiens* cDNA FLJ26002 fis, clone DMC07743, Jul. 31, 2003 and CD249837.1, NIH_MGC_172 *Homo sapiens* cDNA, Unpublished 1999.
GenBank Accession No. NM_206824.1 *Homo sapiens* vitamin K epoxide reductase complex, VKORC1, Aug. 13, 2006.
GenBank Accession No. NP_848715, vitamin K epoxide reductase complex, subunit 1 [Mus musculus], derived from AK003237.1, *Mus musculus* 18-day embryo whole body cDNA, clone:1110001K05, Jul. 10, 2000 and CD774813.1, NIH_BMAP_MHI *Mus musculus* cDNA clone, Jul. 2, 2003.
GenBank Accession No. NT_024812 (5 pages) (Jul. 4, 2003).
Goldsmith et al. "Studies on a Family with Combined Functional Deficiencies of Vitamin K-dependent Coagulation Factors" *J. Clin. Invest.* 69:1253-1260 (1982).
Gossen et al. "Inducible gene expression systems for higher eukaryotic cells" *Current Opinion in Biotechnology* 5:516-520 (1994).
Greaves et al. "Heritable Resistance to Warfarin in Rats" *Nature* 215:877-878 (1967).
Guenthner et al. "Co-purification of Microsomal Epoxide Hydrolase with the Warfarin-Sensitive Vitamin K1 Oxide Reductase of the Vitamin K Cycle" *Biochemical Pharmacology* 55:169-175 (1998).
Gullev et al. "Bleeding Complications to Long-Term Oral Anticoagulant Therapy" *Journal of Thrombosis and Thrombolysis* 1:17-25 (1994).

Hacker et al. "Lack of association between an interleukin-1 receptor antagonist gene polymorphism and ulcerative colitis" *Gut* 40:623-627 (1997).
Hallgren et al. "Carboxylase overexpression effects full carboxylation but poor release and secretion of factor IX: implications for the release of vitamin K-dependent proteins" *Biochemistry* 41(50):15045-55 (2002).
Hallgren et al. "r-VKORC1 Expression in Factor IX BHK Cells Increases Factor IX Carboxylation but is Limited by Saturation of Another Carboxylation Component or by a Shift in the Rate Limiting Step" *Biochemistry* 45(17):5587-5598 (2006).
Hanumanthaiah et al. "Developmental Expression of Vitamin K-Dependent Gamma-Carboxylase Activity in Zebrafish Embryos: Effect of Warfarin" *Blood Cells, Molecules and Diseases* 27(6):992-999 (2001).
Harrington et al. "Pharmacodynamic resistance to warfarin associated with a Val66Met substitution in vitamin K epoxide reductase complex subunit 1" *Thromb Haemost* 93:23-26 (2005).
Hegele. "SNP Judgments and Freedom of Association" *Arterioscler. Thromb. Vasc. Biol.* 22:1058-1061 (2002).
Herlitschka et al. "Overexpression of human prothrombin in permanent cell lines using a dominant selection/amplification fusion marker" *Protein Expr. Purif.* 8(3):358-64 (1996).
Higashi et al. "Association between CYP2C9 genetic variants and anticoagulation-related outcomes during warfarin therapy" *JAMA* 287(13):1690-1698 (2002).
Himly et al. "Defective vaccinia virus as a biologically safe tool for the overproduction of recombinant human secretory proteins" *Protein Expr. Purif.* 14(3):317-26 (1998).
Himmelspach et al. "Recombinant Human Factor X: High Yield Expression and the Role of Furin in Proteolytic Maturation in Vivo and in Vitro" *Thrombosis Research* 97:51-67 (2000).
Hirsh et al. "Antithrombotic therapy in deep vein thrombosis and pulmonary embolism" *Am Heart J.* 123(4 Pt 2):1115-22 (1992).
Hirsh et al. "Oral Anticoagulants: Mechanism of Action, Clinical Effectiveness, and Optimal Therapeutic Range" *Chest* 119:8s-21s (2001).
Horton and Bushwick. "Warfarin Therapy: Evolving Strategies in Anticoagulation" *American Family Physician* 59(3):635-646 (1999).
Houben et al. "Osteocalcin binds tightly to the γ-glutamylcarboxylase at a site distinct from that of the other known vitamin K-dependent proteins" *Biochem. J.* 341:265-269 (1999).
Huisse et al. "Mechanism of the Abnormal Vitamin K-dependent γ-Carboxylation Process in Human Hepatocellular Carcinomas" *Cancer* 74:1533-41 (1994).
ICOS "Factor IX Cell Culture Process" Version 2.0 (12 pages) (2006).
Jackson et al. "Identification of a consensus motif for retention of transmembrane proteins in the endoplasmic reticulum" *The EMBO Journal* 9(10):3153-3162 (1990).
Johnson et al. "Characterization of a Variant Prothrombin in a Patient Congenitally Deficient in Factors II, VII, IX, and X" *British Journal of Haematology* 44:461-469 (1980).
Jones et al. "A cellular DNA-binding protein that activates eukaryotic transcription and DNA replication" *Cell.* 48(1):79-89 (1987).
Jorgensen et al. "Expression of Completely γ-Carboxylated Recombinant Human Prothrombin" *The Journal of Biological Chemistry* 262(14):6729-6734 (1987).
Kaminsky et al. "Correlation of human cytochrome P4502C substrate specificities with primary structure: warfarin as a probe" *Mol Pharmacol.* 43(2):234-239 (1993).
Kaminsky et al. "Human hepatic cytochrome P-450 composition as probed by in vitro microsomal metabolism of warfarin" *Drug Metab Dispos.* 12(4):470-477 (1984).
Kappel and Olson. "Kinetics of Carboxylation of Endogenous and Exogenous Substrates by the Vitamin K-Dependent Carboxylase" *Archives of Biochemistry and Biophysics* 230(1):294-299 (1984).
Accession no. AKQ13996.1 "*Mus musculus* (house mouse) hypothetical protein" ebi.ac.uk 2 pages (created Feb. 8, 2001) (last updated Oct. 7, 2010).

(56) References Cited

OTHER PUBLICATIONS

Accession No. NP_848715.1 "Vitamin K epoxide reductase complex, subunit 1; vitamin K1 epoxide reductase (warfarin-sensitive); phylloquinone epoxide reductase [Mus musculus]" *NCBI* 2 pages (Aug. 25, 2004).
Bandyopadhyay et al. "Conantokin-G Precursor and its Role in γ-Carboxylation by a Vitamin K-dependent Carboxylase from a *Conus* Snail" *The Journal of Biological Chemistry* 273(10):5447-5450 (1998).
Begley et al. "A Conserved Motif within the Vitamin K-dependent Carboxylase Gene is Widely Distributed across Animal Phyla" *The Journal of Biological Chemistry* 275(46):36245-36249 (2000).
Berkner et al. "The physiology of vitamin K nutriture and vitamin K-dependent protein function in atherosclerosis" *Journal of Thrombosis and Haemostasis* 2:2118-2132 (2004).
Bleck et al. "Searching for candidate genes in the new millennium" *Clinical and Experimental Dermatology* 26:279-283 (2001).
Clark et al. "The Secreted Protein Discovery Initiative (SPDI), a Large-Scale Effort to Identify Novel Human Secreted and Transmembrane Proteins: A Bioinformatics Assessment" *Genome Research* 13:2265-2270 (2003).
Cytokines & Cells Encyclopedia—Cope "COS" Jun. 14, 2010 (2 pages).
Cytokines & Cells Encyclopedia—Cope "HEK293" Jun. 14, 2010 (2 pages).
Extended European Search Report corresponding to European Patent Application No. 11851094.0 (10 pages) (Apr. 16, 2014).
GenBank Accession No. AAA88040 "Coagulation factor VII [*Homo sapiens*]" *NCBI* 2 pages (Feb. 13, 1996).
Haack et al. "Conantokin-T" *The Journal of Biological Chemistry* 265(11):6026-6029 (1990).
Kulman et al. "Identification of two novel transmembrane γ-carboxyglutamic acid proteins expressed broadly in fetal and adult tissues" *Proceedings of the National Academy of Sciences* 98(4):1370-1375 (2001).
Letunic et al. "Smart 6: recent updates and new developments" *Nucleic Acids Research* 37:D229-D232 (2009).
Li, Tao "Identification of the Gene for Vitamin K Epoxide Reductase" *University of North Carolina at Chapel Hill Dissertation* (73 pages) (Jun. 2, 2004).
McClure et al. "Post-translational Processing Events in the Secretion Pathway of Human Protein C, a Complex Vitamin K-dependent Antithrombotic Factor" *The Journal of Biological Chemistry* 267(27):19710-19717 (1992).
Nishimoto et al. "Secretion of the Vitamin K-dependent Protein of Bone by Rat Osteosarcoma Cells" *The Journal of Biological Chemistry* 255(14):6579-6583 (1980).
Patton, Aaron "Gateway Cloning Technology: Faster, Easier, More Accurate Cloning" *Gateway Cloning Technology Overview* 4 pages (2000).
Pinto et al. "Cloning of the bone Gla protein gene from the teleost fish *Sparus aurata*. Evidence for overall conservation in gene organization and bone-specific expression from fish to man" *Gene* 270:77-91 (2001).
Sheehan et al. "Demonstration of the extrinsic coagulation pathway in teleostei: Identification of zebrafish coagulation factor VII" *Proceedings of the National Academy of Sciences* 98(15):8768-8773 (2001).
Single Nucleotide Polymorphism (SNP) RefSNP(rs#): rs2359612 *NCBI* (4 pages) (Accessed Apr. 18, 2011).
Single Nucleotide Polymorphism (SNP) SNP(ss) Details: ss3316103 *NCBI* (12 pages) (Sep. 20, 2001).
Sood et al. "Cloning and Characterization of 13 Novel Transcripts and the Human RGS8 Gene from the 1q25 Region Encompassing the Hereditary Prostate Cancer (HPC1) Locus" *Genomics* 73:211-222 (2001).
Swiss Prot Accession No. Q9CRC0 "Vkorc1" Uniprot.org 3 pages (Apr. 12, 2005).
Tanikawa, Tsutomu "Effect of warfarin and diphacinone baits to a warfarin-resistant colony of *Rattus rattus*" *The Japan Society of Medical Entomology and Zoology* 45(2):129-132 (1994).
Tie et al. "Evaluation of warfarin resistance using transcription activator-like effector nucleases-mediated vitamin K epoxide reductase knockout HEK293 cells" *Journal of Thrombosis and Haemostasis* 11:1556-1564 (2013).
Toomajian et al. "Sequence Variation and Haplotype Structure at the Human HFE Locus" *Genetics* 161:1609-1623 (2002).
Tsaioun, Katherine I. "Vitamin K-dependent Proteins in the Developing and Aging Nervous System" *Nutrition Reviews* 57(8):231-240 (1999).
Uhlmann et al. "Antisense Oligonucleotides: A New Therapeutic Principle" *Chemical Reviews* 90(4):543-584 (1990).
Vecsler et al. "Combined genetic profiles of components and regulators of the vitamin K-dependent γ-carboxylation system affect individual sensitivity to warfarin" *Thrombosis and Haemostasis* 95(2):205-211 (2006).
Veenstra et al. "Association of Vitamin K epoxide reductase complex 1 (VKORC1) variants with warfarin dose in a Hong Kong Chinese patent population" *Pharmacogenetics and Genomics* 15(10):687-691 (2005).
Venter et al. "The Sequence of the Human Genome" *Science* 291(5507):1304-1351 (2001).
Vermeer et al. "Vitamin K-Dependent Carboxylase" *Haematologia* 18(2):71-97 (1985).
Vermeer. "γ-Carboxyglutamate-Containing Proteins and the Vitamin K-Dependent Carboxylase" *Biochem J* 266:625-636 (1990).
Vicente et al. "Congenital Deficiency of Vitamin K-Dependent Coagulation Factors and Protein C" *Thrombosis and Haemostasis* (Stuttgart) 51(3):343-346 (1984).
Voet and Voet. *Biochemistry* $2^{nd}$ Ed., John Wiley & Sons, excerpt pp. 1201-1203 (1995).
Voora et al. "Use of Pharmacogenetics to Guide Warfarin Therapy" *Drugs of Today* 40(3):247-257 (2004).
Wadelius et al. "Common *VKORC1* and *GGCX* polymorphisms associated with warfarin dose" *The Pharmacogenomics Journal* 5(4):262-270 (2005).
Wajih et al. "The Inhibitory Effect of Calumenin on the Vitamin K-dependent γ-Carboxylation System" *The Journal of Biological Chemistry* 279(24):25276-25283 (2004).
Wajih et al. "Increased Production of Functional Recombinant Human Clotting Factor IX by Baby Hamster Kidney Cells Engineered to Overexpress VKORC1, the Vitamin K 2,3-Epoxide-reducing Enzyme of the Vitamin K Cycle" *The Journal of Biological Chemistry* 280(36):31603-31607 (2005).
Wajih et al. "siRNA Silencing of Calumenin Enhances Functional Factor IX Production" *Blood* 108(12):3757-3760 (2006).
Wajih et al. "Enhanced Functional Recombinant Factor VII Production by HEK 293 Cells Stably Transfected with VKORC1 Where the Gamma-Carboxylase Inhibitor Calumenin is Stably Suppressed by shRNA Transfection" *Thrombosis Research* 122:405-410 (2008).
Walker et al. "On a Potential Global Role for Vitamin K-Dependent γ-Carboxylation in Animal Systems" *The Journal of Biological Chemistry* 276(11):7769-7774 (2001).
Wallace et al. "A major gene controlling warfarin-resistance in the house mouse" *The Journal of Hygiene*, Cambridge 76:173-181 (1976).
Wallace et al. "Hybridization of synthetic oligodeoxyribonucleotides to Φx174 DNA: the effect of single base pair mismatch" *Nucleic Acids Research* 6(11):3543-3557 (1979).
Wallin et al. "NAD(P)H Dehydrogenase and its Role in the Vitamin K (2-Methyl-3-phytyl-1,4-naphthaquinone)-Dependent Carboxylation Reaction" *Biochemical Journal* 169:95-101 (1978).
Wallin. "No Strict Coupling of Vitamin $K_1$ (2-Methyl-3-phytyl-1,4-naphthoquinone)-Dependent Carboxylation and Vitamin $K_1$ Epoxidation in Detergent-Solubilized Microsomal Fractions from Rat Liver" *Biochemical Journal* 178:513-519 (1979).
Wallin et al. "Vitamin K-Dependent Carboxylation and Vitamin K Epoxidadtion" *Biochemical Journal* 194:983-988 (1981).
Wallin et al. "Vitamin K-Dependent Carboxylation" *the Journal of Biological Chemistry* 257(4):1583-1586 (1982).

(56) References Cited

OTHER PUBLICATIONS

Wallin et al. "Vitamin K-dependent Carboxylation and Vitamin K Metabolism in Liver" *The Journal of Clinical investigation* 76:1879-1884 (1985).
Wallin. "Vitamin K antagonism of coumarin anticoagulation" *Biochemical Journal* 236:685-693 (1986).
Wallin et al. "Warfarin poisoning and vitamin K antagonism in rat and human liver" *Biochemical Journal* 241:389-396 (1987).
Wallin et al. "Purification of Warfarin-Sensitive Vitamin K Epoxide Reductase" *Methods in Enzymology* 282:395-408 (1997).
Wallin et al. "A molecular mechanism for genetic warfarin resistance in the rat" *The FASEB Journal* 15:2542-2544 (2001).
Wallin et al. "Vitamin K 2, 3-epoxide reductase and the vitamin K-dependent gamma-carboxylation system" *Thrombosis Research* 108(4):221-6 (2003).
Wallin et al. "Warfarin and the Vitamin K-Dependent 65-Carboxylation System" *Trends in Molecular Medicine* 10(7):299-302 (2004).
Wallin et al. "VKORC1: A Warfarin-Sensitive Enzyme in Vitamin K Metabolism and Biosynthesis of Vitamin K-Dependent Blood Coagulation Factors" *Vitamins and Hormones* 78:227-246 (2008).
Wang et al. "Identification of a gene encoding a typical γ-carboxyglutamic acid domain in the tunicate *Halocynthia roretzi*" *Journal of Thrombosis and Haemostasis* 1:118-123 (2003).
Wang et al. "VKORC1 Haplotypes Are Associated With Arterial Vascular Diseases (Stroke, Coronary Heart Disease, and Aortic Dissection)" *Circulation* 113(12):1615-1621 (2006).
Ware et al. "Factor IX San Dimas" *The Journal of Biological Chemistry* 264(19):11401-11406 (1989).
Wasley et al. "PACE/Furin Can Process the Vitamin K-dependent Pro-factor IX Precursor within the Secretory Pathway" *The Journal of Biological Chemistry* 2689(12):8458-8465 (1993).
Watson et al. "Recombinant DNA in Medicine" *Recombinant DNA* Chapter 23, 2$^{nd}$ Ed., Scientific American Books, excerpt pp. 453-470 (1992).
Watzke et al. "Factor X Santo Domingo Evidence that the Severe Clinical Phenotype Arises from a Mutation Blocking Secretion" *The Journal of Clinical Investigation* 88:1685-1689 (1991).
Wells et al. "Additivity of Mutational Effects in Proteins" *Biochemistry* 29(37):8509-8517 (1990).
Westhofen et al. "Human Vitamin K 2,3-Epoxide Reductase Complex Subunit 1-Like 1 (VKORC1L1) Mediates Vitamin K-Dependent Intracellular Antioxidant Function" *The Journal of Biological Chemistry* 286(17):15085-15094 (2011).
Wilson et al. "Species Comparison of Vitamin $K_1$ 2,3-Epoxide Reductase Activity in vitro: Kinetics and Warfarin Inhibition" *Toxicology* 189:191-198 (2003).
Winter et al. "Man-made antibodies" *Nature* 349:293-299 (1991).
Wu et al. "In Vitro γ-Carboxylation of a 59-Residue Recombinant Peptide Including the Propeptide and the γ-Carboxyglutamic Acid Domain of Coagulation Factor IX" *The Journal of Biological Chemistry* 265(22):13124-13129 (1990).
Wu et al. "Cloning and Expression of the cDNA for Human gamma-glutamyl carboxylase" *Science* 254(5038):1634-1636 (1991).
Wu et al. "Identification and purification to near homogeneity of the vitamin K-dependent carboxylase" *Proceedings of the National Academy of Sciences, USA* 88:2236-2240 (1991).
Wu et al. "Characterization of the γ-Glutamyl Carboxylase" *Thrombosis and Haemostasis* 78(1):599-604 (1997).
Wu et al. "The Propeptide Binding Site of the Bovine γ-Glutamyl Carboxylase" *The Journal of Biological Chemistry* 272:11718-11722 (1997).
Xie et al. "Molecular basis of ethnic differences in drug disposition and response" *Annual Review of Pharmacology and Toxicology* 41:815-50 (2001).
Xie et al. "CYP2C9 allelic variants: ethnic distribution and functional significance" *Advanced Drug Delivery Reviews* 54(10):1257-1270 (2002).
Yu et al. "Factors determining the maintenance dose of warfarin in Chinese patients" *The Quarterly Journal of Medicine* 89:127-135 (1996).
Yuan et al. "A novel functional VKORC1 promoter polymorphism is associated with inter-individual and inter-ethnic differences in warfarin sensitivity" *Human Molecular Genetics* 14(13):1745-1751 (2005).
Zhang et al. "Role of Individual γ-Carboxyglutamic Acid Residues of Activated Human Protein C in Defining its In Vitro Anticoagulant Activity" *Blood* 80(4):942-952 (1992).
Zhao et al. "Novel *CYP2C9* genetic variants in Asian subjects and their influence on maintenance warfarin dose" *Clinical Pharmacology & Therapeutics* 76(3):210-219 (2004).
Zheng et al. "Inhibition of gene expression by anti-sense oligodeoxynucleotides" *Clinical and Experimental Immunology* 100:380-382 (1995).
Zimmermann et al. "Biochemical Basis of Hereditary Resistance to Warfarin in the Rat" *Biochemical Pharmacology* 23:1033-1040 (1974).
Zwaal et al. "Lipid-protein interactions in blood coagulation" *Biochimica et Biophysica Acta* 1376:433-453 (1998).

\* cited by examiner

FIG. 8

```
VKOR        WILFFVLYDFCIVCITTYAINVSLMW
AR-VKORH    ILSTKLSGSSCLYCLVSAFLSFSLFF
MT-VKORH    FQSLYRIGALCPYCMVVWAVIATLLV
RO-VKORH    FLEPFVIGATCLWCLTSAVIMTGLLW
SY-VKORH    YLMVAVLRQFCMYCTTAIILVAGLGL
```

FIG. 21A
```
MT-VKORH    FQSLYRIGALCPYCMVVWAVIATLLV
CO-VKORH    YSAIYSIGALCPYCMAVWAATLPMFV
SA-VKORH    YQSLYVIGALCPYCMVWAVTIPIFL
```
FIG. 21B
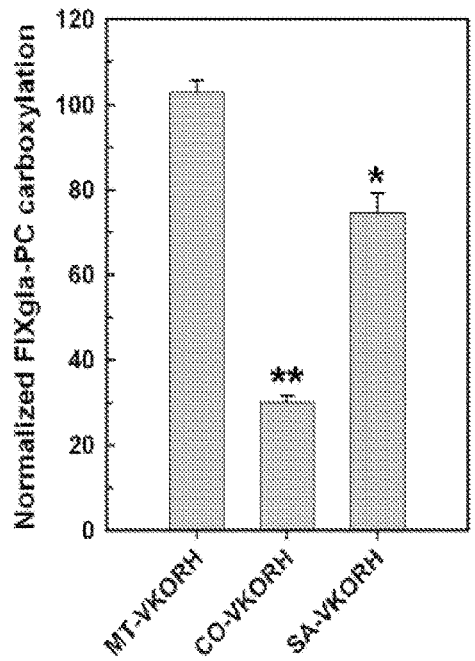
FIG. 21C
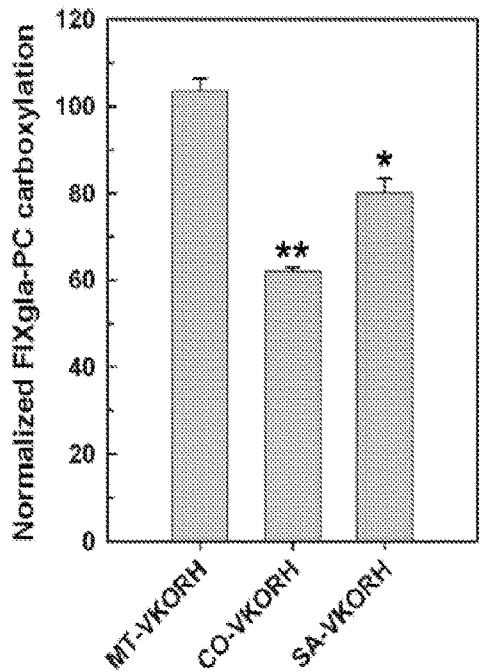

METHODS AND COMPOSITIONS FOR PRODUCING ACTIVE VITAMIN K-DEPENDENT PROTEINS

STATEMENT OF PRIORITY

This application is a 35 U.S.C. §371 national phase entry of PCT Application PCT/US2011/066379, filed Dec. 21, 2011, which claims the benefit, under 35 U.S.C. §119 (e), of U.S. Provisional Application Ser. No. 61/425,652, filed Dec. 21, 2010, U.S. Provisional Application Ser. No. 61/506,436, filed Jul. 11, 2011 and U.S. Provisional Application Ser. No. 61/540,374, filed Sep. 28, 2011, the entire contents of each of which are incorporated by reference herein.

GOVERNMENT SUPPORT

This invention was made with government support under Grant Nos. HL077740, HL048318 and HL06350, awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. §1.821, entitled 5470-572TS_ST25.txt, 79,937 bytes in size, generated on Jun. 9, 2015 and filed via EFS-Web, is provided in lieu of a paper copy. This Sequence Listing is hereby incorporated by reference into the specification for its disclosures.

FIELD OF THE INVENTION

The present invention is directed to isolated nucleic acids, host cells containing the same, and methods of use thereof, in the production of vitamin K dependent proteins.

BACKGROUND OF THE INVENTION

The function of numerous proteins requires the modification of multiple glutamic acid residues to γ-carboxyglutamate. Among these vitamin K-dependent (VKD) coagulation proteins, factor IX (FIX; Christmas factor), factor VII (FVII), and prothrombin are the best known. The observation that a knock-out of the gene for matrix Gla protein results in calcification of the mouse's arteries (Luo et al. (1997) "Spontaneous calcification of arteries and cartilage in mice lacking matrix GLA protein" Nature 386:78-81) emphasizes the importance of the vitamin K cycle for proteins with functions other than coagulation. Moreover, Gas6 and other Gla proteins of unknown function are expressed in neural tissue and warfarin exposure in utero results in mental retardation and facial abnormalities. This is consistent with the observation that the expression of VKD carboxylase, the enzyme that accomplishes the Gla modification, is temporally regulated in a tissue-specific manner with high expression in the nervous system during early embryonic stages. Concomitant with carboxylation, reduced vitamin K, a co-substrate of the reaction, is converted to vitamin K epoxide. Because the amount of vitamin K in the human diet is limited, vitamin K epoxide must be converted back to vitamin K by vitamin K epoxide reductase (VKOR) to prevent its depletion.

VKOR is a polytopic membrane protein of the endoplasmic reticulum (ER). It is responsible for the conversion of vitamin K epoxide (KO) to vitamin K and is highly sensitive to inhibition by coumarin drugs, such as warfarin. Warfarin inhibition of VKOR reduces the availability of reduced vitamin K (vitamin K hydroquinone, $KH_2$), which is a cofactor for γ-glutamyl carboxylase that catalyzes the functionally critical post-translational modification of a family of vitamin K-dependent proteins involved in blood coagulation, bone homeostasis, signal transduction, and cell proliferation. Bioinformatic analyses showed that VKOR is a member of a large family of homologues (VKORH) widely distributed throughout evolution. Characterizations of the human VKOR and VKORH from bacteria have yielded a large amount of structure-function information, but some is contradictory. A four-transmembrane domain (TMD) model for human VKOR was proposed based on the crystal structure of VKORH from *Synechococcus* sp. This model is different from a previous three-TMD topology model in terms of the location of the N-terminus and the conserved cysteine (C43 and C51) loop between the first and second TMD.

The present invention provides methods and compositions for producing vitamin K dependent proteins.

SUMMARY OF THE INVENTION

The present invention provides (1) a method of increasing the amount of carboxylated vitamin K dependent protein in a cell, comprising introducing, into a cell that expresses a first nucleic acid encoding a vitamin K dependent protein, a second nucleic acid comprising a heterologous nucleotide sequence encoding vitamin K epoxide reductase (VKOR), under conditions whereby said first and second nucleic acids are expressed to produce a vitamin K dependent protein and VKOR, respectively, thereby increasing the amount of carboxylated vitamin K dependent protein in the cell.

Additionally provided herein is (2) a method of increasing the carboxylation of a vitamin K dependent protein, comprising introducing, into a cell that expresses a first nucleic acid encoding a vitamin K dependent protein, a second nucleic acid comprising a heterologous nucleotide sequence encoding vitamin K epoxide reductase (VKOR), under conditions whereby said first and second nucleic acids are expressed to produce a vitamin K dependent protein and VKOR, respectively, thereby increasing the carboxylation of the vitamin K dependent protein in the cell.

The present invention also provides (3) a method of producing a carboxylated vitamin K dependent protein in a cell, comprising introducing, into a cell that expresses a first nucleic acid encoding a vitamin K dependent protein, a second nucleic acid comprising a heterologous nucleotide sequence encoding vitamin K epoxide reductase (VKOR), under conditions whereby said first and second nucleic acids are expressed to produce a vitamin K dependent protein and VKOR, respectively, wherein the amount of carboxylated vitamin K dependent protein produced in the cell in the presence of VKOR produced by the second nucleic acid is increased as compared to the amount of carboxylated vitamin K dependent protein produced in the cell in the absence of VKOR produced by the second nucleic acid, thereby producing a carboxylated vitamin K dependent protein in the cell.

In the methods designated (1), (2) and (3) above, the heterologous nucleotide sequence encoding VKOR can be but is not limited to:

1) a nucleotide sequence that encodes an amino acid sequence having at least about 19% identity but not greater than about 79% identity at the amino acid sequence level with a human VKOR amino acid sequence such as the amino acid sequence of GenBank® Accession No. AAS01052 as well as any other human VKOR amino acid sequence now known or later identified, wherein the amino acid sequence has VKOR activity (e.g., at least 10%, 20%, 30%, 40%, 50%, 60%, 70%, 80%, 90%, 100%, 110%, 120%, 130%, 140%, 150%, etc., relative to the activity of a control (e.g., a wild type human VKOR or unmodified human VKOR) as determined according to the methods described in the Examples section herein and as are known in the art;

2) a nucleotide sequence that encodes a *Mycobacterium tuberculosis* VKOR (a nonlimiting example of which is the VKOR having the amino acid sequence provided as GenBank® Accession No. NP_217484);

3) a nucleotide sequence that encodes an *Acropora* VKOR (a nonlimiting example of which is the VKOR having the amino acid sequence provided as GenBank® Accession No. EZ012735);

4) a nucleotide sequence that encodes a *Nematostella* VKOR (a nonlimiting example of which is the VKOR having the amino acid sequence provided as GenBank® Accession No. XP_001627634);

5) a nucleotide sequence that encodes an *Amphioxus* VKOR (a nonlimiting example of which is the VKOR having the amino acid sequence provided as GenBank® Accession No. XP_002611889 (exemplary nucleotide sequence provided as GenBank® Accession No. XM_001611843);

6) a nucleotide sequence that encodes a *Takifugu* VKOR (a nonlimiting example of which is the VKOR having the amino acid sequence provided as GenBank® Accession No. NP_001027838);

7) a nucleotide sequence that encodes a *Ciona* VKOR (a nonlimiting example of which is the VKOR having the amino acid sequence provided as GenBank® Accession No. NP_001073142);

8) a nucleotide sequence that encodes a hamster VKOR (non limiting examples of which include the VKOR having the amino acid sequence of SEQ ID NO:3 obtained from Syrian golden hamster cell line MCB3901 [AV12-664]; Accession No. CRL-9595 and the VKOR having the amino acid sequence provided as GenBank® Accession No. XP_003511033.1);

9) a nucleotide sequence that encodes a *Drosophila* VKOR (a nonlimiting example of which is the VKOR having the amino acid sequence provided as GenBank® Accession No. NP_001014533);

10) a nucleotide sequence that encodes a human VKOR (a nonlimiting example of which is the VKOR having the amino acid sequence provided as GenBank® Accession No. AAS01052), comprising a C51A mutation;

11) a nucleotide sequence that encodes a human VKOR (a nonlimiting example of which is the VKOR having the amino acid sequence provided as GenBank® Accession No. AAS01052), comprising an IV133-134PY mutation;

12) a nucleotide sequence that encodes a human VKOR (a nonlimiting example of which is the VKOR having the amino acid sequence provided as GenBank® Accession No. AAS01052), comprising a C51A mutation and an IV133-134PY mutation;

13) a nucleotide sequence that encodes a human VKOR (a nonlimiting example of which is the VKOR having the amino acid sequence provided as GenBank® Accession No. AAS01052), comprising a V45N mutation;

14) a nucleotide sequence that encodes a human VKOR (a nonlimiting example of which is the VKOR having the amino acid sequence provided as GenBank® Accession No. AAS01052), comprising a substitution of amino acids 44-50 with amino acids DYKDDDDK (SEQ ID NO:37);

15) a nucleotide sequence that encodes a human VKOR comprising a substitution of amino acids 122-139 (WILFFVLYDFCIVCITTY, SEQ ID NO:38) of human VKOR (a nonlimiting example of which is the VKOR having the amino acid sequence provided as GenBank® Accession No. AAS01052) with amino acids 129-146 (FQSLYRIGALCPYCMVVW, SEQ ID NO:39) of *Mycobacterium tuberculosis* VKOR (a nonlimiting example of which is the VKOR having the amino acid sequence provided as GenBank® Accession No. NP_217484);

16) a nucleotide sequence that encodes a human VKOR comprising a substitution of amino acids 122-139 (WILFFVLYDFCIVCITTY, SEQ ID NO:38) of human VKOR (a nonlimiting example of which is the VKOR having the amino acid sequence provided as GenBank® Accession No. AAS01052) with amino acids 185-202 (ILSTKLSGSSCLYCLVSA, SEQ ID NO:40) of *Arabidopsis* VKOR (a nonlimiting example of which is the VKOR having the amino acid sequence provided as GenBank® Accession No. NP_567988);

17) a nucleotide sequence that encodes a human VKOR comprising a substitution of amino acids 122-139 (WILFFVLYDFCIVCITTY, SEQ ID NO:38) of human VKOR (a nonlimiting example of which is the VKOR having the amino acid sequence provided as GenBank® Accession No. AAS01052) with amino acids 120-137 (YLMVAVLRQFCMYCTTAI, SEQ ID NO:41) of *Synechococcus* VKOR (a nonlimiting example of which is the VKOR having the amino acid sequence provided as GenBank® Accession No. YP_478481);

18) a nucleotide sequence that encodes a human VKOR comprising a substitution of amino acids 122-139 (WILFFVLYDFCIVCITTY, SEQ ID NO:38) of human VKOR (a nonlimiting example of which is the VKOR having the amino acid sequence provided as GenBank® Accession No. AAS01052) with amino acids 33-50 (WFQHVMLLKPCVCIYER, SEQ ID NO:42) of a bacterial DsbB enzyme (a nonlimiting example of which is the DsbB enzyme having the amino acid sequence provided as GenBank® Accession No. ZP_03067529); and/or 19) a nucleotide sequence that encodes a human VKOR comprising a substitution of amino acids 122-139 (WILFFVLYDFCIVCITTY, SEQ ID NO:38) of human VKOR (a nonlimiting example of which is the VKOR having the amino acid sequence provided as GenBank® Accession No. AAS01052) with amino acids 300-317 (FLEPFVIGATCLWCLTSA, SEQ ID NO:43) of *Roseiflexus* VKOR (a nonlimiting example of which is the VKOR having the amino acid sequence provided as GenBank® Accession No. YP_001274867).

A further aspect of the present invention is a cell (e.g., a host cell) comprising, consisting essentially of, or consisting of a nucleic acid comprising a heterologous nucleotide sequence encoding a vitamin K epoxide reductase (VKOR) protein (e.g., a recombinant protein) that has at least about 19% identity but not greater than about 79% identity (including 19% 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67% 68%, 69%, 70%, 71%, 72%, 73%, 74%, 75%, 76%, 77%, 78% and 79%) at the amino acid sequence level with a human VKOR amino acid sequence such as the amino acid sequence of GenBank® Accession No. AAS01052 as well as any other human VKOR amino acid sequence (e.g., any other human VKOR variant) now known or later identified, wherein the recombinant protein has VKOR activity (e.g., at least 10%, 20%, 30%, 40%, 50%, 60%, 70%, 80%, 90%, 100%, 110%, 120%, 130%, 140%, 150%, etc., relative to the activity of control (e.g., wild type human VKOR or unmodified human VKOR) as determined according to the methods described in the Examples section herein and as are known in the art.

The present invention additionally provides a cell (e.g., a host cell) comprising, consisting essentially of, or consisting of a nucleic acid comprising a heterologous nucleotide sequence encoding vitamin K epoxide reductase (VKOR) that can be, but is not limited to:

1) a nucleotide sequence that encodes an amino acid sequence having at least about 19% identity but not greater than about 79% identity at the amino acid sequence level with a human VKOR wild type amino acid sequence such as the amino acid sequence of GenBank® Accession No. 2 as well as any other human VKOR wild type amino acid sequence (e.g., any other human VKOR variant) now known or later identified, wherein the recombinant protein has VKOR activity (e.g., at least 10%, 200%, 30%, 40%, 50%, 60%, 70%, 80%, 90%, 100%, 110%, 120%, 130%, 140%, 150%, etc., relative to the activity of control (e.g., wild type human VKOR or unmodified human VKOR) as determined according to the methods described in the Examples section herein and as are known in the art;

2) a nucleotide sequence that encodes a *Mycobacterium tuberculosis* VKOR (a nonlimiting example of which is a VKOR having the amino acid sequence provided as GenBank® Accession No. NP_217484);

3) a nucleotide sequence that encodes an *Acropora* VKOR (a nonlimiting example of which is a VKOR having the amino acid sequence provided as GenBank® Accession No. EZ012735);

4) a nucleotide sequence that encodes a *Nematostella* VKOR (a nonlimiting example of which is a VKOR having the amino acid sequence provided as GenBank® Accession No. XP_001627634);

5) a nucleotide sequence that encodes an *Amphioxus* VKOR (a nonlimiting example of which is a VKOR having the amino acid sequence provided as GenBank® Accession No. XP_002611889 (exemplary nucleotide sequence provided as GenBank® Accession No. XM_001611843).);

6) a nucleotide sequence that encodes a *Takifugu* VKOR (a nonlimiting example of which is a VKOR having the amino acid sequence provided as GenBank® Accession No. NP_001027838);

7) a nucleotide sequence that encodes a *Ciona* VKOR (a nonlimiting example of which is a VKOR having the amino acid sequence provided as GenBank® Accession No. NP_001073142);

8) a nucleotide sequence that encodes a hamster VKOR (non limiting examples of which include the VKOR having the amino acid sequence of SEQ ID NO:3 obtained from Syrian golden hamster cell line MCB3901 [AV12-664]; Accession No. CRL-9595 and the VKOR having the amino acid sequence provided as GenBank® Accession No. XP_003511033.1);

9) a nucleotide sequence that encodes a *Drosophila* VKOR (a nonlimiting example of which is a VKOR having the amino acid sequence provided as GenBank® Accession No. NP_001014533);

10) a nucleotide sequence that encodes a human VKOR (a nonlimiting example of which is a VKOR having the amino acid sequence provided as GenBank® Accession No. AAS01052), comprising a C51A mutation;

11), a nucleotide sequence that encodes a human VKOR (a nonlimiting example of which is a VKOR having the amino acid sequence provided as GenBank® Accession No. AAS01052), comprising an IV133-134PY mutation;

12), a nucleotide sequence that encodes a human VKOR (a nonlimiting example of which is a VKOR having the amino acid sequence provided as GenBank® Accession No. AAS01052) comprising a C51A mutation and an IV133-134PY mutation;

13) a nucleotide sequence that encodes a human VKOR (a nonlimiting example of which is the VKOR having the amino acid sequence provided as GenBank® Accession No. AAS01052), comprising a V45N mutation;

14) a nucleotide sequence that encodes a human VKOR (a nonlimiting example of which is the VKOR having the amino acid sequence provided as GenBank® Accession No. AAS01052), comprising a substitution of amino acids 44-50 with amino acids DYKDDDDK (SEQ ID NO:37);

15) a nucleotide sequence that encodes a human VKOR comprising a substitution of amino acids 122-139 (WILFFVLYDFCIVCITTY, SEQ ID NO:38) of human VKOR (a nonlimiting example of which is a VKOR having the amino acid sequence provided as GenBank® Accession No. AAS01052) with amino acids 129-146 (FQSLYRIGAL-CPYCMVVW, SEQ ID NO:39) of *Mycobacterium tuberculosis* VKOR (a nonlimiting example of which is a VKOR having the amino acid sequence provided as GenBank® Accession No. NP_217484);

16) a nucleotide sequence that encodes a human VKOR comprising a substitution of amino acids 122-139 (WILFFVLYDFCIVITTY, SEQ ID NO:38) of human VKOR (a nonlimiting example of which is a VKOR having the amino acid sequence provided as GenBank® Accession No. AAS01052) with amino acids 185-202 (ILSTKLSGSS-CLYCLVSA, SEQ ID NO:40) of *Arabidopsis* VKOR (a nonlimiting example of which is a VKOR having the amino acid sequence provided as GenBank® Accession No. NP_567988);

17) a nucleotide sequence that encodes a human VKOR comprising a substitution of amino acids 122-139 (WILFFVLYDFCIVCITTY, SEQ ID NO:38) of human VKOR (a nonlimiting example of which is a VKOR having the amino acid sequence provided as GenBank® Accession No. AAS01052) with amino acids 120-137 (YLMVAVL-RQFCMYCTTAI, SEQ ID NO:41) of *Synechococcus* VKOR (a nonlimiting example of which is a VKOR having the amino acid sequence provided as GenBank® Accession No. YP_478481);

18) a nucleotide sequence that encodes a human VKOR comprising a substitution of amino acids 122-139 (WILFFVLYDFCIVCITTY, SEQ ID NO:38) of human VKOR (a nonlimiting example of which is a VKOR having the amino acid sequence provided as GenBank® Accession No. AAS01052) with amino acids 33-50 (WFQHVMLLK-PCVCIYER, SEQ ID NO:42) of a bacterial DsbB enzyme (a nonlimiting example of which is a DsbB enzyme having the amino acid sequence provided as GenBank® Accession No. ZP_03067529); and/or 19) a nucleotide sequence that encodes a human VKOR comprising a substitution of amino acids 122-139 (WILFFVLYDFCIVCITTY, SEQ ID NO:38) of human VKOR (a nonlimiting example of which is a VKOR having the amino acid sequence provided as GenBank® Accession No. AAS01052) with amino acids 300-317 (FLEPFVIGAT-CLWCLTSA, SEQ ID NO:43) of *Roseiflexus* VKOR (a nonlimiting example of which is a VKOR having the amino acid sequence provided as GenBank® Accession No. YP_001274867).

An additional aspect of the present invention is a recombinant nucleic acid comprising a nucleotide sequence encoding vitamin K epoxide reductase (VKOR) as described herein operatively associated with a heterologous promoter. Such a recombinant nucleic acid can be present in a cell (e.g., a transformed cell).

A further aspect of the present invention is a cell that contains and expresses a recombinant nucleic acid as described herein. Such a cell can be a transformed cell. Suitable cells of this invention include but are not limited to, plant, animal, mammal, insect, yeast and bacterial cells.

Any of the recombinant proteins of this invention as described herein (e.g., those enumerated above as 1-17) can have an amount of VKOR activity (e.g., at least 10%, 20%, 30%, 40%, 50%, 60%, 70%, 80%, 90%, 100%, 110%, 120%, 130%, 140%, 150%, etc.), relative to the activity of a control VKOR (e.g., a wild type human VKOR or unmodified VKOR) as determined according to the methods described in the Examples section herein and as are known in the art.

A further aspect of the present invention is a method of making a vitamin K dependent protein, comprising culturing a cell that expresses a nucleotide sequence encoding a vitamin K dependent protein in the presence of vitamin K and produces a vitamin K dependent protein, and then harvesting the vitamin K dependent protein from the culture, the cell containing and expressing a heterologous nucleotide sequence encoding vitamin K epoxide reductase (VKOR) as described herein and producing recombinant VKOR as described herein.

In some embodiments, the cell can further contain and express a heterologous nucleotide sequence encoding vitamin K dependent carboxylase and thereby produce the vitamin K dependent carboxylase as described herein. Thus, the present invention further provides a cell (e.g., a host cell) comprising, consisting essentially of, or consisting of a first heterologous nucleic acid encoding vitamin K dependent carboxylase and a second heterologous nucleic acid encoding vitamin K epoxide reductase. The cell can further comprise a nucleotide sequence encoding a vitamin K dependent protein, which nucleotide sequence encoding the vitamin K dependent protein can be heterologous to the cell (e.g., when the cell is a plant cell or insect cell) or endogenous to the cell (e.g., when the cell is a mammalian cell).

In further embodiments, the present invention provides a method of identifying a substance that regulates activity of *Mycobacterium tuberculosis* vitamin K epoxide reductase (VKOR), comprising determining the activity of *Mycobacterium tuberculosis* VKOR in the presence and absence of the substance by: a) contacting a recombinant *Mycobacterium tuberculosis* VKOR with a reporter protein under conditions whereby carboxylation of the reporter protein by the *Mycobacterium tuberculosis* VKOR can occur; and b) measuring the amount of carboxylation of the reporter protein by *Mycobacterium tuberculosis* VKOR in the presence and absence of the substance, whereby an increase or decrease in the amount of carboxylation of the reporter protein by *Mycobacterium tuberculosis* VKOR as compared to a control identifies the substance as a substance that regulates activity of *Mycobacterium tuberculosis* VKOR Also provided herein is a method of identifying a substance for treating and/or preventing infection and/or disease caused by *Mycobacterium tuberculosis*, comprising determining the activity of *Mycobacterium tuberculosis* VKOR in the presence and absence of the substance by: a) contacting a recombinant *Mycobacterium tuberculosis* VKOR with a reporter protein under conditions whereby carboxylation of the reporter protein by the *Mycobacterium tuberculosis* VKOR can occur; and b) measuring the amount of carboxylation of the reporter protein by *Mycobacterium tuberculosis* VKOR in the presence and absence of the substance whereby a decrease in the amount of carboxylation of the reporter protein by *Mycobacterium tuberculosis* VKOR in the presence of the substance as compared to a control identifies the substance as a substance for treating and/or preventing infection and/or disease caused by *Mycobacterium tuberculosis*.

In one aspect, the present invention provides a method of increasing the amount of carboxylated vitamin K dependent protein in a cell, comprising introducing, into a cell that expresses a first nucleic acid encoding a vitamin K dependent protein, a second nucleic acid comprising a heterologous nucleotide sequence encoding a human vitamin K epoxide reductase (VKOR), (a nonlimiting example of which is the human VKOR having the amino acid sequence of GenBank® Accession No. AAS01052), comprising an R37G mutation, an R35G mutation, an R33G mutation, a K30L mutation, a G9R mutation, a S7R mutation and a G6R mutation, under conditions whereby said first and second nucleic acids are expressed to produce a vitamin K dependent protein and VKOR, respectively, thereby increasing the amount of carboxylated vitamin K dependent protein in the cell.

A further aspect of the present invention is a method of increasing the carboxylation of a vitamin K dependent protein, comprising introducing, into a cell that expresses a first nucleic acid encoding a vitamin K dependent protein, a second nucleic acid comprising a heterologous nucleotide sequence encoding a human vitamin K epoxide reductase (VKOR), (a nonlimiting example of which is the human VKOR having the amino acid sequence of GenBank® Accession No. AAS01052), comprising an R37G mutation, an R35G mutation, an R33G mutation, a K30L mutation, a G9R mutation, a S7R mutation and a G6R mutation, under conditions whereby said first and second nucleic acids are expressed to produce a vitamin K dependent protein and VKOR, respectively, thereby increasing the carboxylation of the vitamin K dependent protein in the cell.

An additional aspect of this invention is a method of producing a carboxylated vitamin K dependent protein in a cell, comprising introducing, into a cell that expresses a first nucleic acid encoding a vitamin K dependent protein, a second nucleic acid comprising a heterologous nucleotide sequence encoding a human vitamin K epoxide reductase (VKOR), (a nonlimiting example of which is the human VKOR having the amino acid sequence of GenBank® Accession No. AAS01052), comprising an R37G mutation, an R35G mutation, an R33G mutation, a K30L mutation, a G9R mutation, a S7R mutation and a G6R mutation, under conditions whereby said first and second nucleic acids are expressed to produce a vitamin K dependent protein and VKOR, respectively, wherein the amount of carboxylated vitamin K dependent protein produced in the cell in the presence of VKOR produced by the second nucleic acid is increased as compared to the amount of carboxylated vitamin K dependent protein produced in the cell in the absence of VKOR produced by the second nucleic acid, thereby producing a carboxylated vitamin K dependent protein in the cell.

In some embodiments of the methods of this invention, the cell can further comprise a third nucleic acid comprising a heterologous nucleotide sequence encoding a vitamin K dependent gamma carboxylase (VKGC), as are well known in the art.

In some embodiments of this invention, the vitamin K dependent protein can be Factor VII, Factor IX, Factor X, Protein C, Protein S, prothrombin and any combination thereof.

In various embodiments of the methods of this invention, the cell can be a plant cell or an insect cell and the first nucleic acid encoding the vitamin K dependent protein can be a heterologous nucleic acid. In some embodiments of the methods of this invention, the cell can be a mammalian cell and the first nucleic acid encoding the vitamin K dependent protein can be an endogenously produced vitamin K dependent protein or the first nucleic acid encoding the vitamin K dependent protein can be a heterologous vitamin K dependent protein.

The present invention further provides an isolated nucleic acid molecule comprising a nucleotide sequence encoding a human vitamin K epoxide reductase (VKOR), (a nonlimiting example of which is the human VKOR having the amino acid sequence of GenBank® Accession No. AAS01052) comprising an R37G mutation, an R35G mutation, an R33G mutation, a K30L mutation, a G9R mutation, a S7R mutation and a G6R mutation.

Further provided herein is a VKOR protein comprising an amino acid sequence produced by translation of a nucleotide sequence encoding a human vitamin K epoxide reductase (VKOR), (a nonlimiting example of which is the human VKOR having the amino acid sequence of GenBank® Accession No. AAS01052) comprising an R37G mutation, an R35G mutation, an R33G mutation, a K30L mutation, a G9R mutation, a S7R mutation and a G6R mutation.

Also provided is a cell (e.g., an isolated cell or a transformed cell) comprising the nucleic acid molecule of this invention and/or the VKOR protein comprising an amino acid sequence of this invention. Additionally provided is a vector comprising the nucleic acid molecule of this invention and in some embodiments, a cell comprising the vector of this invention. In various embodiments, the cell can be a plant cell, an insect cell or a mammalian cell.

These and other aspects of the invention are set forth in more detail in the description of the invention below.

BRIEF DESCRIPTION OF THE DRAWINGS

(FIG. 4A) Cells grown in culture medium with either 11 μM vitamin K (open circles) or 5 μM KO (filled circles) were incubated for 48 h with increasing concentrations of warfarin. The concentration of carboxylated FIXgla-PC in the medium was detected by ELISA. The data are presented as percentages to make the first concentration points of vitamin K and KO coincide. (FIG. 4B) Cells were grown with (open circles) or without (filled circles) 2 μM warfarin in increasing concentrations of vitamin K for 48 h. The concentration of carboxylated reporter protein in the culture medium was measured by ELISA.

(FIG. 5A) Endogenous GGCX activity of $1\times10^6$ HEK293 or AV12 cells was determined as described herein using FLEEL (SEQ ID NO:59) as substrate in the presence of propeptide. (FIG. 5B) Endogenous VKOR activity of $1\times10^7$ HEK293 or AV12 cells was determined as described herein using $K1_{(25)}$ as the HPLC standard.

(FIG. 7A) Warfarin resistant VKOR-Y139F mutant was transiently expressed in HEK293 (black bars) and AV12 cells (gray bars). Thirty hours after transfection, cells were cultured in medium containing 5 μM KO and 2 μM warfarin for 48 h. The concentration of carboxylated FIXgla-PC in the medium was measured by ELISA. The control was the cell line transfected with empty vector, representing endogenous VKOR. (FIG. 7B) AV12 cells (black bars) or AV12 cells that were stably expressing warfarin resistant VKOR-Y139F mutant (gray bars) were cultured in medium containing 5 μM KO (KO) or 5 μM KO and 2 μM warfarin (KO+W) for 48 h. The concentration of carboxylated FIXgla-PC in the medium was measured by ELISA.

FIG. 8. Sequence alignments of VKOR amino acid sequences of 14 diverse species. The VKOR amino acid sequences are: Rat VKOR (SEQ ID NO:1); Mouse VKOR (SEQ ID NO:2); Hamster VKOR (SEQ ID NO:3); Human VKOR (SEQ ID NO:5); *Danio rerio* VKOR (SEQ ID NO:6); *Takifugu* VKOR (SEQ ID NO:7); *Xenopus* VKOR (SEQ ID NO:8); *Acropora* VKOR (SEQ ID NO:9); *Nematostella* VKOR (SEQ ID NO:10); *Amphioxus* VKOR (SEQ ID NO:11); *Ciona* VKOR (SEQ ID NO:13); *Anopheles* VKOR (SEQ ID NO:14); *Drosophila* VKOR (SEQ ID NO:17); and *M. tuberculosis* VKOR (SEQ ID NO:18).

FIG. 11A. Relative activity of *M. tuberculosis* compared to human warfarin resistant VKOR (Y139F). 48 h incubation with 5 µM KO, 2 µM warfarin, FIXgla-PC HEK293 cell line. FIG. 11B. Ability of human VKOR to stimulate carboxylation with VK substrate with inserts from various thioredoxin enzymes. 48 h incubation with 11 µM K, 2 µM warfarin, FIXgla-PC AV-12 cell line. Each sample is made with human VKOR with residues 122-139 replaced with those of bacterial DsbB 33-50, *Mycobacterium tuberculosis* 129-146, *Arabidopsis* 185-202, *Roseiflexus* sp. 300-317, *Synechococcus* 12-137. The readout is carboxlyation of reporter protein. FIG. 11C. Human VKOR with residues 122-139 replaced with analogous residues from other thioredoxin enzymes. Activity with VKOR in HEK293 cells. 48 h incubation with 5 µM KO, 2 µM warfarin, FIXgla-PC HEK293 cell line. Each sample is made with human VKOR with residues 122-139 replaced with those of bacterial DsbB 33-50, *Mycobacterium tuberculosis* 129-146, *Arabidopsis* 185-202, *Roseiflexus* sp. 300-317, *Synechococcus* 120-137. The readout is carboxlyation of reporter protein.

(FIG. 15B) Cell-based activity assay of VKORHs to reduce KO to vitamin K. VKORHs and controls were transiently expressed in FIXgla-PC/HEK293 cells. Cells were cultured in the complete medium containing 5 µM KO and 4 µM warfarin for 48 hours. The concentration of carboxylated FIXgla-PC (Protein C with its gla domain exchanged with factor IX) in the cell culture medium was measured by ELISA and normalized by luciferase activity as described herein.

(FIG. 17A) Individual cysteines in warfarin resistant VKOR (Y139F) were mutated to alanine. These mutant proteins were transiently expressed in FIXgla-PC/HEK293 cells and the enzymatic activity was determined as described in FIGS. 15A-B. The results are shown as black bars with the y-axis on the left. The gray bars represent previous in vitro results (14). (FIG. 17B) Activity assays of the double mutation C43A and C51A (C43/51A), deletion of these two cysteines and the residues between them (C43-51-DEL), and mutation of five cysteines (C16A, C43A, C51A, C85A, and C96A) simultaneously (5C-Mut).

(FIG. 18A) Schematic representation of the proposed membrane topology of human VKOR (23) and MT-VKORH (8). Conserved loop cysteines are indicated by black dots, Y indicates the introduced N-linked glycosylation site. The CXXC redox center (SEQ ID NO:60) is located near the N-terminus of the third transmembrane domain (TMD) in human VKOR and the fourth TMD in MT-VKORH; both face the ER lumen. (FIG. 18B) Localization of the introduced glycosylation site in MT-VKORH by western blot assay. HPC4 tagged MT-VKORH (MT-VKORH) and its glycosylation mutants (NST60: glycosylation site was introduced between cysteine 57 and 65; NSTend: glycosylation site was introduced at the C-terminus) were transiently expressed in HEK293 cells. Cell lysate was treated with or without PNGase F before being subjected to SDS-PAGE. HPC4 tagged protein bands were probed with anti-HPC4 monoclonal antibody and visualized by ECL western blot reagents. (FIG. 18C) Cell-based activity assay of MT-VKORH glycosylation mutants. MT-VKORH and its glycosylation mutants were transiently expressed in FIXgla-PC/HEK293 cells and the enzymatic activity was determined as described in FIGS. 15A-B.

(FIG. 19A) Cell-based activity assay of VKORHs to reduce vitamin K to $KH_2$. VKORHs from different species were transiently expressed in FIXgla-PC/VKOR-Y139F/AV12 cell line and the enzymatic activity was determined as described in FIGS. 15A-B. (FIG. 19B) Warfarin resistant human VKOR and MT-VKORH were transiently expressed in the FIXgla-PC/AV12 cell line and the enzymatic activity was determined as described in FIGS. 15A-B.

(FIG. 20A) Active site sequence alignment of human VKOR and its homologues tested in this study. The sequence used for alignment is from the C-terminus of the second TMD to the C-terminus of the third TMD of human VKOR (SEQ ID NO:50). Conserved residues are highlighted. AR-VKORH: *Arabidopsis* VKORH (SEQ ID NO:51); MT-VKORH: *Mycobacterium tuberculosis* VKORH (SEQ ID NO:52); RO-VKORH: *Roseiflexus* VKORH (SEQ ID NO:53); SY-VKORH: *Synechococcus* VKORH (SEQ ID NO:54). (FIG. 20B) Cell-based activity assay of MT-VKORH, MT-VKORH-P140I/Y141V, human VKOR and human VKOR-I133P/Y134Y. MT-VKORH, human VKOR and the mutant enzymes were transiently expressed in FIXgla-PC/HEK293 cells and the enzymatic activity was determined as described in FIG. 15.

FIGS. 21A-C. Cell-based activity assay of reduction of KO and vitamin K by bacterial VKORHs with sequences similar to MT-VKORH. (FIG. 21A) Active site sequence alignment of MT-VKORH (SEQ ID NO:52) and the other two bacterial VKORHs with similar sequence. Conserved residues are highlighted. Active site cysteines are indicated by arrows. CO-VKORH: *Corynebacterium jeikeium* VKORH (SEQ ID NO:55); SA-VKORH: *Salinispora tropica* VKORH (SEQ ID NO:56). (FIG. 21B) Cell-based assay of reduction of KO to vitamin K by the selected bacterial VKORHs in FIXgla-PC/HEK293. VKORHs were transiently expressed in FIXgla-PC/HEK293 cells and the enzymatic activity was determined as described in FIG. 15. (FIG. 21C) Cell-based activity assay of reduction of vitamin K to $KH_2$ by the selected bacterial VKORHs in FIXgla-PC/VKOR-Y139F/AV12 cells. VKORHs were transiently expressed in FIXgla-PC/HEK293 cells and the enzymatic activity was determined as described in FIGS. 15A-B.

(FIG. 22A) Proposed reaction mechanism of MT-VKORH in *E. coli* protein disulfide bond formation. When a nascent peptide folds to a disulfide linked mature protein, a disulfide bond in the active site of DsbA is reduced to two free cysteines. These cysteines reduce the disulfide bond of the conserved loop cysteines (C57 and C65) of MT-VKORH and in turn those sulfhydryls participate in the intra-molecular reduction of the CXXC redox center (SEQ ID NO:60). When ubiquinone is reduced to ubquinol by MT-VKORH, the CXXC (SEQ ID NO:60) active site cysteines are oxidized back to a disulfide bond. (FIG. 22B) Proposed reaction mechanism of MT-VKORH for reducing vitamin K in mammalian cells. The MT-VKORH disulfide bond of the CXXC (SEQ ID NO:60) active site is directly reduced by an unknown reductant. The reduced form of the enzyme can apparently reduce both KO and vitamin K for VKD carboxylation in mammalian cells.

FIG. 24. Human (SEQ ID NO:5)—*Synechococcus* (SEQ ID NO:58) VKOR alignment.

FIG. 25. *Mycobacterium tuberculosis* (SEQ ID NO: 18)—human (SEQ ID NO:5) VKOR alignment.

FIG. 26. *M. tuberculosis* (SEQ ID NO:18)—*Synechococcus* (SEQ ID NO:58) VKOR alignment.

(FIG. 27A) 48 h incubation with 5 µM warfarin, FIXgla-PC HEK293 cell line (300 µl/well, x-fect). (FIG. 27B) 48 h incubation with 5 µM KO, 4 µM warfarin, FIXgla-PC HEK293 cell line (300 µl/well, x-fect).

(FIG. 28A) Species used were: human, *Mycobacterium tuberculosum*, *Salinaspora tropica* and *Nematostella vectensis*. (FIG. 28B) *Sachoglossus, Acropora, Xenopus, Amphioxus, Nematostella*, human, *Fugu, Ciona*, zebra finch (strongest motif). Also included in the training set (but not picked as having the motif) were *Conexibacter, Synechococcus, Prochlorococcus, Roseiflexus*. Arrows mark small XXX small motif, often found in transmembrane (TM) domains.

(FIG. 29B) 4-TMD Model. N-terminus: Cytoplasm, Cys 43 and 51: ER lumen.

(FIG. 30A) Positively charged residues are four times more abundant on the cytoplasmic side (inside) of membrane proteins as compared to the trans side. (FIG. 30B) Moving of the positively charged residue from the cytoplasmic side to the ER luminal side can result in inversion of TMD orientation.

(FIG. 31A) Arrows show residues modified to alter charge. (FIG. 31B) TMHMM prediction of human VKOR membrane topology-wild type VKOR. (FIG. 31C) TMHMM prediction of human VKOR membrane topology-charge-mutated (CM) VKOR FIG. 32 Relative activity of charge-mutated VKOR (VKOR-CM) compared to control VKOR.

FIG. 34. Sequence alignments of VKOR amino acid sequences of several diverse species. The VKOR amino acid sequences are: Elephant VKOR (SEQ ID NO:44); Anaplopoma VKOR (SEQ ID NO:45); Saccoglossus VKOR (SEQ ID NO:46); Dolphin VKOR (SEQ ID NO:47); Zebra Finch VKOR (SEQ ID NO:48); *D. melanogaster* VKOR (SEQ ID NO:17); *Ciona* VKOR (SEQ ID NO:13); *Takifugu* VKOR (SEQ ID NO:7); Hamster VKOR (SEQ ID NO:3); *Amphioxus* VKOR (SEQ ID NO:11); *Acropora* VKOR (SEQ ID NO:9); Mouse VKOR (SEQ ID NO:2); *Anopheles* VKOR (SEQ ID NO:14); *Danio* VKOR (SEQ ID NO:6); Rat VKOR (SEQ ID NO:1); and Human VKOR (SEQ ID NO:49).

DETAILED DESCRIPTION OF THE INVENTION

Figure 1:
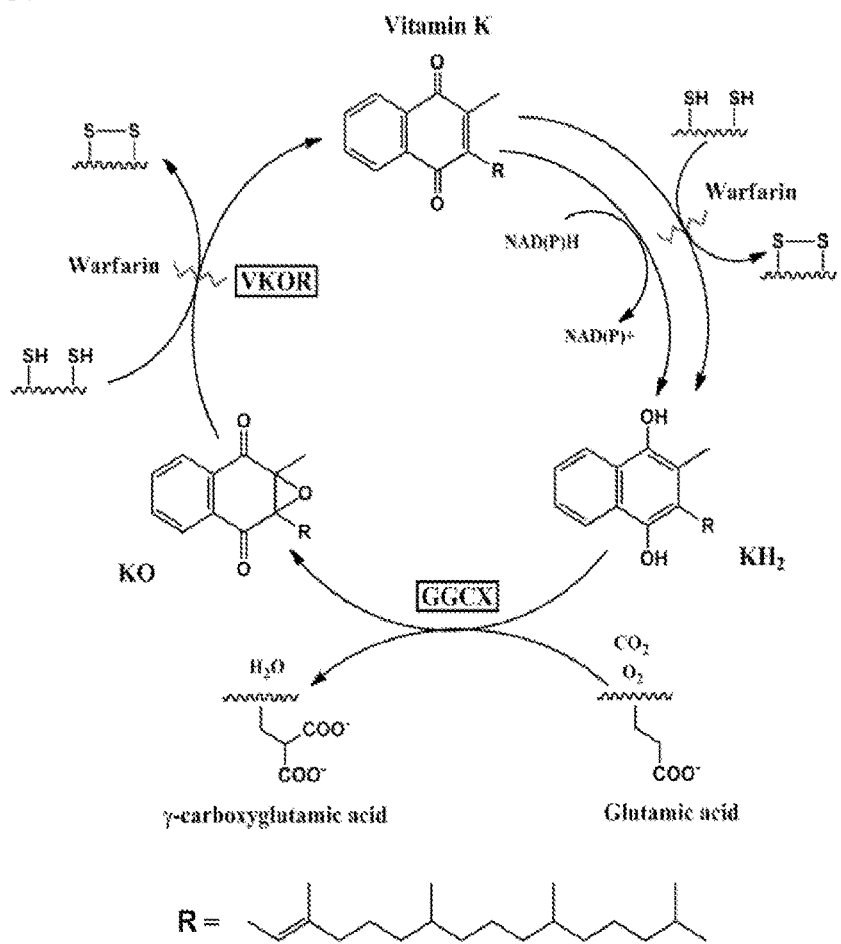
FIG. 1. Vitamin K Cycle. During vitamin K-dependent carboxylation of glutamic acid to γ-carboxyglutamic acid, the reduced form of vitamin K ($KH_2$) is oxidized to vitamin K epoxide (KO) by gamma glutamyl carboxylase (GGCX). KO is reduced to vitamin K by VKOR using the enzyme's two active site cysteine residues. This reaction is sensitive to warfarin inhibition. The reduction of vitamin K to $KH_2$ is carried out in two pathways. One pathway is sensitive to warfarin inhibition and also involves two free cysteine residues in the enzyme active site (VKOR). The second pathway is resistant to warfarin and uses NAD(P)H as a cofactor.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

In some aspects, the present invention is based on the unexpected discovery that recombinant VKOR proteins from highly divergent species can be employed in methods of making an activated (i.e., carboxylated or fully carboxylated) vitamin K dependent protein in a cell, and in some embodiments, with a resulting yield of the activated vitamin K dependent protein being at least about the same or in some cases even greater as compared with the yield of activated vitamin K dependent protein made in a cell (e.g., a control cell) containing a recombinant human VKOR protein (e.g., a wild type human VKOR). Thus, in one embodiment, the present invention provides a method of increasing the amount of carboxylated (e.g., fully carboxylated) vitamin K dependent protein in a cell, comprising introducing, into a cell that expresses a first nucleic acid encoding a vitamin K dependent protein, a second nucleic acid comprising a heterologous nucleotide sequence encoding vitamin K epoxide reductase (VKOR), wherein the heterologous nucleic acid encoding VKOR comprises, consists essentially of or consists of a nucleotide sequence that encodes an amino acid sequence having at least about 19% identity but not greater than about 79% identity (e.g., about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% 61%, 62%, 63%, 64%, 65%, 66%, 67%, 68%, 69%, 70/%, 71%, 72%, 73%, 74%, 75%, 76%, 77%, 78%, 79%, 80%, etc.) with the amino acid sequence of a human VKOR (e.g., the amino acid sequence of GenBank® Accession No. AAS01052), under conditions whereby said first and second nucleic acids are expressed to produce a vitamin K dependent protein and VKOR, respectively, thereby increasing the amount of carboxylated (e.g., fully carboxylated) vitamin K dependent protein in the cell.

Additionally provided herein is a method of increasing the carboxylation of a vitamin K dependent protein, comprising introducing, into a cell that expresses a first nucleic acid encoding a vitamin K dependent protein, a second nucleic acid comprising a heterologous nucleotide sequence encoding vitamin K epoxide reductase (VKOR), wherein the heterologous nucleic acid encoding VKOR comprises, consists essentially of, or consists of a nucleotide sequence that encodes an amino acid sequence having at least 19% identity but not greater than about 79% identity (e.g., about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% 61%, 62%, 63%, 64%, 65%, 66%, 67%, 68%, 69%, 70%, 71%, 72%, 73%, 74%, 75%, 76%, 77%, 78%, 79%, 80%, etc.) with the amino acid sequence of a human VKOR (e.g., the amino acid sequence of GenBank® Accession No. AAS01052), under conditions whereby said first and second nucleic acids are expressed to produce a vitamin K dependent protein and VKOR, respectively, thereby increasing the carboxylation of the vitamin K dependent protein in the cell.

The present invention also provides a method of producing a carboxylated vitamin K dependent protein in a cell, comprising introducing, into a cell that expresses a first nucleic acid encoding a vitamin K dependent protein, a second nucleic acid comprising a heterologous nucleotide sequence encoding vitamin K epoxide reductase (VKOR), wherein the heterologous nucleic acid encoding VKOR comprises, consists essentially of or consists of a nucleotide sequence that encodes an amino acid sequence having at least 19% identity but not greater than about 79% identity (e.g., about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% 61%, 62%, 63%, 64%, 65%, 66%, 67%, 68%, 69%, 70%, 71%, 72%, 73%, 74%, 75%, 76%, 77%, 78%, 79%, 80%, etc.) with the amino acid sequence of a human VKOR (e.g., the amino acid sequence of GenBank® Accession No. AAS01052), under conditions whereby said first and second nucleic acids are expressed to produce a vitamin K dependent protein and VKOR, respectively, wherein the amount of carboxylated vitamin K dependent protein produced in the cell in the presence of VKOR produced by the second nucleic acid is increased as compared to the amount of carboxylated vitamin K dependent protein produced in the cell in the absence of VKOR produced by the second nucleic acid, thereby producing a carboxylated vitamin K dependent protein in the cell.

In further embodiments of the methods of this invention as described above, the heterologous nucleic acid encoding vitamin K epoxide reductase (VKOR; e.g., recombinant VKOR) can be, but is not limited to:

1) a nucleotide sequence that encodes an amino acid sequence having at least 19% identity but not greater than about 79% identity with the amino acid sequence of human VKOR (a nonlimiting example of which is the VKOR having the amino acid sequence set forth as GenBank® Accession No. AAS01052), including any variant of human VKOR;

2) a nucleotide sequence that encodes a *Mycobacterium tuberculosis* VKOR (a nonlimiting example of which is the VKOR having the amino acid sequence set forth as GenBank® Accession No. NP_217484);

3) a nucleotide sequence that encodes an *Acropora* VKOR (a nonlimiting example of which is the VKOR having the amino acid sequence set forth as GenBank® Accession No. EZ012735);

4) a nucleotide sequence that encodes a *Nematostella* VKOR (a nonlimiting example of which is the VKOR having the amino acid sequence set forth as GenBank® Accession No. XP_001627634);

5) a nucleotide sequence that encodes an *Amphioxus* VKOR (a nonlimiting example of which is the VKOR having the amino acid sequence set forth as GenBank® Accession No. XP_002611989 nucleotide sequence: GenBank® Accession No. XM_001611843);

6) a nucleotide sequence that encodes a *Takifugu* VKOR (a nonlimiting example of which is the VKOR having the amino acid sequence set forth as GenBank® Accession No. NP_001027838);

7) a nucleotide sequence that encodes a *Ciona* VKOR (a nonlimiting example of which is the VKOR having the amino acid sequence set forth as GenBank® Accession No. NP_001073142);

8) a nucleotide sequence that encodes a hamster VKOR (non limiting examples of which include the VKOR having the amino acid sequence of SEQ ID NO:3 obtained from Syrian golden hamster cell line MCB3901 [AV12-664]; Accession No. CRL-9595 and the VKOR having the amino acid sequence provided as GenBank® Accession No. XP_003511033.1);

9) a nucleotide sequence that encodes a *Drosophila* VKOR (a nonlimiting example of which is the VKOR having the amino acid sequence set forth as GenBank® Accession No. NP_001014533);

10) a nucleotide sequence that encodes a human VKOR (a nonlimiting example of which is the VKOR having the amino acid sequence set forth as GenBank® Accession No. AAS01052), comprising a C51A mutation;

11) a nucleotide sequence that encodes a human VKOR (a nonlimiting example of which is the VKOR having the amino acid sequence set forth as GenBank® Accession No. AAS01052), comprising an IV133-134PY mutation;

12) a nucleotide sequence that encodes a human VKOR (a nonlimiting example of which is the VKOR having the amino acid sequence set forth as GenBank® Accession No. AAS01052), comprising a C51A mutation and an IV133-134PY mutation;

13) a nucleotide sequence that encodes a human VKOR (a nonlimiting example of which is the VKOR having the amino acid sequence provided as GenBank® Accession No. AAS01052), comprising a V45N mutation;

14) a nucleotide sequence that encodes a human VKOR (a nonlimiting example of which is the VKOR having the amino acid sequence provided as GenBank® Accession No. AAS01052), comprising a substitution of amino acids 44-50 with amino acids DYKDDDDK (SEQ ID NO:37);

15) a nucleotide sequence that encodes a human VKOR comprising a substitution of amino acids 122-139 (WILFFVLYDFCIVCITTY, SEQ ID NO:38) of human VKOR (a nonlimiting example of which is the VKOR having the amino acid sequence set forth as GenBank® Accession No. AAS01052) with amino acids 129-146 (FQSLYRIGALCPYCMVVW, SEQ ID NO:39) of *Mycobacterium tuberculosis* VKOR (a nonlimiting example of which is the VKOR having the amino acid sequence set forth as GenBank® Accession No. NP_217484);

16) a nucleotide sequence that encodes a human VKOR comprising a substitution of amino acids 122-139 (WILFFVLYDFCIVCITTY, SEQ ID NO:38) of human VKOR (a nonlimiting example of which is the VKOR having the amino acid sequence set forth as GenBank® Accession No. AAS01052) with amino acids 185-202 (ILSTKLSGSSCLYCLVSA, SEQ ID NO:40) of *Arabidopsis* VKOR (a nonlimiting example of which is the VKOR having the amino acid sequence set forth as GenBank® Accession No. NP_567988);

17) a nucleotide sequence that encodes a human VKOR comprising a substitution of amino acids 122-139 (WILFFVLYDFCIVCITTY), SEQ ID NO:38 of human VKOR (a nonlimiting example of which is the VKOR having the amino acid sequence set forth as GenBank® Accession No. AAS01052) with amino acids 120-137 (YLMVAVLRQFCMYCTTAI, SEQ ID NO:41) of *Synechococcus* VKOR (a nonlimiting example of which is the VKOR having the amino acid sequence set forth as GenBank® Accession No. YP_478481);

18) a nucleotide sequence that encodes a human VKOR comprising a substitution of amino acids 122-139 (WILFFVLYDFCIVCITTY, SEQ ID NO:38) of human VKOR (a nonlimiting example of which is the VKOR having the amino acid sequence set forth as GenBank® Accession No. AAS01052) with amino acids 33-50 (WFQHVMLLKPCVCIYER, SEQ ID NO:42) of a bacterial DsbB enzyme a nonlimiting example of which is the DsbB enzyme having the amino acid sequence set forth as (GenBank® Accession No. ZP_03067529); and/or 19) a nucleotide sequence that encodes a human VKOR comprising a substitution of amino acids 123-139 (WILFFVLYDFCIVCITTY, SEQ ID NO:38) of human VKOR (a nonlimiting example of which is the VKOR having the amino acid sequence set forth as GenBank® Accession No. AAS01052) with amino acids 300-317 (FLEPFVIGATCLWCLTSA, SEQ ID NO:43) of *Roseiflexus* VKOR (a nonlimiting example of which is the VKOR having the amino acid sequence set forth as GenBank® Accession No. YP_001274867).

In some embodiments of the methods described herein, the cell can further comprise a third nucleic acid, comprising, consisting essentially of or consisting of a nucleotide sequence encoding vitamin K dependent gamma carboxylase (VKGC). The nucleotide sequence and amino acid sequence of the vitamin K dependent gamma carboxylase protein of a variety of species are well known to one of skill in the art and readily accessible via publicly accessible databases such as the GenBank® Database.

In some embodiments, the vitamin K dependent protein of this invention can be a coagulation factor, which can be, but is not limited to Factor VII, Factor IX, Factor X, Protein C, Protein S, prothrombin and any combination thereof. Vitamin K dependent proteins are well known in the art. The nucleotide sequence and amino acid sequence of numerous vitamin K dependent proteins are well known to one of skill in the art and readily accessible via publicly accessible databases such as the GenBank® Database.

An additional aspect of the present invention is a recombinant nucleic acid comprising a nucleotide sequence encoding vitamin K epoxide reductase (VKOR) as described herein operatively associated with a heterologous promoter. Such a recombinant nucleic acid can be present in a cell (e.g., a transformed cell). Thus, a further aspect of the present invention is a cell that contains and expresses a recombinant nucleic acid as described above. Such a cell can be a transformed cell. Suitable cells of this invention include but are not limited to, plant, animal, mammal, insect, yeast and bacterial cells.

In some embodiments of the methods of this invention, when the cell is a plant cell or an insect cell, the first nucleic acid encoding the vitamin K dependent protein can be a heterologous nucleic acid. The production of a heterologous nucleic acid encoding a vitamin K dependent protein and introduction of such heterologous nucleic acid into a cell to produce a recombinant vitamin K dependent protein in the cell are well known in the art.

In some embodiments of the methods of this invention, when the cell is a mammalian cell, the first nucleic acid encoding the vitamin K dependent protein can be a heterologous nucleic acid and/or an endogenous nucleic acid. For example, the mammalian cell can endogenously produce the vitamin K dependent protein of interest and that endogenously produced vitamin K dependent protein is what is activated when recombinant VKOR is present in the mammalian cell. In some embodiments, the mammalian cell can comprise an endogenously produced vitamin k dependent protein and a heterologous (e.g., recombinant) vitamin K dependent protein, both of which can be activated when recombinant VKOR is present in the mammalian cell.

Figure 9:
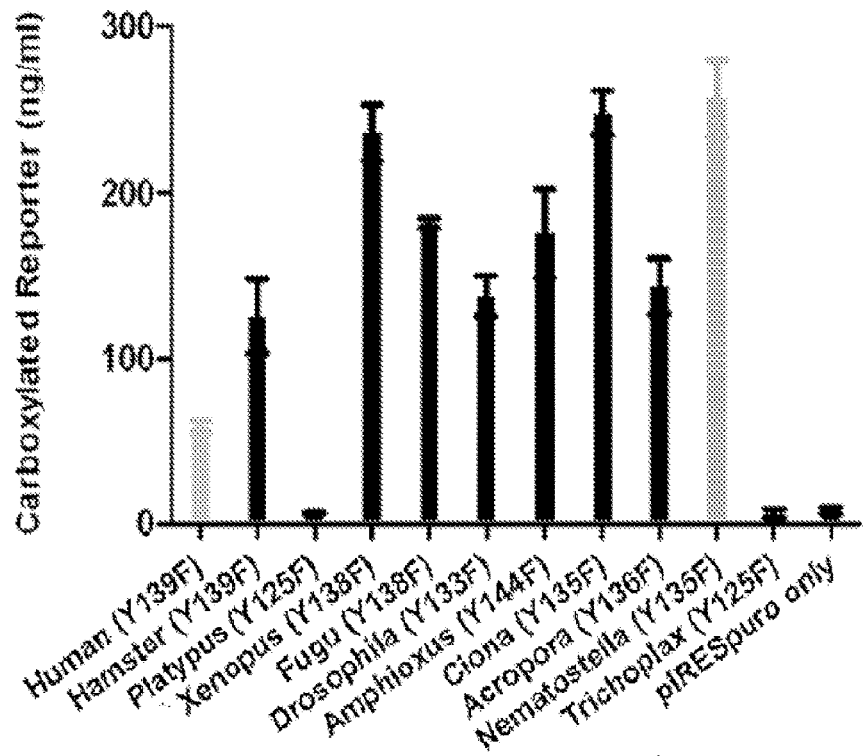
FIG. 9. VKOR activity of several VKOR proteins from diverse species as shown by amount of carboxylated reporter protein according to the cell-based carboxylation assay described herein. 40 h incubation with 5 µM KO, 2 µM warfarin, FIXgla-PC HEK293 cell line.

FIG. 9 shows sequence alignments of the amino acid sequence of the VKOR protein from rat, mouse, human, zebrafish (*Danio* sp.), Fugu fish (*Takifugu* sp.), *Xenopus, Acropora, Nematostella, Amphioxus, Ciona*, mosquito (*Anopheles* sp.), fly (*Drosophila* sp.), and *M. tuberculosis*. The percent identities for these sequences relative to human VKOR are set forth in Table 1. As explained herein, the present invention demonstrates that recombinant VKOR from widely divergent species (e.g., *M. tuberculosis* with only about 19% identity with human VKOR) can be used to activate vitamin K dependent proteins in cells.

In further aspects, the present invention is based on the unexpected discovery that modifying or mutating a human VKOR protein by changing the charge distribution of various residues on either side of the first transmembrane domain results in a VKOR protein with increased ability to produce carboxylated (e.g., fully carboxylated) vitamin K dependent proteins. Thus, in one embodiment, the present invention provides a method of increasing the amount of carboxylated vitamin K dependent protein in a cell, comprising introducing, into a cell that expresses a first nucleic acid encoding a vitamin K dependent protein a second nucleic acid comprising a heterologous nucleotide sequence encoding a human vitamin K epoxide reductase (VKOR), (e.g., identified as having the amino acid sequence of GenBank® Database Accession No. AAS01052), comprising an R37G mutation, an R35G mutation, an R33G mutation, a K30L mutation, a G9R mutation, a S7R mutation and a G6R mutation, under conditions whereby said first and second nucleic acids are expressed to produce a vitamin K dependent protein and VKOR, respectively, thereby increasing the amount of carboxylated vitamin K dependent protein in the cell.

A further embodiment of the present invention is a method of increasing the carboxylation of a vitamin K dependent protein, comprising introducing, into a cell that expresses a first nucleic acid encoding a vitamin K dependent protein, a second nucleic acid comprising a heterologous nucleotide sequence encoding a human vitamin K epoxide reductase (VKOR), (e.g., identified as having the amino acid sequence of GenBank® Database Accession No. AAS01052), comprising an R37G mutation, an R35G mutation, an R33G mutation, a K30L mutation, a G9R mutation, a S7R mutation and a G6R mutation, under conditions whereby said first and second nucleic acids are expressed to produce a vitamin K dependent protein and VKOR, respectively, thereby increasing the carboxylation of the vitamin K dependent protein in the cell.

An additional embodiment of this invention is a method of producing a carboxylated (e.g., fully carboxylated) vitamin K dependent protein in a cell, comprising introducing, into a cell that expresses a first nucleic acid encoding a vitamin K dependent protein, a second nucleic acid comprising a heterologous nucleotide sequence encoding a human vitamin K epoxide reductase (VKOR), (e.g., identified as having the amino acid sequence of GenBank® Database Accession No. AAS01052), comprising an R37G mutation, an R35G mutation, an R33G mutation, a K30L mutation, a G9R mutation, a S7R mutation and a G6R mutation, under conditions whereby said first and second nucleic acids are expressed to produce a vitamin K dependent protein and VKOR, respectively, wherein the amount of carboxylated vitamin K dependent protein produced in the cell in the presence of VKOR produced by the second nucleic acid is increased as compared to the amount of carboxylated vitamin K dependent protein produced in the cell in the absence of VKOR produced by the second nucleic acid, thereby producing a carboxylated vitamin K dependent protein in the cell.

As noted herein, aspects of the present invention are based on the discovery that modification of the charge distribution of various residues on either side of the first transmembrane domain of a human VKOR amino acid sequence can alter the activity of the modified VKOR, resulting, in particular embodiments, in an increased capability of the modified VKOR protein to produce carboxylated vitamin K dependent proteins, as compared with the capability of a non-modified (e.g., wild type human VKOR sequence or a human VKOR sequence lacking modifications to residues 6, 7, 9, 30, 33, 35 and/or 37 as described herein; amino acid numbering based on the amino acid sequence of human VKOR having GenBank® Accession No. AAS01052).

Thus additional embodiments of the present invention include a human VKOR comprising an R37G mutation, an R35G mutation, an R33G mutation, a K30L mutation, a G9R mutation, a S7R mutation and/or a G6R mutation in any combination. Furthermore, the amino acid substitution at residues R37, R35 and/or R33 can be a glycine as described above, or the amino acid substitution at these residues can be with a different amino acid residue that results in the same or a similar effect on charge distribution. For example, glycine is a nonpolar amino acid so substitution at R37, R35 and/or R33 can be done with a different nonpolar amino acid (e.g., alanine (A), valine (V), leucine (L), isoleucine (I), methionine (M), phenylalanine (F), tryptophan (W) or proline (P)).

In yet further embodiments, the human VKOR of this invention can be substituted at K30 with a leucine (L) as described herein, or the substitution at K30 can be with a different amino acid residue that results in the same or similar effect on charge distribution. For example, leucine is a nonpolar amino acid so substitution at K30 can be done with a different nonpolar amino acid (e.g., alanine (A), valine (V), glycine (G), isoleucine (I), methionine (M), phenylalanine (F), tryptophan (W) or proline (P)).

The human VKOR of this invention can also be substituted at G9 and/or G6 with an arginine (R) as described herein, or the substitution at G9 and or G6 can be with a different amino acid residue that results in the same or similar effect on charge distribution. For example, arginine (R) is a positively charged or polar amino acid so substitution at G9 and/or G6 can be with a different positively charged or polar amino acid (e.g., histidine (H), lysine (K), serine (S), threonine (T), cysteine (C), tyrosine (Y), asparagine (N) or glutamine (Q)).

In further embodiments, the human VKOR of this invention can be substituted at S7 with an arginine (R) as described herein or the substitution at S7 can be with a different amino acid residue that results in the same or similar effect on charge distribution. For example, arginine (R) is a positively charged or polar amino acid so substitution at 57 can be with a different positively charged or polar amino acid (e.g., histidine (H), lysine (K), threonine (T), cysteine (C), tyrosine (Y), asparagine (N) or glutamine (Q).

It is also contemplated in this invention that eliminating the positive charges and even possibly introducing negative charges just carboxy-terminal to the first transmembrane domain and/or introducing negative charges into the loop structure (e.g., the loop comprising C43 and C51) of the human VKOR protein could be as effective or even more effective in enhancing the carboxylating activity of VKOR as compared with the amino acid substitutions described herein. Before the first transmembrane domain, the amino terminal portion of all metazoan VKOR molecules is very heterogeneous, making it likely that many additional changes can be made in the amino terminus without hindering the ability of VKOR to stimulate carboxylation. The production and testing of such mutants would be well within the skill in the art.

In various embodiments of this invention, any of the amino acid residue substitutions described herein can be present in any combination in a human VKOR protein of this invention. In particular embodiments, the amino acid residue substitutions described herein can be present in any combination in a human VKOR protein of this invention, wherein the result of the combination of amino acid residue substitutions is a VKOR protein having increased carboxylating activity as compared with a VKOR protein lacking the combination of amino acid residue substitutions. The production and analysis of any of the VKOR proteins of this invention having any of the combinations of amino acid residue substitutions can be carried out according to standard protocols well known in the art. For example, the carboxylating activity of a VKOR protein of this invention can be analyzed and measured according to protocols as set forth, for example in Tie et al. "Functional study of the vitamin K cycle in mammalian cells" *Blood* 117:2967-2974 (Jan. 14, 2011) and Tie et al. "*Mycobacterium tuberculosis* vitamin K epoxide reductase homologue supports vitamin K-dependent carboxylation in mammalian cells" *Antioxid Redox Signal*, e-published Sep. 22, 2011, the entire contents of each of which are incorporated by reference herein.

In some embodiments of the methods described herein, the cell can further comprise a third nucleic acid, comprising, consisting essentially of or consisting of a nucleotide sequence encoding vitamin K dependent gamma carboxylase (VKGC). The nucleotide sequence and amino acid sequence of the vitamin K dependent gamma carboxylase protein of a variety of species are well known to one of skill in the art and readily accessible via publicly accessible databases such as the GenBank® Database.

In some embodiments, the vitamin K dependent protein of this invention can be a coagulation factor, which can be, but is not limited to Factor VII, Factor IX, Factor X, Protein C, Protein S, prothrombin and any combination thereof. Vitamin K dependent proteins are well known in the art. The nucleotide sequence and amino acid sequence of numerous vitamin K dependent proteins are well known to one of skill in the art and readily accessible via publicly accessible databases such as the GenBank® Database.

An additional aspect of the present invention is a recombinant nucleic acid comprising a nucleotide sequence encoding vitamin K epoxide reductase (VKOR) as described herein operatively associated with a heterologous promoter. Such a recombinant nucleic acid can be present in a cell (e.g., a transformed cell). Thus, a further aspect of the present invention is a cell that contains and expresses a recombinant nucleic acid as described above. Such a cell can be a transformed cell. Suitable cells of this invention include but are not limited to, plant, animal, mammal, insect, yeast and bacterial cells.

In some embodiments of the methods of this invention, when the cell is a plant cell or an insect cell, the first nucleic acid encoding the vitamin K dependent protein can be a heterologous nucleic acid. The production of a heterologous nucleic acid encoding a vitamin K dependent protein and introduction of such heterologous nucleic acid into a cell to produce a recombinant vitamin K dependent protein in the cell are well known in the art.

In some embodiments of the methods of this invention, when the cell is a mammalian cell, the first nucleic acid encoding the vitamin K dependent protein can be a heterologous nucleic acid and/or an endogenous nucleic acid. For example, the mammalian cell can endogenously produce the vitamin K dependent protein of interest and that endogenously produced vitamin K dependent protein is what is activated when recombinant VKOR is present in the mammalian cell. In some embodiments, the mammalian cell can comprise an endogenously produced vitamin k dependent protein and a heterologous (e.g., recombinant) vitamin K dependent protein, both of which can be activated when recombinant VKOR is present in the mammalian cell.

DEFINITIONS

As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The term "consisting essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in angiogenesis-stimulating activity of at least about 50% or more as compared to the activity of a polypeptide consisting of the recited sequence.

As used herein, the term "nucleic acid," "nucleic acid molecule" and "nucleotide sequence" encompass both RNA and DNA, including cDNA, genomic DNA, synthetic (e.g., chemically synthesized) DNA and chimeras of RNA and DNA. The nucleic acid molecule or nucleotide sequence may be double-stranded or single-stranded. Where single-stranded, the nucleic acid molecule may be a sense strand or an antisense strand. The nucleic acid molecule may be synthesized using oligonucleotide analogs or derivatives (e.g., inosine or phosphorothioate nucleotides). Such oligonucleotides can be used, for example, to prepare nucleic acid molecules or nucleotide sequences that have altered base-pairing abilities or increased resistance to nucleases.

An "isolated nucleic acid" or "isolated nucleotide sequence" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid or nucleotide sequence includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid gene encoding an additional polypeptide sequence.

The term "isolated" can refer to a nucleic acid, nucleotide sequence or polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose. Furthermore, an "isolated cell" is a cell that has been separated from other components with which it is normally associated in nature. For example, an isolated cell can be a cell in culture medium and/or a cell in a pharmaceutically acceptable carrier of this invention.

The term "oligonucleotide" refers to a nucleotide sequence of at least about five nucleotides to about 300 nucleotides, for example, about 15 to 30 nucleotides, or about 20 to 25 nucleotides, which can be used, for example, as a primer in a PCR amplification and/or as a probe in a hybridization assay or in a microarray. Oligonucleotides may be natural or synthetic, e.g., DNA, RNA, modified backbones, etc.

The term "stringent" as used here refers to hybridization conditions that are commonly understood in the art to define the commodities of the hybridization procedure. Stringency conditions can be low, high or medium, as those terms are commonly know in the art and well recognized by one of ordinary skill. High stringency hybridization conditions that will permit homologous nucleotide sequences to hybridize to a nucleotide sequence as given herein are well known in the art. As one example, hybridization of such sequences to the nucleic acid molecules disclosed herein can be carried out in 25% formamide, 5×SSC, 5×Denhardt's solution and 5% dextran sulfate at 42° C., with wash conditions of 25% formamide, 5×SSC and 0.1% SDS at 42° C., to allow hybridization of sequences of about 60% homology. Another example includes hybridization conditions of 6×SSC, 0.1% SDS at about 45° C., followed by wash conditions of 0.2×SSC, 0.1% SDS at 50-65° C. Another example of stringent conditions is represented by a wash stringency of 0.3 M NaCl, 0.03M sodium citrate, 0.1% SDS at 60-70° C. using a standard hybridization assay (see SAMBROOK et al., EDS., MOLECULAR CLONING: A LABORATORY MANUAL 2d ed. (Cold Spring Harbor, N.Y. 1989, the entire contents of which are incorporated by reference herein). In various embodiments, stringent conditions can include, for example, highly stringent (i.e., high stringency) conditions (e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C.), and/or moderately stringent (i.e., medium stringency) conditions (e.g., washing in 0.2×SSC/0.1% SDS at 42° C.).

Where a particular nucleotide sequence is said to have a specific percent identity to a reference nucleotide sequence, the percent identity is relative to the reference nucleotide sequence. For example, a nucleotide sequence that is 50%, 75%, 85%, 90%, 95% or 99% identical to a reference nucleotide sequence that is 100 bases long can have 50, 75, 85, 90, 95 or 99 bases that are completely identical to a 50, 75, 85, 90, 95 or 99 nucleotide sequence of the reference nucleotide sequence. The nucleotide sequence can also be a 100 base long nucleotide sequence that is 50%, 75%, 85%, 90%, 95% or 99% identical to the reference nucleotide sequence over its entire length. Of course, there are other nucleotide sequences that will also meet the same criteria.

A nucleic acid molecule or nucleotide sequence that is "substantially identical" to a VKOR nucleotide sequence is at least 70%, 75%, 80%, 85% 90%, 95% or 99% identical to the nucleotide sequence encoding a VKOR protein of this invention. For purposes of comparison of nucleic acids, the length of the reference nucleic acid sequence will generally be at least 40 nucleotides, e.g., at least 60 nucleotides or more nucleotides. Sequence identity can be measured using sequence analysis software (e.g., Sequence Analysis Software Package of the Genetics Computer Group, University of Wisconsin Biotechnology Center, 1710 University Avenue, Madison, Wis. 53705).

Furthermore, where a particular amino acid sequence is said to have a specific percent identity to a reference amino acid sequence, the percent identity is relative to the reference amino acid sequence. For example, an amino acid sequence that is 10%, 20%, 30%, 40%, 50%, 75%, 85%, 90%, 95% or 99% identical to a reference amino acid sequence that is 100 amino acid residues long can have 50, 75, 85, 90, 95 or 99 residues that are completely identical to a 50, 75, 85, 90, 95 or 99 residue sequence of the reference amino acid sequence. The amino acid sequence can also be a 100 residue long amino acid sequence that is 50%, 75%, 85%, 90%, 95% or 99% identical to the reference amino acid sequence over its entire length.

As is known in the art, a number of different programs can be used to identify whether a nucleic acid or amino acid has sequence identity or similarity to a known sequence. Sequence identity or similarity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351-360 (1987); the method is similar to that described by Higgins & Sharp, *CABIOS* 5:151-153 (1989).

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program that was obtained from Altschul et al., *Methods in Enzymology,* 266, 460-480 (1996). WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity. An additional useful algorithm is gapped BLAST as reported by Altschul et al. *Nucleic Acids Res.* 25, 3389-3402.

The CLUSTAL program can also be used to determine sequence similarity. This algorithm is described by Higgins et al. (1988) *Gene* 73:237; Higgins et al. (1989) *CABIOS* 5:151-153; Corpet et al. (1988) *Nucleic Acids Res.* 16: 10881-90; Huang et al. (1992) *CABIOS* 8: 155-65; and Pearson et al. (1994) *Meth. Mol. Biol.* 24: 307-331.

In addition, for sequences that contain either more or fewer nucleotides than the nucleic acids disclosed herein, it is understood that in one embodiment, the percentage of sequence identity will be determined based on the number of identical nucleotides in relation to the total number of nucleotide bases. Thus, for example, sequence identity of sequences shorter than a sequence specifically disclosed herein will be determined using the number of nucleotide bases in the shorter sequence, in one embodiment. In percent identity calculations, relative weight is not assigned to various manifestations of sequence variation, such as, insertions, deletions, substitutions, etc.

The VKOR polypeptides of the invention include, but are not limited to, recombinant polypeptides, synthetic peptides and natural polypeptides. The invention also encompasses nucleic acid sequences that encode forms of VKOR polypeptides in which naturally occurring amino acid sequences are altered or deleted. Preferred nucleic acids encode polypeptides that are soluble under normal physiological conditions. Also within the invention are nucleic acids encoding fusion proteins in which all or a portion of VKOR is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells, or to an HPC4 tag to facilitate purification of polypeptides by affinity chromatography or immunoprecipitation. The invention also includes isolated polypeptides (and the nucleic acids that encode these polypeptides) that include a first portion and a second portion; the first portion includes, e.g., all or a portion of a VKOR polypeptide, and the second portion includes, e.g., a detectable marker.

Furthermore, the vitamin K dependent proteins of the invention include, but are not limited to, recombinant polypeptides, synthetic peptides and natural polypeptides. The invention also encompasses nucleic acid sequences that encode forms of vitamin K dependent proteins in which naturally occurring amino acid sequences are altered or deleted. Preferred nucleic acids encode polypeptides that are soluble under normal physiological conditions. Also within the invention are nucleic acids encoding fusion proteins in which all or a portion of vitamin K dependent protein is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells, or to an HPC4 tag to facilitate purification of polypeptides by affinity chromatography or immunoprecipitation. The invention also includes isolated polypeptides (and the nucleic acids that encode these polypeptides) that include a first portion and a second portion; the first portion includes, e.g., all or a portion of a vitamin K dependent protein, and the second portion includes, e.g., a detectable marker.

The fusion partner can be, for example, a polypeptide that facilitates secretion, e.g., a secretory sequence. Such a fused polypeptide is typically referred to as a preprotein. The secretory sequence can be cleaved by the cell to form the mature protein. Also included within the present invention is a nucleotide sequence that encodes VKOR or a vitamin K dependent protein fused to a polypeptide sequence to produce an inactive preprotein. Preproteins can be converted into the active form of the protein by removal of the inactivating sequence.

The invention also includes nucleic acids that hybridize, e.g., under stringent hybridization conditions (as defined herein) to all or a portion of the nucleotide sequence of a VKOR protein of this invention or its complementary sequence. In particular embodiments, the hybridizing portion of the hybridizing nucleic acid is typically at least 15 (e.g., 20, 30, or 50) nucleotides in length. The hybridizing portion of the hybridizing nucleic acid is at least 80%, e.g., at least 95%, at least 98% or 100%, identical to the sequence of a portion or all of a nucleic acid encoding a VKOR polypeptide. Hybridizing nucleic acids of the type described herein can be used, for example, as a cloning probe, a primer (e.g., a PCR primer), or a diagnostic probe. Also included within the invention are small inhibitory RNAs (siRNAs) and/or antisense RNAs that inhibit the function of VKOR, as determined, for example, in an activity assay, as described herein and as is known in the art.

In another embodiment, the invention features cells, e.g., transformed cells, which contain a nucleic acid molecule or nucleotide sequence of this invention. A "transformed cell" is a cell into which (or into an ancestor of which) has been introduced, by means of recombinant nucleic acid techniques, a nucleic acid encoding all or a part of a VKOR polypeptide, and/or a vitamin K dependent protein. Both prokaryotic and eukaryotic cells are included, e.g., bacteria, yeast, insect, mouse, rat, human, plant and the like.

The term "transformation" as used herein refers to the introduction of a heterologous nucleic acid into a cell. Transformation of a cell may be stable or transient. The term "transient transformation" or "transiently transformed" refers to the introduction of one or more heterologous nucleic acids into a cell wherein the heterologous nucleic acid is not heritable from one generation to another.

"Stable transformation" or "stably transformed" refers to the integration of the heterologous nucleic acid into the genome of the cell or incorporation of the heterologous nucleic acid into the cell or cells (e.g., via a plasmid) such that the heterologous nucleic acid is heritable across repeated generations. Thus, in one embodiment of the present invention a stably transformed cell is produced.

Transient transformation may be detected by, for example, an enzyme-linked immunosorbent assay (ELISA) or Western blot, which can detect the presence of a peptide or polypeptide encoded by one or more transgene introduced into a cell. Stable transformation of a cell can be detected by, for example, a Southern blot hybridization assay of genomic DNA of the cell with nucleic acid sequences which specifically hybridize with a nucleotide sequence of a transgene introduced into a cell. Stable transformation of a cell can be detected by, for example, a Northern blot hybridization assay of RNA of the cell with nucleic acid sequences which specifically hybridize with a nucleotide sequence of a transgene introduced into a cell. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

The terms "exogenous" and/or "heterologous" as used herein can include a nucleotide sequence that is not naturally occurring in the nucleic acid construct and/or delivery vector (e.g., virus delivery vector) in which it is contained and can also include a nucleotide sequence that is placed into a non-naturally occurring environment and/or non-naturally occurring position relative to other nucleotide sequences (e.g., by association with a promoter or coding sequence with which it is not naturally associated). For example, a cell of this invention can comprise a heterologous nucleotide sequence encoding a VKOR protein and/or vitamin K dependent protein and said cell can also produce the VKOR protein and/or vitamin K dependent protein endogenously. In other embodiments, a cell of this invention can comprise a heterologous nucleotide sequence encoding a VKOR protein and/or vitamin K dependent protein and said cell may not produce the VKOR protein and/or vitamin K dependent protein endogenously.

The invention also features nucleic acid constructs (e.g., vectors and plasmids) that include a nucleic acid molecule or nucleotide sequence of the invention that is operably linked to a transcription and/or translation control element to enable expression, e.g., expression vectors. By "operably linked" is meant that a selected nucleic acid, e.g., a DNA molecule encoding a VKOR polypeptide and/or a vitamin K dependent protein, is positioned adjacent to one or more regulatory elements, e.g., a promoter, which directs transcription and/or translation of the sequence such that the regulatory elements can control transcription and/or translation of the selected nucleic acid.

The present invention further provides fragments or oligonucleotides of the nucleic acids of this invention, which can be used as primers or probes. Thus, in some embodiments, a fragment or oligonucleotide of this invention is a nucleotide sequence that is at least 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, 750, 800, 850, 900, 1000, 1500, 2000, 2500 or 3000 contiguous nucleotides of a nucleotide sequence encoding a VKOR or vitamin K dependent protein of this invention. Such fragments or oligonucleotides can be detectably labeled or modified, for example, to include and/or incorporate a restriction enzyme cleavage site when employed as a primer in an amplification (e.g., PCR) assay.

The invention also features purified or isolated VKOR polypeptides, such as, for example, a polypeptide comprising, consisting essentially of and/or consisting of the amino acid sequence of the VKOR proteins as described herein or a biologically active fragment or peptide thereof. Such fragments or peptides are typically at least about ten amino acids of the amino acid sequence of a VKOR protein of this invention, (e.g., 15, 20, 25, 30, 35, 40, 45, 50, 55, 60, 65, 75, 85, 95, 100, 125, or 150 amino acids of the amino acid sequence of a VKOR protein of this invention and can be a peptide or fragment of contiguous amino acids of the amino acid sequence of the VKOR protein of this invention. A "biologically active" fragment or peptide of a VKOR protein of this invention is a fragment or peptide of the VKOR protein that has 10%, 20%, 30%, 40%, 50%, 60%, 70%, 80%, 90%, 100%, etc. activity as compared with a human VKOR protein of this invention. The biological activity of a fragment or peptide of this invention can be determined according to the methods provided herein and as are known in the art for identifying VKOR activity. The fragments and peptides of the VKOR protein of this invention can also be active as antigens for the production of antibodies. The identification of epitopes on a fragment or peptide of this invention is carried out by well known protocols and would be within the ordinary skill of one in the art.

As used herein, both "protein" and "polypeptide" mean any chain of amino acids, regardless of length or post-translational modification (e.g., glycosylation, phosphorylation or N-myristylation). Thus, the term "VKOR polypeptide" includes full-length, naturally occurring VKOR proteins, respectively, as well as recombinantly or synthetically produced polypeptides that correspond to a full-length, naturally occurring VKOR protein, or to a portion of a naturally occurring or synthetic VKOR polypeptide.

VKOR proteins of this invention can include a protein substantially identical to all or a portion of a naturally occurring VKOR protein and having VKOR activity as described herein. Proteins that are "substantially identical" to the VKOR proteins described herein have an amino acid sequence that is at least 70%, 75%, 80% or 85% (e.g., 90%, 95% or 99%) identical to the amino acid sequence of the VKOR protein of this invention.

In the case of proteins/polypeptide sequences that are less than 100% identical to a VKOR of this invention, the non-identical positions are preferably, but not necessarily, conservative substitutions for the amino acids of the reference VKOR sequence. Conservative substitutions are well known in the art and typically include, but are not limited to, substitutions within the following groups: glycine and alanine; valine, isoleucine, and leucine; aspartic acid and glutamic acid; asparagine and glutamine; serine and threonine; lysine and arginine; and phenylalanine and tyrosine. Modification of an amino acid sequence to introduce such substitutions is well known in the art, as is the ability to identify variant sequences that contain such substitutions.

A further aspect of the present invention is a method of making a vitamin K dependent protein, comprising culturing a cell that expresses a nucleic acid encoding a vitamin K dependent protein that, in the presence of vitamin K, produces a vitamin K dependent protein; and then harvesting the vitamin K dependent protein from the culture medium, wherein the cell comprises and expresses a heterologous nucleotide sequence encoding a vitamin K epoxide reductase (VKOR) of this invention, thereby producing VKOR. In some embodiments the cell further comprises and expresses a heterologous nucleic acid encoding vitamin K dependent gamma carboxylase, thereby producing vitamin K dependent gamma carboxylase as described herein. In some embodiments, the expression of the VKOR-encoding nucleic acid and the production of the recombinant VKOR of this invention causes the cell to produce greater levels of the vitamin K dependent protein and/or greater levels of active (e.g., fully carboxylated) vitamin K dependent protein than would be produced in the absence of the recombinant VKOR of this invention or in the absence of recombinant VKOR and recombinant vitamin K dependent gamma carboxylase.

Thus, in some embodiments, the present invention also provides a method of producing a vitamin K dependent protein, comprising:

a) introducing into a cell that comprises a nucleotide sequence that encodes a vitamin K dependent protein, a heterologous nucleic acid encoding a nucleic acid comprising a nucleotide sequence encoding a vitamin K epoxide reductase of this invention under conditions whereby the vitamin K dependent protein is produced in the presence of vitamin K and is carboxylated by the recombinant vitamin K epoxide reductase, and b) optionally collecting the vitamin K dependent protein from the cell.

The present invention also provides a method of increasing the amount of carboxylated vitamin K dependent protein in a cell, comprising introducing into a cell that expresses a first nucleic acid encoding a vitamin K dependent protein a second heterologous nucleic acid encoding a vitamin K epoxide reductase (VKOR) of this invention under conditions whereby said first and second nucleic acids are expressed to produce a vitamin K dependent protein and VKOR, respectively.

Further provided herein is a method of increasing the carboxylation of a vitamin K dependent protein, comprising introducing into a cell that expresses a first nucleic acid encoding a vitamin K dependent protein a second heterologous nucleic acid encoding a vitamin K epoxide reductase (VKOR) of this invention under conditions whereby said first and second nucleic acids are expressed to produce a vitamin K dependent protein and VKOR, respectively.

In addition, the present invention provides a method of producing a carboxylated (e.g., fully carboxylated) vitamin K dependent protein in a cell, comprising introducing into a cell that expresses a first nucleic acid encoding a vitamin K dependent protein a second heterologous nucleic acid encoding a vitamin K epoxide reductase (VKOR) of this invention under conditions whereby said first and second nucleic acids are expressed to produce a vitamin K dependent protein and VKOR, respectively, wherein the amount of carboxylated vitamin K dependent protein produced in the cell in the presence of VKOR produced from the heterologous nucleotide sequence is increased as compared to the amount of carboxylated vitamin K dependent protein produced in the cell in the absence of the VKOR of this invention produced from the heterologous nucleotide sequence.

Furthermore, the present invention provides a method of producing a vitamin K dependent protein in a cell, comprising introducing into a cell that expresses a first nucleic acid encoding a vitamin K dependent protein a second nucleic acid comprising a heterologous nucleotide sequence encoding a vitamin K epoxide reductase (VKOR) of this invention under conditions whereby said first and second nucleic acids are expressed to produce a vitamin K dependent protein and VKOR, respectively, wherein 100%, 90%, 80%, 70% or 60% of the vitamin K dependent protein produced in the cell in the presence of VKOR is carboxylated (e.g., fully carboxylated).

Also included herein is a method of producing a vitamin K dependent protein in a cell, comprising introducing into a cell that expresses a first nucleic acid encoding a vitamin K dependent protein a second nucleic acid comprising a heterologous nucleotide sequence encoding a vitamin K epoxide reductase (VKOR) of this invention under conditions whereby said first and second nucleic acids are expressed to produce a vitamin K dependent protein and VKOR, respectively.

In some embodiments of the methods described above, the cell can further comprise a third nucleic acid encoding a vitamin K dependent carboxylase, which can be, but is not limited to, a bovine vitamin K dependent carboxylase. In particular embodiments, the vitamin K-dependent carboxylase is vitamin K gamma glutamyl carboxylase (VKGC).

The VKGC used in the methods of this invention can be VKGC from any vertebrate or invertebrate species that produces VKGC, as are known in the art.

In methods of this invention where the amount of carboxylated vitamin K-dependent protein is increased in a cell in the presence of recombinant VKOR with or without recombinant VKGC, the amount of carboxylated or fully carboxylated vitamin K dependent protein produced in the cell in the presence of recombinant VKOR with or without recombinant VKGC can be increased at least about 10%, 20%, 30%, 40%, 50%, 60%, 70%, 80%, 90% 100% 125% 150%, 200% or 300%, as compared to the amount of carboxylated or fully carboxylated vitamin K dependent protein produced in the cell in the absence of recombinant VKOR with or without VKGC.

By "fully carboxylated" in some embodiments is meant that all sites (or in some embodiments, the majority of sites) on a vitamin K dependent protein that can undergo carboxylation are carboxylated. In some embodiments, fully carboxylated can mean that all vitamin K dependent proteins are carboxylated to some extent and/or that all vitamin K dependent proteins are carboxylated at all or at the majority of carboxylation sites. A carboxylated vitamin K dependent protein or fully carboxylated vitamin K dependent protein is an active or activated protein. By "active protein" or "activated protein" is meant that the vitamin K dependent protein has or is capable of activity in carrying out its biological function (e.g., an enzymatic activity for factor IX or factor X).

The vitamin K dependent protein that can be produced according to the methods of this invention can be any vitamin K dependent protein now known or later identified as such, including but not limited to, Factor VII, Factor VIIA, Factor IX, Factor X, Protein C, activated Protein C, Protein S, bone Gla protein (osteocalcin), matrix Gla protein and prothrombin, including modified versions of such proteins as described herein and as are well known in the art, in any combination.

Any cell that can be transformed with the nucleic acids described herein can be used as described herein, although in some embodiments non-human or even non-mammalian cells can be used. Thus, a cell or cell line of this invention can be, for example, a human cell, an animal cell, a plant cell and/or an insect cell. Nucleic acids encoding vitamin K dependent carboxylase and nucleic acids encoding vitamin K dependent proteins as described herein are well known in the art and their introduction into cells for expression would be carried out according to routine protocols. Thus, in some embodiments, the present invention provides a cell that comprises a nucleic acid (either endogenous or heterologous to the cell) that encodes a vitamin K dependent protein. The vitamin K dependent protein is produced in the cell in the presence of vitamin K. The cell further comprises a heterologous (i.e., exogenous) nucleic acid encoding a recombinant vitamin K epoxide reductase (VKOR) and in some embodiments also a heterologous nucleic acid encoding a recombinant vitamin K dependent carboxylase. The cell can be maintained under conditions known in the art whereby the nucleic acids encoding recombinant VKOR, and in some embodiments, recombinant vitamin K dependent carboxylase, are expressed and recombinant VKOR and in some embodiments, recombinant carboxylase are produced in the cell.

In further embodiments, the present invention provides a method of identifying a substance that regulates activity of *Mycobacterium tuberculosis* vitamin K epoxide reductase (VKOR), comprising determining the activity of *Mycobac-* terium tuberculosis VKOR in the presence and absence of the substance by: a) contacting a recombinant *Mycobacterium tuberculosis* VKOR with a reporter protein under conditions whereby carboxylation of the reporter protein by the *Mycobacterium tuberculosis* VKOR can occur; and b) measuring the amount of carboxylation of the reporter protein by *Mycobacterium tuberculosis* VKOR in the presence and absence of the substance, whereby an increase or decrease, respectively, in the amount of carboxylation of the reporter protein by *Mycobacterium tuberculosis* VKOR in the presence or absence, respectively, of the substance as compared to a control identifies the substance as a substance that regulates activity of *Mycobacterium tuberculosis* VKOR Also provided herein is a method of identifying a substance for treating and/or preventing infection and/or disease caused by *Mycobacterium tuberculosis*, comprising determining the activity of *Mycobacterium tuberculosis* VKOR in the presence and absence of the substance by: a) contacting a recombinant *Mycobacterium tuberculosis* VKOR with a reporter protein under conditions whereby carboxylation of the reporter protein by the *Mycobacterium tuberculosis* VKOR can occur; and b) measuring the amount of carboxylation of the reporter protein by *Mycobacterium tuberculosis* VKOR in the presence and absence of the substance whereby a decrease in the amount of carboxylation of the reporter protein by *Mycobacterium tuberculosis* VKOR in the presence of the substance as compared to a control identifies the substance as a substance for treating and/or preventing infection and/or disease caused by *Mycobacterium tuberculosis*.

In the identifying methods described above, step (a) can be carried out in a cell-free system or in cells in culture and in some embodiments the cells can be mammalian cells, yeast cells, insect cells, etc., as are well known in the art. In some embodiments, the cells are mammalian cells, nonlimiting examples of which include HEK293 cells, AV12 cells, CHO cells, BHK cells, etc., as would be known to one of ordinary skill in the art.

Furthermore, in the methods of this invention, the reporter protein can be any protein that can be carboxylated by VKOR, e.g., any protein comprising a gla domain and propeptide (e.g., Factor VII, Factor IX, Factor X, Protein C, Protein S, prothrombin, Gus6, etc.), as are known in the art. In some embodiments, the reporter protein can be any protein comprising a gla domain and propeptide and/or a protein for which a gla-dependent conformational antibody can be produced. Nonlimiting examples of a reporter protein of this invention include Factor VII, Factor IX, Factor X, Protein C, Protein S, prothrombin, Gus6, Protein C comprising a gla domain and propeptide from Factor IX, protein C comprising a gla domain from Factor VII, protein C comprising a gla domain propeptide from Factor X, protein C comprising a gla domain propeptide from prothrombin, etc., as would be well known in the art.

In some embodiments of the methods of this invention, the amount of carboxylation of the reporter protein by *Mycobacterium tuberculosis* VKOR can be decreased by at least 10% as compared to control (e.g., by at least 5%, at least 10%, at least 15%, at least 20%, at least 25% at least 30%, at least 40%, at least 50%, at least 60%, at least 70%, at least 80%, at least 90%, at least 100% as compared to control).

In some embodiments of the methods of this invention, the amount of carboxylation of the reporter protein by *Mycobacterium tuberculosis* VKOR can be increased by at least 10% as compared to control (e.g., at least 5%, at least 10%, at least 15%, at least 20%, at least 25% at least 30%, at least 40%, at least 50%, at least 60%, at least 70%, at least 80%, at least 90%, at least 100%, at least 150%, at least 200%, at least 300%, at least 400%, at least 500%, as compared to control).

The present invention is more particularly described in the following examples that are intended as illustrative only since numerous modifications and variations therein will be apparent to those skilled in the art. Specifically, it is to be understood that the following examples are not intended to limit the scope of the claims to the invention, but are rather intended to be exemplary of certain embodiments. Any variations in the exemplified methods that occur to the skilled artisan are intended to fall within the scope of the present invention. As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

EXAMPLES

Example I

Study of Activity of VKOR Proteins from Nonhuman Species

This invention applies to additional ways to produce vitamin K dependent proteins (e.g., carboxylated vitamin K dependent proteins). Thus, one aspect of this invention is directed to the discovery that recombinant vitamin K epoxide reductase (VKOR) from highly divergent species can be used to produce vitamin K dependent proteins and to increase carboxylation of vitamin K dependent proteins and in some embodiments such VKOR protein from said highly divergent species is more efficient than its human counterpart in carboxylating a vitamin K dependent protein in cells. The system described herein provides for the measurement of the amount of carboxylation of a reporter protein in a cell based system and the reporter protein in the studies described herein is a chimeric protein C with its Gla domain replaced by that of human factor IX. The amino acid sequence of this chimera is: MAWQLTSLLLFVATWGIS-GTPAPLDSVFSSSERAHQVLRIRKRYNS-GKLEEFVQGNL ERECMEEKCSFEEAREVFENTERT-TEFWKQYVDGDQCLVLPLEHPCASLCCGHGTCI DGIGSFSCDCRSGWEGRFCQREVSFLNCSLDNG-GCTHYCLEEVGWRRCSCAPGYKL GDDLLQCH-PAVKFPCGRPWKRMEKKRSHLKRDTEDQEDQVD-PRLIDGKMTRRGDS PWQVVLLDSKKKLACGAVLIHPSWVLTAAHCM-DESKKLLVRLGEYDLRRWEKWE LDLDIKEVFVHP-NYSKSTTDNDIALLHLAQPATLSQTIVPICLPDS-GLAERELNQAGQE TLVTGWGYHSSREKEAKRNRTFVLNFIKIPVVPH-NECSEVMSNMVSENMLCAGILG DRQ-DACEGDSGGPMVASFH-GTWFLVGLVSWGEGCGLLHNYGVYTKVSRYLDWIH GHIRDKEAPQKSWAP (SEQ ID NO:57) In the studies described herein, the nucleotide sequence encoding this chimera is expressed in HEK293 cells and the degree of carboxylation is determined by the amount of carboxylated reporter secreted into the medium; this is measured by ELISA using a monoclonal antibody specific for the carboxylated form of the Gla domain of factor IX. FIG. 9 shows that recombinant VKOR from *Nematostella* is consistently better at promoting carboxylation of the reporter protein in the human cell line than is the over-expressed recombinant human VKOR. This has been repeatedly demonstrated in more than ten experiments. The *Nematostella* amino acid sequence is only 47.6% identical to the amino acid sequence of human VKOR (FIG. 8 and Table 1), extending the range of functional VKOR sequences considerably.

Figure 34:
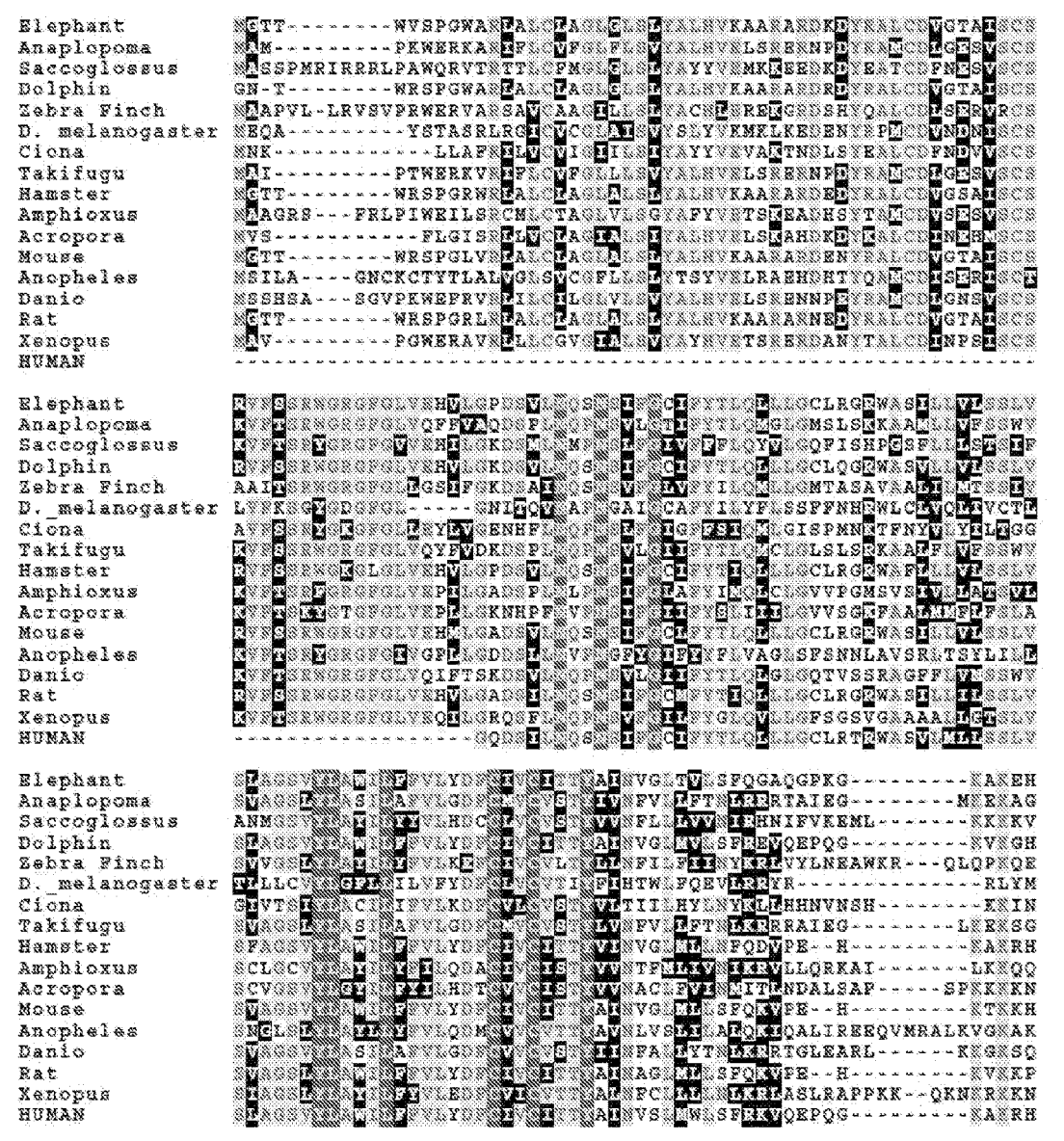

The nucleotide sequence encoding hamster VKOR (SEQ ID NO:3) that was used in the studies described herein was identified from the Syrian golden hamster cell line MCB3901 [AV12-664], ATTC Accession No. CRL-9595™ (referred to herein as "AV12"). The translated protein sequence is approximately 80% identical to humans VKOR (FIG. 8 and Table 1) and this recombinant hamster VKOR has an undiminished ability, compared to recombinant human VKOR, to promote carboxylation of the reporter protein. Further, recombinant VKOR from a different Cnidarian, *Acropora*, also promotes carboxylation of the reporter protein in human cell lines (FIG. 9). Although *Nematostella* and *Acropora* are from the same phyla, their VKOR sequences are only 54% identical to one another (FIG. 8; see also FIG. 34 for additional VKOR sequence alignments).

For all of the VKOR molecules from the different species described herein, the sequences were synthesized by Blue-Heron. The vector used was pIRESpuro 3 from clonetech catalog #631619 (Blue Heron Biotechnology, Bothell, Wash.).

All of the VKOR sequences were made warfarin resistant by substituting the tyrosine at amino acid 139 in the human VKOR sequence with phenylalanine (Y139F). In the non-human species, warfarin resistance was established by substituting out the respective tyrosine homologous to human 139 with phenylalanine. These include Y139 in hamster, Y135 in *Nematostella*, in Y136 in *Acropora*, Y138 in *Xenopus*, Y138 in *Tokifugu*, Y133 in *Drosophila*, Y144 in *Amphioxus*, and Y135 in *Ciona*. VKOR from *Mycobacterium tuberculosis* was resistant to warfarin at the doses employed in these studies, so the amino acid sequence of this VKOR was not modified for warfarin resistance.

In these experiments all of these species had activities that were at least as high as those of the human VKOR sequence and in some cases higher in the in vivo system used. Many of them have sequences that are only about 50% identical and even as low as 19% identical (e.g., *M. tuberculosis*) to human VKOR. The experiments have been repeated a number of times.

By every test so far, the VKOR from *Nematostella* (47.1% identical to human VKOR) is considerably more active than human VKOR itself. In these studies, warfarin is used to eliminate endogenous enzymes in the cell line that is expressing the reporter protein. This means that all of the VKOR variants are rendered warfarin resistant by mutating tyrosine 139 in human VKOR (or its homologue in nonhuman species) to phenylalanine, Y139F. The residue number is slightly different in many species but the homologous tyrosine is modified-unless the tyrosine is naturally not present. The Y139F mutation causes an approximately 50% reduction in the activity of the human VKOR.

Figure 27A:
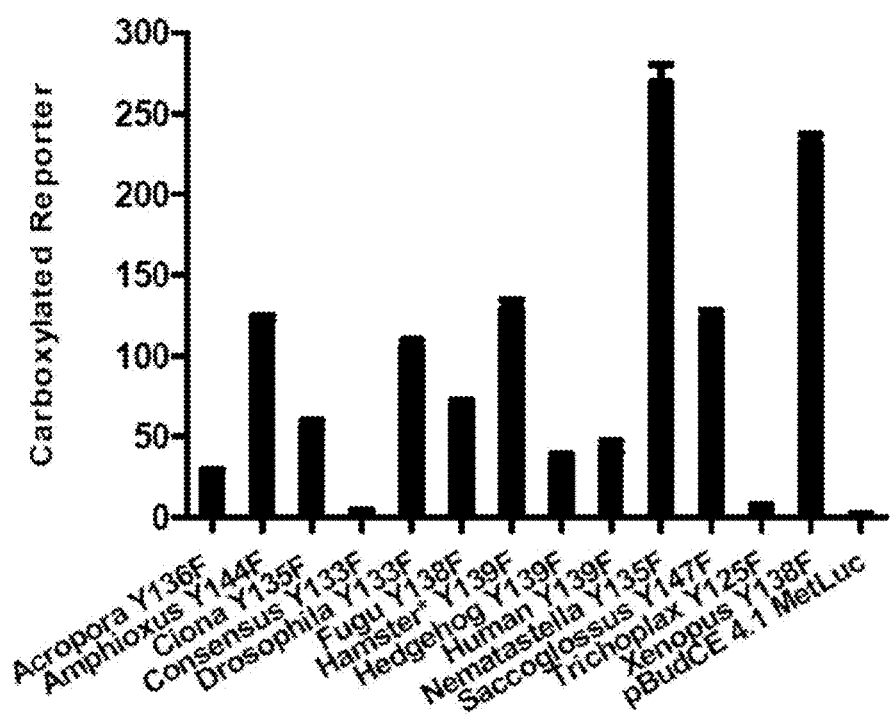
FIGS. 27A-B. ELISA of VKOR activity among diverse species.
Figure 27B:
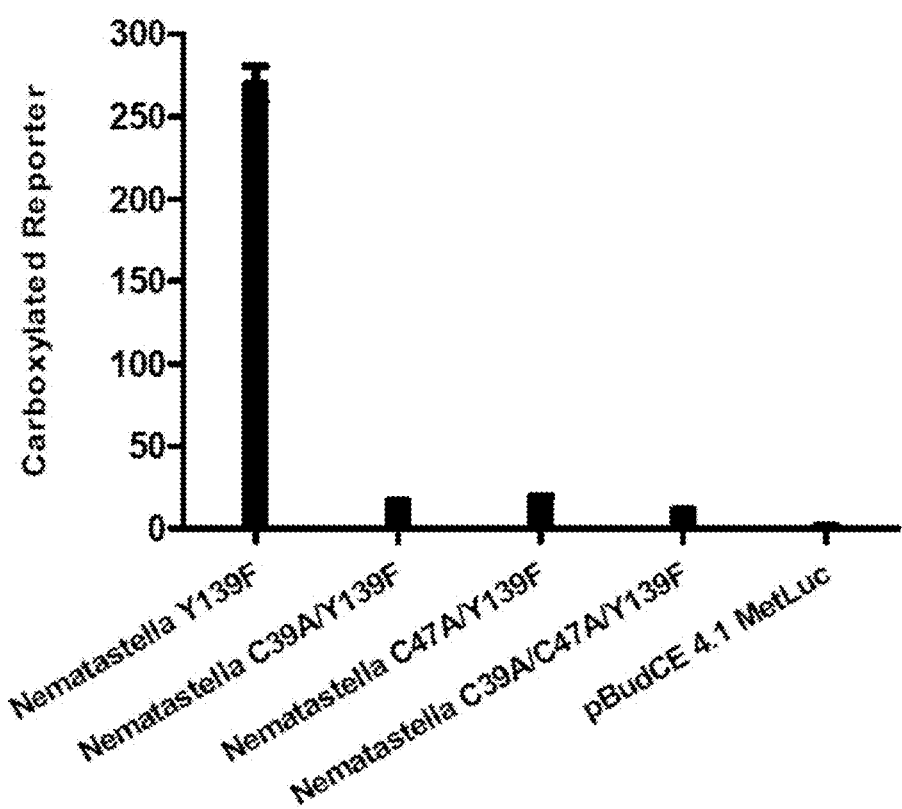

These experiments show that VKOR from these organisms can function in mammalian cells to augment carboxylation of vitamin K-dependent proteins. This study demonstrates that VKOR enzymes from a wide variety of organisms are capable of augmenting carboxylation of vitamin K-dependent proteins in cell culture. In addition to the *Nematostella* results, many other distantly related organisms can also function to promote carboxylation (see, e.g., FIG. 9, FIGS. 27A-B and Table 1) and have the ability to catalyze carboxylation in a cell based system.

Figure 10:
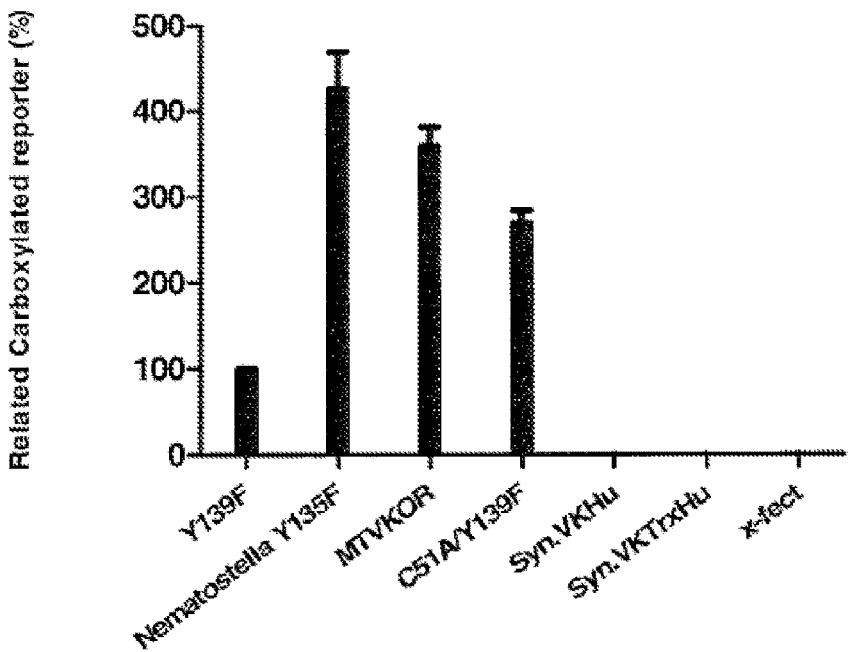
FIG. 10. Relative activity of VKORs as described herein. Y139F: human VKOR rendered warfarin resistant by Y139F mutation; *Nematostella* Y135F: VKOR from *Nematostella* rendered warfarin resistant by Y135F mutation; MTVKOR: *Mycobacterium tuberculosis* VKOR; C51A/Y139F: human VKOR with C51A and Y139F mutations; Syn.VKHu: VKOR from *Synechococcus*; Syn,VKTrxHu: VKOR from *Synechococcus* fused with a thioredoxin type enzyme. FIXgla-PC HEK293 cells, 48 h incubation with 5 µM KO, 2 µM warfarin (x-fect).

In FIG. 10, the availability of different species to catalyze carboxylation of the reporter protein is shown. In this case it is clear that *Nematostella* VKOR (*Nematostella* Y135F) has greater ability to stimulate carboxylation than does the human warfarin resistant control VKOR (Y139F). Surprisingly, *Mycobacterium tuberculosis* VKOR (19.1% identical to human) (MTVKOR) also has greater activity than does the human enzyme. Finally, for this figure, the mutation C51A (C51A/Y139F) in human VKOR also has greater activity than does its control. *Synechococcus* VKOR (Syn.VKHu) exhibited no activity in this reporter system. *Synechococcus* in its native form was fused with a thioredoxin type enzyme (Syn.VKTrxHu) and when this coding region is removed, there is again no carboxylation of the reporter protein.

Figure 11A:
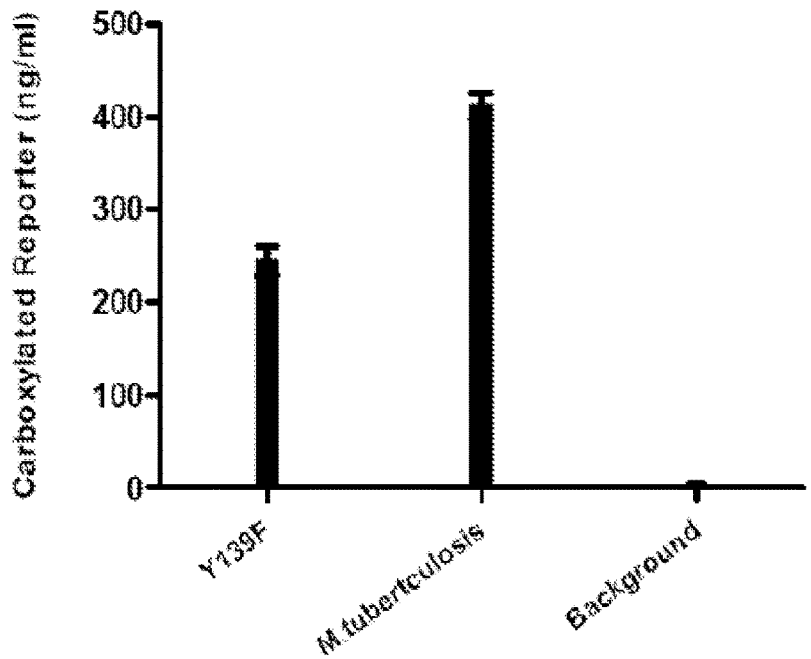
FIGS. 11A-C.
Figure 11B:
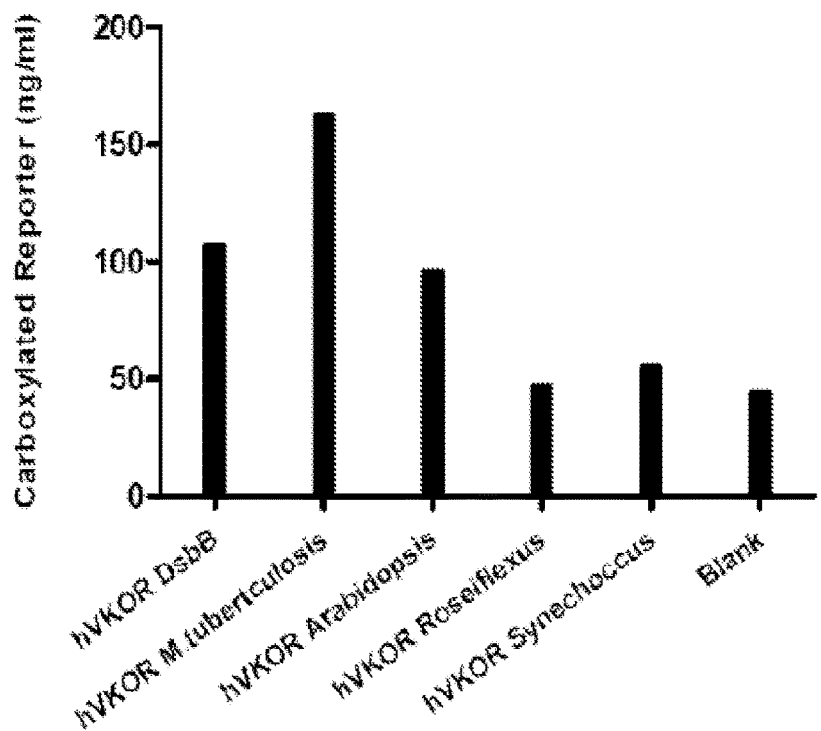
Figure 11C:
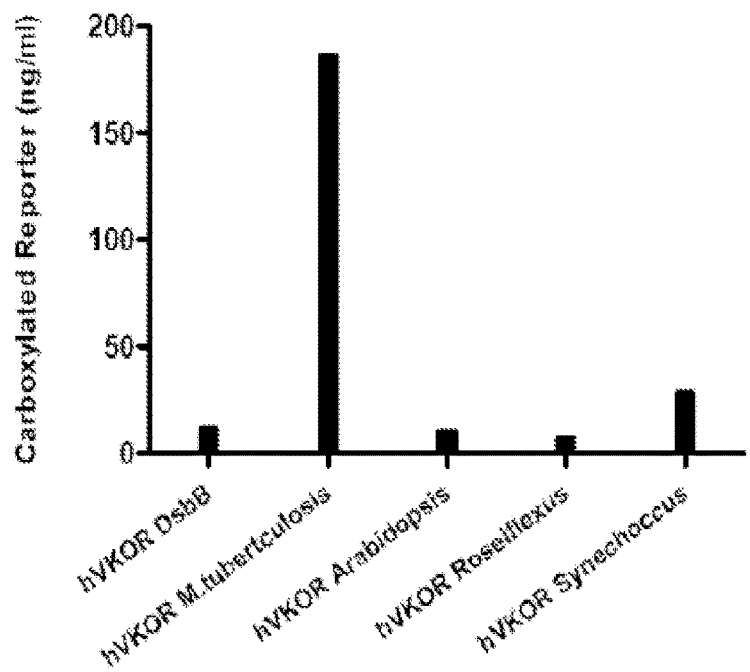

A part of human VKOR was also replaced with sequences from a homologous region of the *Mycobacterium tuberculosis* gene. Specifically amino acid residues 123 to 139 of human VKOR were replaced with amino acid residues 120-146 of *M. tuberculosis* (hVKOR *M. tuberculosis*) and also with residues from other proteins with similar CXXC (SEQ ID NO:60) motifs (*Arabidopsis* (hVKOR *Arabidopsis*), *Synechococcus* (hVKOR *Synechococcus*), *Roseiflexus* (hVKOR *Roseiflexus*) and DsbB protein (hVKOR DsbB); Table 2). Of these, the only molecule with the ability to utilize vitamin K epoxide to carboxylate the reporter protein is *Mycobacterium tuberculosis* (MT) (FIG. 11A). FIG. 11B shows that human VKORs containing the described substitutions from *Arabidopsis* (hVKOR *Arabidopsis*), *M. tuberculosis* (hVKOR *M. tuberculosis*), and even the corresponding region from the bacterial enzyme DsbB (hVKOR DsbB), can utilize vitamin K to produce carboxylated reporter protein. In FIG. 11C, KO is used as a substrate in HEK293 cells and the only VKOR with activity is from *M. tuberculosis*. These studies demonstrate that only the human VKOR substituted with the *M. tuberculosis* domain functions as a VKOR.

Figure 12:
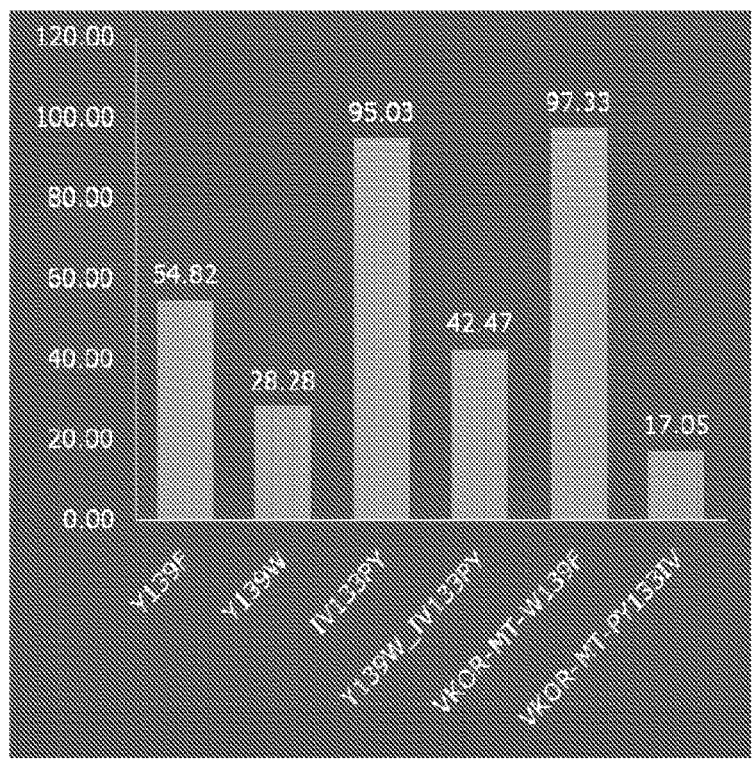
FIG. 12. Amount of carboxylated reporter protein produced in cell-based carboxylation assay described herein using recombinant human VKOR comprising various mutations as described herein.

FIG. 12 shows that an increase in the activity of human VKOR results from substituting PY (the sequence in *Mycobacterium tuberculosis*) for the sequence IV between the active site cysteines 132 and 135 of human VKOR. As noted above, this assay requires the use of warfarin to inhibit endogenous VKOR activity. Therefore, all molecules that were tested have the mutation (at the position homologous to human VKOR Y139F). However it is to be understood that this invention contemplates a VKOR (e.g., human VKOR) with or without a warfarin resistance mutation. This causes a reduction of the activity of human VKOR of approximately 50%. At the level of warfarin used in these assays, the *Mycobacterium tuberculosis* VKOR is naturally resistant to warfarin.

Human VKOR Y139F is shown in the left most column in FIG. 12. The molecule was rendered warfarin resistant by mutating tyrosine 139 to phenylalanine. In the next column, tyrosine 139 was mutated to another aromatic residue, tryptophan (Y139W). This mutation causes a further reduction in the ability of VKOR to convert VKO to VK. The third column from the left shows human VKOR$_{Y139F}$ with the two residues between the active site cysteines mutated from IV to PY (IV133PY). This substitution almost doubles the ability of human VKOR to promote carboxylation of vitamin K-dependent proteins in the mammalian cell system. The fourth column from left shows that changing residue 139 to W and IV at residues 133 and 134 to PY simultaneously (Y139W_IV133PY) does not restore activity to the Y139W VKOR molecule. The fifth column from the left shows that a VKOR molecule with residues 123 to 139 of human VKOR replaced with residues 120-146 of *M. tuberculosis* (VKOR-MT-W139F) but with the tryptophan homologous to Y139 mutated to phenylalanine has strong activity. The column on the right shows that human VKOR with its residues 123-139 replaced by the homologous region from *M. tuberculosis* (VKOR-MT-PY133IV) loses activity when the residues between the active site cysteines (PY) are replaced by the human sequences (IV).

The vector that was used in these experiments was pIRES2 from Clontech but it was modified by removing the DSRed-Express gene and replacing it with the Metridium luciferase gene. The result is a vector that expresses two genes from one transcript.

These data show that bacterial VKOR of *Mycobacterium tuberculosis*, *Nematostella* VKOR and the C51A mutation of human VKOR have VKOR activity. In the case of all the metazoans, the relevant conserved tyrosine residue has been converted to phenylalanine to render it warfarin resistant. In the case of the cysteine 51 mutant (C51A), it as well as the wild-type molecule both have this mutation at residue 139. The *Mycobacterium tuberculosis* VKOR used is naturally resistant to warfarin (in the microgram per ml range). About 50% of the wild-type VKOR activity is observed, so that when human VKOR is compared to *Mycobacterium* VKOR, although the latter has 2 fold greater activity than human VKOR, the human VKOR is about half its normal activity so they are actually probably about the same activity. For the C51A mutation, the activity is about 2 fold greater than WT VKOR and both have the Y139F mutation.

Sequences:

Rat (AAR82917)
(SEQ ID NO: 1)
MGTTWRSPGRLRLALCLAGLALSLYALHVKAARARNEDYRALCDVGTAIS

CSRVFSSRWGRGFGLVEHVLGADSILNQSNSIFGCMFYTIQLLLGCLRGR

WASILLILSSLVSVAGSLYLAWILFFVLYDFCIVCITTYAINAGLMLLSF

QKVPEHKVKKP

Mouse (NP_848715)
(SEQ ID NO: 2)
MGTTWRSPGLVRLALCLAGLALSLYALHVKAARARDENYRALCDVGTAIS

CSRVFSSRWGRGFGLVEHMLGADSVLNQSNSIFGCLFYTLQLLLGCLRGR

WASILLVLSSLVSVAGSVYLAWILFFVLYDFCIVCITTYAINVGLMLLSF

QKVPEHKTKKH

Figure 8:
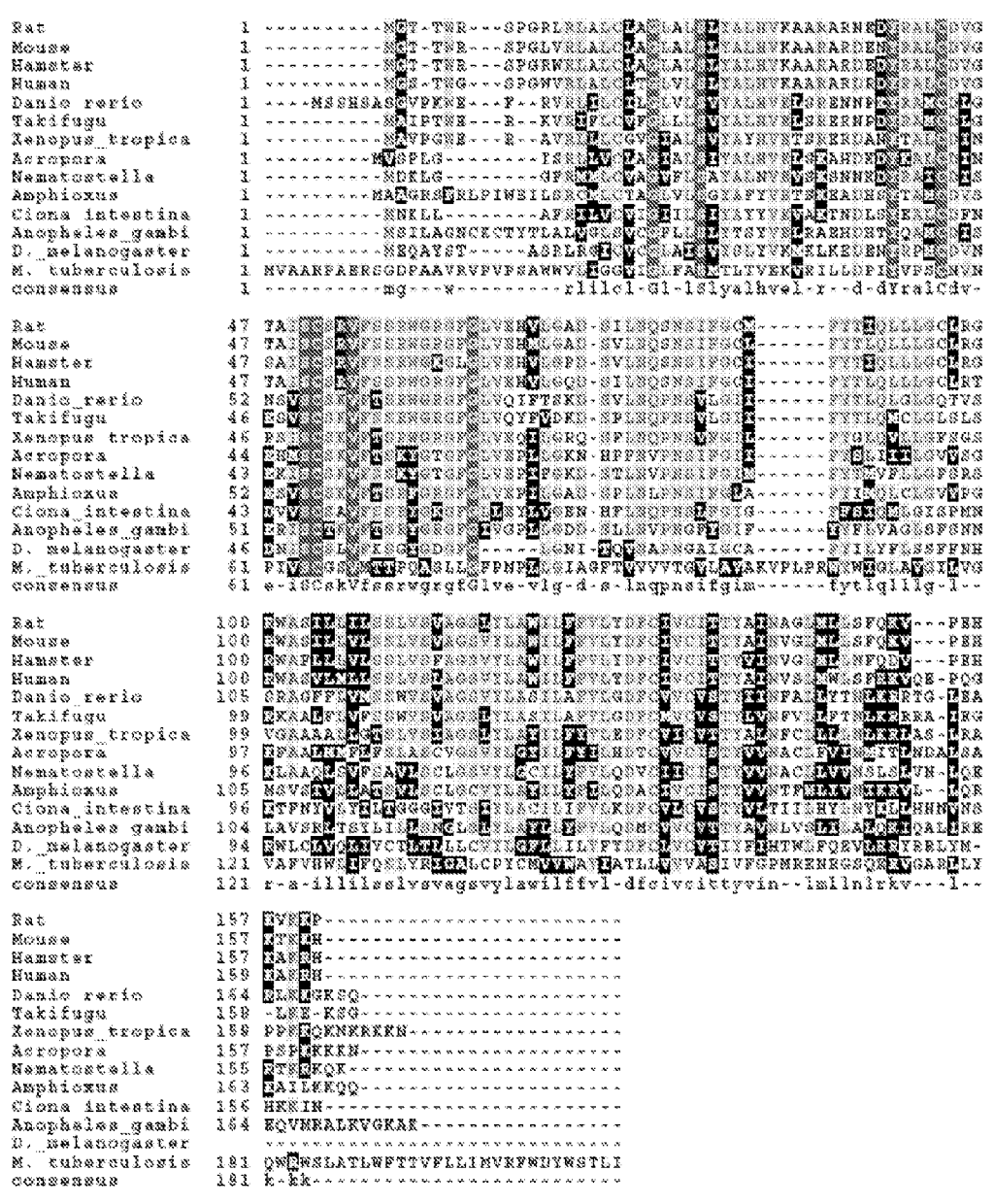

Hamster used in alignment of FIG. 8
(SEQ ID NO: 3)
MGTTWRSPGRWRLALCLAGLALSLYALHVKAARARDEDYRALCDVGSAIS

CSRVFSSRWGKGLGLVEHVLGPDSVLNQNSIFGCIFYTIQLLLGCLRGRW

AFLLLVLSSLVSFAGSVYLAWILFFVLYDFCIVCITTYVIN

*Cricetulus griseus* (Chinese hamster) (XP_003511033.1)
(SEQ ID NO: 4)
MGTTWRSPGR RRLALCLAGL ALSLYALHVK AARARDEDYR

ALCDVGTAIS CSRVFSSRWG KGFGLVEHVL GSDSVLNQSN

SIFGCIFYTI QLLLGCLRGR WASLLLVLSS LVSFAGSVYL

AWILFFVLYD FCIVCITTYA INVGLMLLNF QEVPEHKAKR P

Human (AAS01052)
(SEQ ID NO: 5)
MGSTWGSPGW VRLALCLTGL VLSLYALHVK AARARDRDYR

ALCDVGTAIS CSRVFSSRWG RGFGLVEHVL GQDSILNQSN

SIFGCIFYTL QLLLGCLRTR WASVLMLLSS LVSLAGSVYL

AWILFFVLYD FCIVCITTYA INVSLMWLSF RKVQEPQGKA

KRH

*Danio rerio* (zebrafish, XP_001336460)
(SEQ ID NO: 6)
MSSHSASGVPKWEFRVRLILCILGLVLSVYALHVELSRENNPEYRAMCDL

GNSVSCSKVFTSRWGRGFGLVQIFTSKDSVLNQPNSVLGIIFYTLQLGLG

QTVSSRAGFFLVMSSWVSVAGSVYLASILAFVLGDFCVVCVSTYIINFAL

LYTNLKRRTGLEARLKKGKSQ

*Takifugu* (NP_001027838)
(SEQ ID NO: 7)
MAIPTWERKVRIFLCVFGLLLSVYALHVELSRERNPDYRAMCDLGESVSC

SKVFSSRWGRGFGLVQYFVDKDSPLNQPNSVLGIIFYTLQMCLGLSLSRK

AALFLVFSSWVSVAGSLYLASILAFVLGDFCMVCVSTYLVNFVLLFTNLK

RRRAIEGLKEKSG

*Xenopus* (NP_001006928; NM_001006927)
(SEQ ID NO: 8)
MAVPGWERAVRLLLCGVGIALSVYAYHVETSRERDANYTALCDINPSISC

SKVFTSRWGRGFGLVEQILGRQSFLNQPNSVFGILFYGLQVLLGFSGSVG

AAAALLGTSLVSIAGSLYLAYILFYVLEDFCVICVTTYALNFCLLLLNLK

RLASLRAPPKKQKNKRKKN

*Acropora* (translation of EZ012735)
(SEQ ID NO: 9)
MVSFLGISRLLVCLAGIALSIYALHVELSKAHDKDYKALCDINEHMSCSK

VFTSKYGTGFGLVEPLLGKNHPFNVPNSIFGIIFYSLIIILGVVSGKFAA

LMMFLFSLASCVGSVYLGYILFYILHDTCVVCISTYVVNACLFVINMITL

NDALSAPSPKKKKN

*Nematostella* (XP_001627634)
(SEQ ID NO: 10)
MDKLGGFRMMLCVAGVFLSAYALNVEVSKSNNKDYRAICDISEKISCSKV

FSSKYGTGFGLVEPIFGKDSTLNVPNSIFGIMFYTMVFLLGFSRSKLAAQ

LSVFSAVLSCLGSVYLGCILYFVLQDVCIICISTYVVNACLLVVNSLSLV

NLQERTKRKQK

Amphioxus used in alignment in FIG. 8
(two bolded amino acids are different than
GenBank ® Database sequence shown below)
(SEQ ID NO: 11)
MAAGRSFRLPIWEILSRCMLCTAGLVLSGYAFYVETSKEADHSYTAMCDV

SESVSCSKVFTSRFGRGFGLVEPILGADSPLNLPNSIFGLAFYIMQLCLG

VVPGMSVSIVLLATSVLSCLGCVYLAYILYFILQDACIVCISTYVVNTFM

LIVNIKRVLLQRKAILKKQQ

-continued

Amphioxus (XP_002611889; XM_002611843)
(SEQ ID NO: 12)
MAAGRSFRLPIWEILSRCMLCTAGLVLSGYAFYVETSKEADHSYTAMCDV

SESVSCSKVFTSRFGRGFGLVEPILGADSPLNLPNSIFGLAFYIMQLCLG

VVPGMSVSIVLLATSVLSCLGCVYLAYILYFILQDACIVCISTYVVNTLM

LVVNIKRVLLQRKALLKKQQ

Ciona (NP_001073142)
(SEQ ID NO: 13)
MNKLLAFRILVCVIGIILSIYAYYVEVAKTNDLSYEALCDFNDVVSCSAV

FSSRYGKGLLEYLVGENHFLNQPNSLFGIGFFSIQMLGISPMNKTFNYVL

YILTGGGIVTSIYLACILIFVLKDFCVLCVSTYVLTIILHYLNYKLLHHN

VNSHKKIN

Anopheles (XP_310541)
(SEQ ID NO: 14)
MSILAGNCKCTYTLALVGLSVCGFLLSLYTSYVELRAEHDHTYQAMCDIS

ERISCTKVFTSRYGRGFGIVGPLLGDDSLLNVPNGFYGIFYYFLVAGLSF

SNNLAVSRLTSYLILLSNGLSLYLAYLLYFVLQDMCVVCVTTYAVNLVSL

ILALQKIQALIREEQVMRALKVGKAK

Trichoplax (XM_002107720.1)
(SEQ ID NO: 15)
MSLVGLALSVYALHVETTKESNKNYKAFCDFGASISCSKVFTSKYGKGFG

LIAPIFGQHSSLNQPNSIYGIIFYCIQICLAFHHTLKITRIVLAMSLLSC

IGSFYLAFVLTFVLHDFCLVCVSTYIVNAVVSFLNFKRM

Platypus (XM_001515406.1)
(SEQ ID NO: 16)
MGAWVPTRSARVVGPRALGSRVATAVQPSAVDPDTRHDRIPSLRWGRGFG

LVEMVLGPDSSLNQPNSVFGLLFYSLQLLLGCSRAPWTSVVLALSSLLSL

AGSLYLAWILFFVLHDFCFVCITTYAINVGLALLNYRRLKQAQGKVMKYC

DESSPASSLLERRFYSGGGLRNGGSAASFPFPPATGH

Drosophila (NP_001014533)
(SEQ ID NO: 17)
MEQAYSTASRLRGICVCGLAISVYSLYVKMKLKEDENYRPMCDVNDNISC

SLVFKSGYGDGFGLGNITQVNAPNGAIGCAFYILYFLSSFFNHRWLCLVQ

LIVCTLTLLLCVYLGFLLILVFYDFCLVCVTIYFIHTWLFQEVLRRYRRL

YM

Mycobacterium tuberculosis (NP_217484.1)
(SEQ ID NO: 18)
MVAARPAERSGDPAAVRVPVPSAWWVLIGGVIGLFASMTLTVEKVRILLD

PIYVPSCNVNPIVSCGSVMTTPQASLLGFPNPLLGIAGFTVVVVTGVLAV

AKVPLPRWYWIGLAVGILVGVAFVHWLIFQSLYRIGALCPYCMVVWAVIA

TLLVVVASIVFGPMRENRGSQERVGARLLYQWRWSLATLWFTTVFLLIMV

RFWDYSTLI

Arabidopsis thaliana (NP_567988.1)
(SEQ ID NO: 19)
MMARFVSVSSCQFHFGFREVSPPSVTSYPRRFEVSDRRFPAIPIKCSSSE

PENGEDSAPSLSSSSSSSTSEVSTSNSSTYNWYTGIGGIGMLDTAYLTYL

KVTGSDAFCPIGGGTCGDVLNSDYAVVFGVPLPVIGFVMYGVVTALSAEL

GEGNLPFGISKSNGRFALFGITTAMASASAYFLYILSTKLSGSSCLYCLV

SAFLSFSLFFLSVKDVKLQEIQQVVGLQICLAIIVVASLTASYSTAQPIP

SRSGDIELPYFRTEISSSSSPYAIALAKHLNSIGAKMYGAFWCSHCLEQK

EMFGREAAKELNYVECFPDGYKKGTKILKACADAAIEGFPTWIINDKVLS

GEIELAELAEMTGFSLDQANETNQLQ

Roseiflexus sp. RS-1 (YP_001274867.1)
(SEQ ID NO: 20)
MRRFLLTLIVSCMLTLSLSVASAAATVRAVLFYSPRCGHCHMVISEHLPP

LQQRYGDQLQILMIDVDQAQGAALYREAIAVYAIPEARRGVPTMIISDTV

LVGSVEIPQRLPGLIETLLARGGSDWPPIPGLADLLATVPTSAPAPPTLP

PATAETPPFLRDLPANALAVVVLAGMLLTVMWAGITWSRPAQPPTRWRDR

SIPLLAIGGMAVAAYLTFIETTGAPALCGPVGDCNAVQQSEFARLFGTIP

VGAAGVAGYGAILIVWIVAHLLPGTSGERAALLLPALALIGTLFSIYLTF

LEPFVIGATCLWCLTSAVIMTGLLWLSMPYRQRSTSRGYARR

Synechococcus sp. JA-2-3B'a(2-13) (YP_478481.1)
(SEQ ID NO: 21)
MASYLKLKAQEETWLQRHSRLILAILAGLGSLLTAYLTYTKLTEQPAAFC

TGDGGCDLVLSSRWAEFLGIPTAAVGLLGFLGVLALAVLPDGLPLVKRWR

WPALFGLVSAMTAFEMYMLYLMVAVLRQFCMYCTTAIILVAGLGLVTVLG

HRWLDGGKLAFSYILVAFLTVTTIGVYANQVPPPSPLAVGLAAHLRQIG

GTMYGAYWCPHCQDQKELFGAAFDQVPYVECSPNGPGTPQAQECTEAGIT

SYPTWIINGRTYTGVRSLEALAVASGYPLEEGR

Shigella dysenteriae 1012 DsbB protein
(ZP_03067529.1)
(SEQ ID NO: 22)
MIMLRFLNQCSQGRGAWLLMAFTALALELTALWFQHVMLLKPCVLCIYER

CALFGVLGAALIGAIAPKTPLRYVAMVIWLYSAFRGVQLTYEHTMLQLYP

SPFATCDFMVRFPEWLPLDKWVPQVFVASGDCAERQWDFLGLEMPQWLLG

IFIAYLIVAVLVVISQPFKAKKRDLFGR

Corynebacterium jeikeium K411 (YP_250248.1)
(SEQ ID NO: 23)
MWVWWGREGVSNKESEHMNGLGATKRFGYTFLVLSTIGLIFSALIMHDKV

QMALDPNFEPACTFNEVISCTDVMASDQAATFGFANPFIGMIGFPVMMTL

AVMLIVGAKLPRWIWYCALAGLAFGVAFVHWLAYSAIYSIGALCPYCMAV

WAATLPMFVMTLVHIQREKRREAGEDVAHSALGMPLVVIIAWFLAFTALI

LDQFVF

Salinispora tropica CNB-440 (YP_001157037.1)
(SEQ ID NO: 24)
MTTTANRPVTTPAERHFLAAVTAWVLTIGGAVGLLAAAALTVEKINLLAD

PGYVPTCSINPILSCGSVMNTPQAAVFGFPNPLLGIAGFAVVTTLGVTLL

ATGHLPRWMWLGLQGGVTFGVVFVHWLIYQSLYVIGALCPYCMVVWAVTI

PIFLYTTLQTLRDNTTALPRALRRVTERVARYHSLVLVVWAAFVVVVILH

RFWDYWSTLG

Human VKOR with V45N mutation:
(SEQ ID NO: 25)
MGSTWGSPGWVRLALCLTGLVLSLYALHVKAARARDRDYRALCDNGTAIS

ASRVFSSRWGRGFGLVEHVLGQDSILNQSNSIFGCIFYTLQLLLGCLRTR

-continued

```
WASVLMLLSSLVSLAGSVYLAWILFFVLYDFCIVCITTYAINVSLMWLSF

RKVQEPQGKAKRH

Human VKOR with C51A mutation:
                                           (SEQ ID NO: 26)
MGSTWGSPGWVRLALCLTGLVLSLYALHVKAARARDRDYRALCDVGTAIS

ASRVFSSRWGRGFGLVEHVLGQDSILNQSNSIFGCIFYTLQLLLGCLRTR

WASVLMLLSSLVSLAGSVYLAWILFFVLYDFCIVCITTYAINVSLMWLSF

RKVQEPQGKAKRH

Human VKOR with IV133-134PY mutation:
                                           (SEQ ID NO: 27)
MGSTWGSPGWVRLALCLTGLVLSLYALHVKAARARDRDYRALCDVGTAIS

CSRVFSSRWGRGFGLVEHVLGQDSILNQSNSIFGCIFYTLQLLLGCLRTR

WASVLMLLSSLVSLAGSVYLAWILFFVLYDFCPYCITTYAINVSLMWLSF

RKVQEPQGKAKRH

Human VKOR with IV133-134PY mutation and
C51A mutation:
                                           (SEQ ID NO: 28)
MGSTWGSPGWVRLALCLTGLVLSLYALHVKAARARDRDYRALCDVGTAIS

ASRVFSSRWGRGFGLVEHVLGQDSILNQSNSIFGCIFYTLQLLLGCLRTR

WASVLMLLSSLVSLAGSVYLAWILFFVLYDFCPYCITTYAINVSLMWLSF

RKVQEPQGKAKRH

Human VKOR with amino acids 122-139
substituted with amino acids 129-146 of
M. tuberculosis VKOR
(GenBank ® Database Accession No. NP_217484):
                                           (SEQ ID NO: 29)
MGSTWGSPGWVRLALCLTGLVLSLYALHVKAARARDRDYRALCDVGTAIS

CSRVFSSRWGRGFGLVEHVLGQDSILNQSNSIFGCIFYTLQLLLGCLRTR

WASVLMLLSSLVSLAGSVYLAFQSLYRIGALCPYCMVVWAINVSLMWLSF

RKVQEPQGKAKRH

Human VKOR with amino acids 122-139
substituted with amino acids 185-202 of
Arabidopsis VKOR
(GenBank ® Accession No. NP_567988):
                                           (SEQ ID NO: 30)
MGSTWGSPGWVRLALCLTGLVLSLYALHVKAARARDRDYRALCDVGTAIS

CSRVFSSRWGRGFGLVEHVLGQDSILNQSNSIFGCIFYTLQLLLGCLRTR

WASVLMLLSSLVSLAGSVYLAILSTKLSGSSCLYCLVSAAINVSLMWLSF

RKVQEPQGKAKRH

Human VKOR with amino acids 122-139
substituted with amino acids 120-137 of
Synechococcus VKOR
(GenBank ® Accession No. YP_478481):
                                           (SEQ ID NO: 31)
MGSTWGSPGWVRLALCLTGLVLSLYALHVKAARARDRDYRALCDVGTAIS

CSRVFSSRWGRGFGLVEHVLGQDSILNQSNSIFGCIFYTLQLLLGCLRTR

WASVLMLLSSLVSLAGSVYLAYLMVAVLRQFCMYCTTAIAINVSLMWLSF

RKVQEPQGKAKRH

Human VKOR with amino acids 122-139
substituted with amino acids 33-50 of DsbB
enzyme (GenBank ® Accession No. ZP_03067529):
                                           (SEQ ID NO: 32)
MGSTWGSPGWVRLALCLTGLVLSLYALHVKAARARDRDYRALCDVGTAIS

CSRVFSSRWGRGFGLVEHVLGQDSILNQSNSIFGCIFYTLQLLLGCLRTR

WASVLMLLSSLVSLAGSVYLAWFQHVMLLKPCVLCIYERAINVSLMWLSF

RKVQEPQGKAKRH

Human VKOR with amino acids 122-139
substituted with amino acids 300-317 of
Roseiflexus VKOR
(GenBank ® Accession No. YP_001274867)
                                           (SEQ ID NO: 33)
MGSTWGSPGWVRLALCLTGLVLSLYALHVKAARARDRDYRALCDVGTAIS

CSRVFSSRWGRGFGLVEHVLGQDSILNQSNSIFGCIFYTLQLLLGCLRTR

WASVLMLLSSLVSLAGSVYLAFLEPFVIGATCLWCLTSAAINVSLMWLSF

RKVQEPQGKAKRH

Human VKOR with amino acids 44-50
substituted with amino acids DYKDDDDK
(Flag tag):
                                           (SEQ ID NO: 34)
MGSTWGSPGWVRLALCLTGLVLSLYALHVKAARARDRDYRALCDYKDDDD

KCSRVFSSRWGRGFGLVEHVLGQDSILNQSNSIFGCIFYTLQLLLGCLRT

RWASVLMLLSSLVSLAGSVYLAWILFFVLYDFCIVCITTYAINVSLMWLS

FRKVQEPQGKAKRH

Human VKOR comprising an R37G mutation,
an R35G mutation, an R33G mutation, a
K30L mutation, a G9R mutation, an S7R
mutation and a G6R mutation:
                                           (SEQ ID NO: 35)
MGSTWRRPRWVRLALCLTGLVLSLYALHVLAAGAGDGDYRALCDVGTAIS

CSRVFSSRWGRGFGLVEHVLGQDSILNQSNSIFGCIFYTLQLLLGCLRTR

WASVLMLLSSLVSLAGSVYLAWIFFVLYDFCIVCITTYAINVSLMWLSF

RKVQEPQGKAKRH

Human VKOR comprising an R37 mutation (X₁),
an R35 mutation (X₂), an R33 mutation (X₃),
a K30 mutation (X₄), a G9 mutation (X₅),
an S7 mutation (X₆) and a G6 mutation (X₇):
                                           (SEQ ID NO: 36)
MGSTWX₇X₆PX₅WVRLALCLTGLVLSLYALHVX₄AX₃AX₂DX₁DYRALCDV

GTAISCSRVFSSRWGRGFGLVEHVLGQDSILNQSNSIFGCIFYTLQLLLG

CLRTRWASVLMLLSSLVSLAGSVYLAWILFFVLYDFCIVCITTYA

INVSLMWLSF RKVQEPQGKA KRH,
wherein: X₁ may be G, A, I, L, V, M, F, W or P;
X₂ may be G, A, I, L, V, M, F, W or P;
X₃ may be G, A, I, L, V, M, F, W or P;
X₄ may be L, I, V, A, G, M, F, W or P;
X₅ may be R, H, K, S, T, C, Y, N or Q;
X₆ may be R, H, K, T, C, Y, N or Q;
and X₇ may be R, H, K, S, T, C, Y, N or Q
```

Example II

Studies of Cysteines

Vitamin K hydroquinone (VKH2) is required as a co-factor for the enzyme gamma glutamyl carboxylase, GGCX. GGCX catalyzes the addition of $CO_2$ to the gamma carbon of certain glutamic acids of the vitamin K-dependent proteins. For every Glu modification, VKH2 is converted to vitamin K epoxide (VKO) which must be sequentially converted back to vitamin K (VK) and VKH2 for carboxylation to continue. Vitamin K oxidoreductase (VKOR), a member of the thioredoxin protein family is a 163 amino acid, multi-pass, transmembrane enzyme that converts VKO to VK and can also convert VK to VKH2—although a second enzyme may be a major player in the VK to VKH2 reaction as described herein.

Traditionally, the vitamin K-dependent (VKD) proteins were thought to function mainly in blood coagulation; however, VKD proteins that, e.g., prevent calcification of soft tissues and arteries and that regulate cell growth and inflammation are now known.

VKOR is highly conserved throughout the metazoa and there are apparent bacterial homologs. The most obvious similarity between the metazoan VKORs and the bacterial homologs is that there are two pairs of cysteine residues (numbers 43/51 and 131/135 in human VKOR) that are highly conserved among prokaryotes and eukaryotes. The lone exception is the reported sequence of VKOR of the duck-billed platypus which lacks the cysteines corresponding to 43 and 51 in the human numbering system. The platypus VKOR is inactive in the cell based system described herein for analyzing carboxylation in-vivo.

The bacterial VKOR homologs are particularly interesting because of their relationship to the disulfide bond forming enzymes (Dsb) of *E. coli*. In *E. coli*, DsbA is a soluble enzyme localized to the periplasm and its main function is to oxidize thiols to disulfides in secreted proteins; its metazoan counterpart is the protein disulfide isomerase family. When DsbA catalyzes disulfide formation in proteins in the periplasm, it active site cysteines are reduced. Since the active form is the disulfide, it must be reoxidized to its active disulfide form by DsbB, a four TM integral membrane protein. Interestingly, many bacterial VKOR homologs can complement *E. coli* DsbB.

DsbB of *E. coli* utilizes two pairs of cysteines in its reaction mechanism. In DsbB, it is clear that the cysteines homologous to 43 and 51 of human VKOR accept electrons from reduced proteins in the periplasm becoming reduced to free thiols in the process. These electrons are then shuttled to the active site cysteines, equivalent to cysteines 132 and 135 of human VKOR. These reduced cysteines are then reoxidized by transferring their electrons to ubiquinone. It has been proposed that in human VKOR, cysteine residues 43 and 51 also function to shuttle electrons to the active site cysteines 132 and 135. Because of the conservation of two pairs of cysteines in all of the VKOR molecules, studies were conducted to determine whether, as in bacteria, both pairs of cysteines are required for the in vivo reaction of metazoan VKOR.

Recombinant cysteine mutants of human VKOR have been studied and it has been observed that in vitro, only two cysteines, 132 and 135, are required for its activity. However, because these assay systems used dithiothreitol to reduce VKOR after each reaction cycle, it is possible that these in vitro results do not extend to the in vivo reaction.

Therefore, an assay has been devised to analyze the in vivo function of these cysteine mutant VKORs. This assay is based on quantitation of a carboxylated reporter protein containing the Gla domain of human factor IX expressed in HEK 293 cells, as described herein. Carboxylation of the reporter protein by endogenous VKOR is completely abolished by 4 µM warfarin. However, the ability of the cells to carboxylate the reporter is restored when warfarin resistant recombinant $VKOR_{Y139F}$ is expressed in the presence of 4 µM warfarin. Therefore, all mutant cysteine VKOR molecules were rendered warfarin resistant by introducing the mutation Y139F in addition to the targeted cysteine mutations. The read-out for each mutation is the ability of a HEK293 cell line to produce the carboxylated reporter protein in the presence of 4 µM warfarin.

Because the goal is to determine the relative activity of different mutations, it is necessary to normalize the amount of carboxylated reporter produced in each mutation. However, because most of this work is based upon transient expression of each mutation, correction for transfection efficiency is needed. Transfection efficiency is commonly corrected by co-expressing a marker protein such as luciferase. The amount of carboxylated protein produced, however, is also dependent upon the maximum amount of carboxylated protein the cell is capable of producing; once all of the reporter is carboxylated, no additional signal will be observed. Thus, while the signal from luciferase will continue to increase directly with its increased expression, the reporter signal will be proportional to the amount and specific activity of the introduced VKOR and should saturate. To control for saturation, transfected $VKOR_{Y139F}$ is transfected at different DNA concentrations and the linear range of response is experimentally determined. To control for transfection efficiency, VKOR and luciferase were expressed from either an internal ribosomal entry site vector or from a bi-directional promoter. The ribosomal re-entry vector (pIRES2 DsRed-Express2) uses the internal ribosomal re-entry site of encephalomyocarditis virus. The DS red portion of the vector was replaced with residues of the luciferase from *Metridia*. In this vector two proteins are made from the same mRNA. In one set of constructs the VKOR molecules were transcribed from the promoter while the luciferase was expressed from the ribosomal re-entry site. The reciprocal constructs were also made and expressed. The same relative results were found with each configuration but there less absolute levels of VKOR were seen when translation originated from the ribosomal re-entry site.

Figure 13:
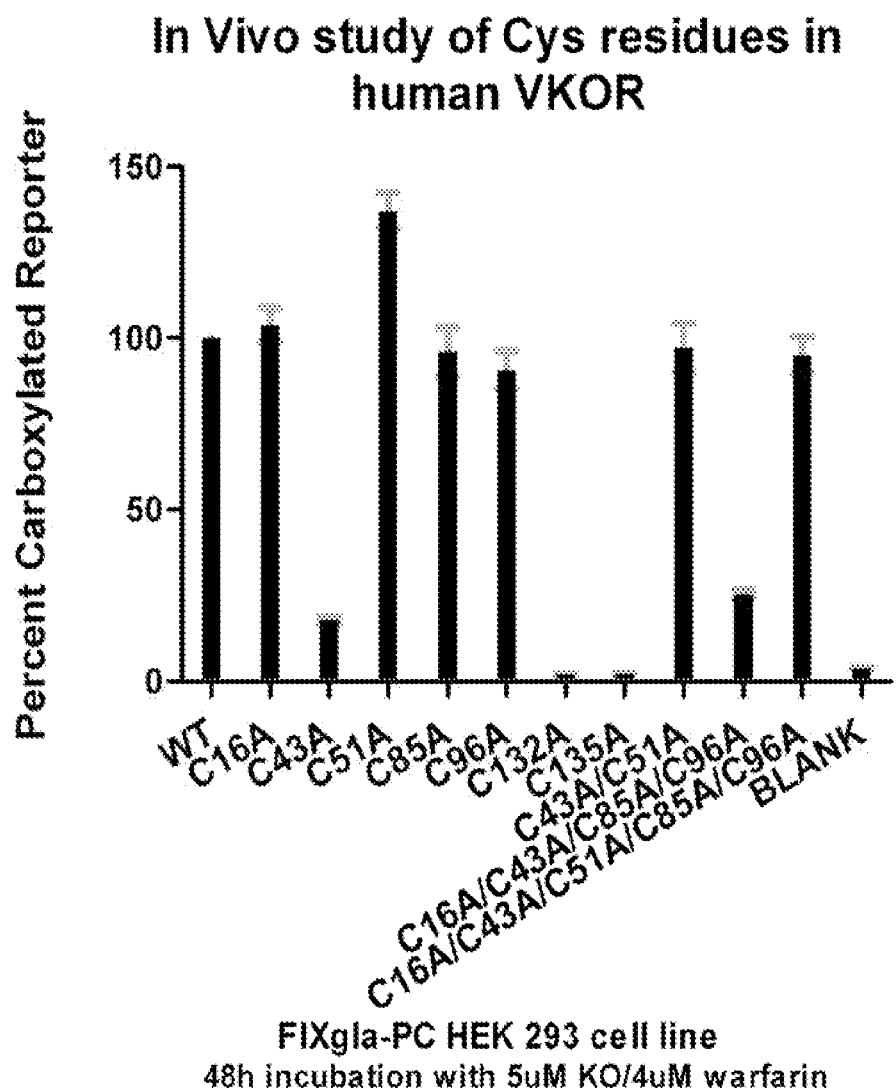
FIG. 13. In vivo study of cysteine residues in human VKOR.

FIG. 13 shows that mutations of active site residues 132 and 135 reduces carboxylation of the reporter protein to background levels. Simultaneous mutation of all 5 non active site cysteines to alanine results in a molecule whose activity is indistinguishable from $VKOR_{Y139F}$, indicating all non active site residues are not essential for the enzyme activity of VKOR. However, mutations of each individual cysteine, indicates otherwise. Mutation of Cys residue 43 results in a molecule with dramatically decreased activity, whether combined with mutations of cysteines 16, 85 and 96 or alone. Simultaneous mutation of residues 43 and 51 restores normal ($VKOR_{Y139F}$) activity; and, a point mutation of 51 alone in $VKOR_{Y139F}$ results in a molecule with greater activity than $VKOR_{Y139F}$.

Figure 28A:
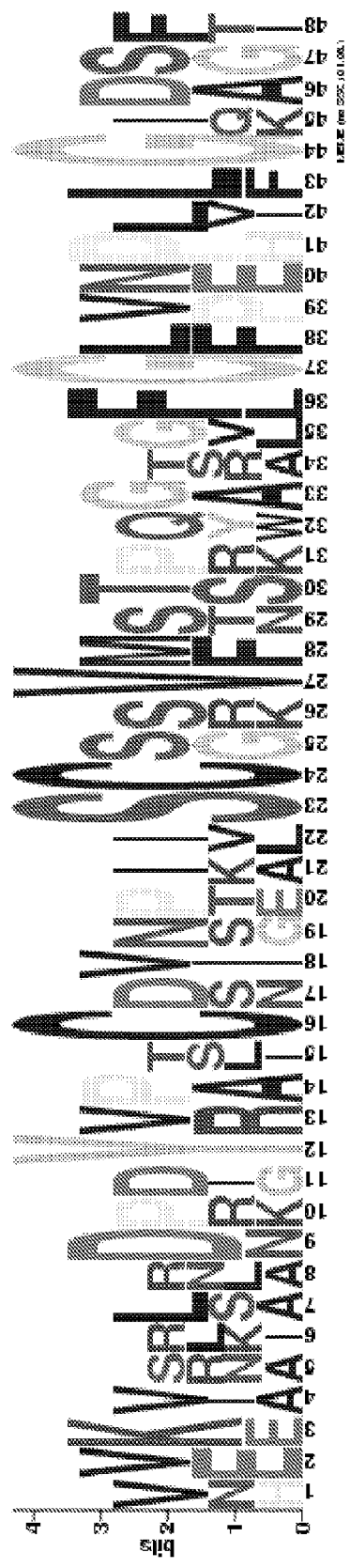
FIGS. 28A-B. Motifs found by Meme Suite.
Figure 28B:
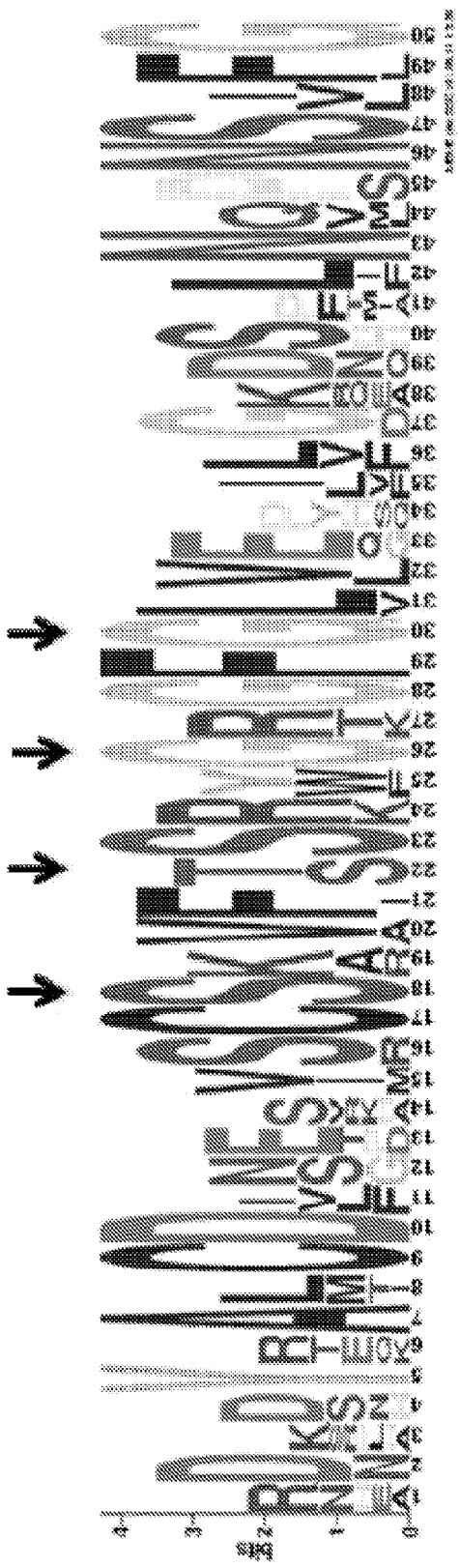

Since these results indicate that cysteines 43 and 51 are not, as in bacterial species, shuttle cysteines, bacterial and metazoan VKORs were further analyzed by comparing conserved motifs within VKORs. The hydrophilic loop containing Cys43 and Cys 51 is the most highly conserved motif (FIG. 14; FIGS. 28A-B).

Figure 14:
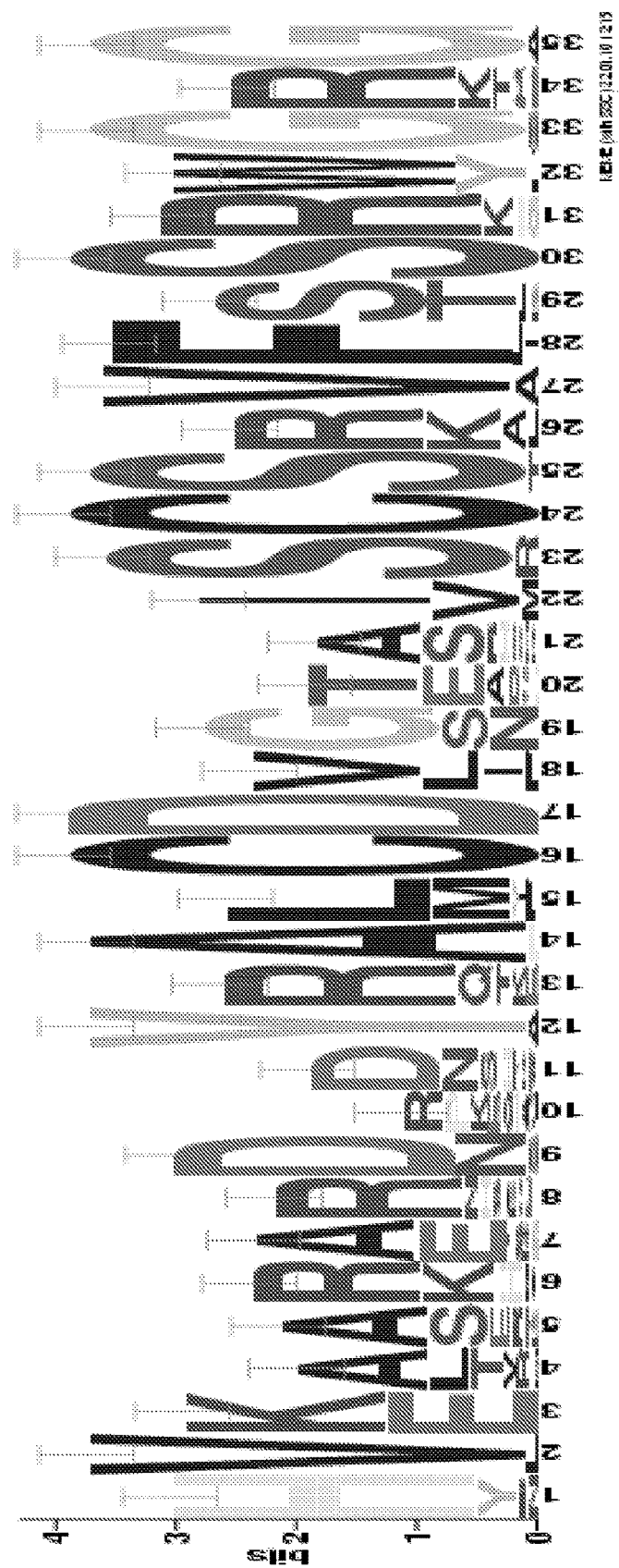
FIG. 14. Comparison of conserved motifs within VKORs.

The motif shown in FIG. 14 was derived from the Motif Suite and the training set used included 35 metazoan species ranging from the primitive *Nematostella, Acropora* and *Trichoplax* through insects, fish, birds, and several mammals and seven bacterial species. Interestingly, although this motif is the most strongly conserved in metazoans, no bacterial species were found to be included in this motif search. If the number of training sequences is changed so that they are more equally balanced between bacterial and metazoan VKORs seven bacterial species, *Corynebacterium* urealyticum, Rhodoccus erythropolis, Saccharopolyspora erythraea and M. tuberculosis also contain this motif.

In conclusion, these results suggest that the mechanism of the metazoan VKORs is significantly different from their bacterial homolog because the conserved cysteines at 43 and 51 are not required for in vivo activity while they are required in the bacterial system.

Example III

Vitamin K Cycle Study in Mammalian Cells

Vitamin K hydroquinone ($KH_2$) is a co-factor for γ-glutamyl carboxylase (GGCX), which catalyzes the post-translational carboxylation of specific glutamic acid residues to γ-carboxyglutamic acid (gla) in a variety of vitamin K-dependent proteins[1]. Gamma-glutamyl carboxylation is essential for the biological functions of vitamin K-dependent proteins involved in blood coagulation, bone metabolism, signal transduction, and cell proliferation. Concomitant with γ-glutamyl carboxylation, $KH_2$ is oxidized to vitamin K 2,3-epoxide (KO). KO must then be converted back to vitamin K (the quinone form) and then $KH_2$ by two separate electron reductions to support the carboxylation reaction. The cyclic production of KO and conversion back to $KH_2$ constitutes the vitamin K cycle (FIG. 1). The only enzymes unequivocally identified as part of the cycle are GGCX and vitamin K epoxide reductase (VKOR)[2].

Identification of the gene encoding VKOR[20,21] has made it possible to study the function of the enzyme at the molecular level. It is now clear that in vitro, VKOR can reduce both KO to vitamin K and vitamin K to $KH_2$. VKOR catalyzes both reactions using the same cysteine residues (132 and 135) at the active site[22,23]. In addition, both reactions are sensitive to warfarin inhibition[23]. It is worth noting that in vitro VKOR converts KO to vitamin K approximately 50 times faster than it converts vitamin K to $KH_2$[23]. Both VKOR and GGCX have been purified and characterized, and the enzymes have very different lipid and/or detergent requirements for activity. This makes studying the interactions and activities of the enzymes together in vitro difficult.

In the present work, a cell-based reporter assay system has been developed that enables the functional study of the complete vitamin K cycle. In this system, a vitamin-K dependent reporter protein is expressed that is easily measured and that reflects the efficiency of vitamin K-dependent carboxylation in vivo. Protein C was used as the reporter for this study. For detection purposes, the gla domain of protein C was replaced with that of factor IX (FIX). This replacement allowed the use of a monoclonal antibody specific for the carboxylated gla domain of FIX for quantitative detection purposes[24,25]. This chimeric reporter protein, FIXgla-PC, was stably expressed in HEK293 cells, which are commonly used for the biosynthesis of vitamin K-dependent proteins, and in AV12 cells, which are less efficient in the carboxylation of vitamin K-dependent proteins[26]. Studies indicate recombinant protein C produced by HEK293 cells is fully carboxylated and even more active than plasma-derived protein C. However, under similar culture conditions, protein C produced by AV12 cells is partially carboxylated with only 20% anticoagulant activity relative to plasma protein C[26]. This indicates that HEK293 and AV12 cells might have different pathways of using vitamin K for making vitamin K-dependent proteins. A study of the contributions of the various enzymes involved in the two-step reduction of KO was carried out by expressing the reporter protein in these two cells lines, and by feeding the cells KO or vitamin K, with or without warfarin, expressing warfarin-resistant VKOR-Y139F, and using dicoumarol to inhibit NQO1.

Materials.

Vitamin $K_1$, warfarin, dicoumarol, and CHAPS were obtained from Sigma-Aldrich (St. Louis, Mo.). Vitamin $K_1$ 2, 3-epoxide was prepared as described previously[27]. Vitamin $K_1$ (10 mg/mL) for cell culture was from Abbott Laboratories (Chicago, Ill.). A vitamin K internal standard for VKOR activity assay, 2-methyl-3(3,7,11,15,19-pentamethyl-2-eicosenyl)-1,4-naphthalenedione (vitamin $K_{1(25)}$), was from GLsynthesis Inc. (Worcester, Mass.). Protein C cDNA clone was from Open Biosystems (Huntsville, Ala.). Mammalian expression vector pcDNA3.1/hygro(+) and Lipofectamine were from Invitrogen (San Diego, Calif.). Mammalian expression vector pCI-neo was from Promega (Madison, Wis.). HEK293 and AV12 cell lines were from ATCC (Manassas, Va.). Mouse anti-carboxylated FIX gla domain monoclonal antibody (α-FIXgla MAb) was obtained from GlaxoSmithKline (Philadelphia, Pa.) and Green Mountain Antibodies (Burlington, Vt.) u. Affinity purified sheep anti-human Protein C IgG and its horseradish peroxidase conjugate were from Affinity Biologicals Inc. (Ancaster, ON Canada).

Construction of the FIXgla-PC Reporter Fusion Protein.

The gene encoding human protein C was amplified by PCR using pCMV-SPORT6-Protein C as a template. The gla domain of protein C (residue 1 to 46) was exchanged with the gla domain of FIX. This FIXgla-PC fusion was subcloned into the mammalian expression vector pcDNA3.1/hygro (+) using the XbaI site to generate the reporter protein expression vector, pcDNA3.1-FIXgla-PC.

Expression of the FIXgla-PC in HEK293 and AV12 Cells.

The FIXgla-PC reporter protein was stably expressed in HEK293 or AV12 cells. Cells were transfected with pcDNA3.1-FIXgla-PC plasmid DNA using Lipofectamine according to the manufacturer's protocol. After selection with 300 µg/ml hygromycin, surviving colonies were picked and screened for high stable expression. Single colonies were cultured in Dulbecco's Modified Eagle's Medium: Nutrient Mixture F-12 (DMEM/F12) supplemented with 10% fetal bovine serum, 11 µM vitamin K, and 1× antibiotics-antimycotics (complete medium) in a 24-well plate for 48 hours. Cell culture medium was collected and directly used for quantification of the secreted carboxylated FIXgla-PC by ELISA. The colony with the highest FIXgla-PC production was selected as the stable cell line to be used for reporter gene expression.

To purify carboxylated FIXgla-PC fusion proteins for use as a standard for ELISA, α-FIXgla MAb was coupled to Affi-Gel 10 (Bio-Rad Laboratories, Hercules, Calif.) according to the manufacturer's protocol. HEK293 cells stably expressing a high level of FIXgla-PC reporter protein were cultured in complete medium supplemented with 11 µM vitamin K. The medium was collected after a 48-hour incubation. Calcium chloride was added to the collected medium to a final concentration of 5 mM. Five hundred ml of the medium was incubated with 1.5 ml of the prepared anti-carboxylated FIXgla domain affinity beads overnight at 4° C. with gentle stirring. The beads were spun down and packed into a 1.5×10 cm column. The column was washed first with 20 mM Tris-HCl, 500 mM NaCl, and 5 mM $CaCl_2$ and then with 20 mM Tris-HCl, 100 mM NaCl, and 5 mM $CaCl_2$. Carboxylated FIXgla-PC reporter protein was eluted with 20 mM Tris-HCl, 100 mM NaCl, and 10 mM EDTA.

To examine the effect of vitamin K, KO, warfarin, or dicoumarol on the carboxylation of the reporter protein, HEK 293 or AV12 cells stably expressing FIXgla-PC were sub-cultured in 24-well plates. When cells were 60-70% confluent, vitamin K, KO, warfarin, or dicoumarol was added to the complete medium and incubated for 48 hours. Cell culture medium was collected and directly used in an ELISA as described in the following section.

FIXgla-PC Measurement in Cell Culture Medium Using ELISA.

The reporter protein in the cell culture medium was quantified by ELISA as described previously with minor modification[29]. To assay for carboxylated FIXgla-PC, a conformation-specific monoclonal antibody that recognizes only the fully carboxylated FIXgla domain in the presence of calcium was used as the coating antibody[28]. 96-well ELISA plates were coated overnight at 4° C. with 100 μL/well α-FIXgla MAb. The concentration of the coating antibodies was 2 μg/ml in 50 mM carbonate buffer (pH 9.6). After being washed 5 times with TBS-T wash buffer (20 mM Tris-HCl, pH 7.6, 150 mM NaCl, and 0.1% Tween 20), the plate was blocked with 0.2% BSA in TBS-T wash buffer for 2 hours at room temperature. Samples and protein standards (0.12-250 ng/mL) with 5 mM $CaCl_2$ were added at 100 μL/well and incubated for 2 hours at room temperature. After being washed with TBS-T wash buffer containing 5 mM $CaCl_2$, sheep anti-human protein C IgG conjugated to horseradish peroxidase (100 μL/well at 1:2500 in TBS-T wash buffer with 5 mM $CaCl_2$) was added to each well and incubated for 45 minutes at room temperature. After the unbound detecting antibody was washed off, 100 μL of ABTS solution (Roche Molecular Biochemicals, Indianapolis, Ind.) was added to each well and the absorbance was determined at 405 nm with a THERMOmax microplate reader (Molecular Devices). The linear range for detection of carboxylated FIXgla-PC was between 0.50 ng/ml and 125 ng/ml ($\gamma=0.9987$) using the logit (OD)-log (FIXgla-PC) plot.

To assay for total reporter protein secreted into the cell culture medium, 96-well ELISA plates were coated with 100 L/well mouse anti-human protein C monoclonal antibody overnight at 4° C. After being washed and blocked as described above, samples and protein standards (0.12-250 ng/mL) were added and incubated for 2 hours at room temperature. After the unbound samples were washed off, sheep anti-human protein C IgG was added to each well and incubated for another 2 hours at room temperature. Then unbound antibody was washed off and the plate was incubated with 100 μL/well rabbit anti-sheep IgG conjugated to horseradish peroxidase for 45 minutes at room temperature. Color development was performed as described above.

Functional Study of Warfarin-Resistant VKOR-Y139F in Established Cell Lines

To study the contribution of VKOR to the vitamin K cycle, a warfarin resistant VKOR mutant, VKOR-Y139F, was cloned into the mammalian expression vector pCI-neo. The resulting plasmid was transiently or stably transfected into the established cell line FIXgla-PC/HEK293 or FIXgla-PC/AV12. The culture medium on the cells transiently expressing VKOR was changed 30 hours post-transfection to complete medium containing 5 μM KO or 5 μM KO with 2 μM warfarin. Cell culture medium was collected after a 48-hour incubation and directly used for ELISA. The stably transfected colony that expressed the highest level of VKOR-Y139F was selected for further study. The effect of over-expressing the VKOR-Y139F mutant on reporter protein carboxylation under different conditions was tested as described herein.

GGCX Activity Assay. GGCX activity was determined by the incorporation of $^{14}CO_2$ into the pentapeptide substrate, FLEEL (SEQ ID NO:59), in the presence of propeptide[30]. $1\times10^6$ of HEK293 or AV12 cell pellets were mixed with 115 μL of ice cold lysis buffer containing 0.5% CHAPS, 25 mM Tris-HCl (pH 7.5), 500 mM NaCl, 4 μM factor IX propeptide, 1.25 mM FLEEL (SEQ ID NO:59) and 1× protease inhibitor cocktail. Samples were placed on ice for 30 minutes with occasional vortexing. The carboxylation reaction was started by the addition of 10 μL of an ice-cold mix of $NaH^{14}CO_3$ (40 μCi/mL) and $KH_2$ (222 μM) to bring the volume to 125 μL. The reaction mix was immediately transferred to a 20° C. water bath and incubated for 45 minutes. The amount of $^{14}CO_2$ incorporation was determined as described previously[31].

VKOR Activity Assay.

VKOR activity was determined as previously described with minor modification[21,32]. HEK293 or AV12 cells (1×10) were collected and re-suspended in 200 μL of ice cold assay buffer containing 25 mM TAPS (pH 8.6), 150 mM NaCl, 30% glycerol, 50 μM KO and 1× protease inhibitor cocktail. Cells were lysed by sonication on ice. The reaction was started by adding 5 mM (final concentration) freshly prepared dithiothreitol (DTT) and incubated at 30° C. in the dark for 45 minutes. The reaction was terminated by the addition of 500 μL isopropanol. The reaction mixture was extracted with 500 μL n-hexane containing 2.52 μM vitamin $K_{1(25)}$ as an internal standard. The upper organic phase containing the vitamins was transferred to a 2-ml brown vial and dried with nitrogen. A total of 500 μL of HPLC mobile phase was added to dissolve the vitamins and the sample was analyzed by HPLC[32].

FIXgla-PC Chimera as a Reporter Protein for Vitamin K-Dependent Carboxylation Efficiency in Living Cells.

To study the vitamin K cycle in vivo, the chimeric reporter protein described above was expressed as a tool for determining the efficiency of in vivo vitamin K-dependent carboxylation. In the presence of vitamin K or KO, secretion of carboxylated reporter protein increased approximately 25-fold (FIG. 2) compared to no additions. Warfarin, an inhibitor of VKOR, eliminated KO-supported carboxylation. In addition, similar levels of carboxylated reporter were secreted independent of the substrate (vitamin K or KO) fed to the cells. As described below, this allowed for the differentiation of some of the functions of the various enzymes involved in the cycle.

Effect of Substrate and/or Warfarin on FIXgla-PC Carboxylation in HEK293 Cells.

Figure 3A:
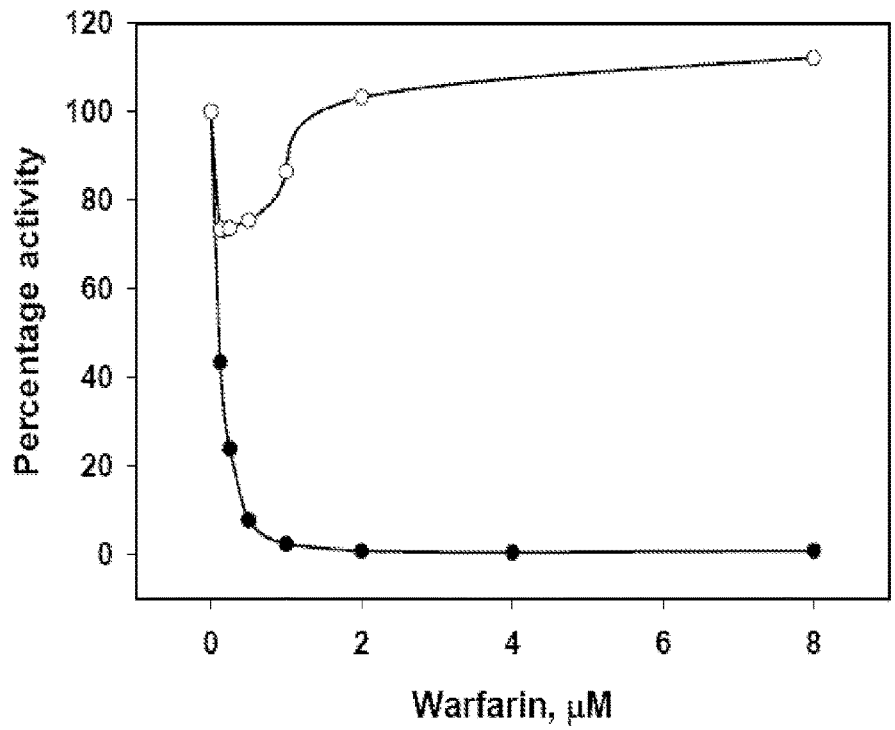
(FIG. 3A) Cells in culture medium with either 11 μM vitamin K (open circles) or 5 μM KO (filled circles) were incubated for 48 h with increasing concentrations of warfarin. The concentration of carboxylated FIXgla-PC in the medium was measured by ELISA. The data are presented as percentages to make the first concentration points of vitamin K and KO coincide.

With KO as substrate, FIXgla-PC carboxylation was completely inhibited by 2 μM warfarin, and 50% inhibition occurred with 0.1 μM warfarin (FIG. 3A). Thus, VKOR, the molecular target for warfarin, is responsible for the reduction of KO in vivo. While warfarin totally inhibited FIXgla-PC carboxylation when HEK293 cells were fed KO, HEK293 cells fed vitamin K produced high (unaffected) levels of carboxylated protein in the presence of warfarin (FIG. 3A). This result suggests that as long as there is enough vitamin K in the medium, inactivation of VKOR by warfarin does not affect the conversion of vitamin K to $KH_2$ by the vitamin K-dependent carboxylation in HEK293 cells. This was confirmed by the result in FIG. 3B, which shows the amount of the carboxylated FIXgla-PC secreted as a function of vitamin K concentration in the presence and absence of warfarin. In the absence of warfarin, carboxylation occurred maximally at 1 μM vitamin K. However, in the presence of warfarin, less than 20% of the carboxylated reporter protein was detected in the medium at 1 μM vitamin K, and maximal carboxylation was detected in the medium at 22 μM vitamin K. The decreased carboxylation efficiency observed at lower vitamin K concentrations in the presence of warfarin might have been due to the inability of cells to either recycle KO or to a low affinity/catalytic efficiency of the warfarin-resistant vitamin K reductase in cells. These results suggest that at high vitamin K concentrations, HEK293 cells efficiently support vitamin K-dependent carboxylation, even when VKOR is inactivated by warfarin. Therefore, there must be a warfarin resistant enzyme that reduces vitamin K to $KH_2$ in HEK293 cells. This enzyme may be the antidotal enzyme that allows patients poisoned with warfarin to be rescued with high doses of vitamin $K^{33,34}$.

Expression of FIXgla-PC in AV12 Cells.

Figure 4A:
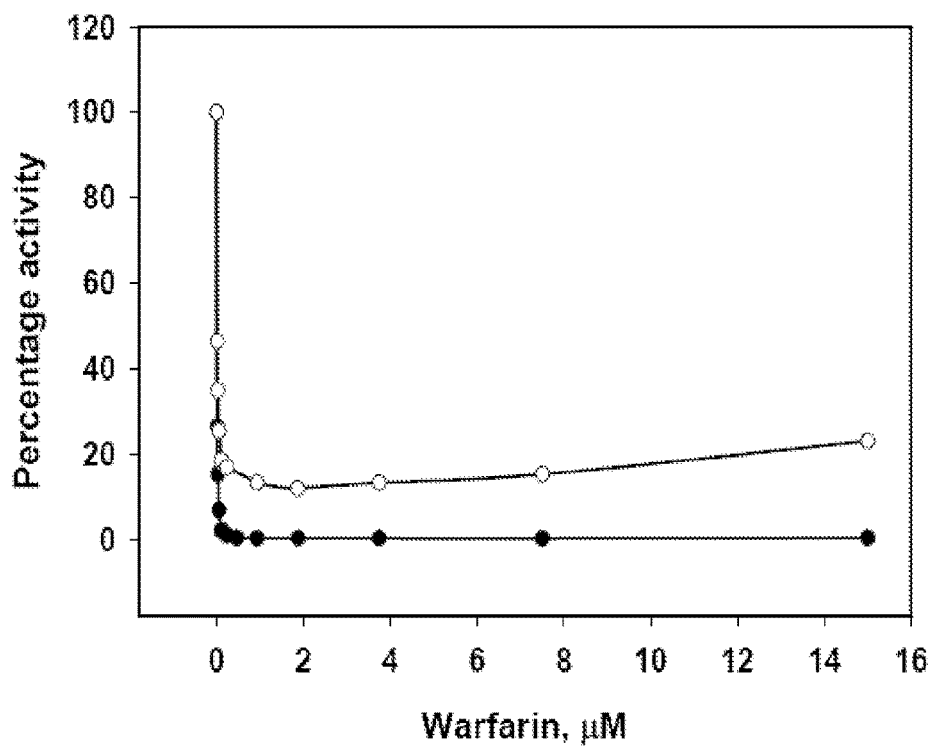
FIGS. 4A-B. Effect of warfarin on FIXgla-PC carboxylation in AV12 cells.
Figure 4B:
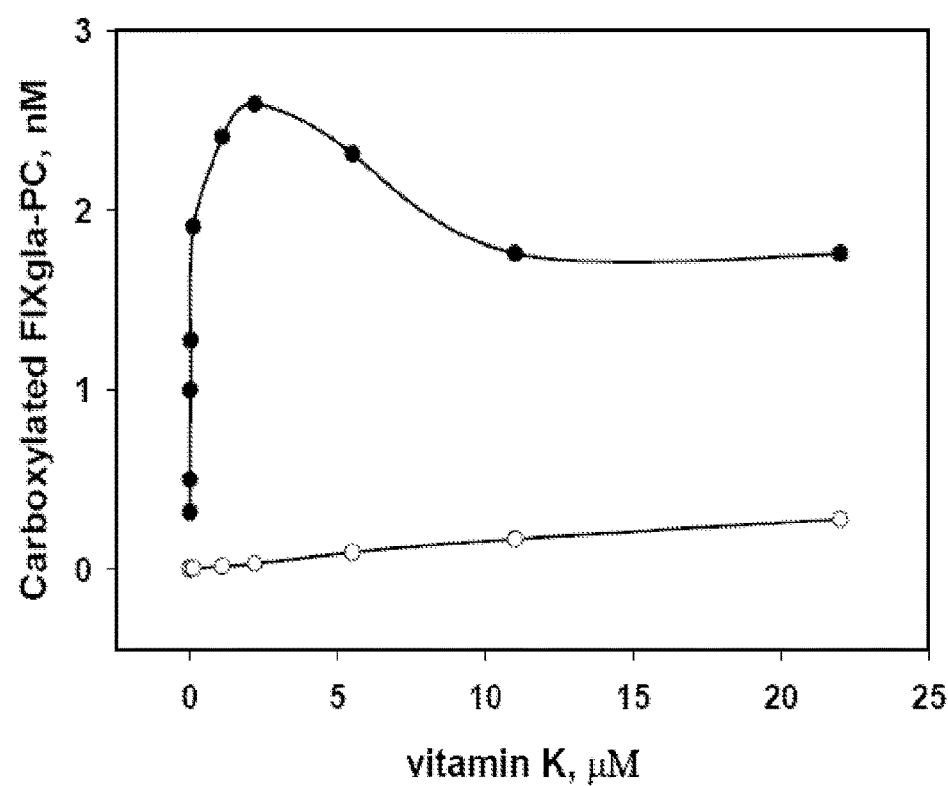

Next, FIXgla-PC was stably expressed in AV12 cells, which carboxylate vitamin K-dependent proteins less efficiently than HEK293 cells[26]. Under similar conditions, AV12 cells produced only about half as much carboxylated protein as HEK293 cells. The effect of warfarin on FIXgla-PC carboxylation in AV12 cells was then tested using KO or vitamin K as the vitamin K source. When KO was used as substrate, the inhibition curve of warfarin on reporter protein carboxylation (FIG. 4A) was similar to that observed in HEK293 cells (FIG. 3A). In AV12 cells, in contrast to HEK293 cells, production of carboxylated reporter protein was significantly inhibited by warfarin when vitamin K was used as substrate (FIG. 4A). In addition, high concentrations of vitamin K did not rescue warfarin inhibition in AV12 cells (FIG. 4B). These results suggest that warfarin-sensitive VKOR is responsible for KO reduction and that the amount of warfarin resistant antidotal enzyme that reduces vitamin K is dramatically less in AV12 cells than in HEK293 cells.

Figure 5A:
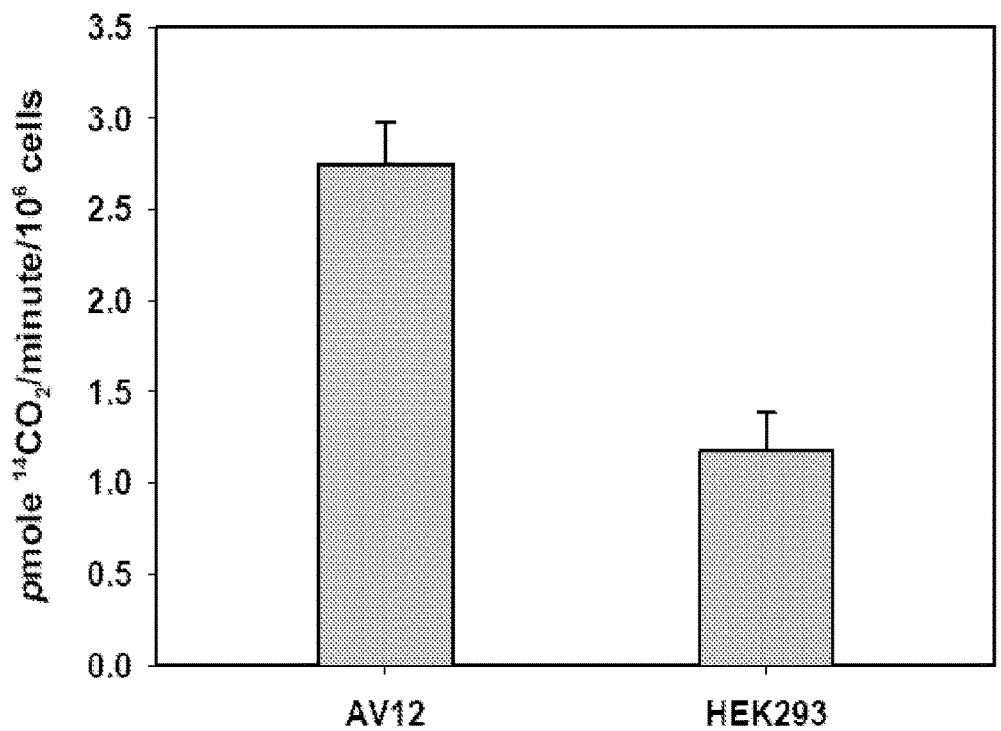
FIGS. 5A-B. Endogenous VKOR and GGCX activity in HEK293 and AV12 cells as measured by in vitro enzymatic activity assay.
Figure 5B:
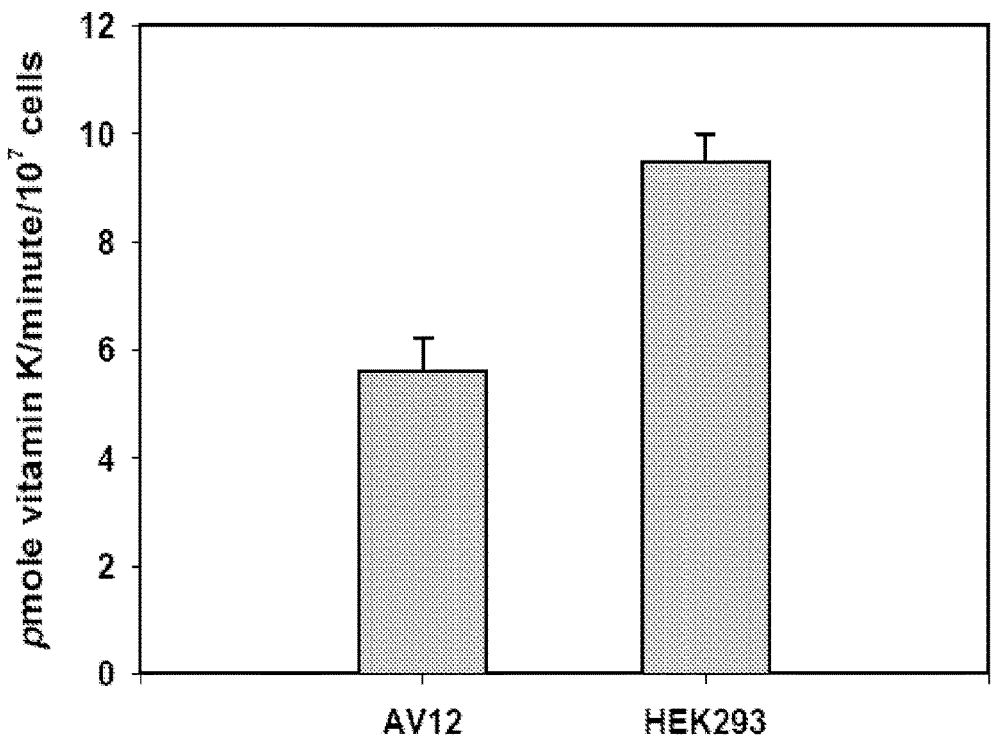

To understand the reason for the differences in carboxylation efficiency between HEK293 and AV12 cells, the in vitro activity of the endogenous VKOR and GGCX was tested in the two cell types (FIG. 5). It was found that GGCX activity was about 3-fold higher in AV12 cells than in HEK293 cells. However, the in vitro VKOR activity of AV12 cells was approximately 66% of that observed in HEK293 cells. The difference between these two cell lines in endogenous VKOR activity correlates with the observation that AV12 cells produce less carboxylated reporter protein than do HEK293 cells. The endogenous GGCX and VKOR activity results agree with the previous observation[35] that the rate of $KH_2$ production rather than the rate of vitamin K-dependent carboxylation can be the rate-limiting step for in vivo vitamin K-dependent protein carboxylation.

Contribution of NQO1 to Vitamin K Reduction.

Figure 6A:
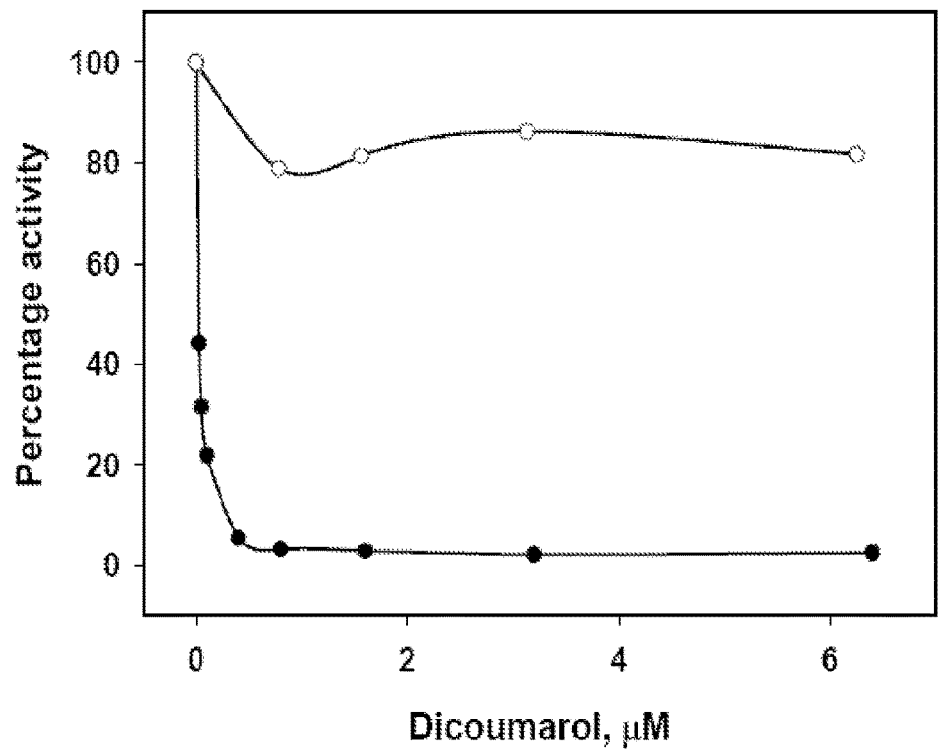
FIGS. 6A-B. Effect of dicoumarol on the carboxylation of the FIXgla-PC in HEK293 and AV12 cells. Increasing concentrations of dicoumarol were added to the cell culture medium with either 11 μM K (open circles) or 5 μM KO (filled circles) and incubated with HEK293 (FIG. 6A) or AV12 (FIG. 6B) cells for 48 hours. The concentration of carboxylated FIXgla-PC in the medium was measured by ELISA. The data are presented as percentages to make the first concentration points of vitamin K and KO coincide.

Dicoumarol-sensitive NQO1 was originally isolated as a vitamin K reductase[36]. Subsequently, it was reported that NQO1 can accomplish the two-electron reduction of vitamin K to $KH_2$ in vitro[11,37]. Therefore, the contribution of NQO1 to the conversion of vitamin K to $KH_2$ was examined in vivo by adding increasing concentrations of dicoumarol to the cell culture medium with either vitamin K or KO as substrate in HEK293 cells. FIG. 6A shows that, as with warfarin, dicoumarol significantly inhibited reporter protein carboxylation when KO was the vitamin K source. This result demonstrates that dicoumarol is a strong inhibitor for VKOR. However, when cells were fed vitamin K, only minimal inhibition was observed. Results from the in vitro assay show that the inhibition constant of dicoumarol for NQO1 is 0.5 nM, while 1.6 μM is required to reach 50% inhibition of NQO1 from the cell-based assay[38]. When the cells were treated with 20 μM dicoumarol, a level reported to almost completely inactivate over-expressed NQO1 in intact cells[38], 60% of the reporter protein was carboxylated. These results suggest that NQO1 contributes minimally to the reduction of vitamin K to $KH_2$ in the vitamin K cycle. Therefore, another, still unidentified dicoumarol/warfarin insensitive enzyme must be the major antidotal enzyme that reduces vitamin K in HEK293 cells.

Figure 6B:
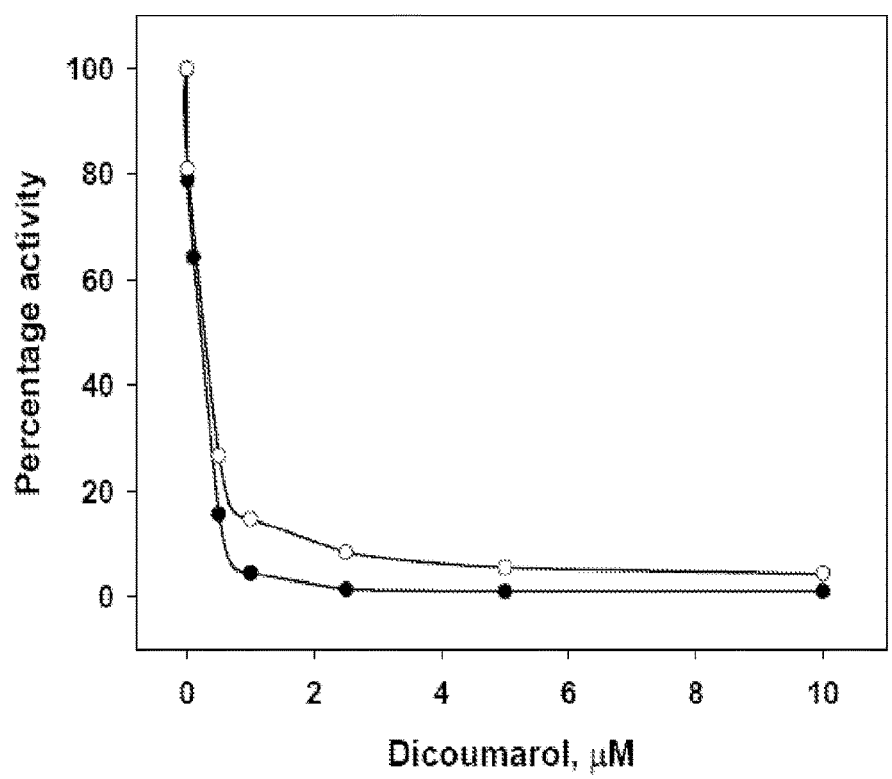

The effect of dicoumarol on reporter protein carboxylation was then tested in AV12 cells. FIG. 6B shows that when KO was the vitamin K source, the inhibition of reporter protein carboxylation by dicoumarol was similar to that in HEK293 cells (FIG. 6A). A significant difference between AV12 cells and HEK293 cells was observed when the cells were grown in the presence of vitamin K; in this case, dicoumarol completely inhibited reporter protein carboxylation in AV12 cells. Moreover, the inhibition curve was similar to that when KO was used as the substrate (FIG. 6B). This result supports the results in FIG. 4A, indicating that unlike HEK293 cells, AV12 cells have very little antidotal enzyme. The ~20% residual activity observed when vitamin K was used as the substrate (FIG. 4A) may have been due to NQO1 activity, which is inhibited by dicoumarol but not by warfarin. Taken together, these data suggest that NQO1 plays a limited role in converting vitamin K to $KH_2$ in the vitamin K cycle in vivo.

Contribution of VKOR to the Reduction of Vitamin K to $KH_2$.

These results confirm that VKOR is responsible for the reduction of KO to vitamin K. To test the ability of VKOR to reduce vitamin K to $KH_2$ in vivo, tyrosine 139 was mutated to phenylalanine (Y139F), which converts VKOR to a warfarin-resistant form[20]. This permitted the inactivation of endogenous VKOR by warfarin while testing the in vivo function of the VKOR-Y139F.

Figure 2:
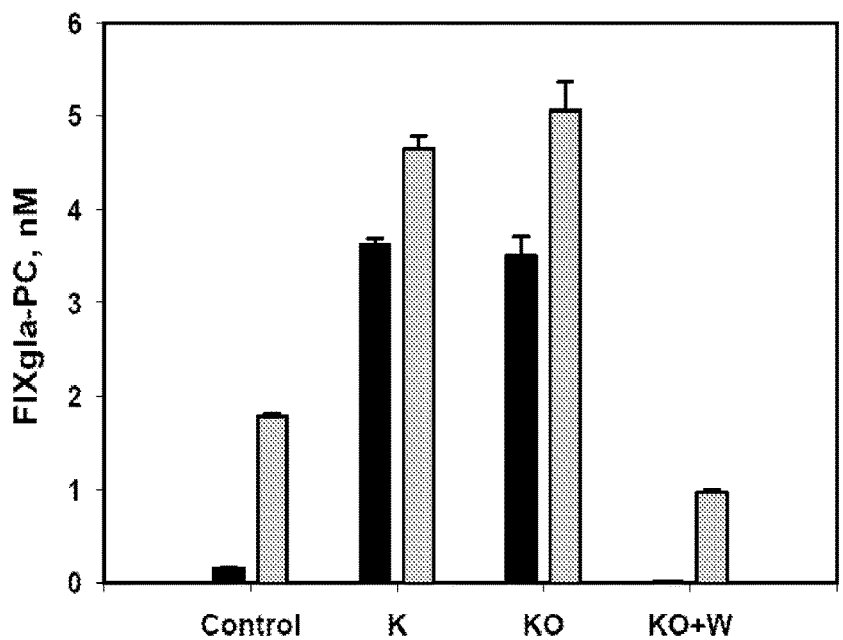
FIG. 2. Effect of vitamin K, KO, and warfarin on FIXgla-PC carboxylation and secretion. Carboxylated (black bar) and total (gray bar) FIXgla-PC secreted from HEK293 cells under different culture conditions was measured by ELISA. Control: complete medium (no added vitamin K); K: complete medium with 11 μM vitamin K; KO: complete medium with 5 μM KO; KO+W: complete medium with 5 μM KO and 2 μM warfarin FIGS. 3A-B. Effect of warfarin on FIXgla-PC carboxylation in HEK 293 cells.
Figure 7A:
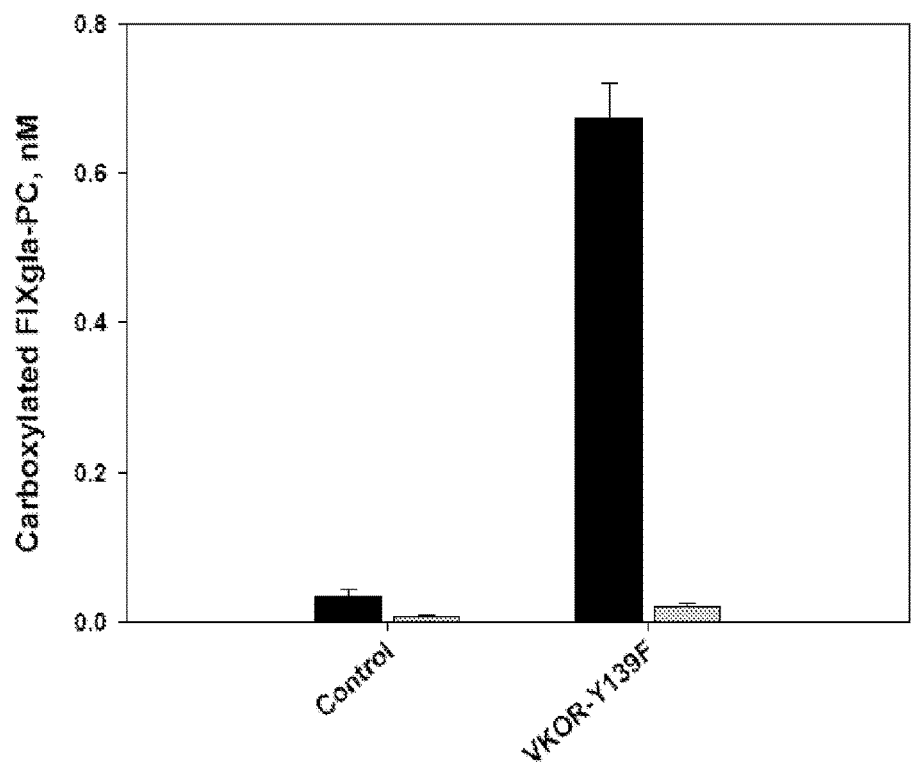
FIGS. 7A-B. Effect of the warfarin resistant VKOR mutant on FIXgla-PC carboxylation.

VKOR-Y139F was transiently expressed in HEK293 and AV12 cells that stably expressed the FIXgla-PC. Cells transfected and not transfected with VKOR-Y139F were grown in complete medium containing 5 μM KO with 2 μM warfarin. As shown in FIG. 7A, 2 μM warfarin inactivated the endogenous VKOR present in the non-transfected cells of both cell lines. Therefore, almost no carboxylated reporter protein was secreted into the medium (control). In cells transiently expressing VKOR-Y139F, significant amounts of carboxylated reporter protein were produced in HEK293 cells (~20-fold increase compared to the control) but not in AV12 cells. It was reasoned that this was because the transiently expressed VKOR-Y139F converted KO to vitamin K in the presence of warfarin. In HEK293 cells, the endogenous warfarin resistant antidotal enzyme further reduced vitamin K to $KH_2$ for the carboxylation reaction. Because there is very little antidotal enzyme present in AV12 cells, warfarin also inactivates the reduction of vitamin K to $KH_2$ (FIG. 4A). However, if VKOR were the major contributor to the conversion of vitamin K to $KH_2$, AV12 cells transiently expressing the VKOR-Y139F mutant should produce significant amounts of carboxylated reporter protein, as observed in HEK293 cells. Therefore, this result indicates that the contribution of VKOR to the reduction of vitamin K to $KH_2$ in vivo is small. In addition, these results suggest that in AV12 cells, a warfarin-sensitive enzyme different from VKOR converts vitamin K to $KH_2$.

Figure 7B:
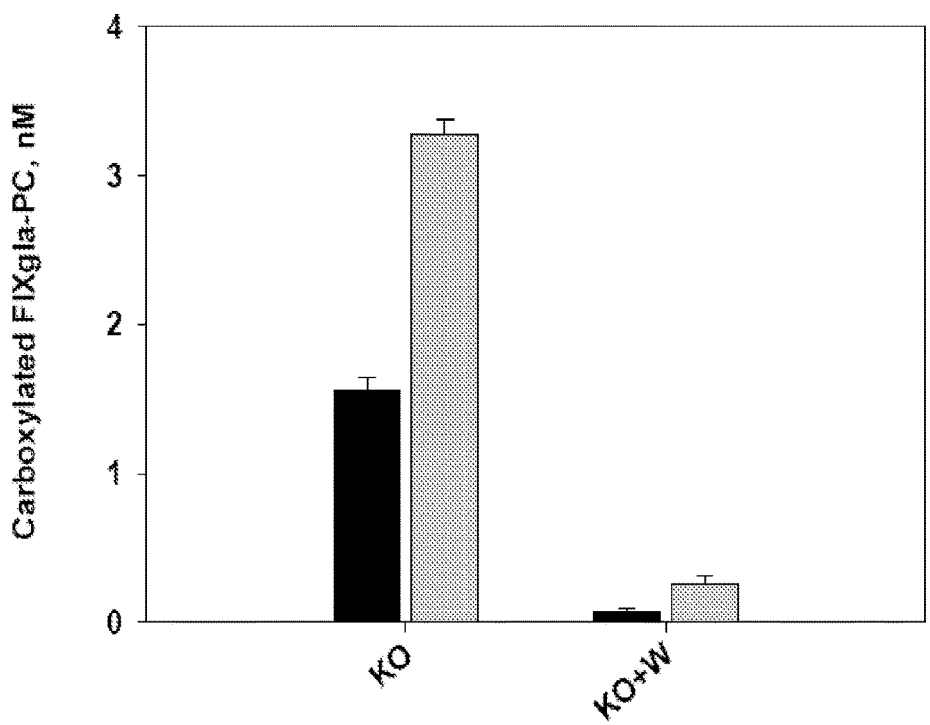

An alternative explanation for why no carboxylated reporter protein was secreted from AV12 cells that transiently expressed VKOR-Y139F could be that VKOR-Y139F is not highly expressed in the cells or the expressed protein is unable to convert KO to vitamin K. To clarify this, VKOR-Y139F was stably expressed in AV12 cells. The colony exhibiting the highest level of VKOR-Y139F expression was chosen for further study. As shown in FIG. 7B, over-expression of VKOR-Y139F increased reporter protein carboxylation approximately two-fold when KO was used as the substrate in the culture medium. This suggests that VKOR-Y139F is a functional protein that is able to reduce KO in AV12 cells. Importantly, warfarin also abolished reporter protein carboxylation in this cell line, which stably over expressed VKOR-Y139F. This evidence further implies that VKOR has a limited ability to convert vitamin K to $KH_2$ in vive.

The initial goal in this study was to develop an in vivo assay that would allow for the study of the function of enzymes involved in the vitamin K cycle, and to identify other enzymes that are important.

The two reductions in the vitamin K cycle were studied by feeding the cells either KO or vitamin K. Cells cultured in medium containing KO and warfarin produced significantly less carboxylated reporter protein (FIGS. 2-4). Since VKOR is the primary target of warfarin, this indicates that the in vivo reduction of KO is mainly carried out by VKOR. In addition, the fact that when fed vitamin K, even in the presence of warfarin, the cells produce a similar amount of carboxylated protein, shows that there is a so-called antidotal enzyme in the HEK293 cells.

Figure 3B:
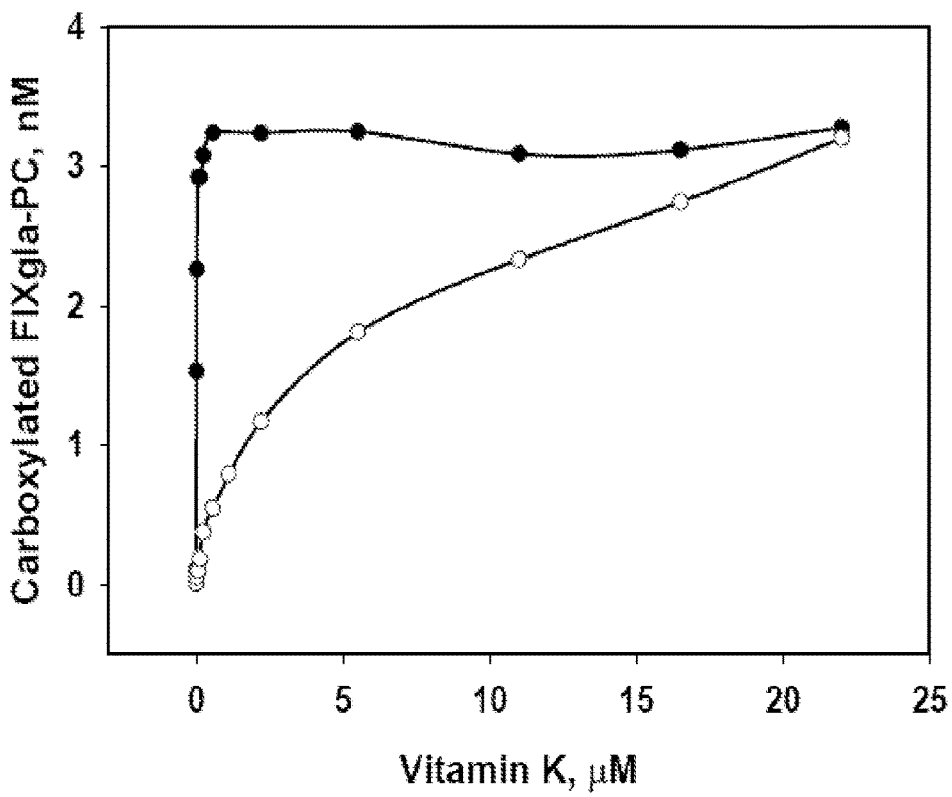
(FIG. 3B) Cells were grown with (open circles) or without (filled circles) 2 μM warfarin in increasing concentrations of vitamin K for 48 h. The concentration of carboxylated FIXgla-PC in the culture medium was measured by ELISA.

The reduction of vitamin K to $KH_2$ has been proposed to be carried out by two pathways[7,40], one accomplished by VKOR, which is sensitive to warfarin inhibition, and the other by NQO1, which is resistant to warfarin inhibition. To clarify the role of NQO1 in the vitamin K cycle, the effect of dicoumarol, an inhibitor of NQO1, was tested on reporter protein carboxylation. When vitamin K was used as the substrate, carboxylation of the reporter protein was decreased by only ~20%. This result suggests that NQO1 is not the antidotal enzyme Unlike in HEK293 cells, warfarin inhibits FIXgla-PC carboxylation in AV12 cells when vitamin K is used as the substrate. High concentrations of vitamin K cannot rescue the inhibition. Different cell types have different mechanisms of vitamin K uptake and metabolism which could affect the amount of reporter protein carboxylation[42,43]. However, in HEK293 cells, maximum carboxylation of FIXgla-PC occurs at 1 µM while in AV12 cells it occurs at 2.5 µM (FIGS. 3B and 4B, respectively). Therefore, it is unlikely that these two cell lines have significant differences in vitamin K uptake. Furthermore, a saturated concentration of vitamin K (11 µM) was used in these experiments. This suggests that with vitamin K as substrate, the different warfarin sensitivities of these two cells are likely due to a lack of antidotal enzyme in AV12 cells. This also implies that the majority of vitamin K reduction in AV12 cells is carried out by a warfarin sensitive pathway.

There seems to be little doubt that VKOR can reduce vitamin K to $KH_2$[2,23]. However, this study with purified VKOR indicated that the rate of conversion of vitamin K to $KH_2$ was considerably slower than the rate of the conversion of KO to vitamin K[23]. In the present study, to test the contribution of VKOR to the reduction of vitamin K to $KH_2$ in vivo, a warfarin resistant VKOR mutant (Y139F) was expressed. When fed KO in the presence of warfarin, HEK293 (Y139F) cells produced carboxylated reporter protein. However, under similar conditions AV12 (Y139F) cells failed to produce significant carboxylated reporter protein. Importantly, VKOR-Y139F is expressed and active in AV12 (Y139F) cells, since the amount of carboxylated reporter protein doubled in the absence of warfarin when these cells were fed KO. Therefore, only the HEK293 (Y139F) cells which have antidotal enzyme can support the complete vitamin K cycle in the presence of warfarin.

Since, in vitro, both KO to vitamin K and vitamin K to $KH_2$ reactions of VKOR are inhibited by warfarin[22,23], the most straightforward conclusion from this result is that the in vivo function of VKOR is to convert KO to vitamin K and that a second enzyme is required to convert vitamin K to $KH_2$.

A second implication of these results is that there must be a warfarin sensitive enzyme, other than VKOR, which converts vitamin K to $KH_2$ in AV12 cells. The existence of a second warfarin sensitive enzyme is unexpected, because Cooper et al. did a retrospective study utilizing 550,000 SNPs from 181 patients and found only polymorphisms in VKOR and cytochrome P450 2C9 affected warfarin dose requirements. Based on that result they concluded that it was unlikely that another enzyme affecting warfarin sensitivity would be found[44]. On the other hand, at present, polymorphisms in VKOR and cytochrome P450 2C9 combine to account for only 30%-60% of the variance in the stabilized warfarin dose distribution[45].

The methods described in this work will be important for further studies of the vitamin K cycle. For example, cell utilization of different forms of vitamin K, i.e., menaquinones versus phylloquinones, may account for some of the hepatic and peripheral carboxylation differences in warfarin sensitivity and response to vitamin K as an antidote to warfarin[46]. On the other hand it is possible that the cells that do not respond to vitamin K treatment during warfarin poisoning may have lower levels of the warfarin-resistant vitamin K reductase (antidotal enzyme). Additionally, there are indications that long-term warfarin therapy may cause unwanted effects of bone fracture and vascular calcification. These problems are apparently due to the inhibition of carboxylation of regulator proteins such as matrix gla protein (MGP) and the growth arrest specific gene 6 product (Gas-6)[47-50]. This cell-based system will be useful in studying these and other questions relating to the vitamin K cycle.

In summary, an in vivo assay system has been established for the functional study of the vitamin K cycle. The two-step reduction of vitamin K can be studied separately using this system by feeding the cells either KO or vitamin K. Evidence is provided in this study of a warfarin sensitive enzyme that converts vitamin K to $KH_2$ that is different from VKOR and the warfarin resistant antidotal enzyme. This antidotal enzyme for vitamin K reduction is probably not NQO1. Finally, this study shows that the main function of VKOR is to convert KO to vitamin K, not vitamin K to $KH_2$.

REFERENCES FOR EXAMPLE III

1. Presnell S R, Stafford D W. The vitamin K-dependent carboxylase. Thromb Haemost. 2002; 87:937-946.
2. Oldenburg J, Marinova M, Muller-Reible C, Watzka M. The vitamin K cycle. Vitam Horm. 2008; 78:35-62.
3. Sherman P A, Sander E G. Vitamin K epoxide reductase: evidence that vitamin K dihydroquinone is a product of vitamin K epoxide reduction. Biochem Biophys Res Commun. 1981; 103:997-1005.
4. Wallin R, Hutson S. Vitamin K-dependent carboxylation. Evidence that at least two microsomal dehydrogenases reduce vitamin K1 to support carboxylation. J Biol Chem. 1982; 257:1583-1586.
5. Gardill S L, Suttie J W. Vitamin K epoxide and quinone reductase activities. Evidence for reduction by a common enzyme. Biochem Pharmacol. 1990; 40:1055-1061.

6. Preusch P C, Smalley D M. Vitamin K1 2,3-epoxide and quinone reduction: mechanism and inhibition. Free Radic Res Commun. 1990; 8:401-415.
7. Wallin R. Vitamin K antagonism of coumarin anticoagulation. A dehydrogenase pathway in rat liver is responsible for the antagonistic effect. Biochem J. 1986; 236: 685-693.
8. Fasco M J, Principe L M. Vitamin K1 hydroquinone formation catalyzed by a microsomal reductase system. Biochem Biophys Res Commun. 1980; 97:1487-1492.
9. Maerki F, Martius C. [Vitamin K reductase, preparation and properties.]. Biochem Z. 1960; 333:111-135.
10. Fasco M J, Principe L M. Vitamin K1 hydroquinone formation catalyzed by DT-diaphorase. Biochem Biophys Res Commun. 1982; 104:187-192.
11. Wallin R, Gebhardt O, Prydz H. NAD(P)H dehydrogenase and its role in the vitamin K (2-methyl-3-phytyl-1, 4-naphthaquinone)-dependent carboxylation reaction. Biochem J. 1978; 169:95-101.
12. Bjornsson T D, Blaschke T F. Vitamin K1 disposition and therapy of warfarin overdose. Lancet. 1978; 2:846-847.
13. Shearer M J, Barkhan P. Vitamin K1 and therapy of massive warfarin overdose. Lancet. 1979; 1:266-267.
14. Ross D, Kepa J K, Winski S L, Beall H D, Anwar A, Siegel D. NAD(P)H:quinone oxidoreductase 1 (NQO1): chemoprotection, bioactivation, gene regulation and genetic polymorphisms. Chem Biol Interact. 2000; 129: 77-97.
15. Brar S S, Kennedy T P, Whorton A R, et al. Reactive oxygen species from NAD(P)H:quinone oxidoreductase constitutively activate NF-kappaB in malignant melanoma cells. Am J Physiol Cell Physiol. 2001; 280:C659-676.
16. Gong X, Gutala R, Jaiswal A K. Quinone oxidoreductases and vitamin K metabolism. Vitam Horm. 2008; 78:85-101.
17. Thijssen H H, Baars L G. Tissue distribution of selective warfarin binding sites in the rat. Biochem Pharmacol. 1991; 42:2181-2186.
18. Ulrich M M, Knapen M H, Herrmann-Erlee M P, Vermeer C. Vitamin K is no antagonist for the action of warfarin in rat osteosarcoma UMR 106. Thromb Res. 1988; 50:27-32.
19. Price P A, Kaneda Y. Vitamin K counteracts the effect of warfarin in liver but not in bone. Thromb Res. 1987; 46:121-131.
20. Rost S, Fregin A, Ivaskevicius V, et al. Mutations in VKORC1 cause warfarin resistance and multiple coagulation factor deficiency type 2. Nature. 2004; 427:537-541.
21. Li T, Chang C Y, Jin D Y, Lin P J, Khvorova A, Stafford D W. Identification of the gene for vitamin K epoxide reductase. Nature. 2004; 427:541-544.
22. Jin D Y, Tie J K, Stafford D W. The conversion of vitamin K epoxide to vitamin K quinone and vitamin K quinone to vitamin K hydroquinone uses the same active site cysteines. Biochemistry. 2007; 46:7279-7283.
23. Chu P H, Huang T Y, Williams J, Stafford D W. Purified vitamin K epoxide reductase alone is sufficient for conversion of vitamin K epoxide to vitamin K and vitamin K to vitamin KH2. Proc Natl Acad Sci USA. 2006; 103: 19308-19313.
24. Sugo T, Mizuguchi J, Kamikubo Y, Matsuda M. Anti-human factor IX monoclonal antibodies specific for calcium ion-induced conformations. Thromb Res. 1990; 58:603-614.
25. Huang M, Furie B C, Furie B. Crystal structure of the calcium-stabilized human factor IX Gla domain bound to a conformation-specific anti-factor IX antibody. J Biol Chem. 2004; 279:14338-14346.
26. Yan S C, Razzano P, Chao Y B, et al. Characterization and novel purification of recombinant human protein C from three mammalian cell lines. Biotechnology (N Y). 1990; 8:655-661.
27. Tishler M, Fieser L F, Wendler N L. Hydro, oxido and other derivatives of vitamin K1 and related compounds. J Am Chem Soc. 1940; 62:2866-2871.
28. Aktimur A, Gabriel M A, Gailani D, Toomey J R. The factor IX gamma-carboxyglutamic acid (Gla) domain is involved in interactions between factor IX and factor XIa. J Biol Chem. 2003; 278:7981-7987.
29. Gui T, Lin H F, Jin D Y, et al. Circulating and binding characteristics of wild-type factor IX and certain Gla domain mutants in vivo. Blood. 2002; 100:153-158.
30. Tie J K, Zheng M Y, Hsiao K L, Perera L, Stafford D W, Straight D L. Transmembrane domain interactions and residue proline 378 are essential for proper structure, especially disulfide bond formation, in the human vitamin K-dependent gamma-glutamyl carboxylase. Biochemistry. 2008; 47:6301-6310.
31. Morris D P, Soute B A, Vermeer C, Stafford D W. Characterization of the purified vitamin K-dependent gamma-glutamyl carboxylase. J Biol Chem. 1993; 268: 8735-8742.
32. Thijssen H H, Soute B A, Vervoort L M, Claessens J G. Paracetamol (acetaminophen) warfarin interaction: NAPQI, the toxic metabolite of paracetamol, is an inhibitor of enzymes in the vitamin K cycle. Thromb Haemost. 2004; 92:797-802.
33. Schurgers L J, Shearer M J, Hamulyak K, Stocklin E, Vermeer C. Effect of vitamin K intake on the stability of oral anticoagulant treatment: dose-response relationships in healthy subjects. Blood. 2004; 104:2682-2689.
34. Lowenthal J, Taylor J D. A method for measuring the activity of compounds with an activity like vitamin K against indirect anticoagulants in rats. Br J Pharmacol Chemother. 1959; 14:14-18.
35. Sun Y M, Jin D Y, Camire R M, Stafford D W. Vitamin K epoxide reductase significantly improves carboxylation in a cell line overexpressing factor X. Blood. 2005; 106:3811-3815.
36. Martius C. [on the Biochemistry of Vitamin K.]. Schweiz Med Wochenschr. 1963; 93:1264-1265.
37. Martius C, Ganser R, Viviani A. The enzymatic reduction of K-vitamins incorporated in the membrane of liposomes. FEBS Lett. 1975; 59:13-14.
38. Lee Y Y, Westphal A H, de Haan L H, Aarts J M, Rietjens I M, van Berkel W J. Human NAD(P)H:quinone oxidoreductase inhibition by flavonoids in living cells. Free Radic Biol Med. 2005; 39:257-265.
39. Lewis A, Ough M, Li L, et al. Treatment of pancreatic cancer cells with dicumarol induces cytotoxicity and oxidative stress. Clin Cancer Res. 2004; 10:4550-4558.
40. Wallin R, Patrick S D, Martin L F. Vitamin K1 reduction in human liver. Location of the coumarin-drug-insensitive enzyme. Biochem J. 1989; 260:879-884.
41. Forthoffer N, Gomez-Diaz C, Bello R I, et al. A novel plasma membrane quinone reductase and NAD(P)H:quinone oxidoreductase 1 are upregulated by serum withdrawal in human promyelocytic HL-60 cells. J Bioenerg Biomembr. 2002; 34:209-219.
42. Shearer M J, Newman P. Metabolism and cell biology of vitamin K. Thromb Haemost. 2008; 100:530-547.

43. Suhara Y, Murakami A, Nakagawa K, Mizuguchi Y, Okano T. Comparative uptake, metabolism, and utilization of menaquinone-4 and phylloquinone in human cultured cell lines. Bioorg Med Chem. 2006; 14:6601-6607.
44. Cooper G M, Johnson J A, Langaee T Y, et al. A genome-wide scan for common genetic variants with a large influence on warfarin maintenance dose. Blood. 2008; 112:1022-1027.
45. Kamali F, Wynne H. Pharmacogenetics of warfarin. Annu Rev Med. 2010; 61:63-75.
46. Spronk H M, Soute B A, Schurgers L J, Thijssen H H, De Mey J G, Vermeer C. Tissue-specific utilization of menaquinone-4 results in the prevention of arterial calcification in warfarin-treated rats. J Vasc Res. 2003; 40:531-537.
47. Danziger J. Vitamin K-dependent proteins, warfarin, and vascular calcification. Clin J Am Soc Nephrol. 2008; 3:1504-1510.
48. Schurgers L J, Cranenburg E C, Vermeer C. Matrix Gla-protein: the calcification inhibitor in need of vitamin K. Thromb Haemost. 2008; 100:593-603.
49. Sato Y, Honda Y, Jun I. Long-term oral anticoagulation therapy and the risk of hip fracture in patients with previous hemispheric infarction and nonrheumatic atrial fibrillation. Cerebrovasc Dis. 2010; 29:73-78.
50. Murshed M, Schinke T, McKee M D, Karsenty G. Extracellular matrix mineralization is regulated locally; different roles of two gla-containing proteins. J Cell Biol. 2004; 165:625-630.

Example IV

*Mycobacterium tuberculosis* Vitamin K Epoxide Reductase Homologue Supports Vitamin K-Dependent Carboxylation in Mammalian Cells Vitamin K epoxide reductase (VKOR) is a critical participant in the production of active forms of reduced vitamin K and is required for modification of vitamin K dependent proteins. Homologues of VKOR (VKORH) exist throughout evolution but in bacteria, they appear to function in oxidative protein folding as well as quinone reduction. In the present study two questions are explored: Do VKORHs function in the vitamin K cycle? Is the pair of loop cysteines, C43 and C51 in human VKOR, highly conserved in all VKORs, essential for the activity of vitamin K epoxide reductase?

A cell-based assay was used to compare the function of VKORHs to that of human VKOR in mammalian cells. What was identified for the first time was a VKORH (from *Mycobacterium tuberculosis*, MT-VKORH) that can function in the mammalian vitamin K cycle with vitamin K epoxide or vitamin K as substrate. Consistent with previous in vitro results, the loop cysteines of human VKOR are not essential for its activity in vivo. Moreover, the corresponding loop cysteines of MT-VKORH (C57 and C65), which are essential for its activity in disulfide bond formation during protein folding in *E. coli*, are not required in the mammalian vitamin K cycle.

These results indicate that VKOR in eukaryotes and VKORH in bacteria, i.e., in their native environments, employ fundamentally different mechanisms for electron transfer to the active site during quinone reduction. However, when either is in the mammalian system both VKORH and VKOR employ a similar mechanism.

Vitamin K epoxide reductase (VKOR) is an endoplasmic reticulum (ER) integral membrane protein (19,24). It is responsible for the conversion of vitamin K epoxide (KO) to vitamin K (a quinone), and can also convert vitamin K to vitamin K hydroquinone ($KH_2$). This series of quinone reductase reactions is an essential part of a redox cycle known as the vitamin K cycle (3). The active form of the vitamin, $KH_2$, is a cofactor for post-translational modification of proteins essential for blood coagulation, bone homeostasis, signal transduction, and cell proliferation (7,29).

VKOR is a member of a large family of homologues (VKORH) widely distributed among vertebrates, invertebrates, plants, bacteria, and archaea (13). All of these enzymes are quinone reductases, but in bacteria they also participate in disulfide bond formation during protein folding. The significance of VKOR's role in the latter process in eukaryotes remains unclear (33). In bacteria, VKORHs are present essentially in strains lacking the quinone reductase (DsB) (8). At least some of these bacterial VKORHs can complement DsbB in *E. coli* DsbB deletion mutant strains (8, 27, 35).

DsbB and VKORHs have two pairs of conserved cysteines which are necessary for catalysis (30,36). The active site, CXXC (SEQ ID NO:60), reduces ubiquinone and a second pair, the loop cysteines, oxidize DsbA to its active form. In DsbB the reduced loop cysteines then shuttle electrons from DsbA to reduce the CXXC (SEQ ID NO:60) to cysteines. In *E. coli* complementation studies, all four conserved cysteine residues in bacterial VKORH are required for activity (20,35). In vitro studies with *Synechococcus* VKORH also support this conclusion (20). Based on these results, an intra-molecular electron transfer pathway between the two pairs of conserved cysteines, similar to that of DsbB, has been proposed for the bacterial VKORHs as well as for mammalian VKOR (20,26).

While the electron flow in DsbB is well established, the mechanism for active site regeneration in VKOR is less clear. Experimental data from site-directed mutagenesis confirms that two conserved cysteine residues, C132 and C135, comprise the CXXC redox center (SEQ ID NO:60) in human VKOR (17, 23, 34). But reports of the function of the other pair of conserved loop cysteine residues, C43 and C51, do not allow a consistent interpretation for their role (17, 22, 23). It appears that VKOR's active site can be reduced in at least two ways. Results from thioredoxin (Trx)/Trx reductase as reductant suggest the loop cysteines are important for activity. On the other hand, with dithiothreitol (DTT) as reductant the loop cysteines do not appear to be essential (17, 23, 34). This latter observation is also true with the *Synechococcus* VKORH (20). This would indicate that the active site can be reduced directly by DTT or indirectly by a mechanism involving the loop cysteines.

The present study employs a cell-based assay for studying the vitamin K cycle (31), to examine whether there are any VKORHs that can support vitamin K dependent (VKD) carboxylation in mammalian cells. Second, in vitro studies concerning the roles of the conserved loop cysteines are extended to this in vivo assay to assess the role of these residues in a milieu in which the enzyme would have to interact with its reduction partner and other forms of the VKORH have a similar electron transfer pathway and membrane structure in mammalian cells compared to that in bacteria.

Materials.

Vitamin $K_1$ and warfarin were obtained from Sigma-Aldrich (St. Louis, Mo.). Luciferase substrate coelenterazine was from Nonalight Technology (Pinetop, Ariz.). Mammalian expression vector pIRES2 DsRed-Express2, secreted Metridia luciferase containing vector pBI-CMV5, and Xfect transfection reagent were from Clontech Laboratories, Inc. (Mountain View, Calif.). The cDNA sequences coding the VKORHs and DsbB used in the study were optimized for mammalian cell expression and chemically synthesized by Blue Heron Biotechnology (Bothell, Wash.). Mouse anti-carboxylated FIX gla domain monoclonal antibody (BC2) was from GlaxoSmithKline (Philadelphia, Pa.) and Green Mountain Antibodies (Burlington, Vt.) (1,10). Horseradish peroxidase conjugated affinity purified sheep anti-human Protein C IgG was from Affinity Biologicals Inc. (Ancaster, ON Canada). Anti-HPC4 monoclonal antibody was from Oklahoma Medical Research Foundation, Oklahoma City, Okla.

DNA Manipulations and Plasmid Constructions.

Mammalian expression vector pIRES2 DsRed-Express2 was used as the basic cloning vector. The red fluorescent protein DsRed-Express2 was replaced by secreted Metridia luciferase which was used as the internal control for normalizing the transient transfection efficiency. The resulting vector pIRES2-Met.Luc was used for expressing all the molecules used in this report. This vector permits both the target protein and the secreted Metridia luciferase to be translated from a single mRNA transcript with a ribosome re-entry site.

All VKORHs and warfarin resistant human VKOR (Y139F) and their mutants were sub-cloned into the EcoRI site of the pIRES2-Met.Luc vector under control of the cytomegalovirus promoter. To create the N-linked glycosylation site in the first periplasmic loop of *Mycobacterium tuberculosis* (MT) VKORH, residues P61 and I62 were mutated to S61 and T62, respectively. Together with residue N60, this introduces a NST sequence between the pair of cysteine residues C57/C65. Due to the short carboxyl terminus of MT-VKORH and the requirement of at least 12 amino acid residues between the glycosylation site and the membrane interface (21), a N-linked glycosylation consensus sequence (NST) with a flexible extension linker (GGSGGSGGS, SEQ ID NO:61) was introduced at the carboxyl terminus of MT-VKORH. All the constructs for glycosylation study have a HPC4 tag at their carboxyl terminus for western blot detection.

In Vivo VKOR Activity Assay.

VKOR in vivo activity was determined with a cell-based assay as described previously (31). Luciferase activity was determined by injecting 50 μl of coelenterazine solution (2 μM in PBS with 300 mM NaCl) to 50 μl of cell culture medium directly. Luminescence emission from the mixture was recorded at 480 nm with a delay of 6 seconds and integration time of 1 second. Transfection efficiency was normalized by the expression of Metridia luciferase in cell culture medium. Abilities of enzymes to use vitamin K and KO to support VKD carboxylation were evaluated as described. One way analysis of variance was used to assess significant differences as indicated. The criterion for statistical significance was set as $P<0.05$ or $0.001$.

Western Blot.

To analyze glycosylation modification of the introduced N-linked glycosylation site in MT-VKORH, mutant proteins were transiently expressed in HEK293 cells. Four-eight hours post-transfection, cells were harvested and lysed in 300 μl PBS with 1% Triton X-100 and 1× protease inhibitor cocktail. For deglycosylation, 1 μL PNGase F (500 U/μL) was added to a 50-μL aliquot of the cell lysate and incubated for 30 minutes at 37° C. Deglycosylated and non-treated samples were directly subjected to SDS-NuPAGE under reducing condition. Western blot analysis was performed as described previously (32).

Investigation of VKORHs' Ability to Support In Vivo VKD Carboxylation with KO as Substrate.

Figure 15A:
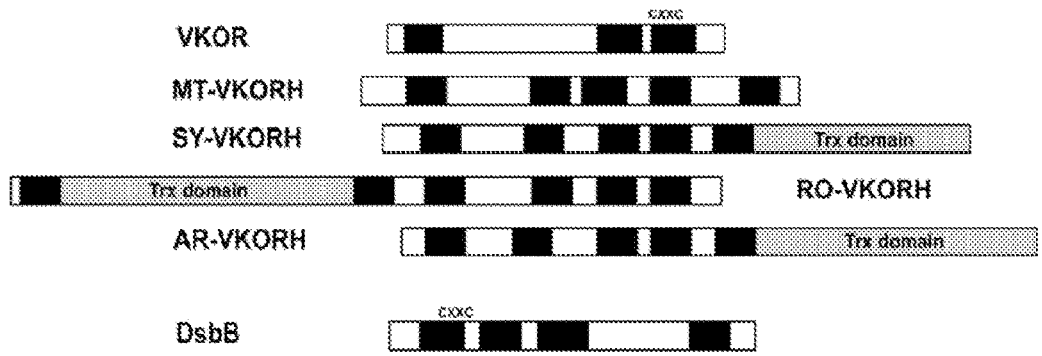
FIGS. 15A-B. Reduction of KO to vitamin K by VKORHs to support VKD carboxylation in HEK293 cells (FIG. 15A) Schematic representation of the vitamin K epoxide reductase homologs (VKORHs) and controls used in this study. The solid bars indicate the transmembrane domain (TMD) predicted by TOPCONS (39) or experimentally determined TMD for human VKOR (23) and DsbB (40). The gray bars indicate the thioredoxin-like (Trx-like) domain. For *Arabidopsis* VKORH, the N-terminal extension that is predicted to encode plastid targeting peptides (19) was removed for the topology prediction. The alignment of VKORHs is based on the TMD containing CXXC redox center (SEQ ID NO:60). MT-VKORH: *Mycobacterium tuberculosis* VKORH; SY-VKORH: *Synechococcus* sp. VKORH; RO-VKORH: *Roseiflexus* sp. RS-1 VKORH; AR-VKORH: *Arabidopsis* VKORH.
Figure 15B:
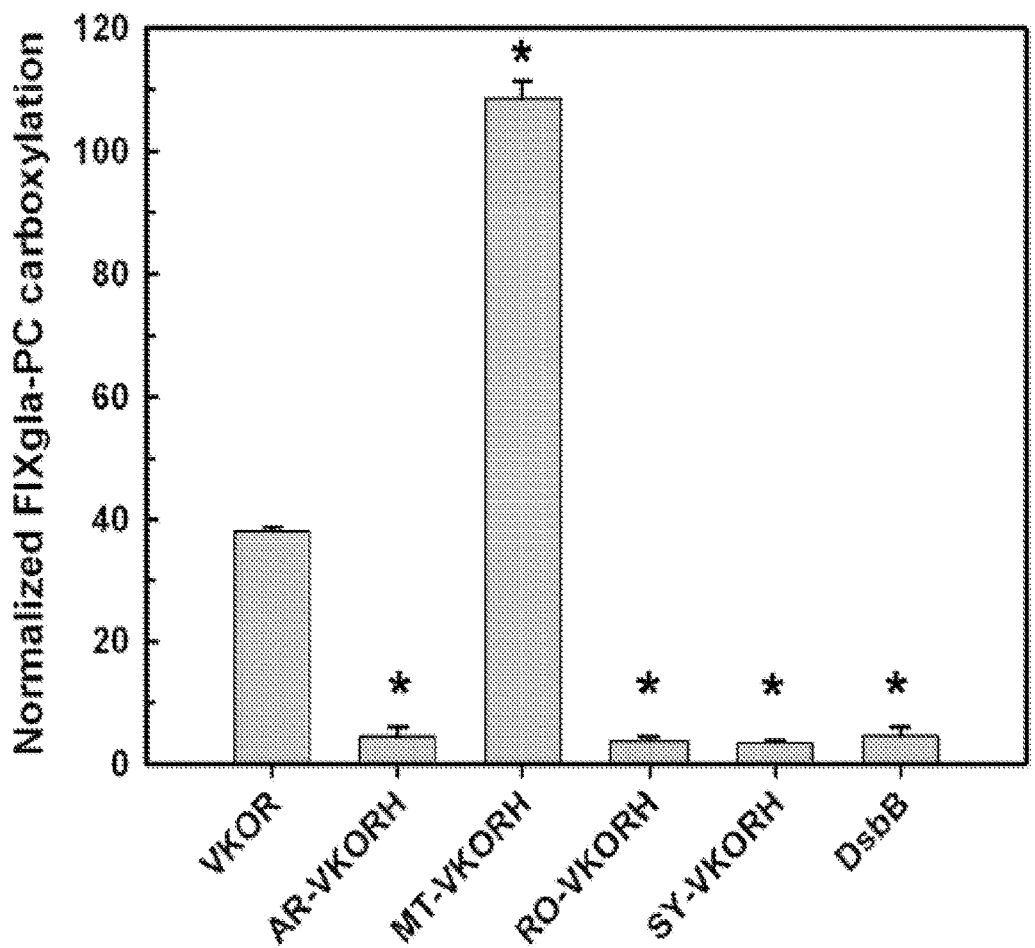

Some VKORHs have certain structural and functional characteristics similar to those of human VKOR (12, 13). The cell-based assay was used to investigate whether these similarities allow some VKORHs to participate in the vitamin K cycle. Initial testing was of VKORHs from four organisms (FIG. 15A): *Arabidopsis thalania* (AR-VKORH), which has vitamin K to $KH_2$ activity and a Trx-like domain at its C-terminus, but is insensitive to warfarin (19), *Mycobacterium tuberculosis* (MT-VKORH), which has no Trx-like domain but is active in *E. coli* protein folding and is reported to be warfarin sensitive (9), *Roseiflexus* sp. (RO-VKORH), which has a N-terminal Trx-like domain, and *Synechococcus* sp. (SY-VKORH), which can reduce vitamin K to $KH_2$ and whose crystal structure has been reported (20). These enzymes were transiently expressed in the established cell line (FIXgla-PC/HEK293) and the cells were cultured in the presence of 5 μM KO and 4 μM warfarin. Of the VKORHs tested, only MT-VKORH supported carboxylation of the reporter protein (FIG. 15B). MT-VKORH has 2.5-fold higher activity than human VKOR-Y139F. Since VKOR-Y139F has ~40% of wild-type activity (18,25); this result suggests that MT-VKORH has activity similar to that of wild-type human VKOR.

The Effect of Cysteine Mutations on MT-VKORHs Ability to Support In Vivo VKD Carboxylation with KO as Substrate.

Figure 16:
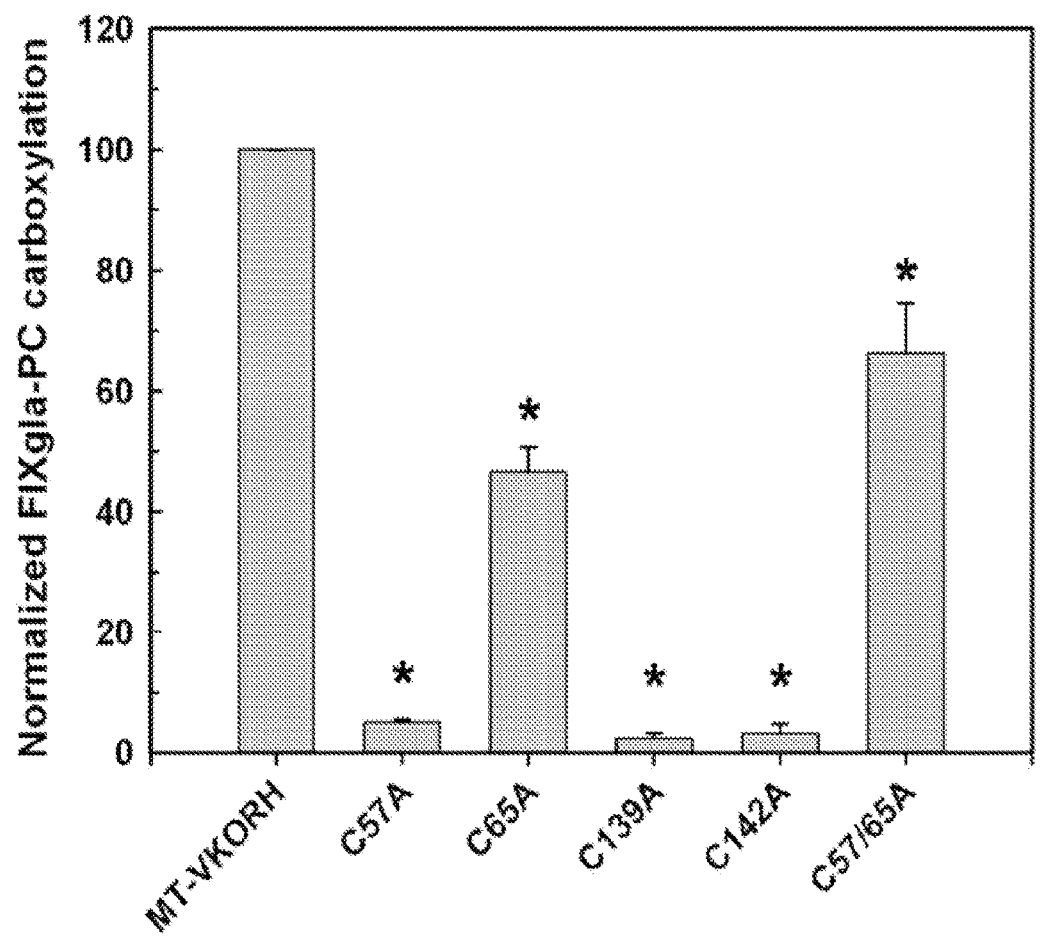
FIG. 16. Reduction of KO to vitamin K by MT-VKORH cysteine mutants to support VKD carboxylation in HEK293 cells. MT-VKORH and its cysteine mutants were transiently expressed in FIXgla-PC/HEK293 cells and the enzymatic activity was determined as described in FIGS. 15A-B.

Both pairs of the conserved cysteines, C57/C65 and C139/C142, in MT-VKORH are essential for complementing DsbB deletion in *E. coli* (35). To examine the importance of these conserved cysteines in the vitamin K cycle, MT-VKORH with alanine mutations at each cysteine (C57A, C65A, C139A, and C142A) as well as with the double mutant, C57A/C65A in FIXgla-PC/HEK293, were transiently expressed. Mutation of either of the cysteines (C139 or C142) in the CXXC redox center (SEQ ID NO:60) abolishes its ability to support VKD carboxylation (FIG. 16). These mutations also abolish MT-VKORH ability to complement DsbB deletion in *E. coli* (8). MT-VKORH C57A mutant has <10% VKD carboxylation activity (FIG. 16). On the other hand, C65A and C57A/C65A mutants retain 50% to 70% activity of the wild-type MT-VKORH. This result suggests that loop cysteines C57/C65 are not directly involved in the reduction of KO in mammalian cells. Thus, the reaction mechanisms utilized for DsbB complementation in *E. coli* (35) and for the conversion of KO to vitamin K in mammalian cells by MT-VKORH appear to be different.

The Effect of Cysteine Mutations on Human VKOR In Vivo Activity.

Figure 17A:
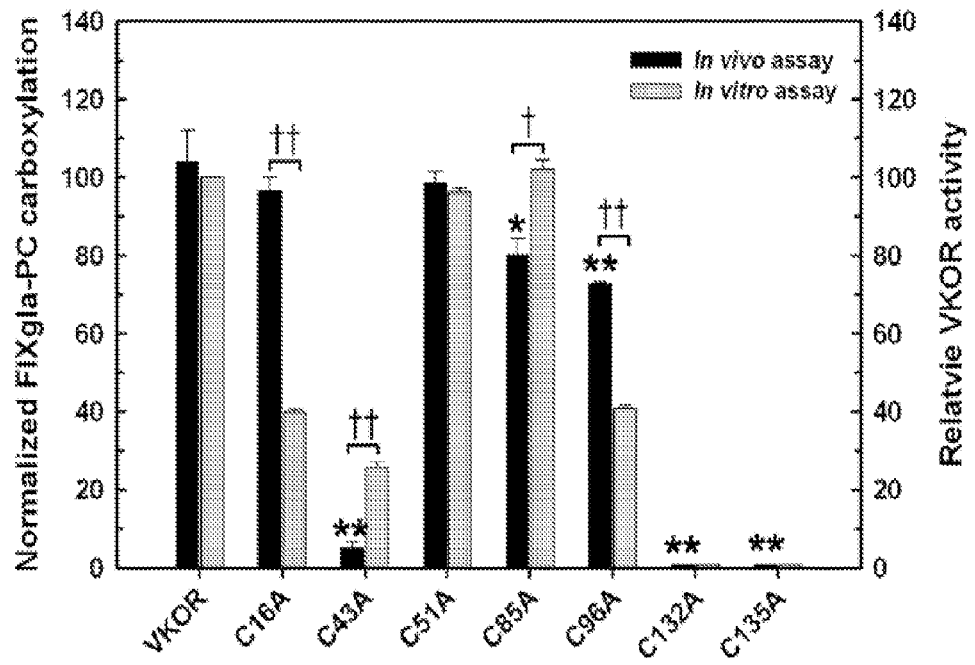
FIGS. 17A-B. Cell-based activity assay of VKOR cysteine mutants.
Figure 17B:
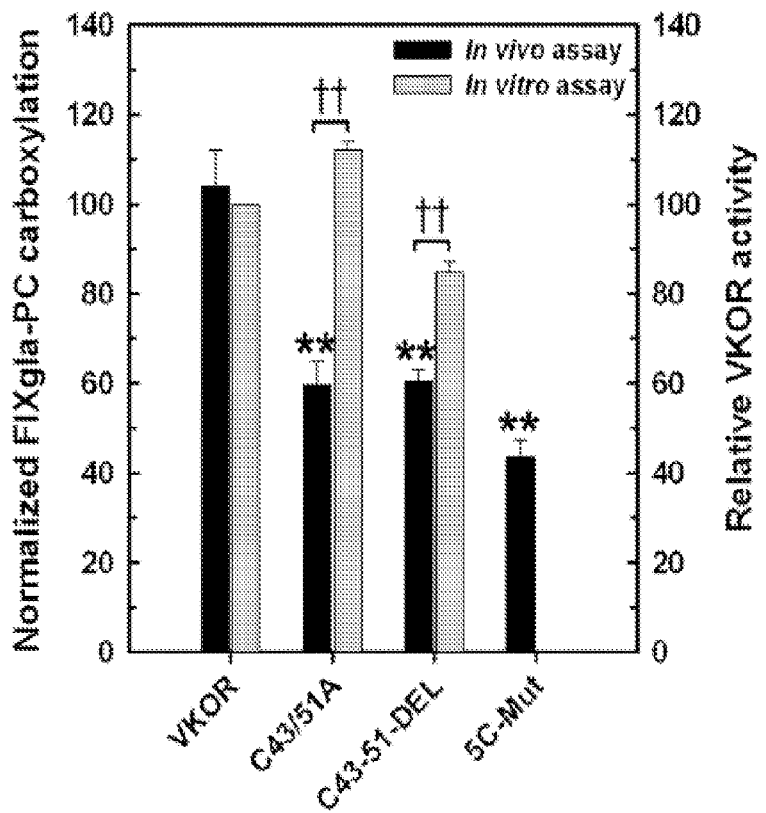

To examine the role of the cysteines in VKOR in vivo, the cysteines were changed to alanines in the warfarin-resistant VKOR-Y139F molecule and these enzymes were transiently expressed in FIXgla-PC/HEK293. The in vivo results (FIG. 17A) are similar to previous in vitro results except that C16A mutation has no effect on activity in vivo but has ~40% activity in the in vitro assay. Only mutations of the active site residues, C132 and C135, reduce activity to background levels. C43A has ~30% activity in the in vitro assay but ~5% activity in the in vivo assay. C51A has activity similar to that of wild-type VKOR in both assays. To confirm the role of C43 and C51, both cysteines were mutated to alanine, or both cysteines and the sequences between them were deleted. As shown (FIG. 17B), in either case the molecule still retains ~60% activity. In addition, mutating all five non-active site cysteines simultaneously to alanine results in a molecule with ~40% activity. These results together suggest that the conserved loop cysteines C43 and C51 are not required for VKOR activity (17).

Cysteine Residues 57 and 65 of MT-VKORH are Located in the ER Lumen.

Figure 18A:
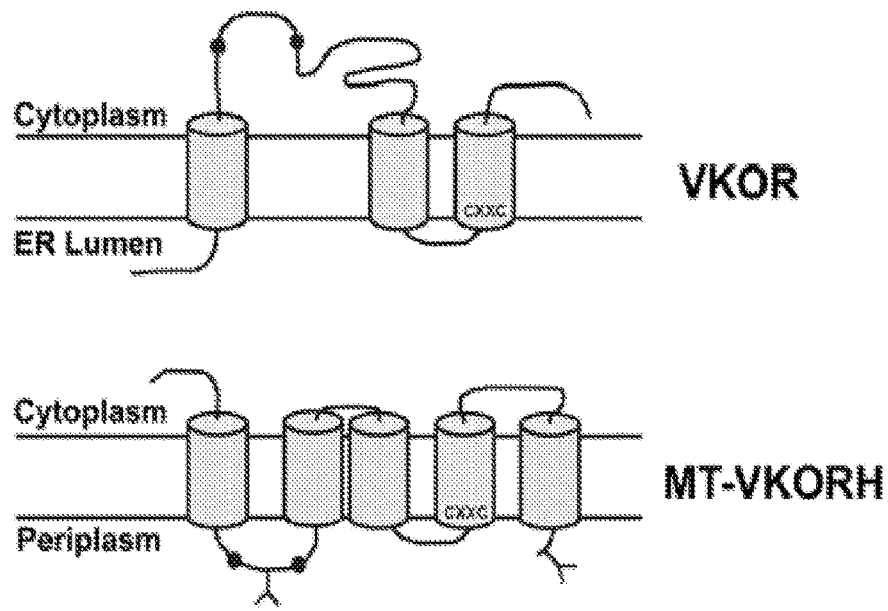
FIGS. 18A-C. Localization of conserved loop cysteines 57/65 and the C-terminus of MT-VKORH by N-linked glycosylation mapping.

Membrane topology studies of MT-VKORH in *E. coli* indicate that C57 and C65 are located in the periplasm, the same side of the bacterial inner membrane as the CXXC redox center (SEQ ID NO:60) (35). According to previous work, the corresponding conserved pair of cysteines 43 and 51 of human VKOR are located in the cytoplasm, i.e., on the opposite side of the ER membrane from the CXXC redox center (SEQ ID NO:60) (32) (FIG. 18A). The function of C57 and C65 of MT-VKORH in reducing KO in mammalian cells appears to be similar to that of C43/C51 of human VKOR, but different than that in *E. coli*. One reason for this might be that MT-VKORH has different membrane topology in *E. coli* and mammalian cells.

Figure 18B:
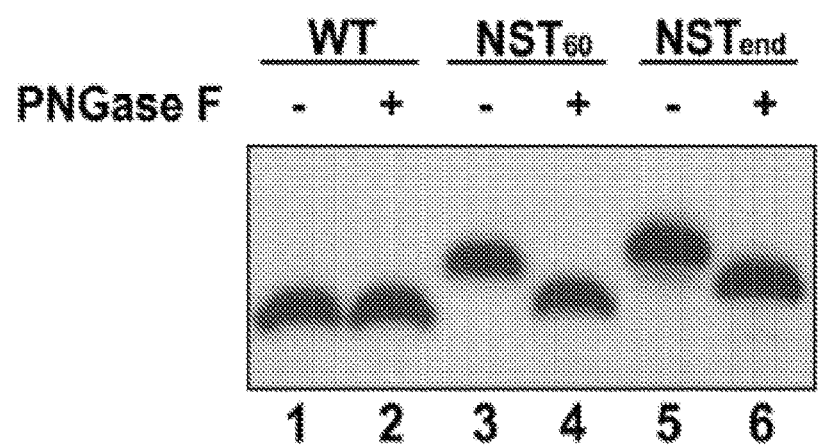
Figure 18C:
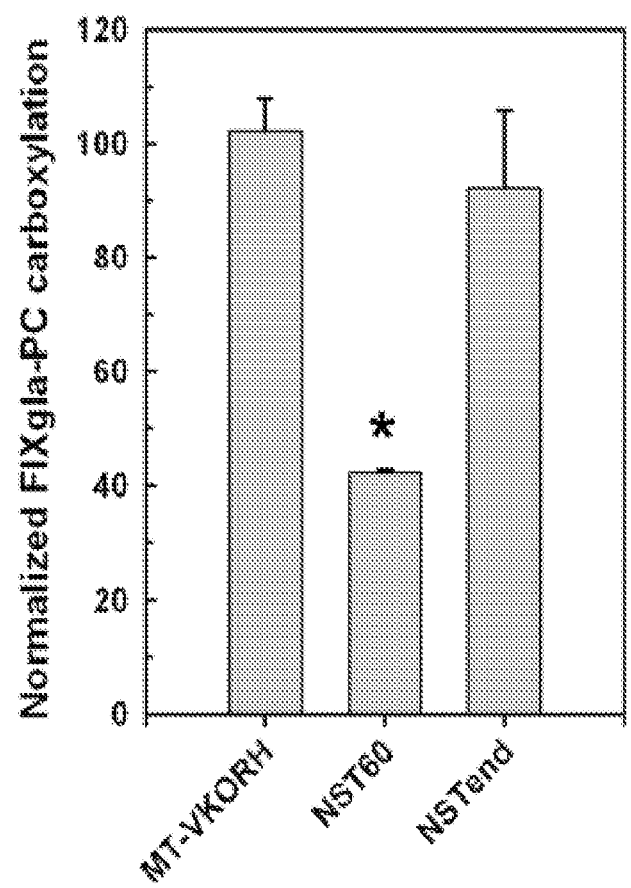

To clarify this issue, the N-linked glycosylation mapping technique (5) was used to determine the MT-VKORH membrane topology in HEK293 cells. These results show that introducing glycosylation sites causes MT-VKORH to migrate slower than wild-type enzyme in SDS-PAGE (FIG. 18B, lanes 3 and 5). These higher molecular weight molecules are sensitive to the endoglycosidase digestion (FIG. 18B, lanes 4 and 6) indicating the introduced sites are glycosylated. Therefore, the cysteine pair C57/C65 and the C-terminus of MT-VKORH are located in the ER lumen, which is consistent with the periplasmic location in bacteria (35). Glycosylation at the C-terminus does not affect MT-VKORH activity, while glycosylation in the loop between C57 and C65 decreases activity 50% compared with that of the wild-type enzyme (FIG. 18C). Together with the cysteine mutation results of human VKOR (FIG. 17), this result further suggests that whether the conserved cysteine pair is located in the cytoplasm or ER lumen, they are not required for the reduction of the CXXC redox center (SEQ ID NO:60).

Support of VKD Carboxylation by VKORH with Vitamin K as Substrate in AV12 Cells.

Figure 19A:
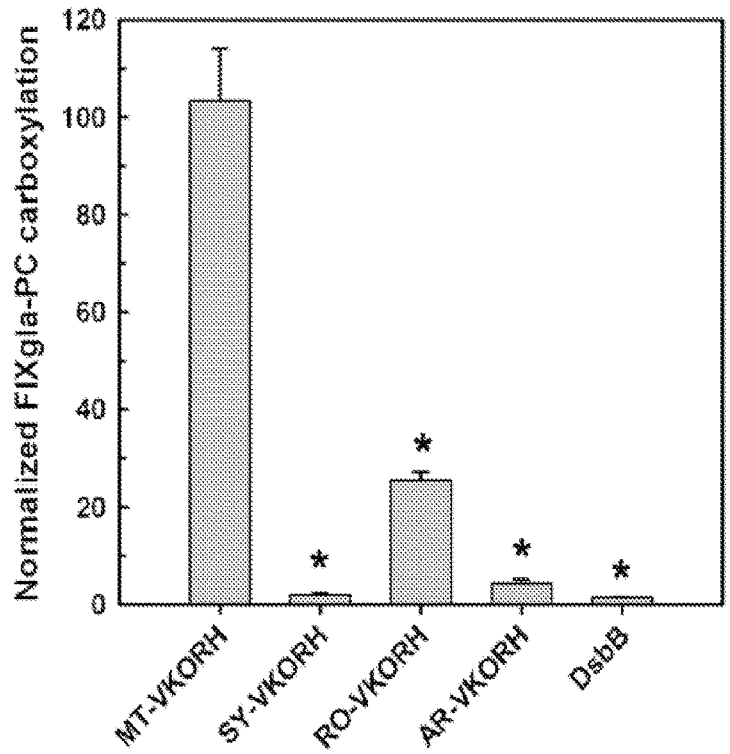
FIGS. 19A-B. Reduction of vitamin K to $KH_2$ by VKORHs to support VKD carboxylation in AV12 cells.

Results to this point indicate that MT-VKORH can reduce KO to vitamin K, but provide no information about its activity for vitamin K to $KH_2$. In contrast to HEK293 cells, which have a warfarin-resistant vitamin K reductase, it was shown that AV12 cells have almost no antidotal enzyme. This makes AV12 cells a good model for investigating enzymes' ability to utilize vitamin K. To determine whether VKORHs can efficiently reduce vitamin K to $KH_2$, and thus support carboxylation, the VKORHs were transiently expressed in FIXgla-PC/AV12 cells stably expressing VKOR-Y139F. It was reasoned that if an enzyme that can efficiently reduce vitamin K to $KH_2$ is introduced, the resulting cell line should produce carboxylated reporter protein when the cells were cultured with KO and warfarin. Of the cell lines transiently expressing VKORHs only those expressing MT-VKORH and RO-VKORH have significant activity (FIG. 19A). VKORHs from *Arabidopsis* and *Synechococcus* can reduce vitamin K in vitro (11,20), but they have no significant activity in the in vivo system.

Figure 19B:
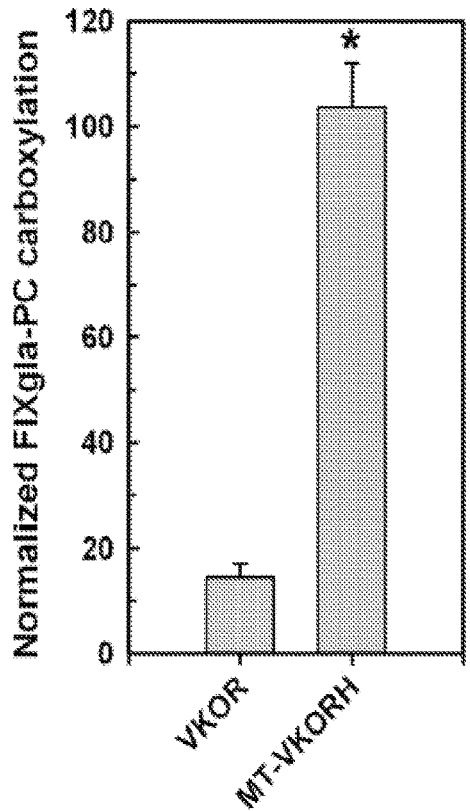

To further confirm MT-VKORH's ability to reduce both KO to vitamin K and vitamin K to $KH_2$, either MT-VKORH or VKOR-Y139F were transiently expressed in FIXgla-PC/AV12 cells that do not stably express VKOR-Y139F. As previously reported, expression of VKOR-Y139F did not support carboxylation of the reporter protein (31). In contrast, expression of MT-VKORH produced significant carboxylated reporter protein (FIG. 19B). This result further supports the conclusion that MT-VKOKH can reduce both KO and vitamin K. It also supports earlier observations that the main function of human VKOR in the vitamin K cycle is to reduce KO to vitamin K but not vitamin K to $KH_2$(31).

The Importance of the Dipeptide Sequence Between the Active Site Cysteines for VKOR Activity.

Figures 20A, 20B:
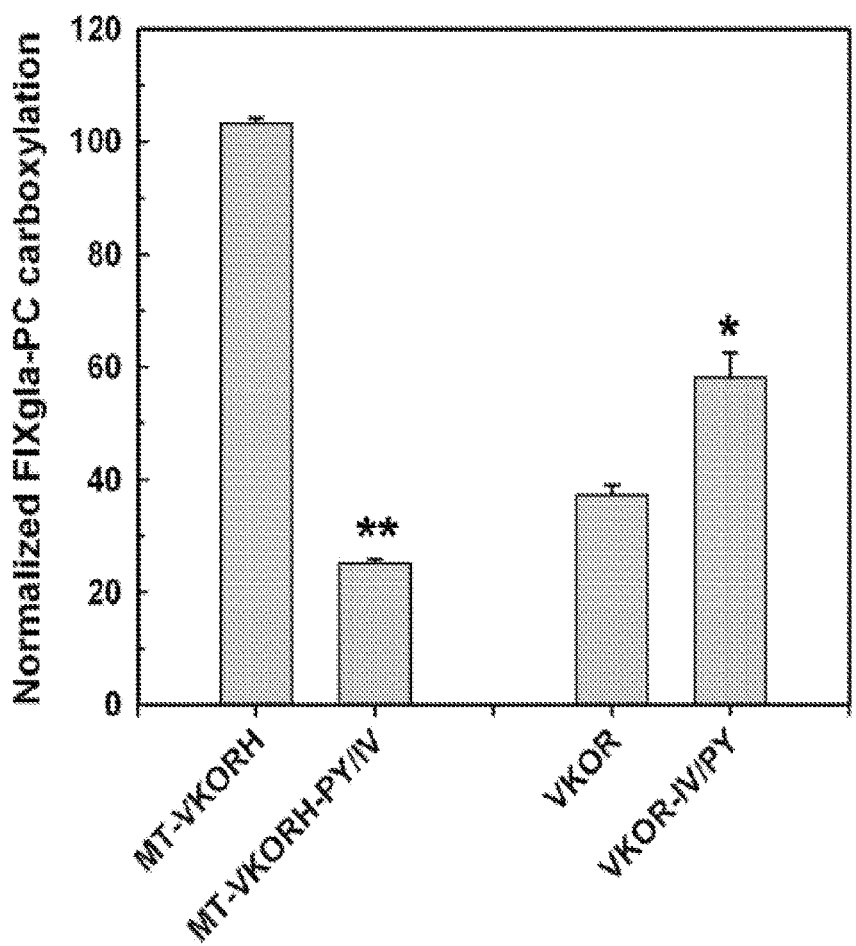
FIGS. 20A-B. Effect of the dipeptide sequence between the two cysteines of the CXXC redox center (SEQ ID NO:60) on VKOR activity.

In enzymes with the redox center, CXXC (SEQ ID NO:60), the dipeptide sequence between the cysteines often plays a crucial role in controlling the enzyme's activity (6,15). VKOR and the VKORHs have different dipeptide sequences in the active site (FIG. 20A). The dipeptide PY in MT-VKORH is a common sequence in the glutaredoxin family's CXXC redox center (SEQ ID NO:60). The PY sequence causes a pKa<4 for the N-terminal nucleophilic cysteine and high reducing potential (12). To test the effect of the dipeptide sequence on enzyme activity, the dipeptide sequences of human VKOR and MT-VKORH were exchanged. With KO as substrate, changing MT-VKORH's PY to IV decreased its activity to less than 30% compared to that of the wild-type enzyme (FIG. 20B). Changing human VKOR's IV to PY caused a modest activity increase.

Reduction of KO and Vitamin K by Other Bacterial VKORHs with Sequences Similar to that of MT-VKORH.

These results suggest that VKORHs without the Trx domain and with the dipeptide sequence PY in the CXXC redox center (SEQ ID NO:60) may be more likely to catalyze both the reduction of KO and vitamin K. To further test this hypothesis, we selected two bacterial VKORHs that meet these criteria; CO-VKORH (From *Corynebacterium jeikeium* K411) and SA-VKORH (From *Salinispora tropica* CNB-440). The CXXC active site sequence (SEQ ID NO:60) and sequences on either side of the active site are conserved in these enzymes (FIG. 21A). As shown, with KO as substrate, SA-VKORH and CO-VKORH have 30% and 70% activity relative to MT-VKORH respectively (FIG. 21B). To determine whether these enzymes can use vitamin K to support carboxylation, they were expressed in FIXgla-PC/VKOR-Y139F/AV12 cell lines. Compared with MT-VKORH, these two VKORHs' ability to reduce vitamin K to $KH_2$ is higher than the KO to vitamin K reduction (FIG. 21C).

Initially three bacterial and one plant (*Arabidopsis*) VKORH, two of which have been reported to reduce vitamin K (2,14), were investigated, to see if any could support VKD carboxylation in vivo. Of these, only MT-VKORH can employ KO in mammalian cells to catalyze carboxylation of our reporter protein (FIG. 15). But with vitamin K as substrate, both MT-VKORH and RO-VKORH (although to a lesser extent) can support VKD carboxylation (FIG. 19). This result is particularly interesting; first because MT-VKORH is the only non-eukaryotic enzyme shown to reduce KO to vitamin K; second because, as opposed to VKOR, it efficiently uses either KO or vitamin K as substrate; and finally the active sites of both MT-VKORH and RO-VKORH can be reduced in vivo by the physiologic reductant for VKOR. This result also allowed for a comparison of the structure-function characteristics of human VKOR with a bacterial enzyme in a system where they are both active.

When MT-VKORH complements DsbB deletion mutants in *E. coli*, both the active site cysteines and the loop cysteines are important for this function (35). In contrast, these results indicate that, like the VKOR (FIG. 17), only the active site cysteines are required for MT-VKORH function in mammalian cell VKD carboxylation, (FIG. 16). According to previous results, the human VKOR (32) loop cysteines are in the cytoplasm, but according to Wang et al. the MT-VKORH (35) loop cysteines are located in the periplasm of E. coli. Therefore a possible explanation for the different results in E. coli and this system concerning the loop cysteines is that MT-VKORH has a different membrane topology in HEK293 cells than in E. coli. These results show this is not the case (FIG. 18). These results indicate that there are at least two mechanisms by which the active site of the reductases can be reduced.

Figure 22A:
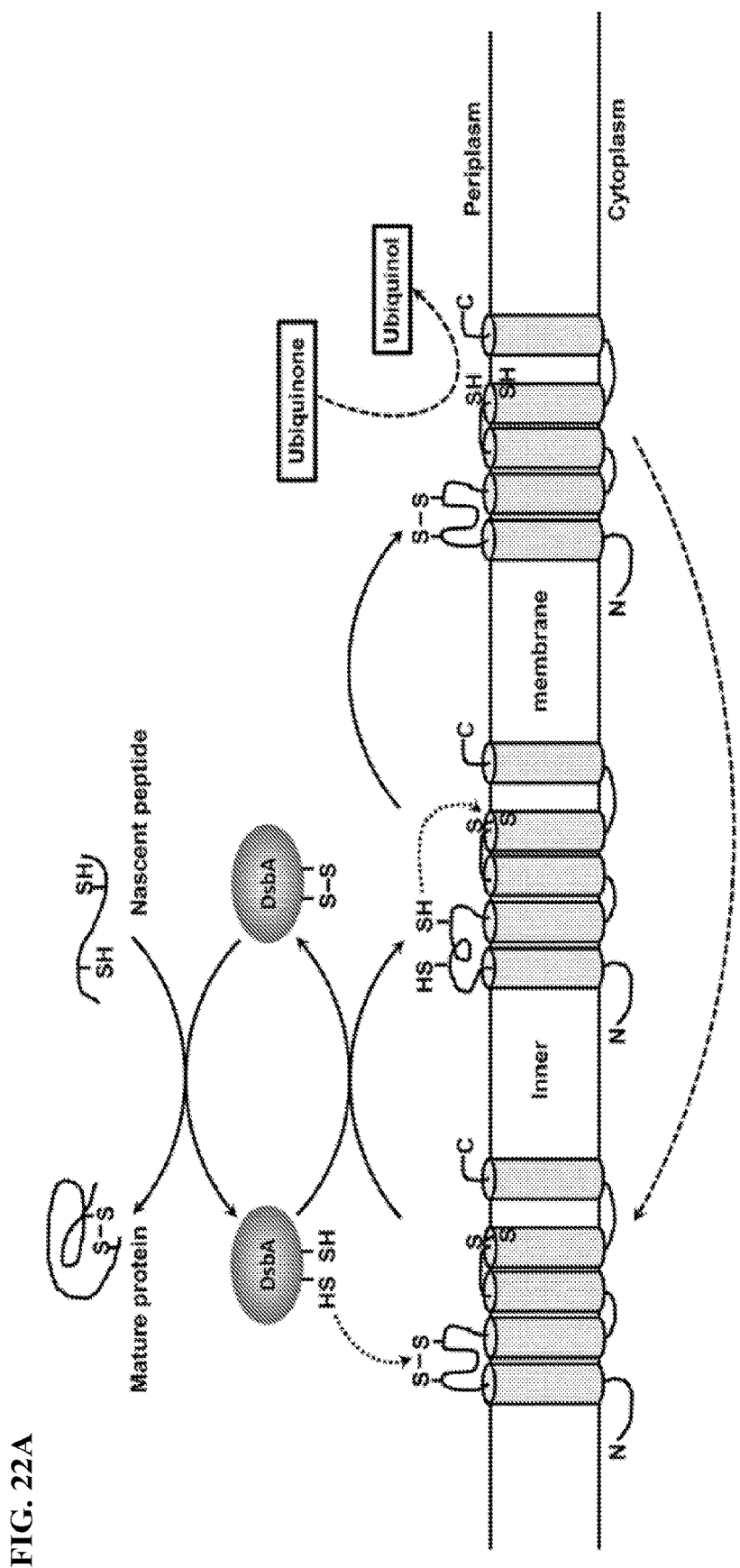
FIGS. 22A-B. Proposed reaction mechanism of MT-VKORH in the reduction of ubiquinone and vitamin K.
Figure 22B:
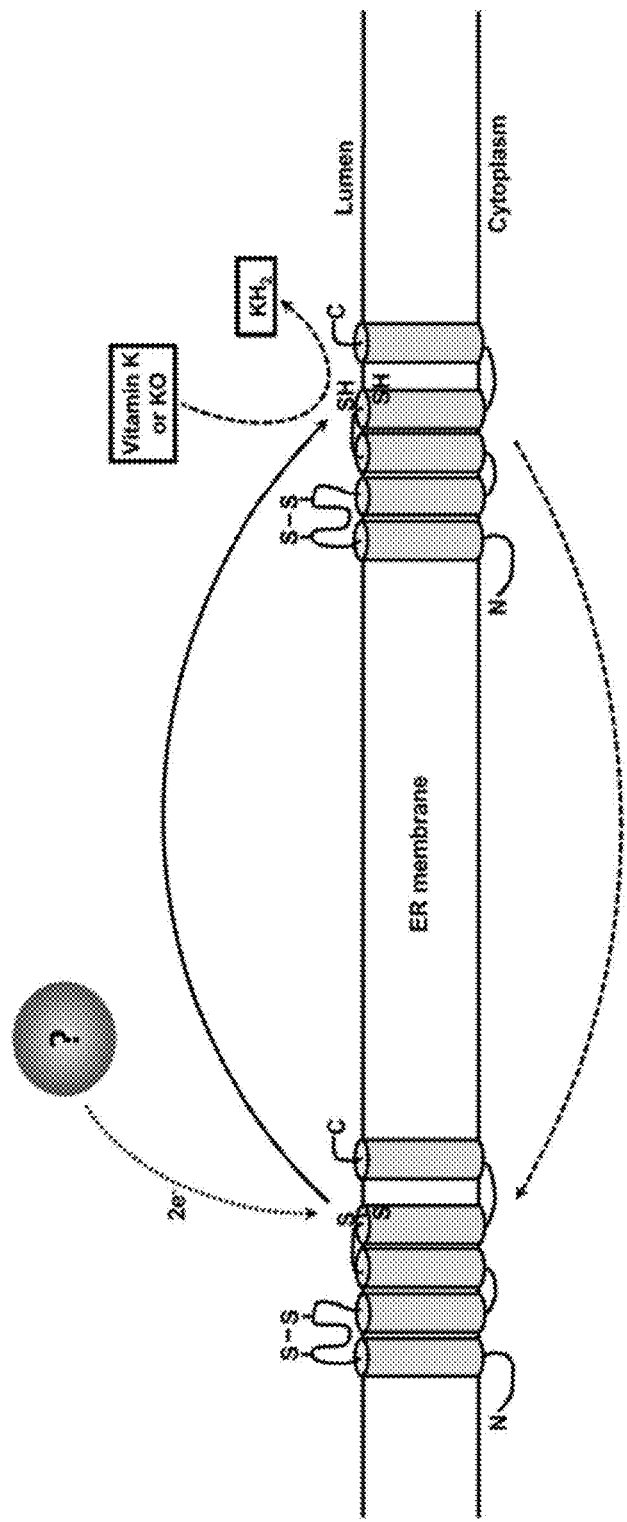

In the bacteria periplasm, the loop must interact with DsbA to support disulfide formation during protein folding which is necessary for cell motility. During this process it in turn reduces the active site CXXC (SEQ ID NO:60) to complete a cycle to the active enzyme. On the other hand, the mammalian loop apparently plays only a secondary role in any reducing cycle other than that of vitamin K. If this were not the case, it seems likely that warfarin treatment might affect important cellular functions other than vitamin K production and cause negative physiological effects. In addition, the murine knockout of VKOR would not be viable when fed vitamin K (28). This suggests that in the mammalian system reduction of the active site CXXC (SEQ ID NO:60) must be catalyzed directly and inter-molecularly by an as yet unidentified reducing protein/molecule (FIG. 22).

As mentioned above, in contrast to VKOR, the MT-VKORH can efficiently use either KO or vitamin K as substrate in carboxylation. One reason for this could be the difference of the dipeptide sequence in the CXXC redox center (SEQ ID NO:60). The dipeptide between the two cysteines plays a crucial role in controlling the enzyme activity by an effect on the pKa of the N-terminal cysteine (6,15). In VKOR, the dipeptide is IV; while in MTVKORH it is PY (FIG. 20A). The PY sequence causes a low pKa (<4) for the N-terminal nucleophilic cysteine and a high redox potential for the active site (12). When the dipeptides were exchanged between MT-VKORH and human VKOR the mutant MTVKORH had significantly lower activity with KO, but the effect on VKOR was modest indicating that other unidentified structural features are important in VKOR.

To study the importance of the sequence adjacent to the active site, two other bacterial VKORH with sequences similar to that of MT-VKORH were tested. Both enzymes supported VKD carboxylation with KO or vitamin K as substrate (FIG. 21). These results indicate that the dipeptide sequence and adjacent residues are important for in vivo reduction of vitamin K. It is interesting to note that the homologues that support both reductions have conserved sequences surrounding the active site that are quite different from that of VKOR (FIG. 19A).

In summary, these studies have shown that VKORH from *Mycobacterium tuberculosis* can reduce both KO and vitamin K to support VKD carboxylation in mammalian cells. In contrast to its function in oxidative protein folding in *E. coli*, the conserved loop cysteines are apparently dispensable for supporting VKD carboxylation in mammalian cells. In addition it appears in the mammalian system that membrane topology, as long as the active site is in the ER lumen, does not affect enzyme activity. These results indicate that MT-VKORH can function by two physiologically relevant mechanisms depending on its cellular environment.

REFERENCES FOR EXAMPLE IV

1. Aktimur A, Gabriel M A, Gailani D, Toomey J R. The factor IX gammacarboxyglutamic acid (Gla) domain is involved in interactions between factor IX and factor XIa. *J Biol Chem* 278:7981-7, 2003.
2. Bartlett G J, Porter C T, Borkakoti N, Thornton J M. Analysis of catalytic residues in enzyme active sites. *J Mol Biol* 324:105-21, 2002.
3. Bell R G, Matschiner J T. Warfarin and the inhibition of vitamin K activity by an oxide metabolite. *Nature* 237: 32-3, 1972.
4. Bernsel A, Viklund H, Hennerdal A, Elofsson A. TOPCONS: consensus prediction of membrane protein topology. *Nucleic Acids Res* 37:W465-8, 2009.
5. Chavez R A, Hall Z W. The transmembrane topology of the amino terminus of the alpha subunit of the nicotinic acetylcholine receptor. *J Biol Chem* 266:15532-8, 1991.
6. Chivers P T, Prehoda K E, Raines R T. The CXXC motif: a rheostat in the active site. *Biochemistry* 36:4061-6, 1997.
7. Danziger J. Vitamin K-dependent proteins, warfarin, and vascular calcification. *Clin J Am Soc Nephrol* 3:1504-10, 2008.
8. Dutton R J, Boyd D, Berkmen M, Beckwith J. Bacterial species exhibit diversity in their mechanisms and capacity for protein disulfide bond formation. *Proc Natl Acad Sci USA* 105:11933-8, 2008.
9. Dutton R J, Wayman A, Wei J R, Rubin E J, Beckwith J, Boyd D. Inhibition of bacterial disulfide bond formation by the anticoagulant warfarin. *Proc Natl Acad Sci USA* 107:297-301, 2010.
10. Feuerstein G Z, Patel A, Toomey J R, Bugelski P, Nichols A J, Church W R, Valocik R, Koster P, Baker A, Blackburn M N. Antithrombotic efficacy of a novel murine antihuman factor IX antibody in rats. *Arterioscler Thromb Vasc Biol* 19:2554-62, 1999.
11. Furt F, Oostende C, Widhalm J R, Dale M A, Wertz J, Basset G J. A bimodular oxidoreductase mediates the specific reduction of phylloquinone (vitamin K(1)) in chloroplasts. *Plant J* 64:38-46, 2010.
12. Gan Z R, Sardana M K, Jacobs J W, Polokoff M A. Yeast thioltransferase—the active site cysteines display differential reactivity. *Arch Biochem Biophys* 282:110-5, 1990.
13. Goodstadt L, Ponting C P. Vitamin K epoxide reductase: homology, active site and catalytic mechanism. *Trends Biochem Sci* 29:289-92, 2004.
14. Holliday G L, Mitchell J B, Thornton J M. Understanding the functional roles of amino acid residues in enzyme catalysis. *J Mol Biol* 390:560-77, 2009.
15. Huber-Wunderlich M, Glockshuber R. A single dipeptide sequence modulates the redox properties of a whole enzyme family. *Fold Des* 3:161-71, 1998.
16. Jander G, Martin N L, Beckwith J. Two cysteines in each periplasmic domain of the membrane protein DsbB are required for its function in protein disulfide bond formation. *Embo J* 13:5121-7, 1994.
17. Jin D Y, Tie J K, Stafford D W. The conversion of vitamin K epoxide to vitamin K quinone and vitamin K quinone to vitamin K hydroquinone uses the same active site cysteines. *Biochemistry* 46:7279-83, 2007.
18. Lasseur R, Longin-Sauvageon C, Videmann B, Billeret M, Berny P, Benoit E. Warfarin resistance in a French strain of rats. *J Biochem Mol Toxicol* 19:379-85, 2005.
19. Li T, Chang C Y, Jin D Y, Lin P J, Khvorova A, Stafford D W. Identification of the gene for vitamin K epoxide reductase. *Nature* 427:541-4, 2004.
20. Li W, Schulman S, Dutton R J, Boyd D, Beckwith J, Rapoport T A. Structure of a bacterial homologue of vitamin K epoxide reductase. *Nature* 463:507-12, 2010.

21. Nilsson I M, von Heijne G. Determination of the distance between the oligosaccharyltransferase active site and the endoplasmic reticulum membrane. *J Biol Chem* 268:5798-801, 1993.
22. Rishavy M A, Usubalieva A, Hallgren K W, Berkner K L. Novel insight into the mechanism of the vitamin K oxidoreductase (VKOR): electron relay through Cys43 and Cys51 reduces VKOR to allow vitamin K reduction and facilitation of vitamin K-dependent protein carboxylation. *J Biol Chem* 286:7267-78, 2011.
23. Rost S, Fregin A, Hunerberg M, Bevans C G, Muller C R, Oldenburg J. Site directed mutagenesis of coumarin-type anticoagulant-sensitive VKORC1: evidence that highly conserved amino acids define structural requirements for enzymatic activity and inhibition by warfarin. *Thromb Haemost* 94:780-6, 2005.
24. Rost S, Fregin A, Ivaskevicius V, Conzelmann E, Hortnagel K, Pelz H J, Lappegard K, Seifried E, Scharrer I, Tuddenham E G, Muller C R, Strom T M, Oldenburg J. Mutations in VKORC1 cause warfarin resistance and multiple coagulation factor deficiency type 2. *Nature* 427:537-41, 2004.
25. Rost S, Pelz H J, Menzel S, MacNicoll A D, Leon V, Song K J, Jakel T, Oldenburg J, Muller C R. Novel mutations in the VKORC1 gene of wild rats and mice—a response to 50 years of selection pressure by warfarin? *BMC Genet* 10:4, 2009.
26. Schulman S, Wang B, Li W, Rapoport T A. Vitamin K epoxide reductase prefers ER membrane-anchored thioredoxin-like redox partners. *Proc Natl Acad Sci USA* 107:15027-32, 2010.
27. Singh A K, Bhattacharyya-Pakrasi M, Pakrasi H B. Identification of an atypical membrane protein involved in the formation of protein disulfide bonds in oxygenic photosynthetic organisms. *J Biol Chem* 283:15762-70, 2008.
28. Spohn G, Kleinridders A, Wunderlich F T, Watzka M, Zaucke F, Blumbach K, Geisen C, Seifried E, Muller C, Paulsson M, Bruning J C, Oldenburg J. VKORC1 deficiency in mice causes early postnatal lethality due to severe bleeding. *Thromb Haemost* 101:1044-50, 2009.
29. Stafford D W. The vitamin K cycle. *J Thromb Haemost* 3:1873-8, 2005.
30. Tapley T L, Eichner T, Gleiter S, Ballou D P, Bardwell J C. Kinetic characterization of the disulfide bond-forming enzyme DsbB. *J Biol Chem* 282:10263-71, 2007.
31. Tie J K, Jin D Y, Straight D L, Stafford D W. Functional study of the vitamin K cycle in mammalian cells. *Blood* 117:2967-74, 2011.
32. Tie J K, Nicchitta C, von Heijne G, Stafford D W. Membrane topology mapping of vitamin K epoxide reductase by in vitro translation/cotranslocation. *J Biol Chem* 280:16410-6, 2005.
33. Wajih N, Hutson S M, Wallin R. Disulfide-dependent protein folding is linked to operation of the vitamin K cycle in the endoplasmic reticulum. A protein disulfide isomerase-VKORC1 redox enzyme complex appears to be responsible for vitamin K1 2,3-epoxide reduction. *J Biol Chem* 282:2626-35, 2007.
34. Wajih N, Sane D C, Hutson S M, Wallin R. Engineering of a recombinant vitamin K-dependent gamma-carboxylation system with enhanced gammacarboxyglutamic acid forming capacity: evidence for a functional CXXC redox center in the system. *J Biol Chem* 280:10540-7, 2005.
35. Wang X, Dutton R J, Beckwith J, Boyd D. Membrane Topology and Mutational Analysis of *Mycobacterium tuberculosis* VKOR, a Protein Involved in Disulfide Bond Formation and a Homologue of Human Vitamin K Epoxide Reductase. *Antioxid Redox Signal* 14:1413-20, 2011.
36. Zhou Y, Cierpicki T, Jimenez R H, Lukasik S M, Ellena J F, Cafiso D S, Kadokura H, Beckwith J, Bushweller J H. NMR solution structure of the integral membrane enzyme DsbB: functional insights into DsbB-catalyzed disulfide bond formation. *Mol Cell* 31:896-908, 2008.

Example 5

Vitamin K Epoxide Reductases with Modified Membrane Topology and Increased Activity Methods: To further confirm the topological structure of human VKOR and to better understand its reaction mechanism, fluorescence protease protection assays and selective chemical modification of the endogenous cysteines were used to probe the membrane topology of human VKOR in mammalian, HEK 293 cells.

Figure 29A:
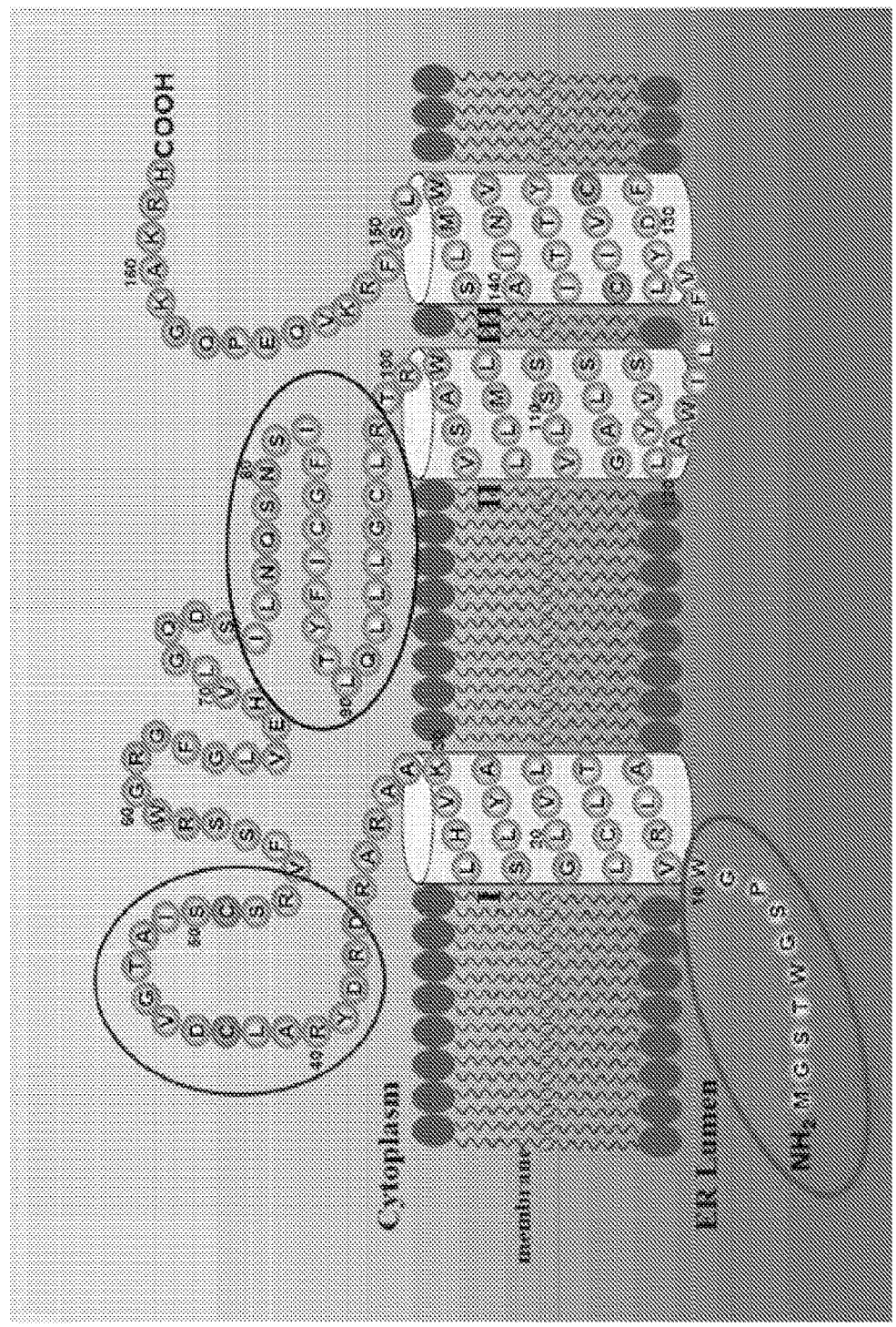
FIGS. 29A-B. Transmembrane domain models of human VKOR (SEQ ID NO:5) (FIG. 29A) 3-TMD Model. N-terminus: ER lumen, Cys 43 and 51: Cytoplasm.
Figure 29B:
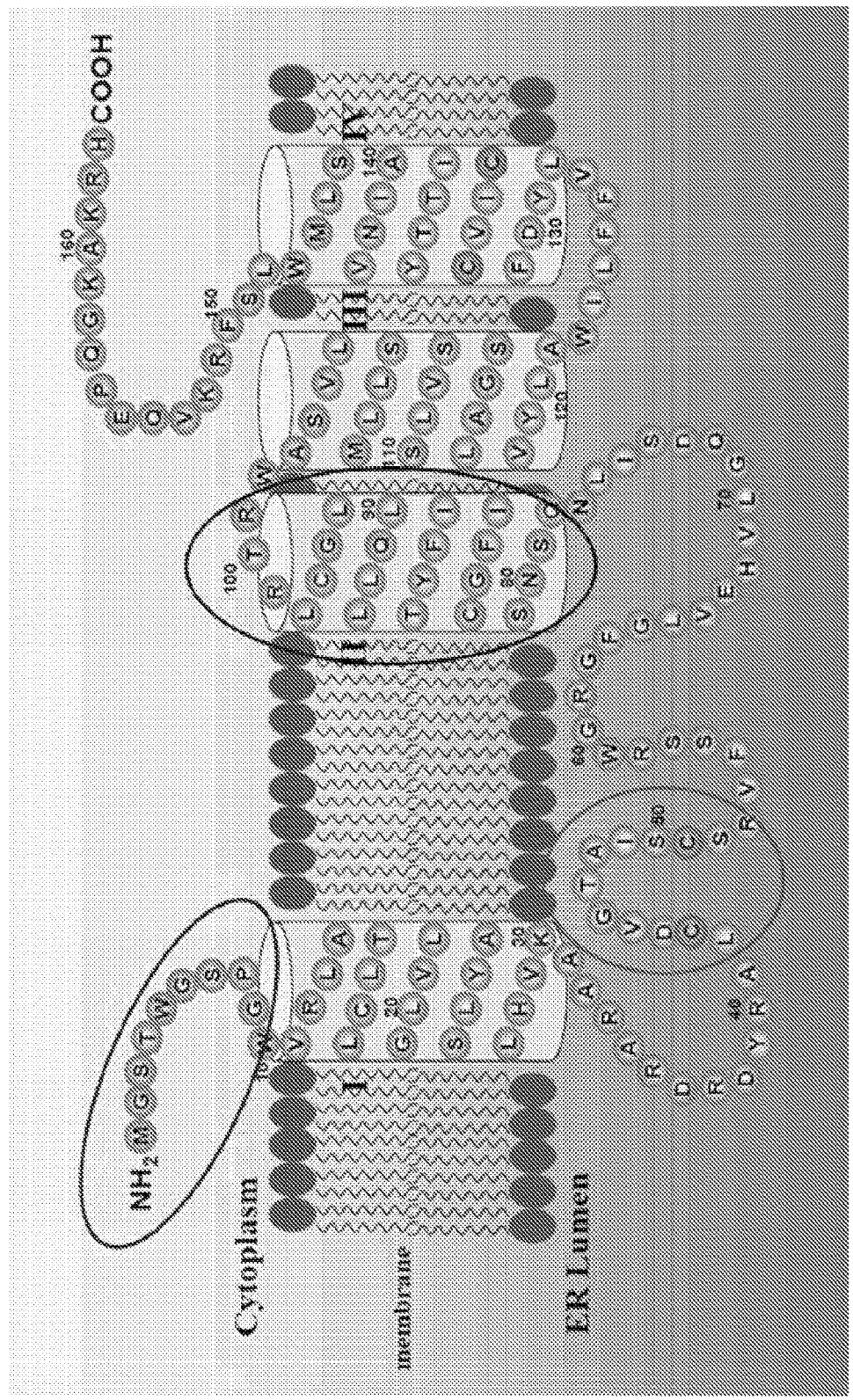

Results: The present results support the previously reported three-TMD model [see FIG. 29A (three TMD model) and FIG. 29B (four TMD model] suggesting that the N-terminus of VKOR is located in the ER lumen and the conserved cysteine loop is located in the cytoplasm. In addition, the membrane topology of the VKOR paralogue, VKORC1L1, has been examined. In contrast to VKOR, VKORC1L1 has four TMDs, which is similar to the membrane topology of the VKOR domain of *Synechococcus*. This topological model places the conserved cysteine loop in the ER lumen. Cell-based in vivo activity assays indicate that both VKOR and VKORC1L1 are active in the vitamin K cycle.

Conclusion: VKOR and VKORC1L1 have different membrane topologies. Whether the loop cysteines are located in the ER lumen or the cytoplasm, they are not directly involved in catalysis.

This aspect of the present invention is directed to modifying or mutating human VKOR to increase its ability to produce carboxylated vitamin K dependent proteins (e.g., increased amount of carboxylated vitamin K dependent proteins as compared to a human VKOR protein that does not have the modifications and/or mutations of this invention). Specifically, the charge distribution of several residues on either side of the first transmembrane domain has been changed. Since there are an excess of positive charges on what is believed to be the cytoplasmic side of the membrane, these residues have been altered in the following way; specifically arginines 33, 35, and 37 were changed to glycine and lysine 30 was changed to leucine. On the other side of the first transmembrane domain glycine 6, serine 7, and glycine 9 were changed to arginines. These changes appear to have changed the topology of human VKOR and also increase the ability of the human VKOR to carboxylate a vitamin K dependent reporter protein by approximately fourfold (see pages 67-69).

Figures 24, 25:
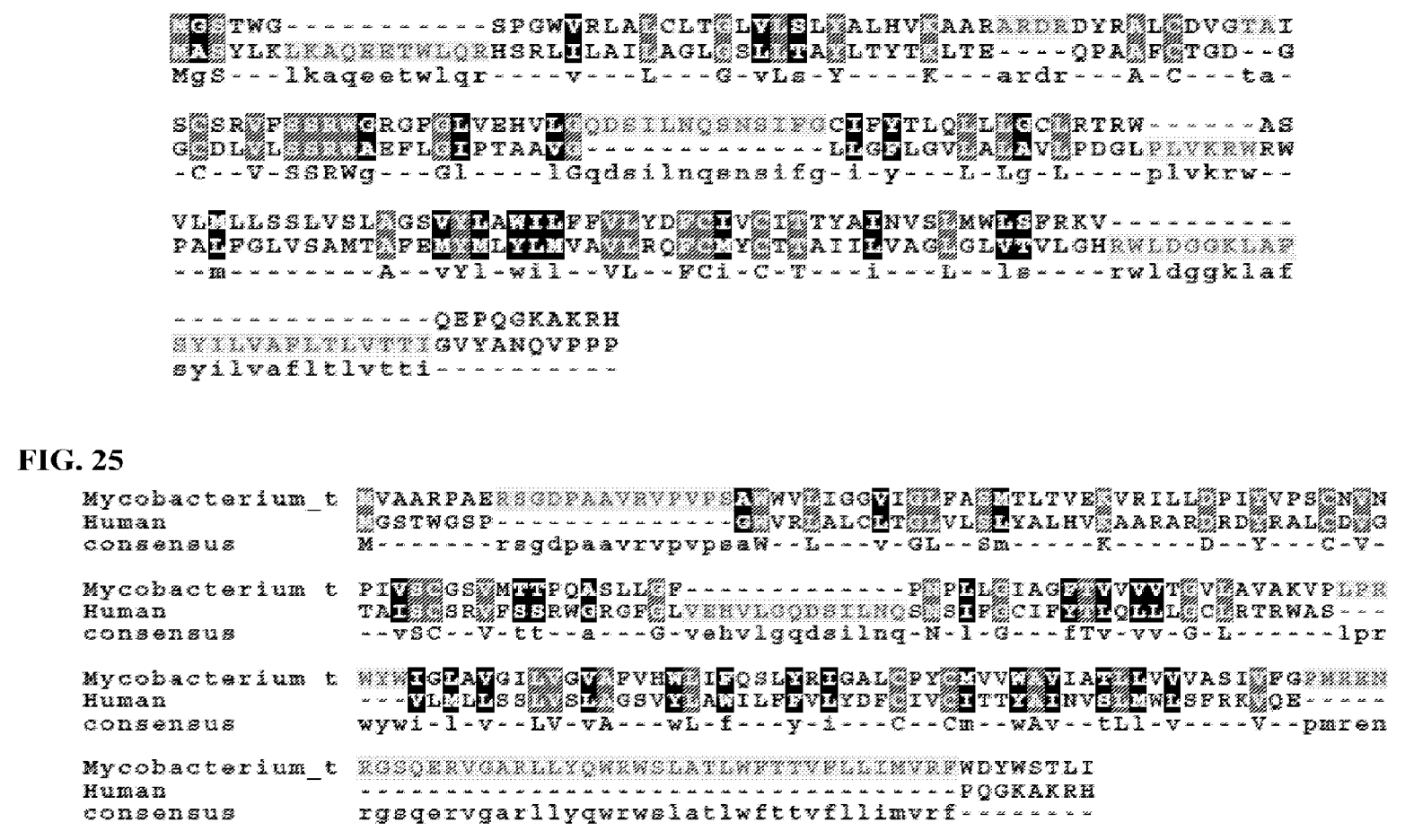
Figure 26:
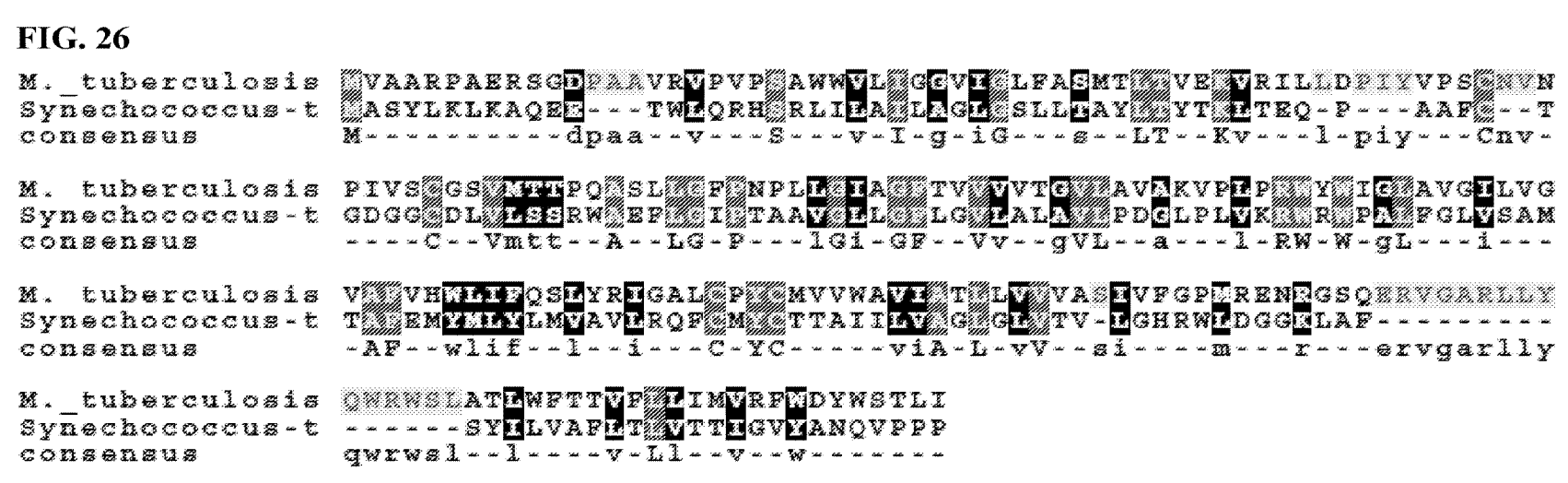
Figure 30A:
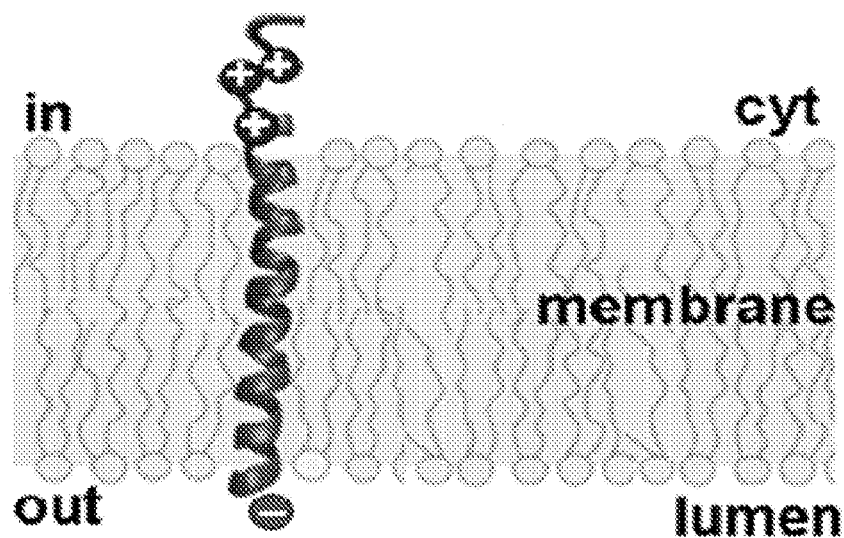
FIGS. 30A-B. Positive Inside Rule. The orientation of the transmembrane helix is primarily determined by the charged residues flanking the hydrophobic core.
Figure 30B:
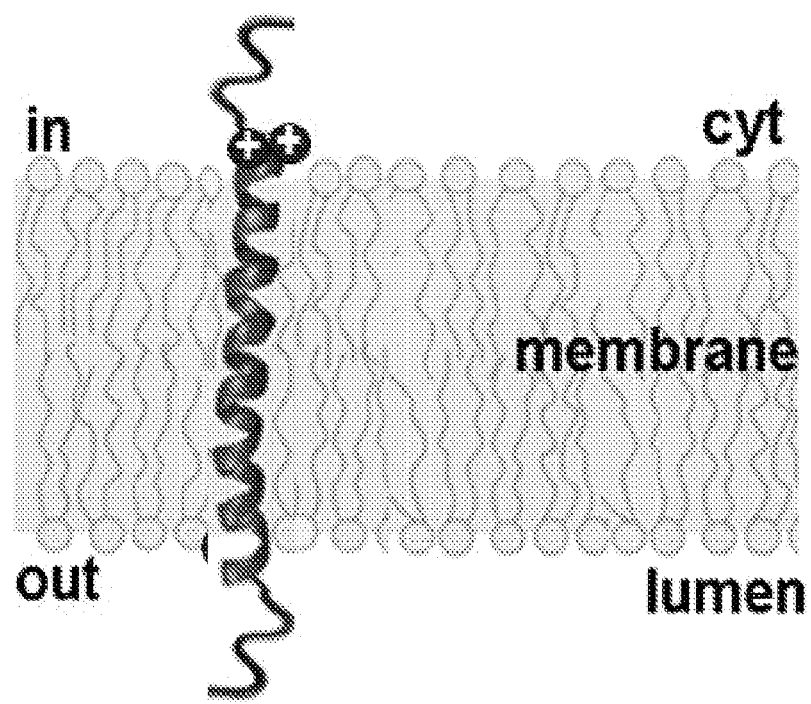

FIGS. 30A-B demonstrate the positive inside rule. The major discoveries relating to the positive inside rule were initiated by von Heijne. The orientation of the transmembrane helix is primarily determined by the charged residues flanking the hydrophobic core. Positively charged residues are four times more abundant on the cytoplasmic side (inside) of membrane proteins as compared to the trans side. Moving of the positively charged residue from the cytoplasmic side to the ER luminal side can result in inversion of TMD orientation. FIGS. 24, 25 and 26 show alignments of VKORs from human, *Mycobacterium* and *Synechococcus*. In human VKOR, there are five positive charges very close to TMD1 (see FIG. 31A) and there are three a little farther out in the human VKOR sequence. These charges indicate an excess of positive charges and indicate that this loop would likely reside in the cytoplasm. The VKOR sequence of *Synechococcus* has only two positive charges in the same segment and has four positive charges amino terminal to TMD1. Changing these residues is expected to result in a molecule with an altered amino terminus and altered transmembrane domain topology.

Figure 31A:
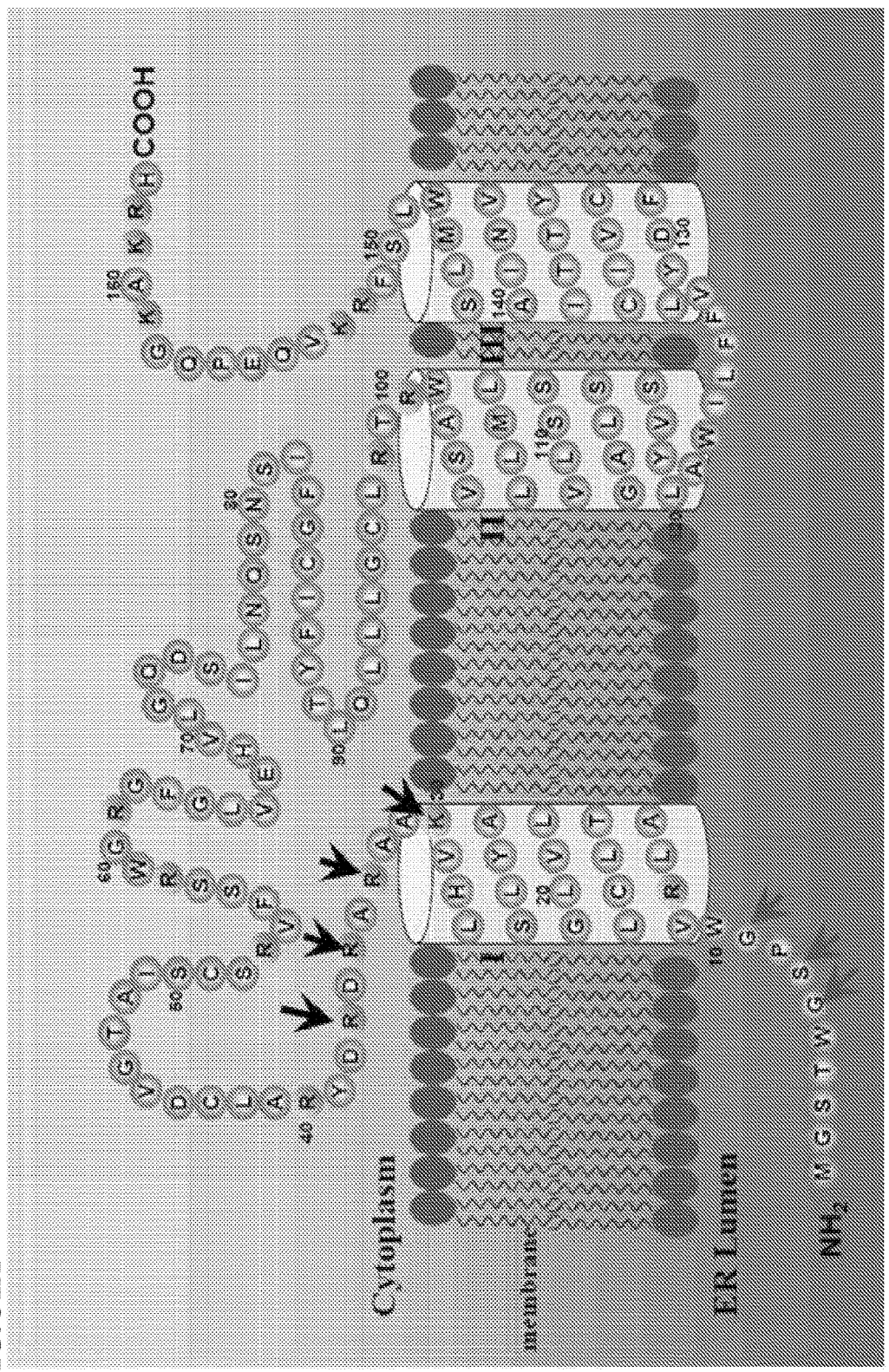
FIGS. 31A-C. Changing the charge distributions flanking TMD1 may alter the membrane topology of human VKOR (SEQ ID NO:5).
Figure 31B:
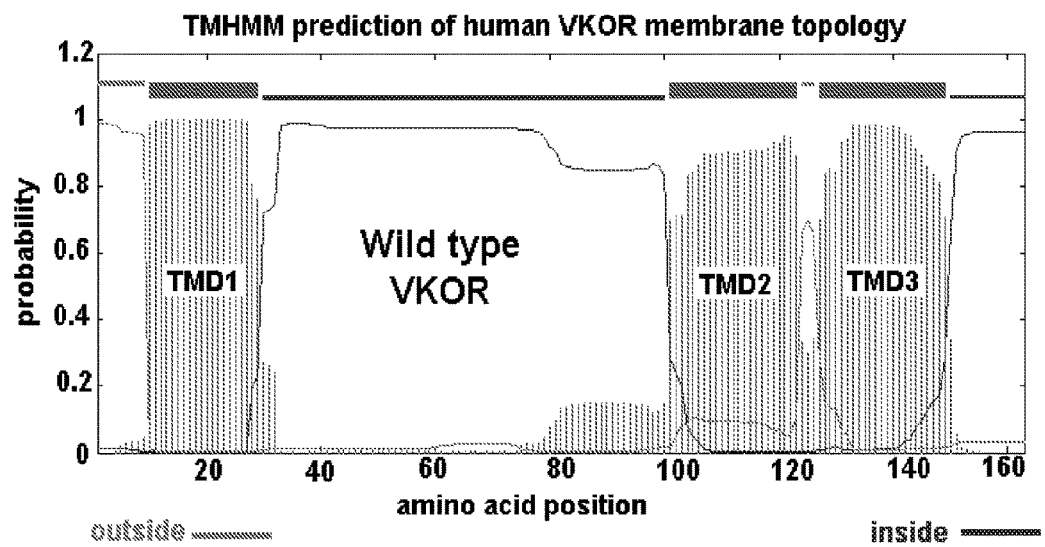
Figure 31C:
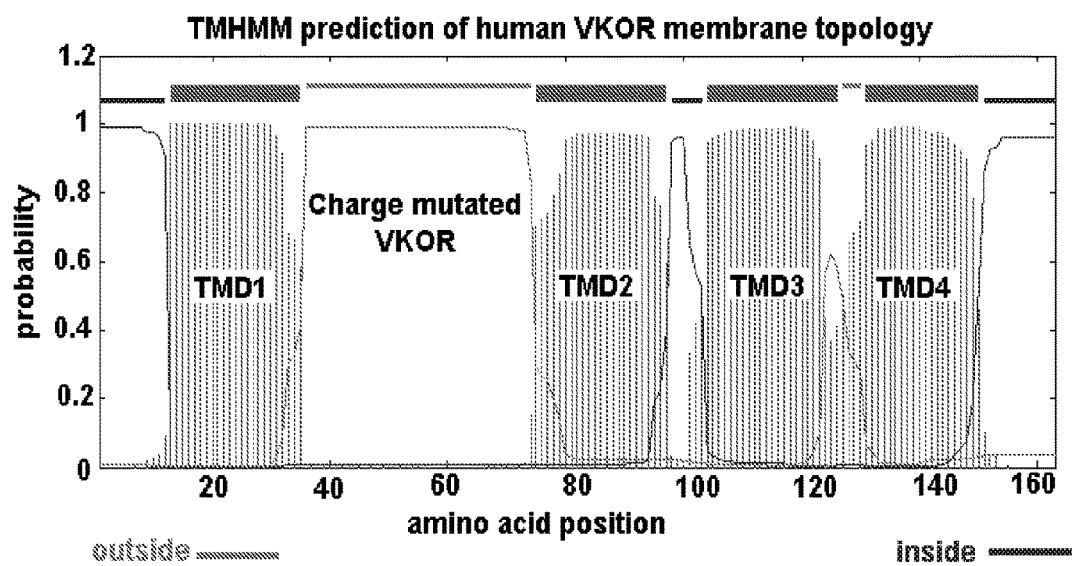

FIG. 31B shows the prediction of wild type human VKOR topologies and FIG. 31C shows the predicted topologies after mutations. In FIG. 31A, the residues that were changed are designated by arrows. These changes are described above.

Figure 32:
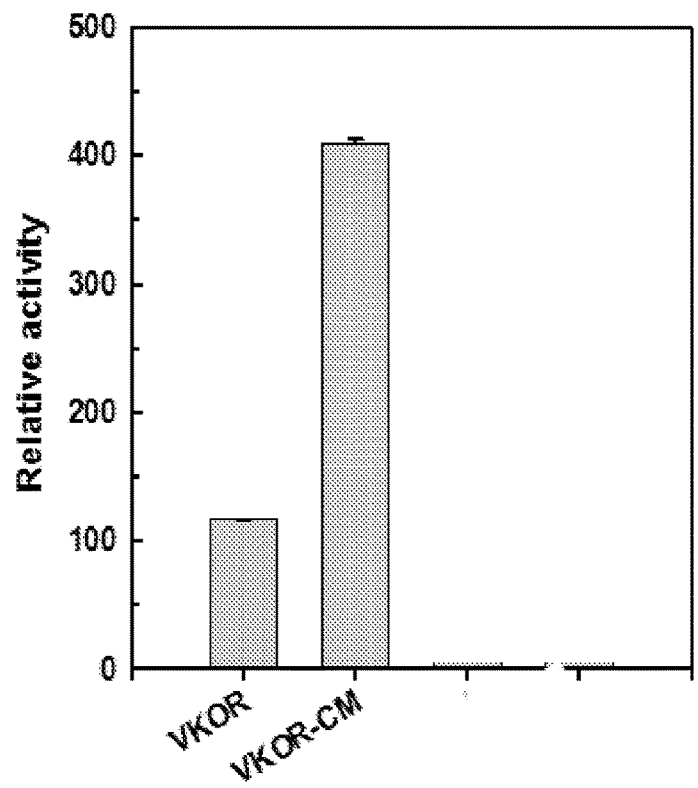

FIG. 32 shows that the mutations that were made convert human VKOR to a molecule about four times more active than wild type VKOR.

Figure 33:
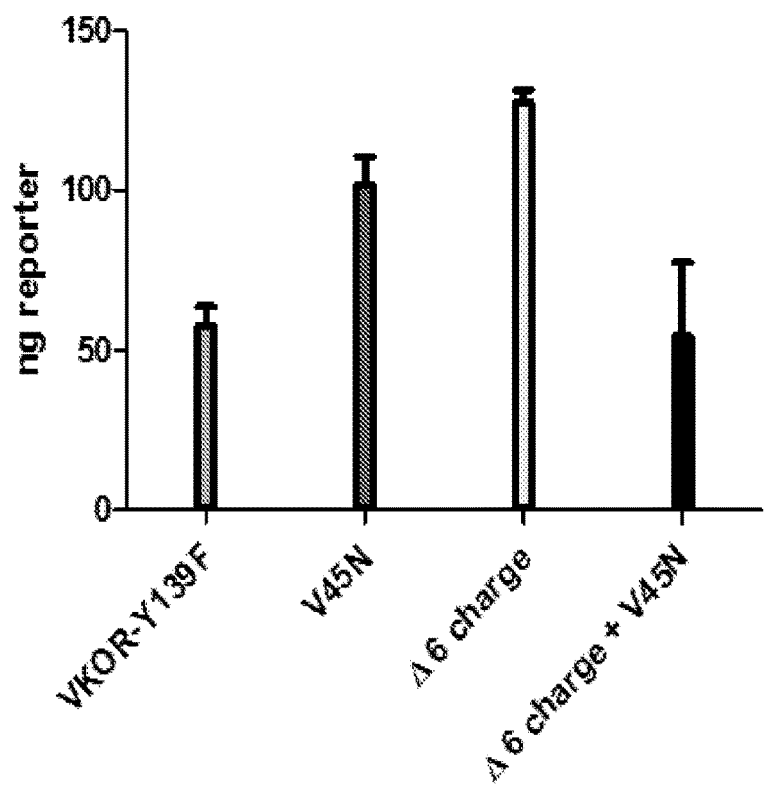
FIG. 33. Activity of human VKOR modified by a V45N substitution, which introduces an additional glycosylation site. Δ6 charge describes a human VKOR modified at six amino acid residues to alter the charge of the protein as described herein.

Further included in this invention is a human VKOR protein comprising a V45N substitution, which introduces an additional glycosylation site. A human VKOR protein comprising this substitution has increased carboxylation activity as shown in FIG. 33. This human VKOR can be employed in the methods of this invention. This human VKOR can comprise any of the mutations described herein in any combination.

Figure 23:
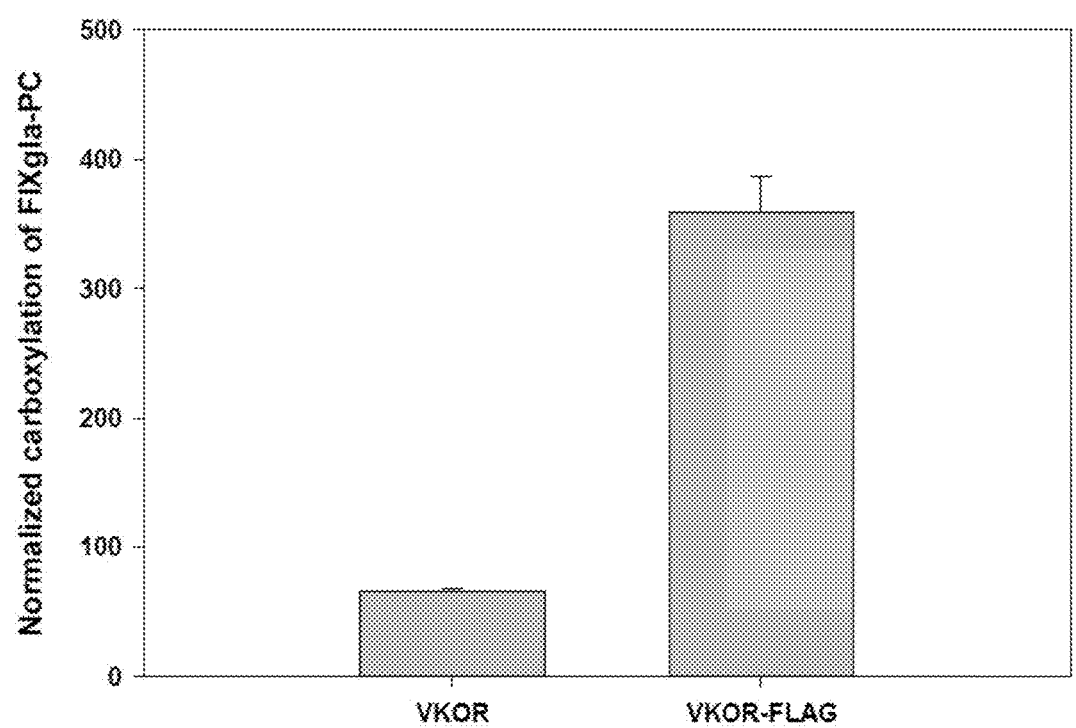
FIG. 23. Effect of exchange of FLAG tag with cysteine loop on VKOR activity. The VKOR cysteine loop sequence D44VGTAIS50 (amino acids 44-50 of the amino acid sequence of VKOR as provided, for example as GenBank® Database Accession No. AAS01052) was replaced with FLAG tag sequence DYKDDDDK (SEQ ID NO:37) and the resulting protein was tested for carboxylation activity as described herein.

Also included in this invention is a human VKOR protein comprising a substitution of amino acids 44-50 (DVGTAIS, SEQ ID NO:62) with the amino acid sequence DYKDDDDK (SEQ ID NO:37, FLAG tag sequence). The increased activity of this VKOR mutant is shown in FIG. 23.

The foregoing is illustrative of the present invention, and is not to be construed as limiting thereof. The invention is defined by the following claims, with equivalents of the claims to be included therein.

All publications, patent applications, patents, patent publications, GenBank® database accession numbers and other references cited herein are incorporated by reference in their entireties for the teachings relevant to the sentence and/or paragraph in which the reference is presented.

TABLE 1

| Organism | Compared to: | % Identity | Relative activity: Human Y139F |
|---|---|---|---|
| Human | *Mycobacterium tuberculosis* | 19.9 | Yes, greater |
| Human | *Acropora* | 46.1 | Yes, greater |
| Human | *Nematostella* | 47.1 | Yes, greater |
| Human | *Anopheles* | 38.8 | NA |
| Human | Hamster | ~80.0 | Yes, greater |
| Human | *Takifugu* | 45.7 | Yes, greater |
| Human | *Xenopus tropicalis* | 50.9 | Yes, greater |
| Human | Mouse | 83.0 | NA |
| Human | *Ciona* | 37.6 | Yes, greater |
| Human | *Amphioxus* | 38.7 | Yes, greater |
| Human | *Danio rerio* | 45.7 | NA |
| Human | Rat | 82.8 | NA |
| Human | *Drosophila* | 36.2 | NA |
| Human | Platypus | 44.6 | No |
| Human | *Trichoplax* | 42.3 | No |

TABLE 2

```
                                              (SEQ ID NO: 38)
Human                  122-WILFFVLYDFCIVCITTY-139

(SEQ ID NO: 43)
Roseiflexus sp. RS-1   300-FLEPFVIGATCLWCLTSA-317

(SEQ ID NO: 41)
Synechococcus          120-YLMVAVLRQFCMYCTTAI-137

(SEQ ID NO: 40)
Arabidopsis            185-ILSTKLSGSSCLYCLVSA-202

(SEQ ID NO: 39)
M tuberculosis         129-FQSLYRIGALCPYCMVVW-146

(SEQ ID NO: 42)
DsbB                    33-WFQHVMLLKPCVLCIYER- 50
```

That which is claimed is:

1. A method of increasing the amount of carboxylated vitamin K dependent protein in a mammalian cell, comprising introducing, into a mammalian cell that expresses a first nucleic acid encoding a vitamin K dependent protein, a second nucleic acid comprising a heterologous nucleotide sequence encoding vitamin K epoxide reductase (VKOR), wherein the heterologous nucleotide sequence encoding VKOR is a nucleotide sequence that encodes a *Nematostella* VKOR, under conditions whereby said first and second nucleic acids are expressed to produce a vitamin K dependent protein and VKOR, respectively, thereby increasing the amount of carboxylated vitamin K dependent protein in the mammalian cell.

2. The method of claim 1, wherein the cell further comprises a third nucleic acid comprising a heterologous nucleotide sequence encoding a vitamin K dependent carboxylase.

\* \* \* \* \*

UNITED STATES PATENT AND TRADEMARK OFFICE
CERTIFICATE OF CORRECTION

PATENT NO. : 9,631,002 B2
APPLICATION NO. : 13/997008
DATED : April 25, 2017
INVENTOR(S) : Tie et al.

Page 1 of 2

It is certified that error appears in the above-identified patent and that said Letters Patent is hereby corrected as shown below:

On the Title Page

Item [56]:
Page 7, Other Publications, Column 2, 17th entry:
  Insert -- Jin et al. "The Conversion of Vitamin K Epoxide to Vitamin K Quinone and Vitamin K Quinone to Vitamin K Hydroquionone Uses the Same Active Site Cysteines" *Biochemistry* 46:7279-7283 (2007) --

Page 7, Other Publications, Column 2, last entry:
  Delete "Accession No. AKQ13996.1" and insert -- Accession No. AK013996.1 --

Page 9, Other Publications, Column 1, 7th entry, Wallin et al.:
  Delete "Vitamin K-Dependent *6s* –Carboxylation" and insert -- Vitamin K-Dependent $\gamma$–Carboxylation --

In the Specification

Column 5, Line 24: Delete "10%, 200%, 30%" and insert -- 10%, 20%, 30% --

Column 20, Line 46: Delete "tion at 57 can" and insert -- tion at S7 can --

Column 35, (SEQ ID No: 3), Line 60: Insert the following to the last line of the sequence:
  -- VGLMLLNFQDVPEHKAKRH --

Column 40, Lines 21 and 22: Delete "amino acids DYKDDDDK (Flag tag)" and insert -- amino acids DYKDDDDK (SEQ ID No:37, Flag tag) --

Column 45, Line 40: Delete "L/well mouse" and insert -- µL/well mouse --

Signed and Sealed this
Fourteenth Day of August, 2018

Andrei Iancu
*Director of the United States Patent and Trademark Office*

Column 46, Line 18: Delete "AV12 cells (1×10)" and insert -- AV12 cells ($1\times10^7$) --

Column 49, Line 10: Delete "in vive." and insert -- in vivo. --

Column 55, Line 32: Delete "P61 and 162 were" and insert -- P61 and I62 were --

SEQUENCE LISTING

```
<160> NUMBER OF SEQ ID NOS: 62

<210> SEQ ID NO 1
<211> LENGTH: 161
<212> TYPE: PRT
<213> ORGANISM: Rattus norvegicus

<400> SEQUENCE: 1

Met Gly Thr Thr Trp Arg Ser Pro Gly Arg Leu Arg Leu Ala Leu Cys
1               5                   10                  15

Leu Ala Gly Leu Ala Leu Ser Leu Tyr Ala Leu His Val Lys Ala Ala
            20                  25                  30

Arg Ala Arg Asn Glu Asp Tyr Arg Ala Leu Cys Asp Val Gly Thr Ala
        35                  40                  45

Ile Ser Cys Ser Arg Val Phe Ser Ser Arg Trp Gly Arg Gly Phe Gly
    50                  55                  60

Leu Val Glu His Val Leu Gly Ala Asp Ser Ile Leu Asn Gln Ser Asn
65                  70                  75                  80

Ser Ile Phe Gly Cys Met Phe Tyr Thr Ile Gln Leu Leu Leu Gly Cys
                85                  90                  95

Leu Arg Gly Arg Trp Ala Ser Ile Leu Leu Ile Leu Ser Ser Leu Val
```

```
                  100                 105                 110
Ser Val Ala Gly Ser Leu Tyr Leu Ala Trp Ile Leu Phe Phe Val Leu
            115                 120                 125

Tyr Asp Phe Cys Ile Val Cys Ile Thr Thr Tyr Ala Ile Asn Ala Gly
            130                 135                 140

Leu Met Leu Leu Ser Phe Gln Lys Val Pro Glu His Lys Val Lys Lys
145                 150                 155                 160

Pro

<210> SEQ ID NO 2
<211> LENGTH: 161
<212> TYPE: PRT
<213> ORGANISM: Mus musculus

<400> SEQUENCE: 2

Met Gly Thr Thr Trp Arg Ser Pro Gly Leu Val Arg Leu Ala Leu Cys
1               5                   10                  15

Leu Ala Gly Leu Ala Leu Ser Leu Tyr Ala Leu His Val Lys Ala Ala
            20                  25                  30

Arg Ala Arg Asp Glu Asn Tyr Arg Ala Leu Cys Asp Val Gly Thr Ala
        35                  40                  45

Ile Ser Cys Ser Arg Val Phe Ser Ser Arg Trp Gly Arg Gly Phe Gly
50                  55                  60

Leu Val Glu His Met Leu Gly Ala Asp Ser Val Leu Asn Gln Ser Asn
65                  70                  75                  80

Ser Ile Phe Gly Cys Leu Phe Tyr Thr Leu Gln Leu Leu Leu Gly Cys
                85                  90                  95

Leu Arg Gly Arg Trp Ala Ser Ile Leu Leu Val Leu Ser Ser Leu Val
            100                 105                 110

Ser Val Ala Gly Ser Val Tyr Leu Ala Trp Ile Leu Phe Phe Val Leu
            115                 120                 125

Tyr Asp Phe Cys Ile Val Cys Ile Thr Thr Tyr Ala Ile Asn Val Gly
            130                 135                 140

Leu Met Leu Leu Ser Phe Gln Lys Val Pro Glu His Lys Thr Lys Lys
145                 150                 155                 160

His

<210> SEQ ID NO 3
<211> LENGTH: 160
<212> TYPE: PRT
<213> ORGANISM: Cricetulus griseus

<400> SEQUENCE: 3

Met Gly Thr Thr Trp Arg Ser Pro Gly Arg Trp Arg Leu Ala Leu Cys
1               5                   10                  15

Leu Ala Gly Leu Ala Leu Ser Leu Tyr Ala Leu His Val Lys Ala Ala
            20                  25                  30

Arg Ala Arg Asp Glu Asp Tyr Arg Ala Leu Cys Asp Val Gly Ser Ala
        35                  40                  45

Ile Ser Cys Ser Arg Val Phe Ser Ser Arg Trp Gly Lys Gly Leu Gly
50                  55                  60

Leu Val Glu His Val Leu Gly Pro Asp Ser Val Leu Asn Gln Asn Ser
65                  70                  75                  80

Ile Phe Gly Cys Ile Phe Tyr Thr Ile Gln Leu Leu Leu Gly Cys Leu
                85                  90                  95
```

```
Arg Gly Arg Trp Ala Phe Leu Leu Val Leu Ser Ser Leu Val Ser
            100                 105                 110

Phe Ala Gly Ser Val Tyr Leu Ala Trp Ile Leu Phe Val Leu Tyr
        115                 120                 125

Asp Phe Cys Ile Val Cys Ile Thr Thr Tyr Val Ile Asn Val Gly Leu
130                 135                 140

Met Leu Leu Asn Phe Gln Asp Val Pro Glu His Lys Ala Lys Arg His
145                 150                 155                 160

<210> SEQ ID NO 4
<211> LENGTH: 161
<212> TYPE: PRT
<213> ORGANISM: Cricetulus griseus

<400> SEQUENCE: 4

Met Gly Thr Thr Trp Arg Ser Pro Gly Arg Arg Leu Ala Leu Cys
1               5                   10                  15

Leu Ala Gly Leu Ala Leu Ser Leu Tyr Ala Leu His Val Lys Ala Ala
            20                  25                  30

Arg Ala Arg Asp Glu Asp Tyr Arg Ala Leu Cys Asp Val Gly Thr Ala
        35                  40                  45

Ile Ser Cys Ser Arg Val Phe Ser Ser Arg Trp Gly Lys Gly Phe Gly
    50                  55                  60

Leu Val Glu His Val Leu Gly Ser Asp Ser Val Leu Asn Gln Ser Asn
65                  70                  75                  80

Ser Ile Phe Gly Cys Ile Phe Tyr Thr Ile Gln Leu Leu Leu Gly Cys
                85                  90                  95

Leu Arg Gly Arg Trp Ala Ser Leu Leu Val Leu Ser Ser Leu Val
            100                 105                 110

Ser Phe Ala Gly Ser Val Tyr Leu Ala Trp Ile Leu Phe Phe Val Leu
        115                 120                 125

Tyr Asp Phe Cys Ile Val Cys Ile Thr Thr Tyr Ala Ile Asn Val Gly
    130                 135                 140

Leu Met Leu Leu Asn Phe Gln Glu Val Pro Glu His Lys Ala Lys Arg
145                 150                 155                 160

Pro

<210> SEQ ID NO 5
<211> LENGTH: 163
<212> TYPE: PRT
<213> ORGANISM: Homo sapiens

<400> SEQUENCE: 5

Met Gly Ser Thr Trp Gly Ser Pro Gly Trp Val Arg Leu Ala Leu Cys
1               5                   10                  15

Leu Thr Gly Leu Val Leu Ser Leu Tyr Ala Leu His Val Lys Ala Ala
            20                  25                  30

Arg Ala Arg Asp Arg Asp Tyr Arg Ala Leu Cys Asp Val Gly Thr Ala
        35                  40                  45

Ile Ser Cys Ser Arg Val Phe Ser Ser Arg Trp Gly Arg Gly Phe Gly
    50                  55                  60

Leu Val Glu His Val Leu Gly Gln Asp Ser Ile Leu Asn Gln Ser Asn
65                  70                  75                  80

Ser Ile Phe Gly Cys Ile Phe Tyr Thr Leu Gln Leu Leu Leu Gly Cys
                85                  90                  95

Leu Arg Thr Arg Trp Ala Ser Val Leu Met Leu Leu Ser Ser Leu Val
```

```
              100                 105                 110
Ser Leu Ala Gly Ser Val Tyr Leu Ala Trp Ile Leu Phe Val Leu
            115                 120                 125

Tyr Asp Phe Cys Ile Val Cys Ile Thr Thr Tyr Ala Ile Asn Val Ser
130                 135                 140

Leu Met Trp Leu Ser Phe Arg Lys Val Gln Glu Pro Gln Gly Lys Ala
145                 150                 155                 160

Lys Arg His

<210> SEQ ID NO 6
<211> LENGTH: 171
<212> TYPE: PRT
<213> ORGANISM: Danio rerio

<400> SEQUENCE: 6

Met Ser Ser His Ser Ala Ser Gly Val Pro Lys Trp Glu Phe Arg Val
1               5                   10                  15

Arg Leu Ile Leu Cys Ile Leu Gly Leu Val Leu Ser Val Tyr Ala Leu
            20                  25                  30

His Val Glu Leu Ser Arg Glu Asn Asn Pro Glu Tyr Arg Ala Met Cys
        35                  40                  45

Asp Leu Gly Asn Ser Val Ser Cys Ser Lys Val Phe Thr Ser Arg Trp
50                  55                  60

Gly Arg Gly Phe Gly Leu Val Gln Ile Phe Thr Ser Lys Asp Ser Val
65                  70                  75                  80

Leu Asn Gln Pro Asn Ser Val Leu Gly Ile Ile Phe Tyr Thr Leu Gln
                85                  90                  95

Leu Gly Leu Gly Gln Thr Val Ser Ser Arg Ala Gly Phe Phe Leu Val
            100                 105                 110

Met Ser Ser Trp Val Ser Val Ala Gly Ser Val Tyr Leu Ala Ser Ile
        115                 120                 125

Leu Ala Phe Val Leu Gly Asp Phe Cys Val Val Cys Ser Thr Tyr
    130                 135                 140

Ile Ile Asn Phe Ala Leu Leu Tyr Thr Asn Leu Lys Arg Arg Thr Gly
145                 150                 155                 160

Leu Glu Ala Arg Leu Lys Lys Gly Lys Ser Gln
                165                 170

<210> SEQ ID NO 7
<211> LENGTH: 163
<212> TYPE: PRT
<213> ORGANISM: Takifugu rubripes

<400> SEQUENCE: 7

Met Ala Ile Pro Thr Trp Glu Arg Lys Val Arg Ile Phe Leu Cys Val
1               5                   10                  15

Phe Gly Leu Leu Leu Ser Val Tyr Ala Leu His Val Glu Leu Ser Arg
            20                  25                  30

Glu Arg Asn Pro Asp Tyr Arg Ala Met Cys Asp Leu Gly Glu Ser Val
        35                  40                  45

Ser Cys Ser Lys Val Phe Ser Arg Trp Gly Arg Gly Phe Gly Leu
    50                  55                  60

Val Gln Tyr Phe Val Asp Lys Asp Ser Pro Leu Asn Gln Pro Asn Ser
65                  70                  75                  80

Val Leu Gly Ile Ile Phe Tyr Thr Leu Gln Met Cys Leu Gly Leu Ser
                85                  90                  95
```

-continued

```
Leu Ser Arg Lys Ala Ala Leu Phe Leu Val Phe Ser Ser Trp Val Ser
            100                 105                 110

Val Ala Gly Ser Leu Tyr Leu Ala Ser Ile Leu Ala Phe Val Leu Gly
            115                 120                 125

Asp Phe Cys Met Val Cys Val Ser Thr Tyr Leu Val Asn Phe Val Leu
            130                 135                 140

Leu Phe Thr Asn Leu Lys Arg Arg Ala Ile Glu Gly Leu Lys Glu
145                 150                 155                 160

Lys Ser Gly

<210> SEQ ID NO 8
<211> LENGTH: 169
<212> TYPE: PRT
<213> ORGANISM: Xenopus (Silurana) tropicalis

<400> SEQUENCE: 8

Met Ala Val Pro Gly Trp Glu Arg Ala Val Arg Leu Leu Leu Cys Gly
1               5                   10                  15

Val Gly Ile Ala Leu Ser Val Tyr Ala Tyr His Val Glu Thr Ser Arg
            20                  25                  30

Glu Arg Asp Ala Asn Tyr Thr Ala Leu Cys Asp Ile Asn Pro Ser Ile
        35                  40                  45

Ser Cys Ser Lys Val Phe Thr Ser Arg Trp Gly Arg Gly Phe Gly Leu
    50                  55                  60

Val Glu Gln Ile Leu Gly Arg Gln Ser Phe Leu Asn Gln Pro Asn Ser
65                  70                  75                  80

Val Phe Gly Ile Leu Phe Tyr Gly Leu Gln Val Leu Leu Gly Phe Ser
                85                  90                  95

Gly Ser Val Gly Ala Ala Ala Leu Leu Gly Thr Ser Leu Val Ser
            100                 105                 110

Ile Ala Gly Ser Leu Tyr Leu Ala Tyr Ile Leu Phe Tyr Val Leu Glu
            115                 120                 125

Asp Phe Cys Val Ile Cys Val Thr Thr Tyr Ala Leu Asn Phe Cys Leu
            130                 135                 140

Leu Leu Leu Asn Leu Lys Arg Leu Ala Ser Leu Arg Ala Pro Pro Lys
145                 150                 155                 160

Lys Gln Lys Asn Lys Arg Lys Lys Asn
                165

<210> SEQ ID NO 9
<211> LENGTH: 164
<212> TYPE: PRT
<213> ORGANISM: Acropora millepora

<400> SEQUENCE: 9

Met Val Ser Phe Leu Gly Ile Ser Arg Leu Leu Val Cys Leu Ala Gly
1               5                   10                  15

Ile Ala Leu Ser Ile Tyr Ala Leu His Val Glu Leu Ser Lys Ala His
            20                  25                  30

Asp Lys Asp Tyr Lys Ala Leu Cys Asp Ile Asn Glu His Met Ser Cys
        35                  40                  45

Ser Lys Val Phe Thr Ser Lys Tyr Gly Thr Gly Phe Gly Leu Val Glu
    50                  55                  60

Pro Leu Leu Gly Lys Asn His Pro Phe Asn Val Pro Asn Ser Ile Phe
65                  70                  75                  80
```

```
Gly Ile Ile Phe Tyr Ser Leu Ile Ile Leu Gly Val Val Ser Gly
                85                  90                  95

Lys Phe Ala Ala Leu Met Met Phe Leu Phe Ser Leu Ala Ser Cys Val
            100                 105                 110

Gly Ser Val Tyr Leu Gly Tyr Ile Leu Phe Tyr Ile Leu His Asp Thr
            115                 120                 125

Cys Val Val Cys Ile Ser Thr Tyr Val Val Asn Ala Cys Leu Phe Val
            130                 135                 140

Ile Asn Met Ile Thr Leu Asn Asp Ala Leu Ser Ala Pro Ser Pro Lys
145                 150                 155                 160

Lys Lys Lys Asn
```

<210> SEQ ID NO 10
<211> LENGTH: 161
<212> TYPE: PRT
<213> ORGANISM: Nematostella vectensis

<400> SEQUENCE: 10

```
Met Asp Lys Leu Gly Gly Phe Arg Met Met Leu Cys Val Ala Gly Val
1               5                   10                  15

Phe Leu Ser Ala Tyr Ala Leu Asn Val Glu Val Ser Lys Ser Asn Asn
            20                  25                  30

Lys Asp Tyr Arg Ala Ile Cys Asp Ile Ser Glu Lys Ile Ser Cys Ser
        35                  40                  45

Lys Val Phe Ser Ser Lys Tyr Gly Thr Gly Phe Gly Leu Val Glu Pro
50                  55                  60

Ile Phe Gly Lys Asp Ser Thr Leu Asn Val Pro Asn Ser Ile Phe Gly
65                  70                  75                  80

Ile Met Phe Tyr Thr Met Val Phe Leu Leu Gly Phe Ser Arg Ser Lys
                85                  90                  95

Leu Ala Ala Gln Leu Ser Val Phe Ser Ala Val Leu Ser Cys Leu Gly
            100                 105                 110

Ser Val Tyr Leu Gly Cys Ile Leu Tyr Phe Val Leu Gln Asp Val Cys
            115                 120                 125

Ile Ile Cys Ile Ser Thr Tyr Val Val Asn Ala Cys Leu Leu Val Val
            130                 135                 140

Asn Ser Leu Ser Leu Val Asn Leu Gln Glu Arg Thr Lys Arg Lys Gln
145                 150                 155                 160

Lys
```

<210> SEQ ID NO 11
<211> LENGTH: 170
<212> TYPE: PRT
<213> ORGANISM: Branchiostoma floridae

<400> SEQUENCE: 11

```
Met Ala Ala Gly Arg Ser Phe Arg Leu Pro Ile Trp Glu Ile Leu Ser
1               5                   10                  15

Arg Cys Met Leu Cys Thr Ala Gly Leu Val Leu Ser Gly Tyr Ala Phe
            20                  25                  30

Tyr Val Glu Thr Ser Lys Glu Ala Asp His Ser Tyr Thr Ala Met Cys
        35                  40                  45

Asp Val Ser Glu Ser Val Ser Cys Ser Lys Val Phe Thr Ser Arg Phe
50                  55                  60

Gly Arg Gly Phe Gly Leu Val Glu Pro Ile Leu Gly Ala Asp Ser Pro
65                  70                  75                  80
```

```
Leu Asn Leu Pro Asn Ser Ile Phe Gly Leu Ala Phe Tyr Ile Met Gln
                85                  90                  95

Leu Cys Leu Gly Val Val Pro Gly Met Ser Val Ser Ile Val Leu Leu
            100                 105                 110

Ala Thr Ser Val Leu Ser Cys Leu Gly Cys Val Tyr Leu Ala Tyr Ile
        115                 120                 125

Leu Tyr Phe Ile Leu Gln Asp Ala Cys Ile Val Cys Ile Ser Thr Tyr
    130                 135                 140

Val Val Asn Thr Phe Met Leu Ile Val Asn Ile Lys Arg Val Leu Leu
145                 150                 155                 160

Gln Arg Lys Ala Ile Leu Lys Lys Gln Gln
                165                 170

<210> SEQ ID NO 12
<211> LENGTH: 170
<212> TYPE: PRT
<213> ORGANISM: Branchiostoma floridae

<400> SEQUENCE: 12

Met Ala Ala Gly Arg Ser Phe Arg Leu Pro Ile Trp Glu Ile Leu Ser
1               5                   10                  15

Arg Cys Met Leu Cys Thr Ala Gly Leu Val Leu Ser Gly Tyr Ala Phe
            20                  25                  30

Tyr Val Glu Thr Ser Lys Glu Ala Asp His Ser Tyr Thr Ala Met Cys
        35                  40                  45

Asp Val Ser Glu Ser Val Ser Cys Ser Lys Val Phe Thr Ser Arg Phe
    50                  55                  60

Gly Arg Gly Phe Gly Leu Val Glu Pro Ile Leu Gly Ala Asp Ser Pro
65                  70                  75                  80

Leu Asn Leu Pro Asn Ser Ile Phe Gly Leu Ala Phe Tyr Ile Met Gln
                85                  90                  95

Leu Cys Leu Gly Val Val Pro Gly Met Ser Val Ser Ile Val Leu Leu
            100                 105                 110

Ala Thr Ser Val Leu Ser Cys Leu Gly Cys Val Tyr Leu Ala Tyr Ile
        115                 120                 125

Leu Tyr Phe Ile Leu Gln Asp Ala Cys Ile Val Cys Ile Ser Thr Tyr
    130                 135                 140

Val Val Asn Thr Leu Met Leu Val Val Asn Ile Lys Arg Val Leu Leu
145                 150                 155                 160

Gln Arg Lys Ala Leu Leu Lys Lys Gln Gln
                165                 170

<210> SEQ ID NO 13
<211> LENGTH: 158
<212> TYPE: PRT
<213> ORGANISM: Ciona intestinalis

<400> SEQUENCE: 13

Met Asn Lys Leu Leu Ala Phe Arg Ile Leu Val Cys Val Ile Gly Ile
1               5                   10                  15

Ile Leu Ser Ile Tyr Ala Tyr Tyr Val Glu Val Ala Lys Thr Asn Asp
            20                  25                  30

Leu Ser Tyr Glu Ala Leu Cys Asp Phe Asn Asp Val Val Ser Cys Ser
        35                  40                  45

Ala Val Phe Ser Ser Arg Tyr Gly Lys Gly Leu Leu Glu Tyr Leu Val
    50                  55                  60
```

Gly Glu Asn His Phe Leu Asn Gln Pro Asn Ser Leu Phe Gly Ile Gly
65                  70                  75                  80

Phe Phe Ser Ile Gln Met Leu Gly Ile Ser Pro Met Asn Lys Thr Phe
                85                  90                  95

Asn Tyr Val Leu Tyr Ile Leu Thr Gly Gly Gly Ile Val Thr Ser Ile
            100                 105                 110

Tyr Leu Ala Cys Ile Leu Ile Phe Val Leu Lys Asp Phe Cys Val Leu
        115                 120                 125

Cys Val Ser Thr Tyr Val Leu Thr Ile Ile Leu His Tyr Leu Asn Tyr
130                 135                 140

Lys Leu Leu His His Asn Val Asn Ser His Lys Lys Ile Asn
145                 150                 155

<210> SEQ ID NO 14
<211> LENGTH: 176
<212> TYPE: PRT
<213> ORGANISM: Anopheles gambiae

<400> SEQUENCE: 14

Met Ser Ile Leu Ala Gly Asn Cys Lys Cys Thr Tyr Thr Leu Ala Leu
1               5                   10                  15

Val Gly Leu Ser Val Cys Gly Phe Leu Leu Ser Leu Tyr Thr Ser Tyr
            20                  25                  30

Val Glu Leu Arg Ala Glu His Asp His Thr Tyr Gln Ala Met Cys Asp
        35                  40                  45

Ile Ser Glu Arg Ile Ser Cys Thr Lys Val Phe Thr Ser Arg Tyr Gly
    50                  55                  60

Arg Gly Phe Gly Ile Val Gly Pro Leu Gly Asp Asp Ser Leu Leu
65                  70                  75                  80

Asn Val Pro Asn Gly Phe Tyr Gly Ile Phe Tyr Tyr Phe Leu Val Ala
                85                  90                  95

Gly Leu Ser Phe Ser Asn Asn Leu Ala Val Ser Arg Leu Thr Ser Tyr
            100                 105                 110

Leu Ile Leu Leu Ser Asn Gly Leu Ser Leu Tyr Leu Ala Tyr Leu Leu
        115                 120                 125

Tyr Phe Val Leu Gln Asp Met Cys Val Val Cys Val Thr Thr Tyr Ala
130                 135                 140

Val Asn Leu Val Ser Leu Ile Leu Ala Leu Gln Lys Ile Gln Ala Leu
145                 150                 155                 160

Ile Arg Glu Glu Gln Val Met Arg Ala Leu Lys Val Gly Lys Ala Lys
                165                 170                 175

<210> SEQ ID NO 15
<211> LENGTH: 170
<212> TYPE: PRT
<213> ORGANISM: Trichoplax adhaerens

<400> SEQUENCE: 15

Met Ala Ala Gly Arg Ser Phe Arg Leu Pro Ile Trp Glu Ile Leu Ser
1               5                   10                  15

Arg Cys Met Leu Cys Thr Ala Gly Leu Val Leu Ser Gly Tyr Ala Phe
            20                  25                  30

Tyr Val Glu Thr Ser Lys Glu Ala Asp His Ser Tyr Thr Ala Met Cys
        35                  40                  45

Asp Val Ser Glu Ser Val Ser Cys Ser Lys Val Phe Thr Ser Arg Phe
    50                  55                  60

```
Gly Arg Gly Phe Gly Leu Val Glu Pro Ile Leu Gly Ala Asp Ser Pro
 65                  70                  75                  80

Leu Asn Leu Pro Asn Ser Ile Phe Gly Leu Ala Phe Tyr Ile Met Gln
                 85                  90                  95

Leu Cys Leu Gly Val Val Pro Gly Met Ser Val Ser Ile Val Leu Leu
            100                 105                 110

Ala Thr Ser Val Leu Ser Cys Leu Gly Cys Val Tyr Leu Ala Tyr Ile
        115                 120                 125

Leu Tyr Phe Ile Leu Gln Asp Ala Cys Ile Val Cys Ile Ser Thr Tyr
    130                 135                 140

Val Val Asn Thr Leu Met Leu Val Val Asn Ile Lys Arg Val Leu Leu
145                 150                 155                 160

Gln Arg Lys Ala Leu Leu Lys Lys Gln Gln
                165                 170

<210> SEQ ID NO 16
<211> LENGTH: 187
<212> TYPE: PRT
<213> ORGANISM: Ornithorhynchus anatinus

<400> SEQUENCE: 16

Met Gly Ala Trp Val Pro Thr Arg Ser Ala Arg Val Val Gly Pro Arg
1                5                  10                  15

Ala Leu Gly Ser Arg Val Ala Thr Ala Val Gln Pro Ser Ala Val Asp
            20                  25                  30

Pro Asp Thr Arg His Asp Arg Ile Pro Ser Leu Arg Trp Gly Arg Gly
        35                  40                  45

Phe Gly Leu Val Glu Met Val Leu Gly Pro Asp Ser Ser Leu Asn Gln
    50                  55                  60

Pro Asn Ser Val Phe Gly Leu Leu Phe Tyr Ser Leu Gln Leu Leu Leu
65                  70                  75                  80

Gly Cys Ser Arg Ala Pro Trp Thr Ser Val Val Leu Ala Leu Ser Ser
                85                  90                  95

Leu Leu Ser Leu Ala Gly Ser Leu Tyr Leu Ala Trp Ile Leu Phe Phe
            100                 105                 110

Val Leu His Asp Phe Cys Phe Val Cys Ile Thr Thr Tyr Ala Ile Asn
        115                 120                 125

Val Gly Leu Ala Leu Leu Asn Tyr Arg Arg Leu Lys Gln Ala Gln Gly
    130                 135                 140

Lys Val Met Lys Tyr Cys Asp Glu Ser Ser Pro Ala Ser Ser Leu Leu
145                 150                 155                 160

Glu Arg Arg Phe Tyr Ser Gly Gly Leu Arg Asn Gly Gly Ser Ala
                165                 170                 175

Ala Ser Phe Pro Phe Pro Pro Ala Thr Gly His
            180                 185

<210> SEQ ID NO 17
<211> LENGTH: 152
<212> TYPE: PRT
<213> ORGANISM: Drosophila melanogaster

<400> SEQUENCE: 17

Met Glu Gln Ala Tyr Ser Thr Ala Ser Arg Leu Arg Gly Ile Cys Val
1                5                  10                  15

Cys Gly Leu Ala Ile Ser Val Tyr Ser Leu Tyr Val Lys Met Lys Leu
            20                  25                  30
```

```
Lys Glu Asp Glu Asn Tyr Arg Pro Met Cys Asp Val Asn Asp Asn Ile
        35                  40                  45

Ser Cys Ser Leu Val Phe Lys Ser Gly Tyr Gly Asp Gly Phe Gly Leu
 50                  55                  60

Gly Asn Ile Thr Gln Val Asn Ala Pro Asn Gly Ala Ile Gly Cys Ala
65                   70                  75                  80

Phe Tyr Ile Leu Tyr Phe Leu Ser Ser Phe Phe Asn His Arg Trp Leu
                85                  90                  95

Cys Leu Val Gln Leu Ile Val Cys Thr Leu Thr Leu Leu Cys Val
                100                 105                 110

Tyr Leu Gly Phe Leu Leu Ile Leu Val Phe Tyr Asp Phe Cys Leu Val
            115                 120                 125

Cys Val Thr Ile Tyr Phe Ile His Thr Trp Leu Phe Gln Glu Val Leu
        130                 135                 140

Arg Arg Tyr Arg Arg Leu Tyr Met
145                 150

<210> SEQ ID NO 18
<211> LENGTH: 209
<212> TYPE: PRT
<213> ORGANISM: Mycobacterium tuberculosis

<400> SEQUENCE: 18

Met Val Ala Ala Arg Pro Ala Glu Arg Ser Gly Asp Pro Ala Ala Val
1               5                   10                  15

Arg Val Pro Val Pro Ser Ala Trp Trp Val Leu Ile Gly Gly Val Ile
            20                  25                  30

Gly Leu Phe Ala Ser Met Thr Leu Thr Val Glu Lys Val Arg Ile Leu
        35                  40                  45

Leu Asp Pro Ile Tyr Val Pro Ser Cys Asn Val Asn Pro Ile Val Ser
 50                  55                  60

Cys Gly Ser Val Met Thr Thr Pro Gln Ala Ser Leu Leu Gly Phe Pro
65                   70                  75                  80

Asn Pro Leu Leu Gly Ile Ala Gly Phe Thr Val Val Val Val Thr Gly
                85                  90                  95

Val Leu Ala Val Ala Lys Val Pro Leu Pro Arg Trp Tyr Trp Ile Gly
            100                 105                 110

Leu Ala Val Gly Ile Leu Val Gly Val Ala Phe Val His Trp Leu Ile
        115                 120                 125

Phe Gln Ser Leu Tyr Arg Ile Gly Ala Leu Cys Pro Tyr Cys Met Val
    130                 135                 140

Val Trp Ala Val Ile Ala Thr Leu Leu Val Val Val Ala Ser Ile Val
145                 150                 155                 160

Phe Gly Pro Met Arg Glu Asn Arg Gly Ser Gln Arg Val Gly Ala
                165                 170                 175

Arg Leu Tyr Gln Trp Arg Trp Ser Leu Ala Thr Leu Trp Phe Thr
            180                 185                 190

Thr Val Phe Leu Leu Ile Met Val Arg Phe Trp Asp Tyr Ser Thr Leu
        195                 200                 205

Ile

<210> SEQ ID NO 19
<211> LENGTH: 350
<212> TYPE: PRT
<213> ORGANISM: Arabidopsis thaliana
```

<400> SEQUENCE: 19

```
Met Met Ala Arg Phe Val Ser Val Ser Ser Cys Gln Phe His Phe Gly
1               5                   10                  15

Phe Arg Glu Val Ser Pro Pro Ser Val Thr Ser Tyr Pro Arg Arg Phe
            20                  25                  30

Glu Val Ser Asp Arg Arg Phe Pro Ala Ile Pro Ile Lys Cys Ser Ser
        35                  40                  45

Ser Glu Pro Glu Asn Gly Glu Asp Ser Ala Pro Ser Leu Ser Ser Ser
    50                  55                  60

Ser Ser Ser Ser Thr Ser Glu Val Ser Thr Ser Asn Ser Ser Thr Tyr
65                  70                  75                  80

Asn Trp Tyr Thr Gly Ile Gly Gly Ile Gly Met Leu Asp Thr Ala Tyr
                85                  90                  95

Leu Thr Tyr Leu Lys Val Thr Gly Ser Asp Ala Phe Cys Pro Ile Gly
            100                 105                 110

Gly Gly Thr Cys Gly Asp Val Leu Asn Ser Asp Tyr Ala Val Val Phe
        115                 120                 125

Gly Val Pro Leu Pro Val Ile Gly Phe Val Met Tyr Gly Val Val Thr
130                 135                 140

Ala Leu Ser Ala Glu Leu Gly Glu Gly Asn Leu Pro Phe Gly Ile Ser
145                 150                 155                 160

Lys Ser Asn Gly Arg Phe Ala Leu Phe Gly Ile Thr Thr Ala Met Ala
                165                 170                 175

Ser Ala Ser Ala Tyr Phe Leu Tyr Ile Leu Ser Thr Lys Leu Ser Gly
            180                 185                 190

Ser Ser Cys Leu Tyr Cys Leu Val Ser Ala Phe Leu Ser Phe Ser Leu
        195                 200                 205

Phe Phe Leu Ser Val Lys Asp Val Lys Leu Gln Glu Ile Gln Gln Val
210                 215                 220

Val Gly Leu Gln Ile Cys Leu Ala Ile Ile Val Val Ala Ser Leu Thr
225                 230                 235                 240

Ala Ser Tyr Ser Thr Ala Gln Pro Ile Pro Ser Arg Ser Gly Asp Ile
                245                 250                 255

Glu Leu Pro Tyr Phe Arg Thr Glu Ile Ser Ser Ser Ser Pro Tyr
            260                 265                 270

Ala Ile Ala Leu Ala Lys His Leu Asn Ser Ile Gly Ala Lys Met Tyr
        275                 280                 285

Gly Ala Phe Trp Cys Ser His Cys Leu Glu Gln Lys Glu Met Phe Gly
290                 295                 300

Arg Glu Ala Ala Lys Glu Leu Asn Tyr Val Glu Cys Phe Pro Asp Gly
305                 310                 315                 320

Tyr Lys Lys Gly Thr Lys Ile Leu Lys Ala Cys Ala Asp Ala Ala Ile
                325                 330                 335

Glu Gly Phe Pro Thr Trp Ile Ile Asn Asp Lys Val Leu Ser
            340                 345                 350

<210> SEQ ID NO 20
<211> LENGTH: 342
<212> TYPE: PRT
<213> ORGANISM: Roseiflexus sp. RS-1

<400> SEQUENCE: 20

Met Arg Arg Phe Leu Leu Thr Leu Ile Val Ser Cys Met Leu Thr Leu
1               5                   10                  15
```

Ser Leu Ser Val Ala Ser Ala Ala Thr Val Arg Ala Val Leu Phe
            20                  25                  30

Tyr Ser Pro Arg Cys Gly His Cys His Met Val Ile Ser Glu His Leu
        35                  40                  45

Pro Pro Leu Gln Gln Arg Tyr Gly Asp Gln Leu Gln Ile Leu Met Ile
    50                  55                  60

Asp Val Asp Gln Ala Gln Gly Ala Ala Leu Tyr Arg Glu Ala Ile Ala
65                  70                  75                  80

Val Tyr Ala Ile Pro Glu Ala Arg Arg Gly Val Pro Thr Met Ile Ile
                85                  90                  95

Ser Asp Thr Val Leu Val Gly Ser Val Glu Ile Pro Gln Arg Leu Pro
            100                 105                 110

Gly Leu Ile Glu Thr Leu Leu Ala Arg Gly Gly Ser Asp Trp Pro Pro
        115                 120                 125

Ile Pro Gly Leu Ala Asp Leu Leu Ala Thr Val Pro Thr Ser Ala Pro
130                 135                 140

Ala Pro Pro Thr Leu Pro Pro Ala Thr Ala Glu Thr Pro Pro Phe Leu
145                 150                 155                 160

Arg Asp Leu Pro Ala Asn Ala Leu Ala Val Val Val Leu Ala Gly Met
                165                 170                 175

Leu Leu Thr Val Met Trp Ala Gly Ile Thr Trp Ser Arg Pro Ala Gln
            180                 185                 190

Pro Pro Thr Arg Trp Arg Asp Arg Ser Ile Pro Leu Leu Ala Ile Gly
        195                 200                 205

Gly Met Ala Val Ala Ala Tyr Leu Thr Phe Ile Glu Thr Thr Gly Ala
210                 215                 220

Pro Ala Leu Cys Gly Pro Val Gly Asp Cys Asn Ala Val Gln Gln Ser
225                 230                 235                 240

Glu Phe Ala Arg Leu Phe Gly Thr Ile Pro Val Gly Ala Ala Gly Val
                245                 250                 255

Ala Gly Tyr Gly Ala Ile Leu Ile Val Trp Ile Val Ala His Leu Leu
            260                 265                 270

Pro Gly Thr Ser Gly Glu Arg Ala Ala Leu Leu Leu Pro Ala Leu Ala
        275                 280                 285

Leu Ile Gly Thr Leu Phe Ser Ile Tyr Leu Thr Phe Leu Glu Pro Phe
290                 295                 300

Val Ile Gly Ala Thr Cys Leu Trp Cys Leu Thr Ser Ala Val Ile Met
305                 310                 315                 320

Thr Gly Leu Leu Trp Leu Ser Met Pro Tyr Arg Gln Arg Ser Thr Ser
                325                 330                 335

Arg Gly Tyr Ala Arg Arg
            340

<210> SEQ ID NO 21
<211> LENGTH: 283
<212> TYPE: PRT
<213> ORGANISM: Synechococcus sp. JA-2-3B'a(2-13)

<400> SEQUENCE: 21

Met Ala Ser Tyr Leu Lys Leu Lys Ala Gln Glu Glu Thr Trp Leu Gln
1               5                   10                  15

Arg His Ser Arg Leu Ile Leu Ala Ile Leu Ala Gly Leu Gly Ser Leu
            20                  25                  30

Leu Thr Ala Tyr Leu Thr Tyr Thr Lys Leu Thr Glu Gln Pro Ala Ala

```
        35                  40                  45

Phe Cys Thr Gly Asp Gly Gly Cys Asp Leu Val Leu Ser Ser Arg Trp
    50                  55                  60

Ala Glu Phe Leu Gly Ile Pro Thr Ala Ala Val Gly Leu Leu Gly Phe
65                  70                  75                  80

Leu Gly Val Leu Ala Leu Ala Val Leu Pro Asp Gly Leu Pro Leu Val
                85                  90                  95

Lys Arg Trp Arg Trp Pro Ala Leu Phe Gly Leu Val Ser Ala Met Thr
            100                 105                 110

Ala Phe Glu Met Tyr Met Leu Tyr Leu Met Val Ala Val Leu Arg Gln
        115                 120                 125

Phe Cys Met Tyr Cys Thr Thr Ala Ile Ile Leu Val Ala Gly Leu Gly
    130                 135                 140

Leu Val Thr Val Leu Gly His Arg Trp Leu Asp Gly Gly Lys Leu Ala
145                 150                 155                 160
Phe Ser Tyr Ile Leu Val Ala Phe Leu Thr Leu Val Thr Thr Ile Gly
                165                 170                 175

Val Tyr Ala Asn Gln Val Pro Pro Pro Ser Pro Leu Ala Val Gly Leu
            180                 185                 190

Ala Ala His Leu Arg Gln Ile Gly Gly Thr Met Tyr Gly Ala Tyr Trp
        195                 200                 205

Cys Pro His Cys Gln Asp Gln Lys Glu Leu Phe Gly Ala Ala Phe Asp
    210                 215                 220

Gln Val Pro Tyr Val Glu Cys Ser Pro Asn Gly Pro Gly Thr Pro Gln
225                 230                 235                 240
Ala Gln Glu Cys Thr Glu Ala Gly Ile Thr Ser Tyr Pro Thr Trp Ile
                245                 250                 255
Ile Asn Gly Arg Thr Tyr Thr Gly Val Arg Ser Leu Glu Ala Leu Ala
            260                 265                 270

Val Ala Ser Gly Tyr Pro Leu Glu Glu Gly Arg
        275                 280

<210> SEQ ID NO 22
<211> LENGTH: 178
<212> TYPE: PRT
<213> ORGANISM: Shigella dysenteriae

<400> SEQUENCE: 22

Met Ile Met Leu Arg Phe Leu Asn Gln Cys Ser Gln Gly Arg Gly Ala
1               5                   10                  15

Trp Leu Leu Met Ala Phe Thr Ala Leu Ala Leu Glu Leu Thr Ala Leu
            20                  25                  30

Trp Phe Gln His Val Met Leu Leu Lys Pro Cys Val Leu Cys Ile Tyr
        35                  40                  45

Glu Arg Cys Ala Leu Phe Gly Val Leu Gly Ala Ala Leu Ile Gly Ala
    50                  55                  60

Ile Ala Pro Lys Thr Pro Leu Arg Tyr Val Ala Met Val Ile Trp Leu
65                  70                  75                  80

Tyr Ser Ala Phe Arg Gly Val Gln Leu Thr Tyr Glu His Thr Met Leu
                85                  90                  95

Gln Leu Tyr Pro Ser Pro Phe Ala Thr Cys Asp Phe Met Val Arg Phe
            100                 105                 110

Pro Glu Trp Leu Pro Leu Asp Lys Trp Val Pro Gln Val Phe Val Ala
        115                 120                 125

Ser Gly Asp Cys Ala Glu Arg Gln Trp Asp Phe Leu Gly Leu Glu Met
    130                 135                 140

Pro Gln Trp Leu Leu Gly Ile Phe Ile Ala Tyr Leu Ile Val Ala Val
145                 150                 155                 160

Leu Val Val Ile Ser Gln Pro Phe Lys Ala Lys Lys Arg Asp Leu Phe
                165                 170                 175

Gly Arg

<210> SEQ ID NO 23
<211> LENGTH: 206
<212> TYPE: PRT
<213> ORGANISM: Corynebacterium jeikeium

<400> SEQUENCE: 23

Met Trp Val Trp Trp Gly Arg Glu Gly Val Ser Asn Lys Glu Ser Glu
1               5                   10                  15

His Met Asn Gly Leu Gly Ala Thr Lys Arg Phe Gly Tyr Thr Phe Leu
            20                  25                  30

Val Leu Ser Thr Ile Gly Leu Ile Phe Ser Ala Leu Ile Met His Asp
        35                  40                  45

Lys Val Gln Met Ala Leu Asp Pro Asn Phe Glu Pro Ala Cys Thr Phe
50                  55                  60

Asn Glu Val Ile Ser Cys Thr Asp Val Met Ala Ser Asp Gln Ala Ala
65                  70                  75                  80

Thr Phe Gly Phe Ala Asn Pro Phe Ile Gly Met Ile Gly Phe Pro Val
            85                  90                  95

Met Met Thr Leu Ala Val Met Leu Ile Val Gly Ala Lys Leu Pro Arg
            100                 105                 110

Trp Ile Trp Tyr Cys Ala Leu Ala Gly Leu Ala Phe Gly Val Ala Phe
        115                 120                 125

Val His Trp Leu Ala Tyr Ser Ala Ile Tyr Ser Ile Gly Ala Leu Cys
130                 135                 140

Pro Tyr Cys Met Ala Val Trp Ala Ala Thr Leu Pro Met Phe Val Met
145                 150                 155                 160

Thr Leu Val His Ile Gln Arg Glu Lys Arg Arg Glu Ala Gly Glu Asp
                165                 170                 175

Val Ala His Ser Ala Leu Gly Met Pro Leu Val Val Ile Ile Ala Trp
            180                 185                 190

Phe Leu Ala Phe Thr Ala Leu Ile Leu Asp Gln Phe Val Phe
        195                 200                 205

<210> SEQ ID NO 24
<211> LENGTH: 210
<212> TYPE: PRT
<213> ORGANISM: Salinispora tropica CNB-440

<400> SEQUENCE: 24

Met Thr Thr Thr Ala Asn Arg Pro Val Thr Thr Pro Ala Glu Arg His
1               5                   10                  15

Phe Leu Ala Ala Val Thr Ala Trp Val Leu Thr Ile Gly Gly Ala Val
            20                  25                  30

Gly Leu Leu Ala Ala Ala Ala Leu Thr Val Glu Lys Ile Asn Leu Leu
        35                  40                  45

Ala Asp Pro Gly Tyr Val Pro Thr Cys Ser Ile Asn Pro Ile Leu Ser
50                  55                  60

Cys Gly Ser Val Met Asn Thr Pro Gln Ala Ala Val Phe Gly Phe Pro

```
            65                  70                  75                  80
Asn Pro Leu Leu Gly Ile Ala Gly Phe Ala Val Val Thr Thr Leu Gly
                85                  90                  95

Val Thr Leu Leu Ala Thr Gly His Leu Pro Arg Trp Met Trp Leu Gly
                100                 105                 110

Leu Gln Gly Gly Val Thr Phe Gly Val Val Phe Val His Trp Leu Ile
                115                 120                 125

Tyr Gln Ser Leu Tyr Val Ile Gly Ala Leu Cys Pro Tyr Cys Met Val
                130                 135                 140

Val Trp Ala Val Thr Ile Pro Ile Phe Leu Tyr Thr Thr Leu Gln Thr
145                 150                 155                 160

Leu Arg Asp Asn Thr Thr Ala Leu Pro Arg Ala Leu Arg Arg Val Thr
                165                 170                 175

Glu Arg Val Ala Arg Tyr His Ser Leu Val Leu Val Val Trp Ala Ala
                180                 185                 190

Phe Val Val Val Ile Leu His Arg Phe Trp Asp Tyr Trp Ser Thr
                195                 200                 205

Leu Gly
    210

<210> SEQ ID NO 25
<211> LENGTH: 163
<212> TYPE: PRT
<213> ORGANISM: Artificial
<220> FEATURE:
<223> OTHER INFORMATION: Human VKOR with V45N mutation

<400> SEQUENCE: 25

Met Gly Ser Thr Trp Gly Ser Pro Gly Trp Val Arg Leu Ala Leu Cys
1               5                   10                  15

Leu Thr Gly Leu Val Leu Ser Leu Tyr Ala Leu His Val Lys Ala Ala
                20                  25                  30

Arg Ala Arg Asp Arg Asp Tyr Arg Ala Leu Cys Asp Asn Gly Thr Ala
                35                  40                  45

Ile Ser Ala Ser Arg Val Phe Ser Ser Arg Trp Gly Arg Gly Phe Gly
50                  55                  60

Leu Val Glu His Val Leu Gly Gln Asp Ser Ile Leu Asn Gln Ser Asn
65                  70                  75                  80

Ser Ile Phe Gly Cys Ile Phe Tyr Thr Leu Gln Leu Leu Leu Gly Cys
                85                  90                  95

Leu Arg Thr Arg Trp Ala Ser Val Leu Met Leu Leu Ser Ser Leu Val
                100                 105                 110

Ser Leu Ala Gly Ser Val Tyr Leu Ala Trp Ile Leu Phe Phe Val Leu
                115                 120                 125

Tyr Asp Phe Cys Ile Val Cys Ile Thr Thr Tyr Ala Ile Asn Val Ser
                130                 135                 140

Leu Met Trp Leu Ser Phe Arg Lys Val Gln Glu Pro Gln Gly Lys Ala
145                 150                 155                 160

Lys Arg His

<210> SEQ ID NO 26
<211> LENGTH: 163
<212> TYPE: PRT
<213> ORGANISM: Artificial
<220> FEATURE:
<223> OTHER INFORMATION: Human VKOR with C51A mutation
```

<400> SEQUENCE: 26

```
Met Gly Ser Thr Trp Gly Ser Pro Gly Trp Val Arg Leu Ala Leu Cys
1               5                   10                  15
Leu Thr Gly Leu Val Leu Ser Leu Tyr Ala Leu His Val Lys Ala Ala
            20                  25                  30
Arg Ala Arg Asp Arg Asp Tyr Arg Ala Leu Cys Asp Val Gly Thr Ala
        35                  40                  45
Ile Ser Ala Ser Arg Val Phe Ser Ser Arg Trp Gly Arg Gly Phe Gly
    50                  55                  60
Leu Val Glu His Val Leu Gly Gln Asp Ser Ile Leu Asn Gln Ser Asn
65                  70                  75                  80
Ser Ile Phe Gly Cys Ile Phe Tyr Thr Leu Gln Leu Leu Gly Cys
                85                  90                  95
Leu Arg Thr Arg Trp Ala Ser Val Leu Met Leu Leu Ser Ser Leu Val
                100                 105                 110
Ser Leu Ala Gly Ser Val Tyr Leu Ala Trp Ile Leu Phe Phe Val Leu
            115                 120                 125
Tyr Asp Phe Cys Ile Val Cys Ile Thr Thr Tyr Ala Ile Asn Val Ser
        130                 135                 140
Leu Met Trp Leu Ser Phe Arg Lys Val Gln Glu Pro Gln Gly Lys Ala
145                 150                 155                 160
Lys Arg His
```

<210> SEQ ID NO 27
<211> LENGTH: 163
<212> TYPE: PRT
<213> ORGANISM: Artificial
<220> FEATURE:
<223> OTHER INFORMATION: Human VKOR with IV133-134PY mutation

<400> SEQUENCE: 27

```
Met Gly Ser Thr Trp Gly Ser Pro Gly Trp Val Arg Leu Ala Leu Cys
1               5                   10                  15
Leu Thr Gly Leu Val Leu Ser Leu Tyr Ala Leu His Val Lys Ala Ala
            20                  25                  30
Arg Ala Arg Asp Arg Asp Tyr Arg Ala Leu Cys Asp Val Gly Thr Ala
        35                  40                  45
Ile Ser Cys Ser Arg Val Phe Ser Ser Arg Trp Gly Arg Gly Phe Gly
    50                  55                  60
Leu Val Glu His Val Leu Gly Gln Asp Ser Ile Leu Asn Gln Ser Asn
65                  70                  75                  80
Ser Ile Phe Gly Cys Ile Phe Tyr Thr Leu Gln Leu Leu Gly Cys
                85                  90                  95
Leu Arg Thr Arg Trp Ala Ser Val Leu Met Leu Leu Ser Ser Leu Val
                100                 105                 110
Ser Leu Ala Gly Ser Val Tyr Leu Ala Trp Ile Leu Phe Phe Val Leu
            115                 120                 125
Tyr Asp Phe Cys Pro Tyr Cys Ile Thr Thr Tyr Ala Ile Asn Val Ser
        130                 135                 140
Leu Met Trp Leu Ser Phe Arg Lys Val Gln Glu Pro Gln Gly Lys Ala
145                 150                 155                 160
Lys Arg His
```

<210> SEQ ID NO 28
<211> LENGTH: 163

```
<212> TYPE: PRT
<213> ORGANISM: Artificial
<220> FEATURE:
<223> OTHER INFORMATION: Human VKOR with IV133-134PY mutation and C51A
      mutation

<400> SEQUENCE: 28

Met Gly Ser Thr Trp Gly Ser Pro Gly Trp Val Arg Leu Ala Leu Cys
1               5                   10                  15

Leu Thr Gly Leu Val Leu Ser Leu Tyr Ala Leu His Val Lys Ala Ala
            20                  25                  30

Arg Ala Arg Asp Arg Asp Tyr Arg Ala Leu Cys Asp Val Gly Thr Ala
        35                  40                  45

Ile Ser Ala Ser Arg Val Phe Ser Ser Arg Trp Gly Arg Gly Phe Gly
    50                  55                  60

Leu Val Glu His Val Leu Gly Gln Asp Ser Ile Leu Asn Gln Ser Asn
65                  70                  75                  80

Ser Ile Phe Gly Cys Ile Phe Tyr Thr Leu Gln Leu Leu Leu Gly Cys
                85                  90                  95

Leu Arg Thr Arg Trp Ala Ser Val Leu Met Leu Leu Ser Ser Leu Val
            100                 105                 110

Ser Leu Ala Gly Ser Val Tyr Leu Ala Trp Ile Leu Phe Phe Val Leu
        115                 120                 125

Tyr Asp Phe Cys Pro Tyr Cys Ile Thr Thr Tyr Ala Ile Asn Val Ser
130                 135                 140

Leu Met Trp Leu Ser Phe Arg Lys Val Gln Glu Pro Gln Gly Lys Ala
145                 150                 155                 160

Lys Arg His

<210> SEQ ID NO 29
<211> LENGTH: 163
<212> TYPE: PRT
<213> ORGANISM: Artificial
<220> FEATURE:
<223> OTHER INFORMATION: Human VKOR with amino acids 122-139 substituted
      with amino acids 129-146 of M. tuberculosis VKOR (RefSeq accession
      no. NP_217484)

<400> SEQUENCE: 29

Met Gly Ser Thr Trp Gly Ser Pro Gly Trp Val Arg Leu Ala Leu Cys
1               5                   10                  15

Leu Thr Gly Leu Val Leu Ser Leu Tyr Ala Leu His Val Lys Ala Ala
            20                  25                  30

Arg Ala Arg Asp Arg Asp Tyr Arg Ala Leu Cys Asp Val Gly Thr Ala
        35                  40                  45

Ile Ser Cys Ser Arg Val Phe Ser Ser Arg Trp Gly Arg Gly Phe Gly
    50                  55                  60

Leu Val Glu His Val Leu Gly Gln Asp Ser Ile Leu Asn Gln Ser Asn
65                  70                  75                  80

Ser Ile Phe Gly Cys Ile Phe Tyr Thr Leu Gln Leu Leu Leu Gly Cys
                85                  90                  95

Leu Arg Thr Arg Trp Ala Ser Val Leu Met Leu Leu Ser Ser Leu Val
            100                 105                 110

Ser Leu Ala Gly Ser Val Tyr Leu Ala Phe Gln Ser Leu Tyr Arg Ile
        115                 120                 125

Gly Ala Leu Cys Pro Tyr Cys Met Val Val Trp Ala Ile Asn Val Ser
130                 135                 140
```

```
Leu Met Trp Leu Ser Phe Arg Lys Val Gln Glu Pro Gln Gly Lys Ala
145                 150                 155                 160

Lys Arg His

<210> SEQ ID NO 30
<211> LENGTH: 163
<212> TYPE: PRT
<213> ORGANISM: Artificial
<220> FEATURE:
<223> OTHER INFORMATION: Human VKOR with amino acids 122-139 substituted
      with amino acids 185-202 of A. thaliana VKOR (RefSeq accession no.
      NP_567988)

<400> SEQUENCE: 30

Met Gly Ser Thr Trp Gly Ser Pro Gly Trp Val Arg Leu Ala Leu Cys
1               5                   10                  15

Leu Thr Gly Leu Val Leu Ser Leu Tyr Ala Leu His Val Lys Ala Ala
            20                  25                  30

Arg Ala Arg Asp Arg Asp Tyr Arg Ala Leu Cys Asp Val Gly Thr Ala
        35                  40                  45

Ile Ser Cys Ser Arg Val Phe Ser Ser Arg Trp Gly Arg Gly Phe Gly
    50                  55                  60

Leu Val Glu His Val Leu Gly Gln Asp Ser Ile Leu Asn Gln Ser Asn
65                  70                  75                  80

Ser Ile Phe Gly Cys Ile Phe Tyr Thr Leu Gln Leu Leu Leu Gly Cys
                85                  90                  95

Leu Arg Thr Arg Trp Ala Ser Val Leu Met Leu Leu Ser Ser Leu Val
            100                 105                 110

Ser Leu Ala Gly Ser Val Tyr Leu Ala Ile Leu Ser Thr Lys Leu Ser
        115                 120                 125

Gly Ser Ser Cys Leu Tyr Cys Leu Val Ser Ala Ala Ile Asn Val Ser
    130                 135                 140

Leu Met Trp Leu Ser Phe Arg Lys Val Gln Glu Pro Gln Gly Lys Ala
145                 150                 155                 160

Lys Arg His

<210> SEQ ID NO 31
<211> LENGTH: 163
<212> TYPE: PRT
<213> ORGANISM: Artificial
<220> FEATURE:
<223> OTHER INFORMATION: Human VKOR with amino acids 122-139 substituted
      with amino acids 120-137 of Synechococcus sp. JA-2-3B'a(2-13) VKOR
      (RefSeq accession no. YP_478481)

<400> SEQUENCE: 31

Met Gly Ser Thr Trp Gly Ser Pro Gly Trp Val Arg Leu Ala Leu Cys
1               5                   10                  15

Leu Thr Gly Leu Val Leu Ser Leu Tyr Ala Leu His Val Lys Ala Ala
            20                  25                  30

Arg Ala Arg Asp Arg Asp Tyr Arg Ala Leu Cys Asp Val Gly Thr Ala
        35                  40                  45

Ile Ser Cys Ser Arg Val Phe Ser Ser Arg Trp Gly Arg Gly Phe Gly
    50                  55                  60

Leu Val Glu His Val Leu Gly Gln Asp Ser Ile Leu Asn Gln Ser Asn
65                  70                  75                  80

Ser Ile Phe Gly Cys Ile Phe Tyr Thr Leu Gln Leu Leu Leu Gly Cys
                85                  90                  95
```

```
Leu Arg Thr Arg Trp Ala Ser Val Leu Met Leu Ser Ser Leu Val
            100                 105                 110

Ser Leu Ala Gly Ser Val Tyr Leu Ala Tyr Leu Met Val Ala Val Leu
        115                 120                 125

Arg Gln Phe Cys Met Tyr Cys Thr Thr Ala Ile Ala Ile Asn Val Ser
    130                 135                 140

Leu Met Trp Leu Ser Phe Arg Lys Val Gln Glu Pro Gln Gly Lys Ala
145                 150                 155                 160

Lys Arg His

<210> SEQ ID NO 32
<211> LENGTH: 163
<212> TYPE: PRT
<213> ORGANISM: Artificial
<220> FEATURE:
<223> OTHER INFORMATION: Human VKOR with amino acids 122-139 substituted
      with amino acids 33-50 of DsbB enzyme (RefSeq accession no.
      ZP_03067529)

<400> SEQUENCE: 32

```
Ile Ser Cys Ser Arg Val Phe Ser Ser Arg Trp Gly Arg Gly Phe Gly
 50                  55                  60
Leu Val Glu His Val Leu Gly Gln Asp Ser Ile Leu Asn Gln Ser Asn
 65                  70                  75                  80
Ser Ile Phe Gly Cys Ile Phe Tyr Thr Leu Gln Leu Leu Gly Cys
             85                  90                  95
Leu Arg Thr Arg Trp Ala Ser Val Leu Met Leu Ser Ser Leu Val
             100                 105                 110
Ser Leu Ala Gly Ser Val Tyr Leu Ala Phe Leu Glu Pro Phe Val Ile
                 115                 120                 125
Gly Ala Thr Cys Leu Trp Cys Leu Thr Ser Ala Ile Asn Val Ser
     130                 135                 140
Leu Met Trp Leu Ser Phe Arg Lys Val Gln Glu Pro Gln Gly Lys Ala
 145                 150                 155                 160
Lys Arg His
```

```
<210> SEQ ID NO 34
<211> LENGTH: 164
<212> TYPE: PRT
<213> ORGANISM: Artificial
<220> FEATURE:
<223> OTHER INFORMATION: Human VKOR with amino acids 44-50 substituted
      with amino acids DYKDDDDK (Flag tag)

<400> SEQUENCE: 34

Met Gly Ser Thr Trp Gly Ser Pro Gly Trp Val Arg Leu Ala Leu Cys
 1               5                  10                  15
Leu Thr Gly Leu Val Leu Ser Leu Tyr Ala Leu His Val Lys Ala Ala
                 20                  25                  30
Arg Ala Arg Asp Arg Asp Tyr Arg Ala Leu Cys Asp Tyr Lys Asp Asp
             35                  40                  45
Asp Asp Lys Cys Ser Arg Val Phe Ser Ser Arg Trp Gly Arg Gly Phe
 50                  55                  60
Gly Leu Val Glu His Val Leu Gly Gln Asp Ser Ile Leu Asn Gln Ser
 65                  70                  75                  80
Asn Ser Ile Phe Gly Cys Ile Phe Tyr Thr Leu Gln Leu Leu Leu Gly
             85                  90                  95
Cys Leu Arg Thr Arg Trp Ala Ser Val Leu Met Leu Ser Ser Leu
             100                 105                 110
Val Ser Leu Ala Gly Ser Val Tyr Leu Ala Trp Ile Leu Phe Phe Val
                 115                 120                 125
Leu Tyr Asp Phe Cys Ile Val Cys Ile Thr Thr Tyr Ala Ile Asn Val
 130                 135                 140
Ser Leu Met Trp Leu Ser Phe Arg Lys Val Gln Glu Pro Gln Gly Lys
 145                 150                 155                 160
Ala Lys Arg His
```

```
<210> SEQ ID NO 35
<211> LENGTH: 163
<212> TYPE: PRT
<213> ORGANISM: Artificial
<220> FEATURE:
<223> OTHER INFORMATION: Human VKOR comprising an R37G mutation, an R35G
      mutation, an R33G mutation, a K30L mutation, a G9R mutation, an
      S7R mutation and a G6R mutation

<400> SEQUENCE: 35

Met Gly Ser Thr Trp Arg Arg Pro Arg Trp Val Arg Leu Ala Leu Cys
```

```
                1               5                  10                    15
Leu Thr Gly Leu Val Leu Ser Leu Tyr Ala Leu His Val Leu Ala Ala
            20                  25                  30

Gly Ala Gly Asp Gly Asp Tyr Arg Ala Leu Cys Asp Val Gly Thr Ala
            35                  40                  45

Ile Ser Cys Ser Arg Val Phe Ser Ser Arg Trp Gly Arg Gly Phe Gly
 50                  55                  60

Leu Val Glu His Val Leu Gly Gln Asp Ser Ile Leu Asn Gln Ser Asn
 65                  70                  75                  80

Ser Ile Phe Gly Cys Ile Phe Tyr Thr Leu Gln Leu Leu Gly Cys
                 85                  90                  95

Leu Arg Thr Arg Trp Ala Ser Val Leu Met Leu Leu Ser Ser Leu Val
            100                 105                 110

Ser Leu Ala Gly Ser Val Tyr Leu Ala Trp Ile Leu Phe Phe Val Leu
            115                 120                 125

Tyr Asp Phe Cys Ile Val Cys Ile Thr Thr Tyr Ala Ile Asn Val Ser
            130                 135                 140

Leu Met Trp Leu Ser Phe Arg Lys Val Gln Glu Pro Gln Gly Lys Ala
145                 150                 155                 160

Lys Arg His

<210> SEQ ID NO 36
<211> LENGTH: 163
<212> TYPE: PRT
<213> ORGANISM: Artificial
<220> FEATURE:
<223> OTHER INFORMATION: Human VKOR comprising an R37 mutation, an R35
      mutation, an R33 mutation, a K30 mutation, a G9 mutation, an S7
      mutation and a G6 mutation
<220> FEATURE:
<221> NAME/KEY: MISC_FEATURE
<222> LOCATION: (6)..(6)
<223> OTHER INFORMATION: Xaa may be G, A, I, L, V, M, F, W or P
<220> FEATURE:
<221> NAME/KEY: MISC_FEATURE
<222> LOCATION: (7)..(7)
<223> OTHER INFORMATION: Xaa may be G, A, I, L, V, M, F, W or P
<220> FEATURE:
<221> NAME/KEY: MISC_FEATURE
<222> LOCATION: (9)..(9)
<223> OTHER INFORMATION: Xaa may be G, A, I, L, V, M, F, W or P
<220> FEATURE:
<221> NAME/KEY: MISC_FEATURE
<222> LOCATION: (30)..(30)
<223> OTHER INFORMATION: Xaa may be L, I, V, A, G, M, F, W or P
<220> FEATURE:
<221> NAME/KEY: MISC_FEATURE
<222> LOCATION: (33)..(33)
<223> OTHER INFORMATION: Xaa may be R, H, K, S, T, C, Y, N or Q
<220> FEATURE:
<221> NAME/KEY: MISC_FEATURE
<222> LOCATION: (35)..(35)
<223> OTHER INFORMATION: Xaa may be R, H, K, T, C, Y, N or Q
<220> FEATURE:
<221> NAME/KEY: MISC_FEATURE
<222> LOCATION: (37)..(37)
<223> OTHER INFORMATION: Xaa may be R, H, K, S, T, C, Y, N or Q

<400> SEQUENCE: 36

Met Gly Ser Thr Trp Xaa Xaa Pro Xaa Trp Val Arg Leu Ala Leu Cys
 1               5                  10                  15

Leu Thr Gly Leu Val Leu Ser Leu Tyr Ala Leu His Val Xaa Ala Ala
            20                  25                  30

Xaa Ala Xaa Asp Xaa Asp Tyr Arg Ala Leu Cys Asp Val Gly Thr Ala
            35                  40                  45
```

```
Ile Ser Cys Ser Arg Val Phe Ser Arg Trp Gly Arg Gly Phe Gly
        50                  55                  60

Leu Val Glu His Val Leu Gly Gln Asp Ser Ile Leu Asn Gln Ser Asn
 65                  70                  75                  80

Ser Ile Phe Gly Cys Ile Phe Tyr Thr Leu Gln Leu Leu Gly Cys
                85                  90                  95

Leu Arg Thr Arg Trp Ala Ser Val Leu Met Leu Ser Ser Leu Val
            100                 105                 110

Ser Leu Ala Gly Ser Val Tyr Leu Ala Trp Ile Leu Phe Phe Val Leu
            115                 120                 125

Tyr Asp Phe Cys Ile Val Cys Ile Thr Thr Tyr Ala Ile Asn Val Ser
            130                 135                 140

Leu Met Trp Leu Ser Phe Arg Lys Val Gln Glu Pro Gln Gly Lys Ala
145                 150                 155                 160

Lys Arg His
```

<210> SEQ ID NO 37
<211> LENGTH: 8
<212> TYPE: PRT
<213> ORGANISM: Artificial
<220> FEATURE:
<223> OTHER INFORMATION: FLAG tag sequence

<400> SEQUENCE: 37

```
Asp Tyr Lys Asp Asp Asp Asp Lys
 1               5
```

<210> SEQ ID NO 38
<211> LENGTH: 18
<212> TYPE: PRT
<213> ORGANISM: Homo sapiens

<400> SEQUENCE: 38

```
Trp Ile Leu Phe Phe Val Leu Tyr Asp Phe Cys Ile Val Cys Ile Thr
 1               5                   10                  15

Thr Tyr
```

<210> SEQ ID NO 39
<211> LENGTH: 18
<212> TYPE: PRT
<213> ORGANISM: Mycobacterium tuberculosis

<400> SEQUENCE: 39

```
Phe Gln Ser Leu Tyr Arg Ile Gly Ala Leu Cys Pro Tyr Cys Met Val
 1               5                   10                  15

Val Trp
```

<210> SEQ ID NO 40
<211> LENGTH: 18
<212> TYPE: PRT
<213> ORGANISM: Arabidopsis thaliana

<400> SEQUENCE: 40

```
Ile Leu Ser Thr Lys Leu Ser Gly Ser Ser Cys Leu Tyr Cys Leu Val
 1               5                   10                  15

Ser Ala
```

<210> SEQ ID NO 41
<211> LENGTH: 18

```
<212> TYPE: PRT
<213> ORGANISM: Synechococcus sp. JA-2-3B'a(2-13)

<400> SEQUENCE: 41

Tyr Leu Met Val Ala Val Leu Arg Gln Phe Cys Met Tyr Cys Thr Thr
1               5                   10                  15

Ala Ile

<210> SEQ ID NO 42
<211> LENGTH: 18
<212> TYPE: PRT
<213> ORGANISM: Shigella dysenteriae

<400> SEQUENCE: 42

Trp Phe Gln His Val Met Leu Leu Lys Pro Cys Val Leu Cys Ile Tyr
1               5                   10                  15

Glu Arg

<210> SEQ ID NO 43
<211> LENGTH: 18
<212> TYPE: PRT
<213> ORGANISM: Roseiflexus sp. RS-1

<400> SEQUENCE: 43

Phe Leu Glu Pro Phe Val Ile Gly Ala Thr Cys Leu Trp Cys Leu Thr
1               5                   10                  15

Ser Ala

<210> SEQ ID NO 44
<211> LENGTH: 163
<212> TYPE: PRT
<213> ORGANISM: Loxodonta africana

<400> SEQUENCE: 44

Met Gly Thr Thr Trp Val Ser Pro Gly Trp Ala Arg Leu Ala Leu Cys
1               5                   10                  15

Leu Ala Gly Leu Gly Leu Ser Leu Tyr Ala Leu His Val Lys Ala Ala
                20                  25                  30

Arg Ala Arg Asp Lys Asp Tyr Arg Ala Leu Cys Asp Val Gly Thr Ala
            35                  40                  45

Ile Ser Cys Ser Arg Val Phe Ser Ser Arg Trp Gly Arg Gly Phe Gly
        50                  55                  60

Leu Val Glu His Val Leu Gly Pro Asp Ser Val Leu Asn Gln Ser Asn
65                  70                  75                  80

Ser Ile Phe Gly Cys Ile Phe Tyr Thr Leu Gln Leu Leu Leu Gly Cys
                85                  90                  95

Leu Arg Gly Arg Trp Ala Ser Ile Leu Leu Val Leu Ser Ser Leu Val
            100                 105                 110

Ser Leu Ala Gly Ser Val Tyr Leu Ala Trp Ile Leu Phe Phe Val Leu
        115                 120                 125

Tyr Asp Phe Cys Ile Val Cys Ile Thr Thr Tyr Ala Ile Asn Val Gly
    130                 135                 140

Leu Thr Val Leu Ser Phe Gln Gly Ala Gln Gly Pro Lys Gly Lys Ala
145                 150                 155                 160

Lys Glu His

<210> SEQ ID NO 45
<211> LENGTH: 163
```

<212> TYPE: PRT
<213> ORGANISM: Anoplopoma fimbria

<400> SEQUENCE: 45

Met Ala Met Pro Lys Trp Glu Arg Lys Ala Arg Ile Phe Leu Cys Val
1               5                   10                  15

Phe Gly Leu Phe Leu Ser Val Tyr Ala Leu His Val Glu Leu Ser Arg
            20                  25                  30

Glu Arg Asn Pro Asp Tyr Arg Ala Met Cys Asp Leu Gly Glu Ser Val
        35                  40                  45

Ser Cys Ser Lys Val Phe Thr Ser Arg Trp Gly Arg Gly Phe Gly Leu
    50                  55                  60

Val Gln Phe Phe Val Ala Gln Asp Ser Pro Leu Asn Gln Pro Asn Ser
65                  70                  75                  80

Val Leu Gly Thr Ile Phe Tyr Thr Leu Gln Met Gly Leu Gly Met Ser
                85                  90                  95

Leu Ser Lys Lys Ala Ala Met Leu Leu Val Phe Ser Ser Trp Val Ser
            100                 105                 110

Val Ala Gly Ser Leu Tyr Leu Ala Ser Ile Leu Ala Phe Val Leu Gly
        115                 120                 125

Asp Phe Cys Met Val Cys Val Ser Thr Tyr Ile Val Asn Phe Val Leu
    130                 135                 140

Leu Phe Thr Asn Leu Arg Arg Arg Thr Ala Ile Glu Gly Met Lys Glu
145                 150                 155                 160

Lys Ala Gly

<210> SEQ ID NO 46
<211> LENGTH: 173
<212> TYPE: PRT
<213> ORGANISM: Saccoglossus kowalevskii

<400> SEQUENCE: 46

Met Ala Ser Ser Pro Met Arg Ile Arg Arg Leu Pro Ala Trp Gln
1               5                   10                  15

Arg Val Thr Arg Thr Thr Leu Cys Phe Met Gly Leu Gly Leu Ser Leu
            20                  25                  30

Tyr Ala Tyr Tyr Val Glu Met Lys Lys Glu Glu Asp Lys Asp Tyr Glu
        35                  40                  45

Ala Thr Cys Asp Phe Asn Glu Ser Val Ser Cys Ser Lys Val Phe Thr
    50                  55                  60

Ser Arg Tyr Gly Arg Gly Phe Gly Val Val Glu His Ile Leu Gly Lys
65                  70                  75                  80

Asp Ser Met Leu Asn Met Pro Asn Ser Leu Phe Gly Ile Val Phe Phe
                85                  90                  95

Phe Leu Gln Tyr Val Leu Gly Gln Phe Ile Ser His Pro Gly Ser Phe
            100                 105                 110

Leu Leu Leu Ser Thr Ser Ile Phe Ala Asn Met Gly Ser Val Tyr Leu
        115                 120                 125

Ala Tyr Ile Leu Tyr Tyr Val Leu His Asp Cys Cys Leu Val Cys Val
    130                 135                 140

Ser Thr Tyr Val Val Asn Phe Leu Leu Leu Val Val Asn Ile Arg His
145                 150                 155                 160

Asn Ile Phe Val Lys Glu Met Leu Lys Lys Lys Val
                165                 170

```
<210> SEQ ID NO 47
<211> LENGTH: 163
<212> TYPE: PRT
<213> ORGANISM: Tursiops truncatus

<400> SEQUENCE: 47

Gly Asn Thr Trp Arg Ser Pro Trp Gly Trp Ala Arg Leu Ala Leu Cys
1               5                   10                  15

Leu Ala Gly Leu Gly Leu Ser Leu Tyr Ala Leu His Val Lys Ala Ala
                20                  25                  30

Arg Ala Arg Asp Arg Asp Tyr Arg Ala Leu Cys Asp Val Gly Thr Ala
            35                  40                  45

Ile Ser Cys Ser Arg Val Phe Ser Ser Arg Trp Gly Arg Gly Phe Gly
        50                  55                  60

Leu Val Glu His Val Leu Gly Lys Asp Ser Val Leu Asn Gln Ser Asn
65                  70                  75                  80

Ser Ile Phe Gly Cys Ile Phe Tyr Thr Leu Gln Leu Leu Gly Cys
                    85                  90                  95

Leu Gln Gly Arg Trp Ala Ser Val Leu Val Leu Ser Ser Leu Val
                100                 105                 110

Ser Leu Ala Gly Ser Val Tyr Leu Ala Trp Ile Leu Phe Phe Val Leu
                115                 120                 125

Tyr Asp Phe Cys Ile Val Cys Ile Thr Thr Tyr Ala Ile Asn Val Gly
            130                 135                 140

Leu Met Val Leu Ser Phe Arg Glu Val Gln Glu Pro Gln Gly Lys Val
145                 150                 155                 160

Lys Gly His

<210> SEQ ID NO 48
<211> LENGTH: 176
<212> TYPE: PRT
<213> ORGANISM: Taeniopygia guttata

<400> SEQUENCE: 48

Met Ala Ala Pro Val Leu Leu Arg Val Ser Val Pro Arg Trp Glu Arg
1               5                   10                  15

Val Ala Arg Ser Ala Val Cys Ala Ala Gly Ile Leu Ser Leu Tyr
                20                  25                  30

Ala Cys His Leu Glu Arg Glu Lys Gly Arg Asp Ser His Tyr Gln Ala
            35                  40                  45

Leu Cys Asp Leu Ser Glu Arg Val Arg Cys Ser Ala Ala Ile Thr Ser
        50                  55                  60

Arg Trp Gly Arg Gly Phe Gly Leu Leu Gly Ser Ile Phe Gly Lys Asp
65                  70                  75                  80

Ser Ala Ile Asn Gln Ser Asn Ser Val Phe Gly Leu Val Phe Tyr Ile
                    85                  90                  95

Leu Gln Met Leu Leu Gly Met Thr Ala Ser Ala Val Ala Ala Leu Ile
                100                 105                 110

Leu Met Thr Ser Ser Ile Val Ser Val Val Gly Ser Leu Tyr Leu Ala
                115                 120                 125

Tyr Ile Leu Tyr Phe Val Leu Lys Glu Phe Cys Ile Val Cys Val Leu
            130                 135                 140

Thr Tyr Leu Leu Asn Phe Ile Leu Phe Ile Ile Asn Tyr Lys Arg Leu
145                 150                 155                 160

Val Tyr Leu Asn Glu Ala Trp Lys Arg Gln Leu Gln Pro Lys Gln Glu
                165                 170                 175
```

-continued

<210> SEQ ID NO 49
<211> LENGTH: 93
<212> TYPE: PRT
<213> ORGANISM: Homo sapiens

<400> SEQUENCE: 49

Gly Gln Asp Ser Ile Leu Asn Gln Ser Asn Ser Ile Phe Gly Cys Ile
1               5                   10                  15

Phe Tyr Thr Leu Gln Leu Leu Leu Gly Cys Leu Arg Thr Arg Trp Ala
            20                  25                  30

Ser Val Leu Met Leu Leu Ser Ser Leu Val Ser Leu Ala Gly Ser Val
        35                  40                  45

Tyr Leu Ala Trp Ile Leu Phe Phe Val Leu Tyr Asp Phe Cys Ile Val
    50                  55                  60

Cys Ile Thr Thr Tyr Ala Ile Asn Val Ser Leu Met Trp Leu Ser Phe
65                  70                  75                  80

Arg Lys Val Gln Glu Pro Gln Gly Lys Ala Lys Arg His
                85                  90

<210> SEQ ID NO 50
<211> LENGTH: 26
<212> TYPE: PRT
<213> ORGANISM: Homo sapiens

<400> SEQUENCE: 50

Trp Ile Leu Phe Phe Val Leu Tyr Asp Phe Cys Ile Val Cys Ile Thr
1               5                   10                  15

Thr Tyr Ala Ile Asn Val Ser Leu Met Trp
            20                  25

<210> SEQ ID NO 51
<211> LENGTH: 26
<212> TYPE: PRT
<213> ORGANISM: Arabidopsis thaliana

<400> SEQUENCE: 51

Ile Leu Ser Thr Lys Leu Ser Gly Ser Ser Cys Leu Tyr Cys Leu Val
1               5                   10                  15

Ser Ala Phe Leu Ser Phe Ser Leu Phe Phe
            20                  25

<210> SEQ ID NO 52
<211> LENGTH: 26
<212> TYPE: PRT
<213> ORGANISM: Mycobacterium tuberculosis

<400> SEQUENCE: 52

Phe Gln Ser Leu Tyr Arg Ile Gly Ala Leu Cys Pro Tyr Cys Met Val
1               5                   10                  15

Val Trp Ala Val Ile Ala Thr Leu Leu Val
            20                  25

<210> SEQ ID NO 53
<211> LENGTH: 26
<212> TYPE: PRT
<213> ORGANISM: Roseiflexus sp. RS-1

<400> SEQUENCE: 53

Phe Leu Glu Pro Phe Val Ile Gly Ala Thr Cys Leu Trp Cys Leu Thr
1               5                   10                  15

Ser Ala Val Ile Met Thr Gly Leu Leu Trp
            20                  25

<210> SEQ ID NO 54
<211> LENGTH: 26
<212> TYPE: PRT
<213> ORGANISM: Synechococcus sp. JA-2-3B'a(2-13)

<400> SEQUENCE: 54

Tyr Leu Met Val Ala Val Leu Arg Gln Phe Cys Met Tyr Cys Thr Thr
1               5                   10                  15

Ala Ile Ile Leu Val Ala Gly Leu Gly Leu
            20                  25

<210> SEQ ID NO 55
<211> LENGTH: 26
<212> TYPE: PRT
<213> ORGANISM: Corynebacterium jeikeium

<400> SEQUENCE: 55

Tyr Ser Ala Ile Tyr Ser Ile Gly Ala Leu Cys Pro Tyr Cys Met Ala
1               5                   10                  15

Val Trp Ala Ala Thr Leu Pro Met Phe Val
            20                  25

<210> SEQ ID NO 56
<211> LENGTH: 26
<212> TYPE: PRT
<213> ORGANISM: Salinispora tropica CNB-440

<400> SEQUENCE: 56

Tyr Gln Ser Leu Tyr Val Ile Gly Ala Leu Cys Pro Tyr Cys Met Val
1               5                   10                  15

Val Trp Ala Val Thr Ile Pro Ile Phe Leu
            20                  25

<210> SEQ ID NO 57
<211> LENGTH: 463
<212> TYPE: PRT
<213> ORGANISM: Artificial
<220> FEATURE:
<223> OTHER INFORMATION: Chimeric protein C sequence

<400> SEQUENCE: 57

Met Ala Trp Gln Leu Thr Ser Leu Leu Leu Phe Val Ala Thr Trp Gly
1               5                   10                  15

Ile Ser Gly Thr Pro Ala Pro Leu Asp Ser Val Phe Ser Ser Ser Glu
            20                  25                  30

Arg Ala His Gln Val Leu Arg Ile Arg Lys Arg Tyr Asn Ser Gly Lys
        35                  40                  45

Leu Glu Glu Phe Val Gln Gly Asn Leu Glu Arg Glu Cys Met Glu Glu
    50                  55                  60

Lys Cys Ser Phe Glu Glu Ala Arg Glu Val Phe Glu Asn Thr Glu Arg
65                  70                  75                  80

Thr Thr Glu Phe Trp Lys Gln Tyr Val Asp Gly Asp Gln Cys Leu Val
                85                  90                  95

Leu Pro Leu Glu His Pro Cys Ala Ser Leu Cys Cys Gly His Gly Thr
            100                 105                 110

Cys Ile Asp Gly Ile Gly Ser Phe Ser Cys Asp Cys Arg Ser Gly Trp
        115                 120                 125

Glu Gly Arg Phe Cys Gln Arg Glu Val Ser Phe Leu Asn Cys Ser Leu
            130                 135                 140

Asp Asn Gly Gly Cys Thr His Tyr Cys Leu Glu Val Gly Trp Arg
145                 150                 155                 160

Arg Cys Ser Cys Ala Pro Gly Tyr Lys Leu Gly Asp Asp Leu Leu Gln
                165                 170                 175

Cys His Pro Ala Val Lys Phe Pro Cys Gly Arg Pro Trp Lys Arg Met
                180                 185                 190

Glu Lys Lys Arg Ser His Leu Lys Arg Asp Thr Glu Asp Gln Glu Asp
            195                 200                 205

Gln Val Asp Pro Arg Leu Ile Asp Gly Lys Met Thr Arg Arg Gly Asp
210                 215                 220

Ser Pro Trp Gln Val Val Leu Asp Ser Lys Lys Leu Ala Cys
225                 230                 235                 240

Gly Ala Val Leu Ile His Pro Ser Trp Val Leu Thr Ala Ala His Cys
                245                 250                 255

Met Asp Glu Ser Lys Lys Leu Leu Val Arg Leu Gly Glu Tyr Asp Leu
            260                 265                 270

Arg Arg Trp Glu Lys Trp Glu Leu Asp Leu Asp Ile Lys Glu Val Phe
            275                 280                 285

Val His Pro Asn Tyr Ser Lys Ser Thr Thr Asp Asn Asp Ile Ala Leu
290                 295                 300

Leu His Leu Ala Gln Pro Ala Thr Leu Ser Gln Thr Ile Val Pro Ile
305                 310                 315                 320

Cys Leu Pro Asp Ser Gly Leu Ala Glu Arg Glu Leu Asn Gln Ala Gly
                325                 330                 335

Gln Glu Thr Leu Val Thr Gly Trp Gly Tyr His Ser Ser Arg Glu Lys
            340                 345                 350

Glu Ala Lys Arg Asn Arg Thr Phe Val Leu Asn Phe Ile Lys Ile Pro
            355                 360                 365

Val Val Pro His Asn Glu Cys Ser Glu Val Met Ser Asn Met Val Ser
370                 375                 380

Glu Asn Met Leu Cys Ala Gly Ile Leu Gly Asp Arg Gln Asp Ala Cys
385                 390                 395                 400

Glu Gly Asp Ser Gly Gly Pro Met Val Ala Ser Phe His Gly Thr Trp
                405                 410                 415

Phe Leu Val Gly Leu Val Ser Trp Gly Glu Gly Cys Gly Leu Leu His
            420                 425                 430

Asn Tyr Gly Val Tyr Thr Lys Val Ser Arg Tyr Leu Asp Trp Ile His
            435                 440                 445

Gly His Ile Arg Asp Lys Glu Ala Pro Gln Lys Ser Trp Ala Pro
450                 455                 460

<210> SEQ ID NO 58
<211> LENGTH: 185
<212> TYPE: PRT
<213> ORGANISM: Synechococcus sp. JA-2-3B'a(2-13)

<400> SEQUENCE: 58

Met Ala Ser Tyr Leu Lys Leu Lys Ala Gln Glu Glu Thr Trp Leu Gln
1               5                   10                  15

Arg His Ser Arg Leu Ile Leu Ala Ile Leu Ala Gly Leu Gly Ser Leu
            20                  25                  30

Leu Thr Ala Tyr Leu Thr Tyr Thr Lys Leu Thr Glu Gln Pro Ala Ala

```
                  35                  40                  45

Phe Cys Thr Gly Asp Gly Gly Cys Asp Leu Val Leu Ser Ser Arg Trp
 50                  55                  60

Ala Glu Phe Leu Gly Ile Pro Thr Ala Ala Val Gly Leu Leu Gly Phe
 65                  70                  75                  80

Leu Gly Val Leu Ala Leu Ala Val Leu Pro Asp Gly Leu Pro Leu Val
                 85                  90                  95

Lys Arg Trp Arg Trp Pro Ala Leu Phe Gly Leu Val Ser Ala Met Thr
                100                 105                 110

Ala Phe Glu Met Tyr Met Leu Tyr Leu Met Val Ala Val Leu Arg Gln
                115                 120                 125

Phe Cys Met Tyr Cys Thr Thr Ala Ile Ile Leu Val Ala Gly Leu Gly
                130                 135                 140

Leu Val Thr Val Leu Gly His Arg Trp Leu Asp Gly Gly Lys Leu Ala
145                 150                 155                 160

Phe Ser Tyr Ile Leu Val Ala Phe Leu Thr Leu Val Thr Thr Ile Gly
                165                 170                 175

Val Tyr Ala Asn Gln Val Pro Pro Pro
                180                 185

<210> SEQ ID NO 59
<211> LENGTH: 5
<212> TYPE: PRT
<213> ORGANISM: Artificial
<220> FEATURE:
<223> OTHER INFORMATION: GGCX pentapeptide substrate sequence

<400> SEQUENCE: 59

Phe Leu Glu Glu Leu
1               5

<210> SEQ ID NO 60
<211> LENGTH: 4
<212> TYPE: PRT
<213> ORGANISM: Artificial
<220> FEATURE:
<223> OTHER INFORMATION: VKOR active site concensus sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 60

Cys Xaa Xaa Cys
1

<210> SEQ ID NO 61
<211> LENGTH: 9
<212> TYPE: PRT
<213> ORGANISM: Artificial
<220> FEATURE:
<223> OTHER INFORMATION: Flexible extension linker sequence

<400> SEQUENCE: 61

Gly Gly Ser Gly Gly Ser Gly Gly Ser
1               5

<210> SEQ ID NO 62
<211> LENGTH: 7
<212> TYPE: PRT
<213> ORGANISM: Homo sapiens
<220> FEATURE:
<221> NAME/KEY: MISC_FEATURE
```

-continued

```
<222> LOCATION: (1)..(7)
<223> OTHER INFORMATION: Amino acids 44-50 of human VKOR

<400> SEQUENCE: 62

Asp Val Gly Thr Ala Ile Ser
1               5
```